(12) United States Patent
Boyette et al.

(10) Patent No.: US 11,957,583 B2
(45) Date of Patent: Apr. 16, 2024

(54) SYSTEM AND METHOD FOR CARDIAC VALVE REPAIR

(71) Applicant: Versa Vascular Inc., Santa Cruz, CA (US)

(72) Inventors: Jeremy J. Boyette, Woodside, CA (US); Daniel T. Wallace, Santa Cruz, CA (US); Juan Granada, Upper Saddle River, NJ (US); Peter W. Gregg, Santa Cruz, CA (US); Spencer C. Noe, San Miguel, CA (US); Evelyn N. Haynes, Los Gatos, CA (US); Andrew Backus, Santa Cruz, CA (US)

(73) Assignee: VERSA VASCULAR INC., Santa Cruz, CA (US)

( * ) Notice: Subject to any disclaimer, the term of this patent is extended or adjusted under 35 U.S.C. 154(b) by 0 days.

(21) Appl. No.: 18/206,577

(22) Filed: Jun. 6, 2023

(65) Prior Publication Data

US 2023/0320854 A1    Oct. 12, 2023

Related U.S. Application Data

(63) Continuation-in-part of application No. 17/550,660, filed on Dec. 14, 2021, which is a continuation-in-part of application No. 17/227,847, filed on Apr. 12, 2021, now Pat. No. 11,266,502.

(60) Provisional application No. 63/349,222, filed on Jun. 6, 2022, provisional application No. 63/125,035, filed on Dec. 14, 2020.

(51) Int. Cl.
*A61F 2/24* (2006.01)

(52) U.S. Cl.
CPC .......... *A61F 2/2436* (2013.01); *A61F 2/2439* (2013.01)

(58) Field of Classification Search
CPC ............................ A61F 2/2436; A61F 2/2439
See application file for complete search history.

(56) References Cited

U.S. PATENT DOCUMENTS

| | | | |
|---|---|---|---|
| 10,070,858 B2 * | 9/2018 | Shelton, IV | A61B 50/3001 |
| 10,136,993 B1 * | 11/2018 | Metchik | A61F 2/2466 |
| 10,898,325 B2 * | 1/2021 | Calomeni | A61F 2/2436 |
| 11,058,411 B2 * | 7/2021 | Bar | A61F 2/2409 |
| 2011/0137335 A1 * | 6/2011 | Hallisey | A61F 2/012 606/200 |
| 2012/0109181 A1 * | 5/2012 | Hallisey | A61F 2/01 606/200 |

(Continued)

OTHER PUBLICATIONS

International Search Report and Written Opinion, PCT/US2023/024623, dated Oct. 4, 2023, 12 pgs.

*Primary Examiner* — Phong Son H Dang
(74) *Attorney, Agent, or Firm* — Polsinelli PC

(57) ABSTRACT

A delivery device for cardiac valve repair implants includes a delivery catheter and an extension member protruding from a distal end of the delivery catheter. The delivery device further includes a control arm assembly having pairs of control arms. Each pair includes a proximal control arm drivable from a handle assembly of the delivery device and a distal arm coupled to a distal end of the proximal control arm and a distal end of the extension member. Proximally driving each of the proximal control arms of the control arm assembly results in expansion of the control arm assembly and corresponding expansion of a cardiac valve repair implant coupled to the control arm assembly.

30 Claims, 133 Drawing Sheets

(56) References Cited

U.S. PATENT DOCUMENTS

| | | | |
|---|---|---|---|
| 2012/0323174 A1 | 12/2012 | Shih | |
| 2015/0148896 A1* | 5/2015 | Karapetian | A61F 2/88 623/2.11 |
| 2016/0113766 A1* | 4/2016 | Ganesan | A61F 2/2427 623/2.11 |
| 2018/0021044 A1* | 1/2018 | Miller | A61B 17/12031 606/142 |
| 2019/0029818 A1* | 1/2019 | Siegel | B29C 49/26 |
| 2019/0029827 A1* | 1/2019 | Bar | A61F 2/24 |
| 2019/0029854 A1 | 1/2019 | Calomeni et al. | |
| 2019/0142580 A1* | 5/2019 | Delgado | A61F 2/2445 623/2.1 |
| 2019/0254824 A1* | 8/2019 | Bar | A61F 2/2427 |
| 2021/0361428 A1* | 11/2021 | Dixon | A61F 2/2466 |
| 2022/0313433 A1* | 10/2022 | Ma | A61F 2/246 |

\* cited by examiner

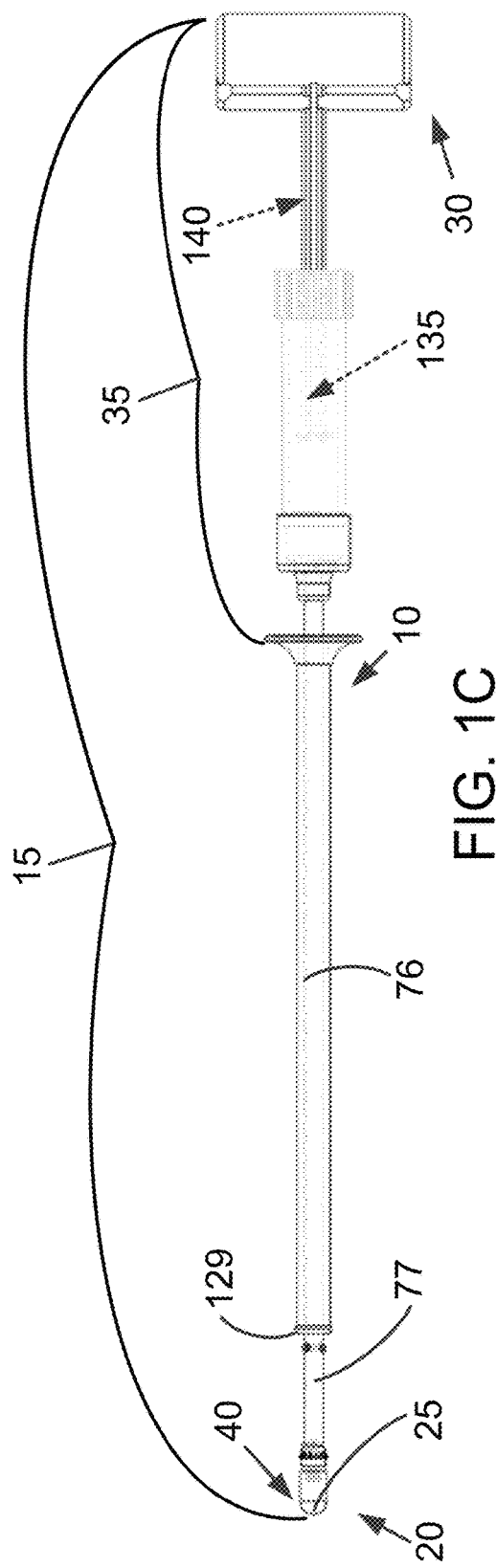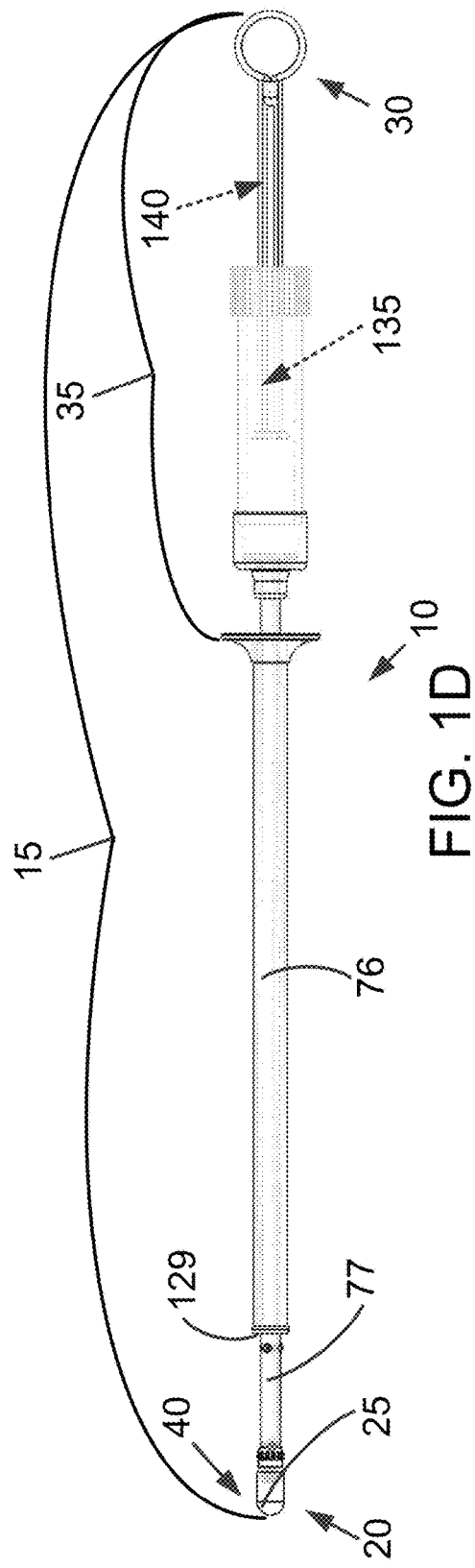

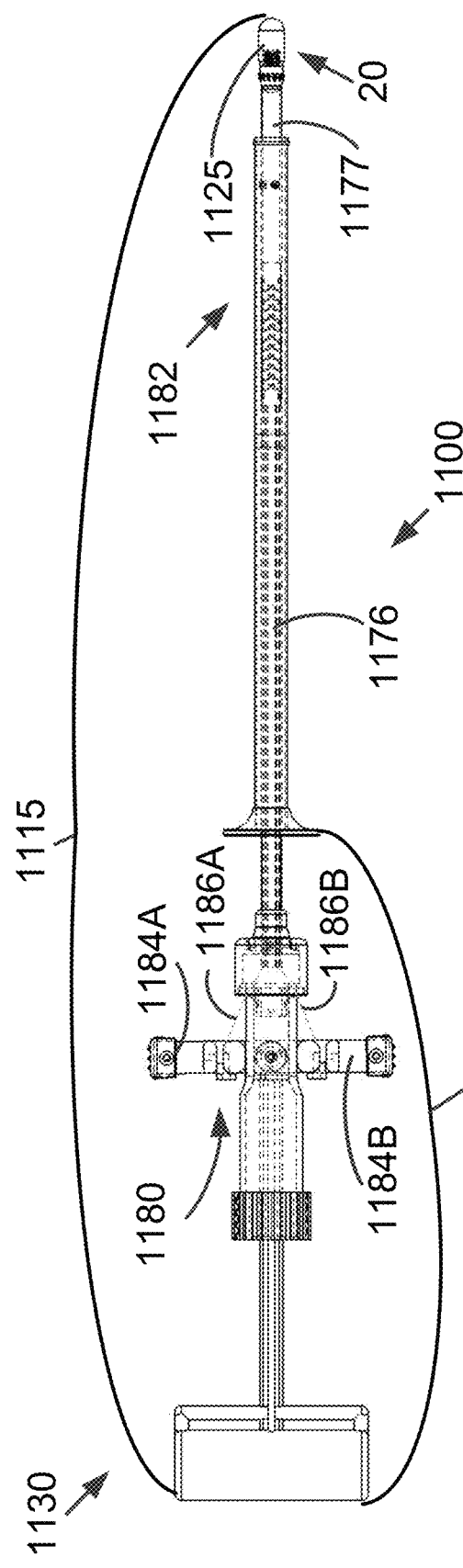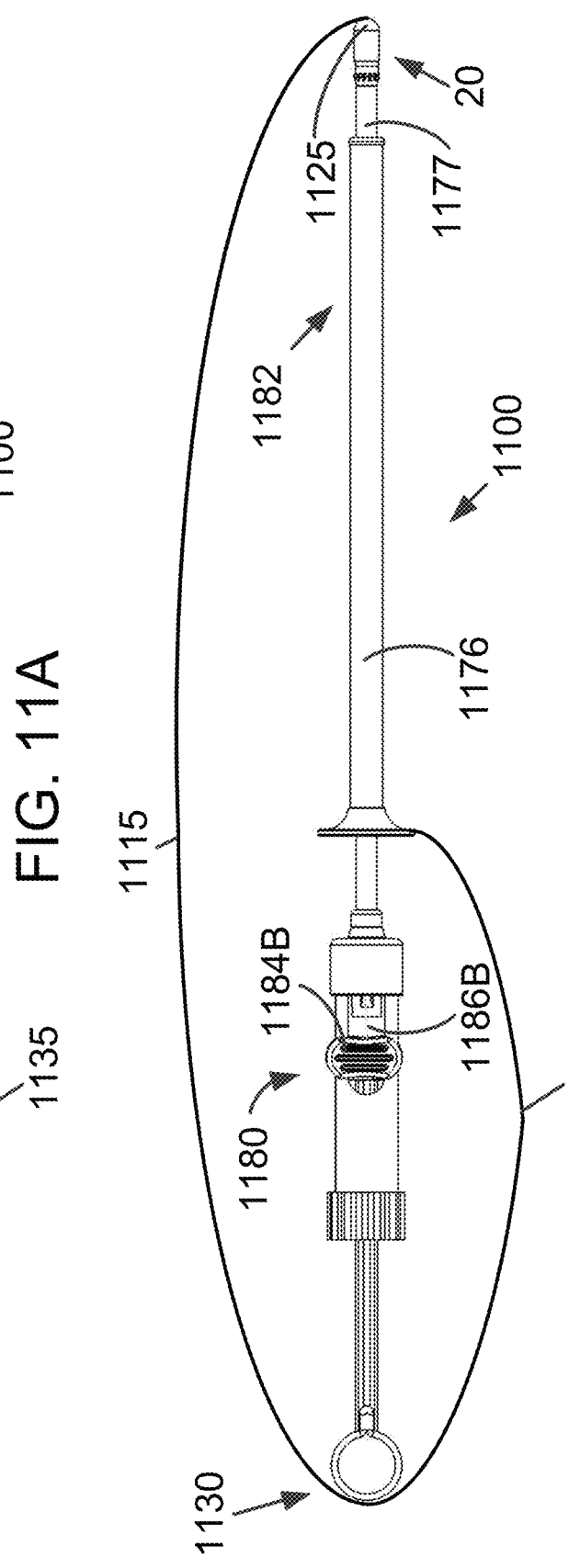
FIG. 11A
FIG. 11B

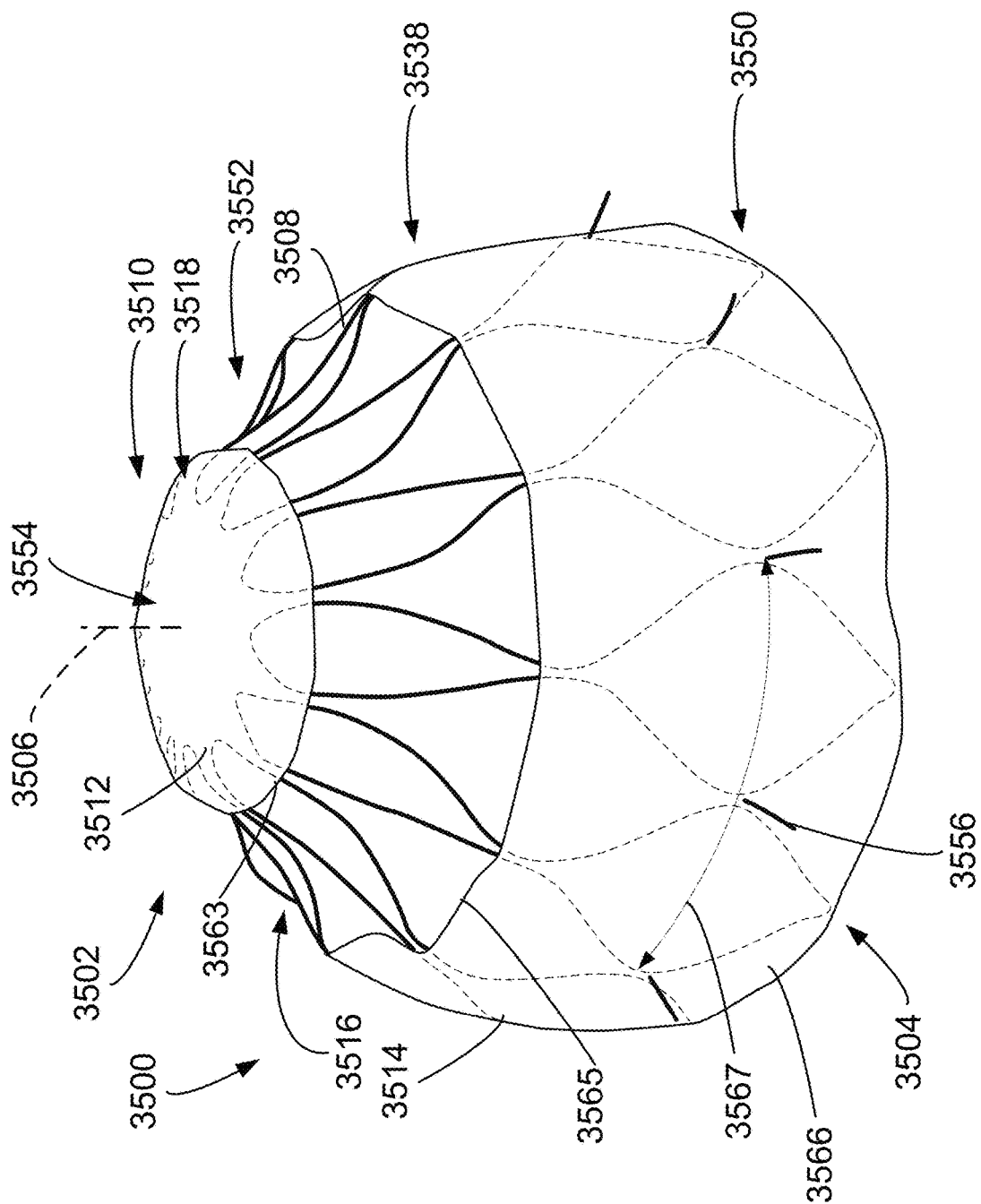

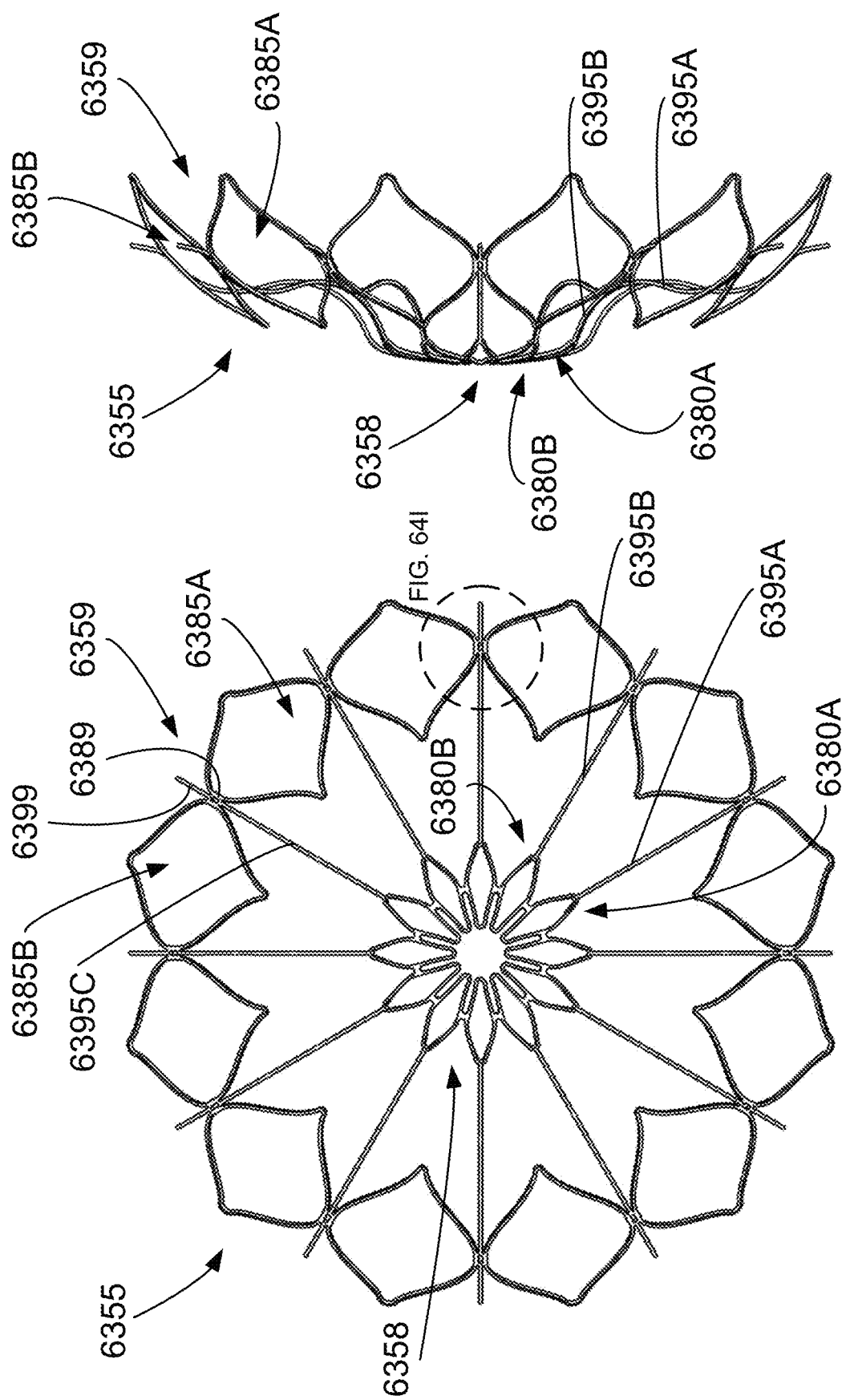

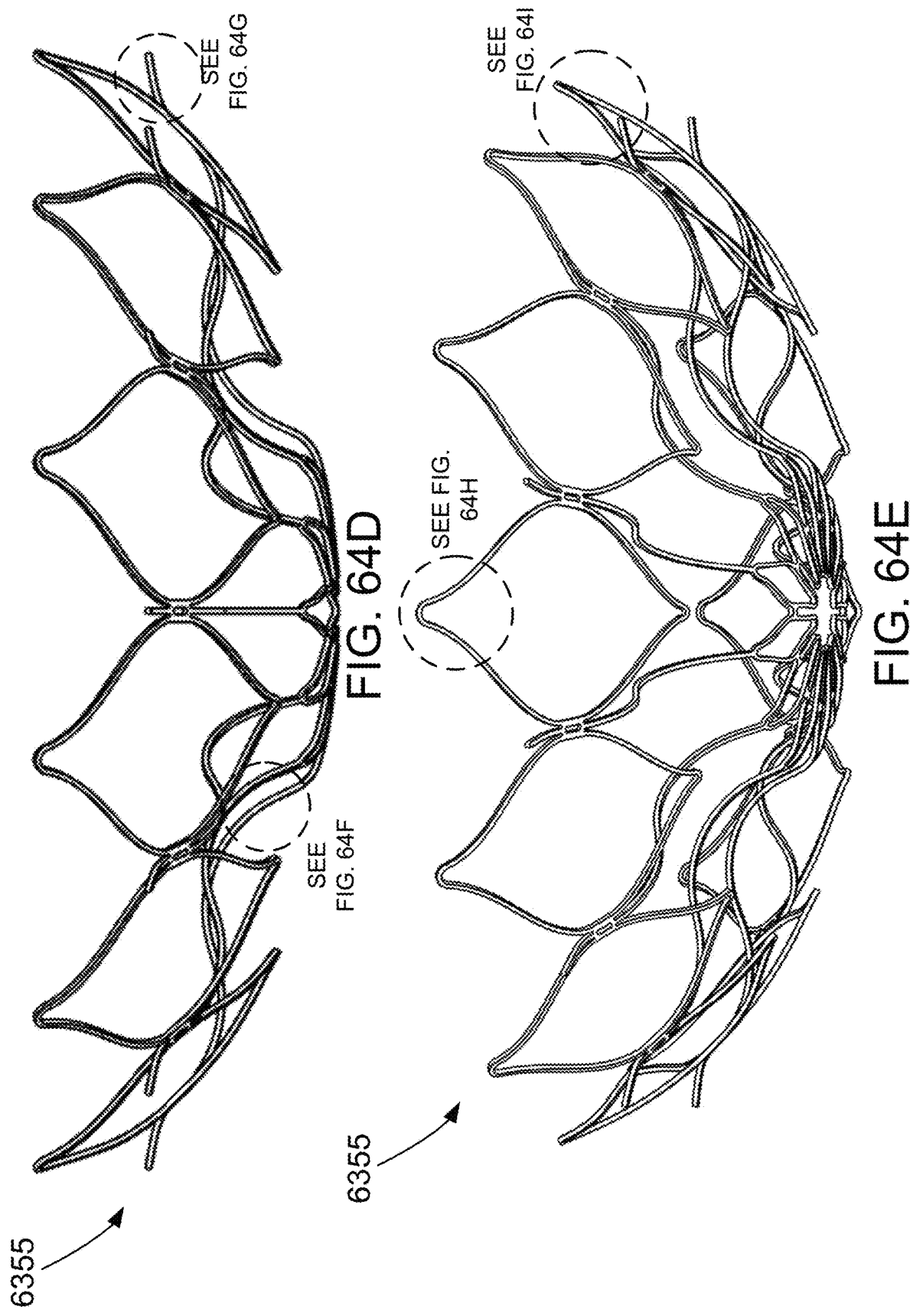

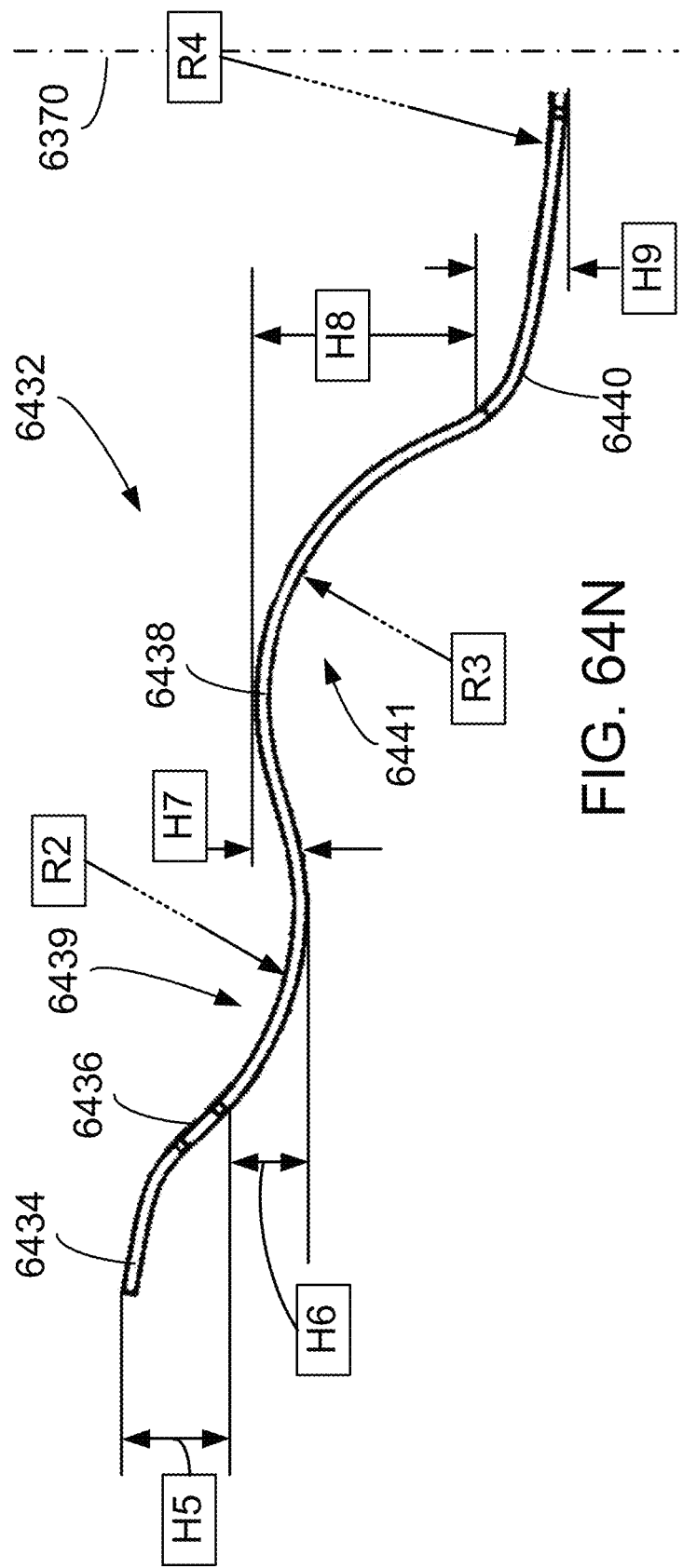

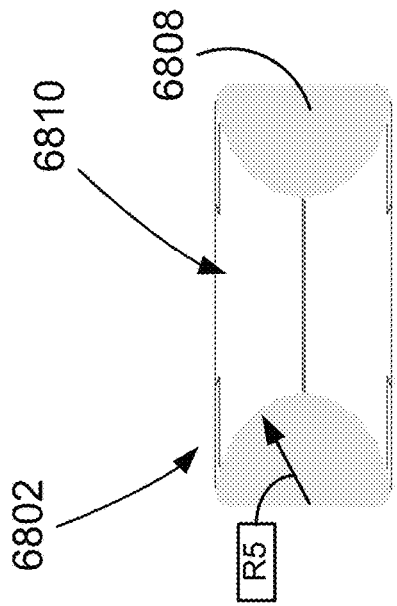
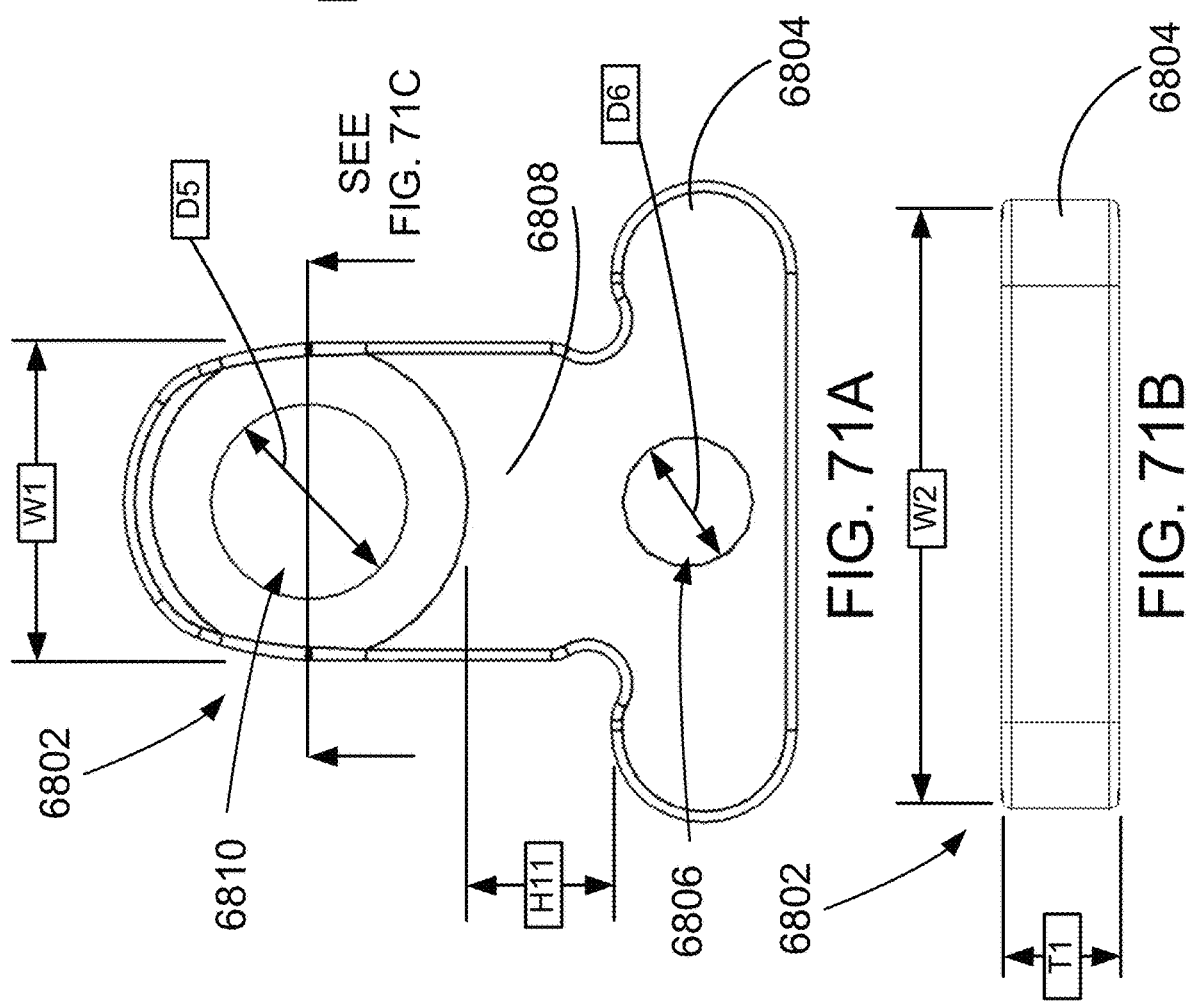

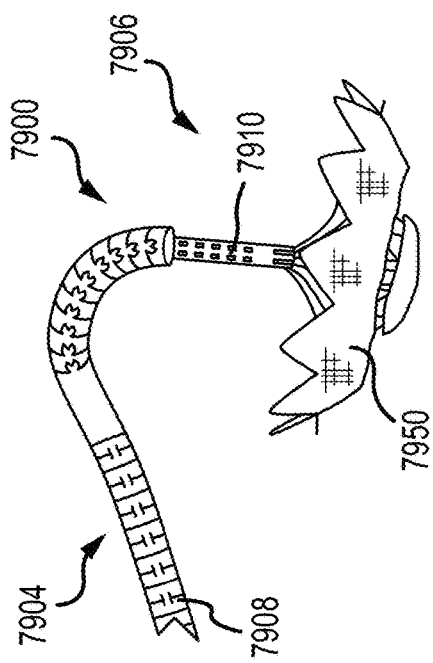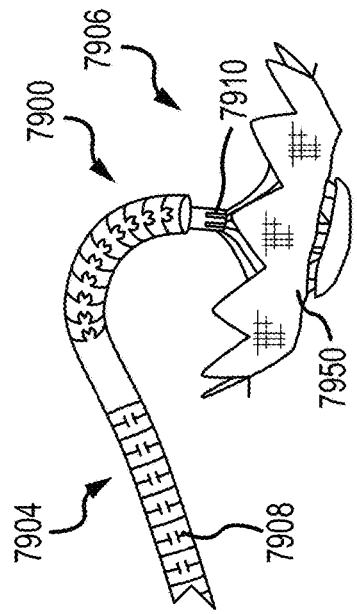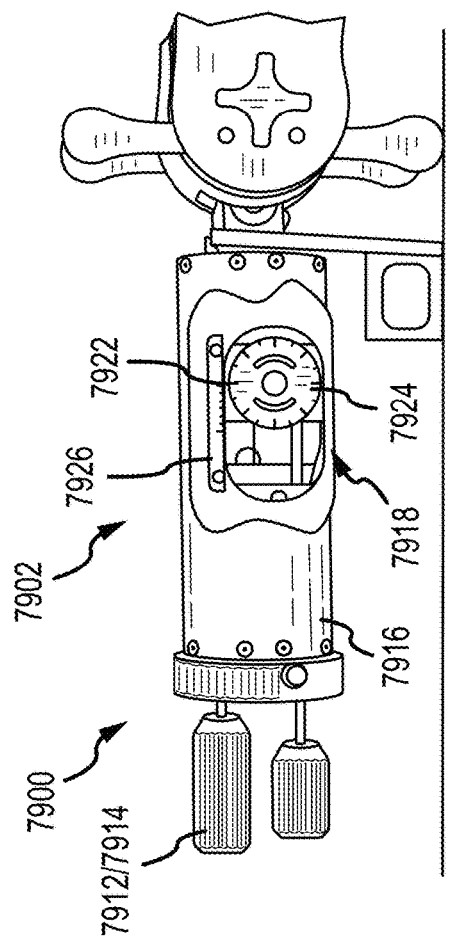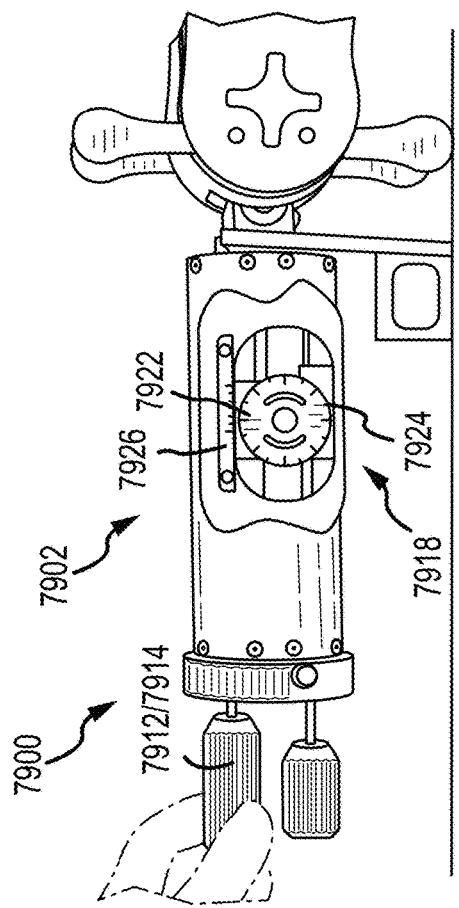

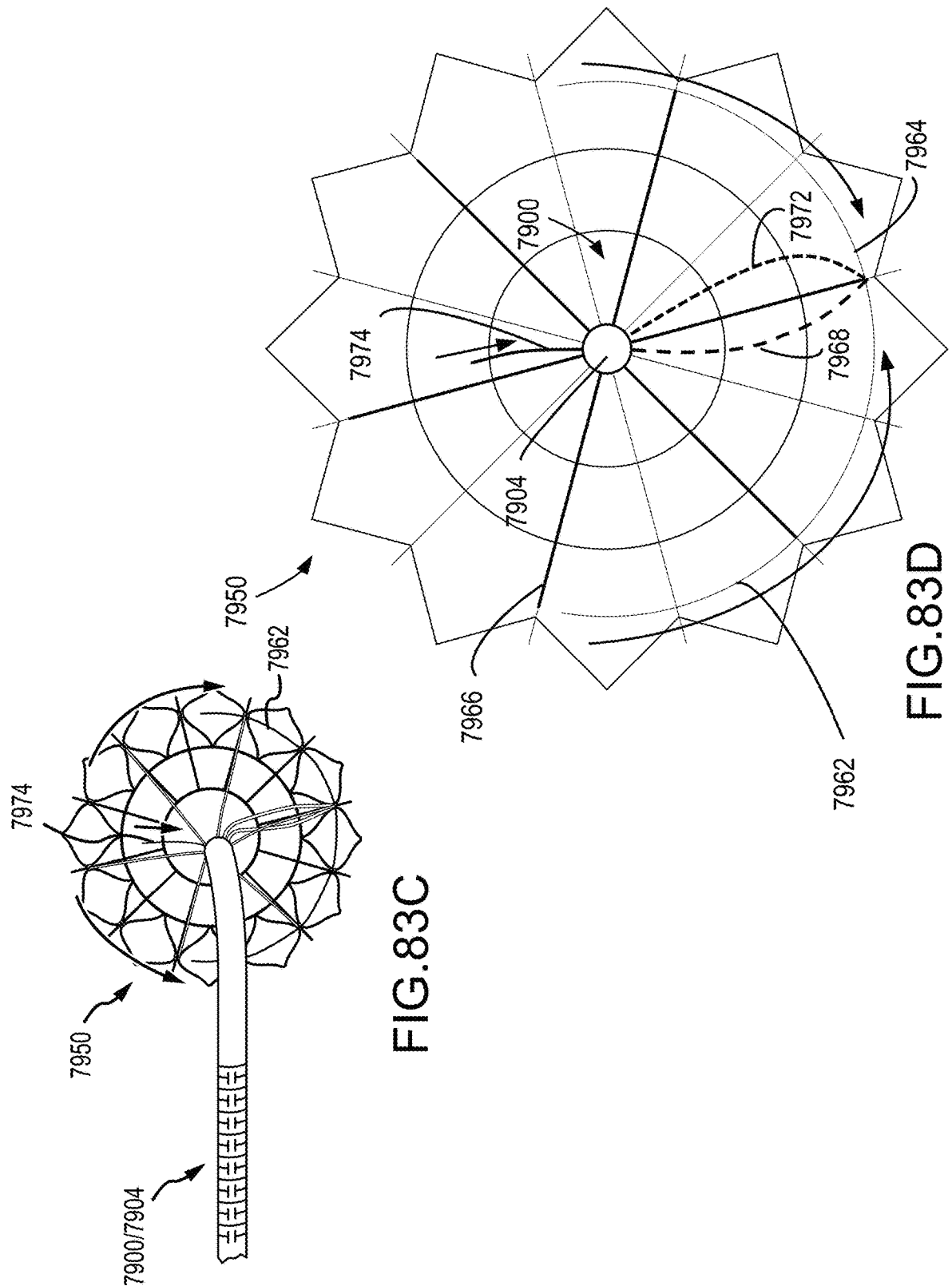

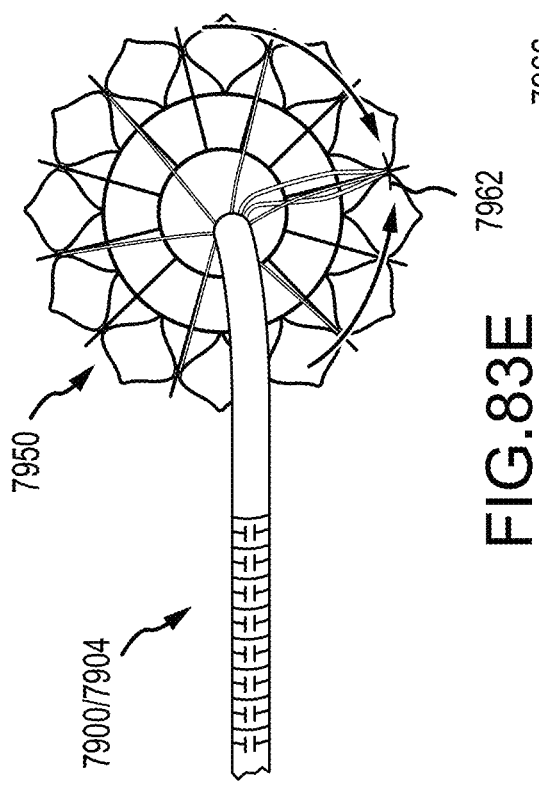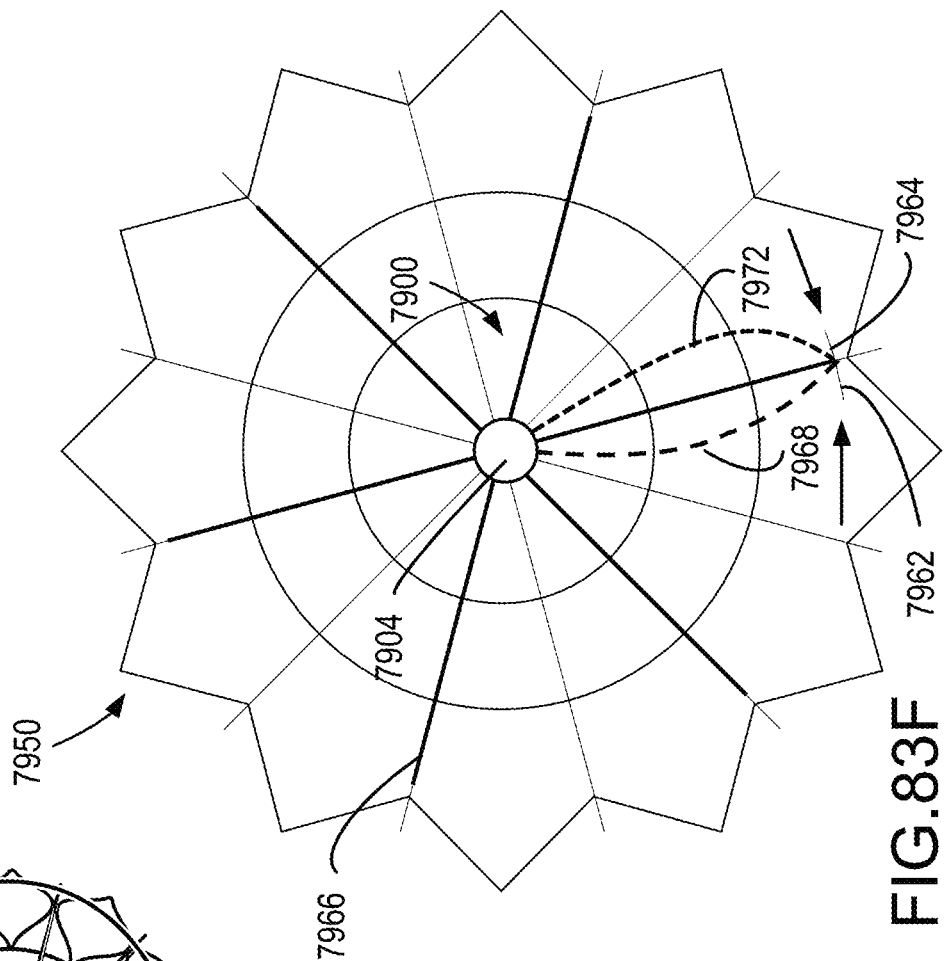
FIG. 83E
FIG. 83F

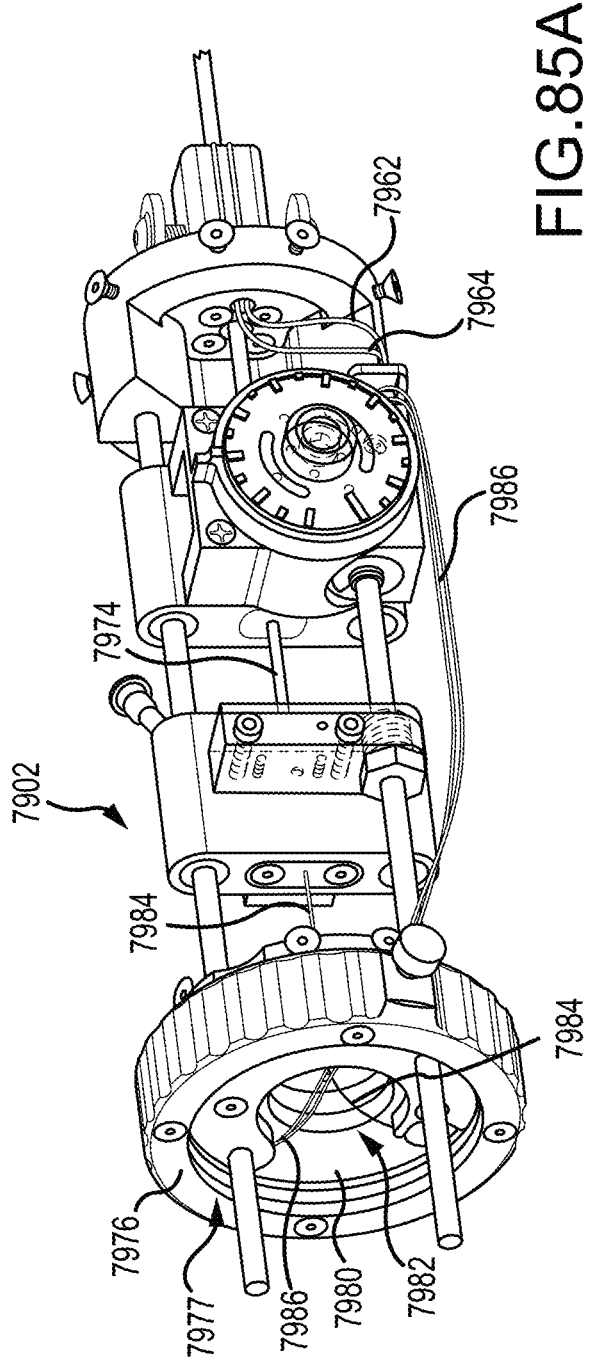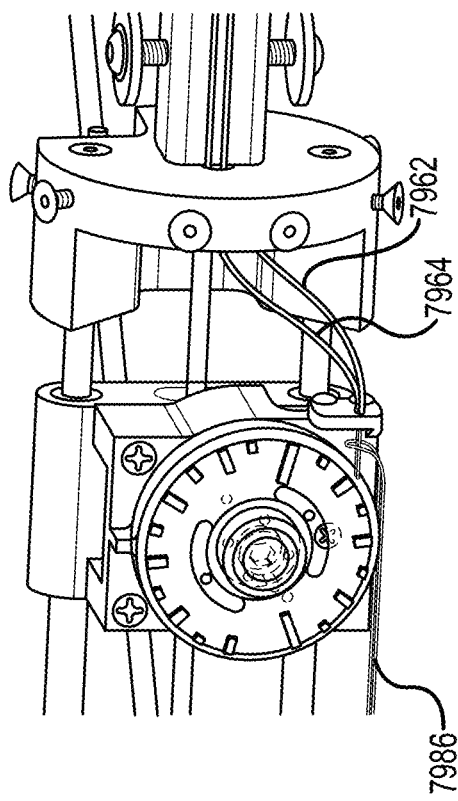

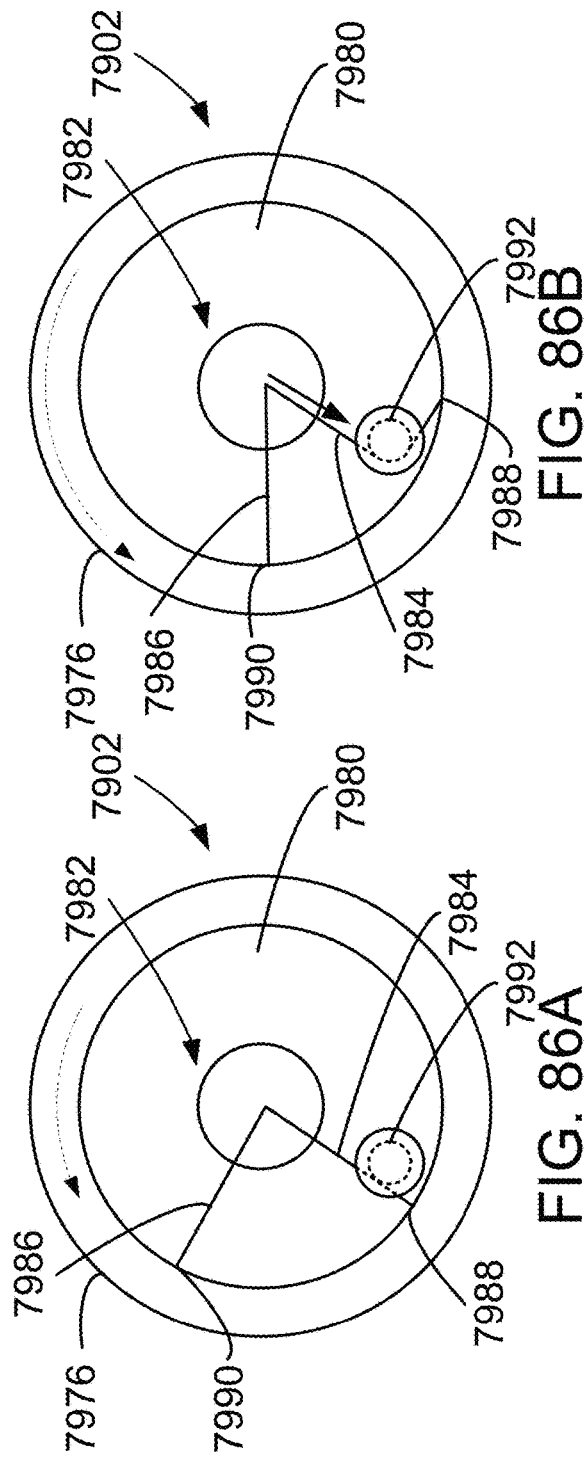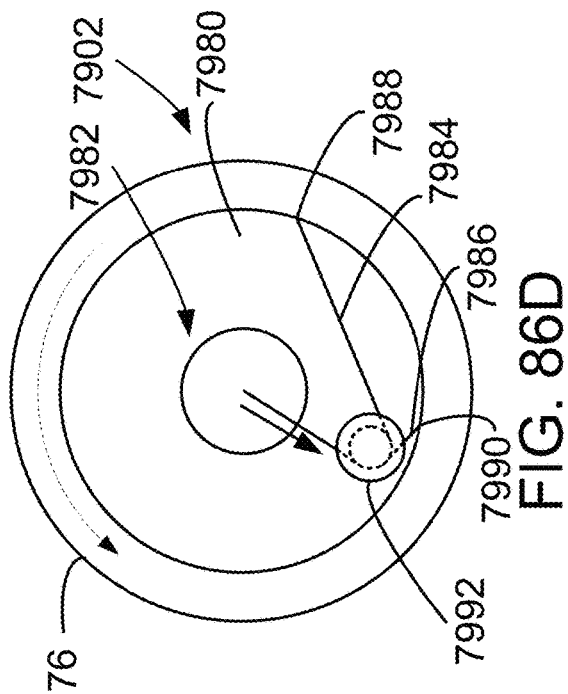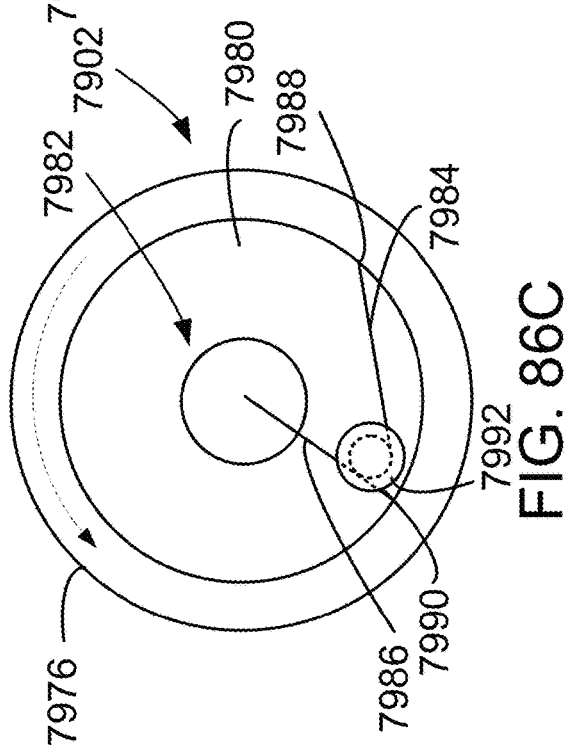

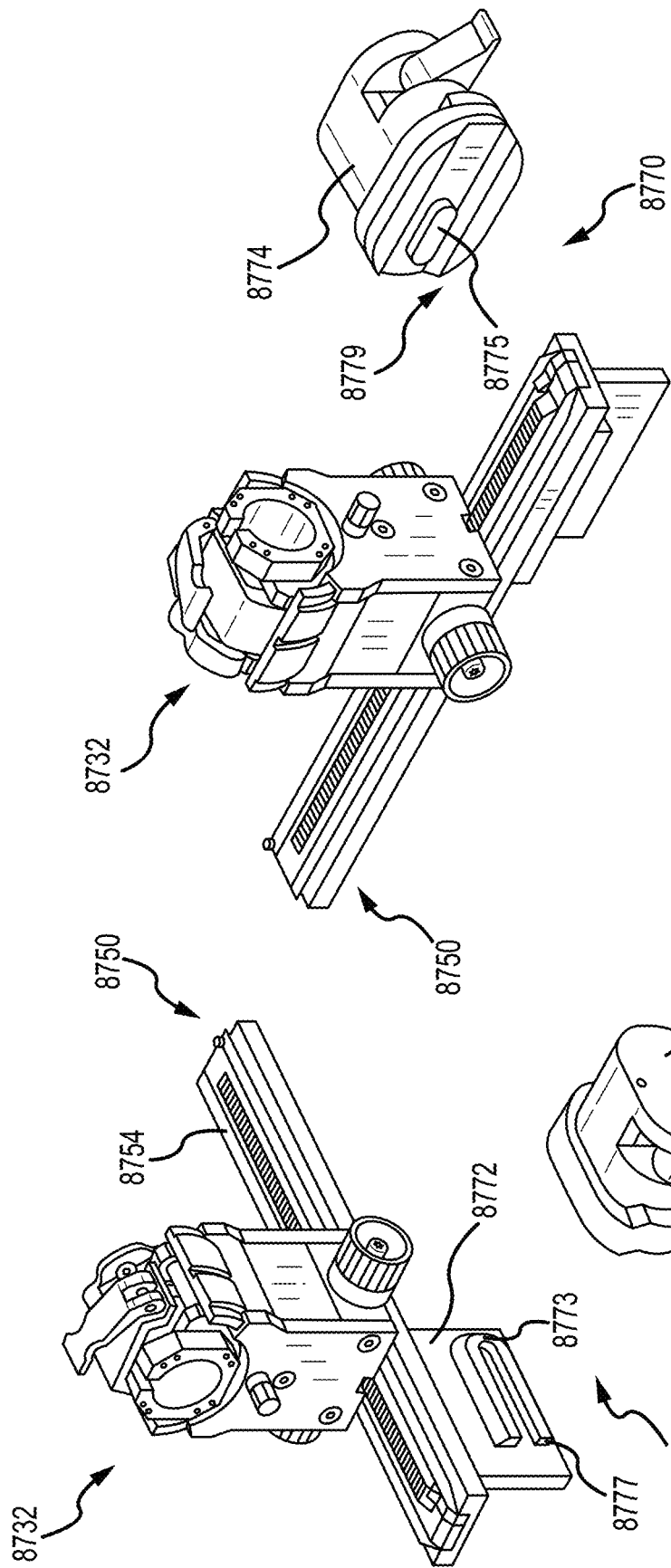

SYSTEM AND METHOD FOR CARDIAC VALVE REPAIR

CROSS-REFERENCE TO RELATED APPLICATIONS

This application is a continuation-in-part of U.S. patent application Ser. No. 17/550,660, filed Dec. 14, 2021, which is a continuation-in-part of U.S. patent application Ser. No. 17/227,847, filed Apr. 12, 2021, now U.S. Pat. No. 11,266, 502 and titled "System and Method for Cardiac Valve Repair", which is related to and claims priority under 35 U.S.C. § 119(e) from U.S. Patent Application No. 63/125, 035, filed Dec. 14, 2020, and titled "System and Method for Cardiac Valve Repair".

This application is also related to and claims priority under 35 U.S.C. § 119(e) from U.S. Patent Application No. 63/349,222, filed Jun. 6, 2022.

The entire contents of each of the foregoing applications are incorporated herein by reference for all purposes.

FIELD

The present disclosure relates to medical systems and methods for repairing a cardiac valve. More specifically, the present disclosure pertains to a cardiac valve repair implant that is minimally invasively deliverable and implantable via an associated minimally invasive delivery tool.

BACKGROUND

Cardiac valve regurgitation occurs when a cardiac valve does not close completely, causing blood to leak back through the valve. The causes of regurgitation may vary. Functional regurgitation is caused by changes to the heart geometry near the valve, where, for example, the heart enlarges, inducing both geometrical distortion around the valve annulus and insufficient leaflet coaptation during valve closure.

Degenerative regurgitation is caused by a disease of the valve itself, where, for example, the leaflets may thicken and be unable to seal completely. In both cases, the patient suffers because high-pressure blood in the ventricle regurgitates through the valve into the low-pressure venous system.

Surgical repair and replacement may successfully treat tricuspid and mitral regurgitation, but surgery is costly and traumatic. Specifically, the surgical treatments require general anesthesia, a stopped heart with extracorporeal bypass, and either valve replacement or repair. The surgical treatments require painful recovery over a period of approximately three weeks. As a result, surgical treatment is often not performed because cost, recovery time, pain, and, for older patients, mortality risk may be prohibitive.

Cardiac valves may also be repaired via percutaneous systems and methods. For example, a percutaneous treatment may navigate a Nitinol clip between the valve leaflets to permanently clip the leaflets together. The percutaneous clip procedure results in a relatively pain-free recovery within days, and this procedure has successfully treated hundreds of thousands mitral regurgitation patients. Unfortunately, the percutaneous clip procedure is costly and difficult to perform, particularly by inexperienced operators. Further, the feasibility of the percutaneous clip procedure for the tricuspid valve is unproven and may be less effective in a three-leaflet valve. In addition, the mechanisms of valvular regurgitation are multiple and fixing a single mechanism of disease (e.g., leaflet grasping) may temporarily reduce the severity of regurgitation but not improve the natural history of the disease (e.g., deterioration over time).

Accordingly, there is a need for a system for repairing a cardiac valve that is simple to deliver, targets several disease components simultaneously, and improves overall results as compared to conventional treatments. There is also a need for a method of making such a repair.

SUMMARY

In one aspect of the present disclosure, a delivery device for cardiac valve repair implants is provided. The delivery device includes a delivery catheter, an extension member protruding from a distal end of the delivery catheter and a control arm assembly releasably coupleable to a valve repair implant. The control arm assembly includes a control arm pair that further includes a distal control arm coupled to and extending proximally from a distal end of the extension member and a proximal control arm coupled the distal control arm, the proximal control arm extendable from the distal end of the delivery catheter to laterally expand the control arm assembly.

In another aspect of the present disclosure, another delivery device for cardiac valve repair implants is provided. The delivery device includes a delivery catheter, an extension member protruding from a distal end of the delivery catheter and a control arm assembly releasably coupleable to a valve repair implant. The control arm assembly includes multiple control arm pairs distributed circumferentially about the extension member. Each control arm pair includes a distal control arm coupled to and extending proximally from a distal end of the extension member and a proximal control arm coupled to the distal control arm, the proximal control arm extendable from the distal end of the delivery catheter to laterally expand the control arm assembly.

In another aspect of the present disclosure, a delivery device for cardiac valve repair implants is provided. The delivery device includes a delivery catheter, an extension member protruding from a distal end of the delivery catheter and a control arm assembly releasably coupleable to a valve repair implant. The control arm assembly includes a control arm pair that further includes a distal control arm coupled to and extending proximally from a distal end of the extension member and a proximal control arm coupled the distal control arm, the proximal control arm extendable from the distal end of the delivery catheter to laterally expand the control arm assembly. The delivery catheter further includes a distal portion including multiple, independently steerable sections.

BRIEF DESCRIPTION OF THE DRAWINGS

FIGS. 1A-1D are illustrations of a system for repairing a cardiac valve, the system including a minimally invasive delivery tool and an implantable cardiac valve repair implant supported on a distal end of the delivery tool and that is deliverable and implantable via the delivery tool.

FIGS. 11A-11C are illustrations of a system for repairing a cardiac valve and, more specifically, a plan view, side elevation view, and a plan view illustrating a range of motion of a delivery tool of the system, respectively.

FIG. 35B is a second distal-end view of the implant of FIG. 35A including each of inner and outer sheets.

FIGS. 70 and FIGS. 71A-71C are views of the eyelets of FIGS. 69A-69B.

FIGS. 79A and 79B are elevation views of a handle assembly and a distal end of a delivery system illustrating distal extension of an implant coupled to the delivery system.

FIGS. 79C and 79D are elevation views of the handle assembly and the distal end of the delivery system illustrating distal retraction of the implant coupled to the delivery system.

FIGS. 83A-83H are proximal views of an implant coupled to a delivery system during progressive stages of an implant release sequence.

FIGS. 85A and 85B are internal views of the handle assembly of FIG. 84.

FIG. 86A-86D proximal internal views of the handle assembly of FIG. 84 during progressive stages of an implant release sequence.

FIGS. 87D and 87E are isometric views of a rail assembly, carriage assembly, and interface of the mounting assembly of FIG. 87A in a decoupled state.

FIG. 89 is a side view of the distal portion of the delivery device of FIG. 88A with the control arm assembly in a collapsed and retracted configuration.

FIG. 90 is a flow chart illustrating an example method of delivering a cardiac valve repair implant according to this disclosure.

DETAILED DESCRIPTION

Figure 1A:
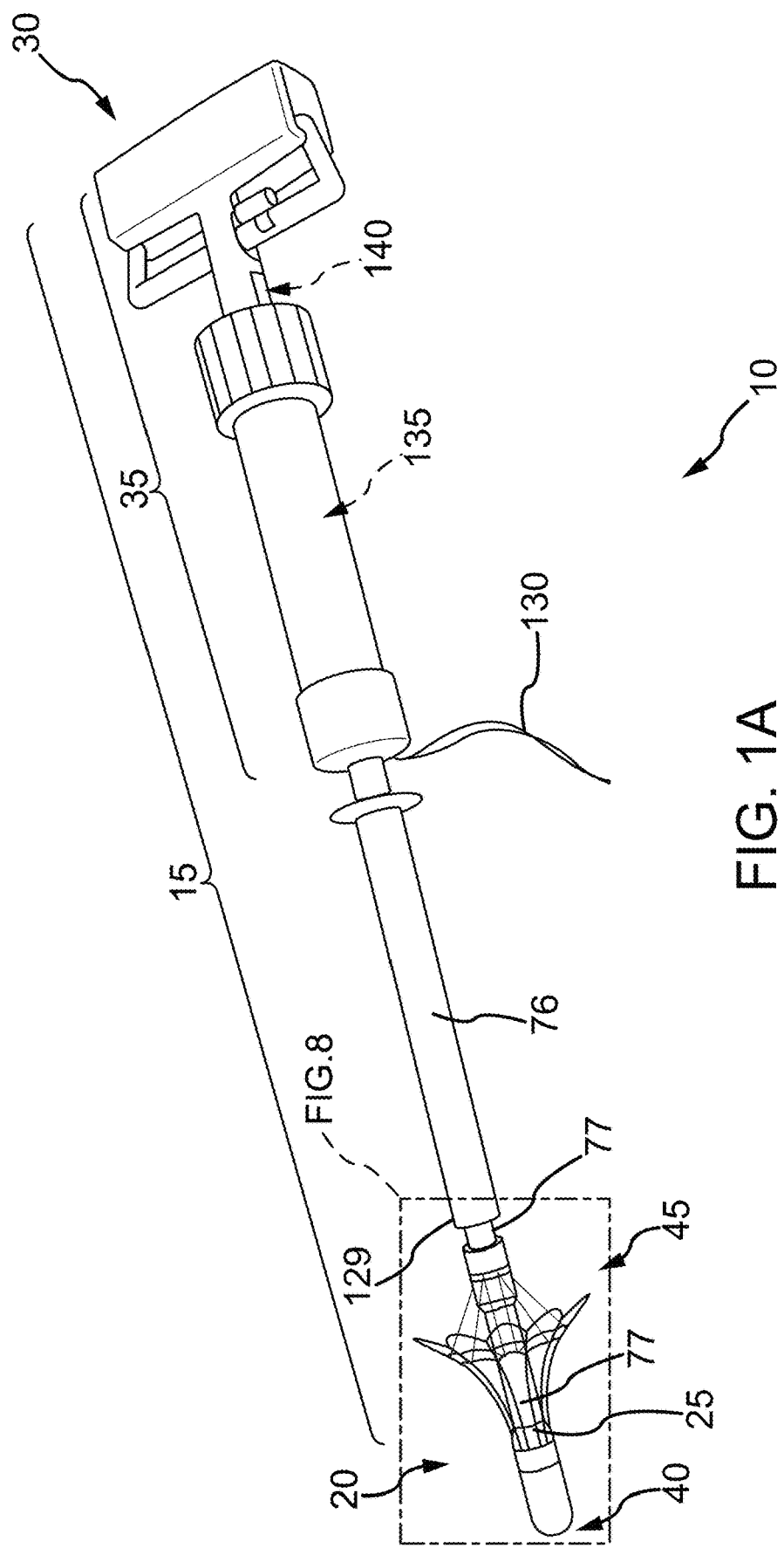
Figure 1B:
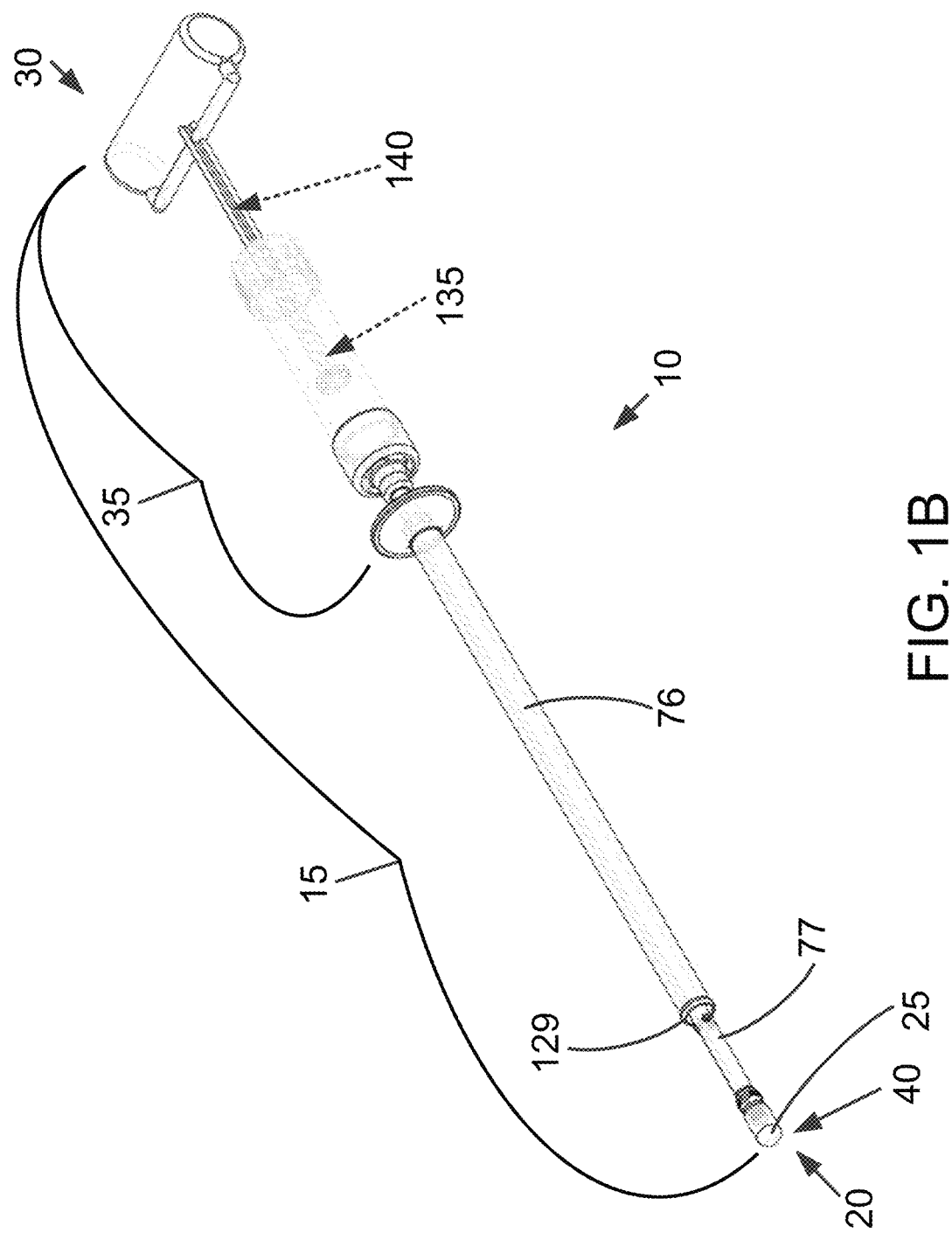

Fora brief overview of the cardiac valve repair system 10 disclosed herein, reference is made to FIGS. 1A-1D. In particular, FIG. 1A is an illustration of the cardiac valve repair system 10 while FIGS. 1B-1D are isometric, plan, and side elevation views, respectively of the valve repair system 10. As can be understood from FIG. 1A, the system 10 includes a delivery and deployment tool 15 and an implantable cardiac valve repair device or implant 20 supported on a distal end 25 of the tool 15. The tool 15 includes a proximal end 30 opposite the tool distal end 25. The tool proximal end 30 includes a control handle 35 used by a physician to manipulate the tool 15 in positioning the implant 20 at the target site and deploying the implant 20 within the target site, which is a cardiac valve in need of repair, as discussed in detail later in this Detailed Description. In one embodiment, the tool 15 is used for minimally invasive delivery and deployment of the implant 20 in the cardiac valve in need of repair.

The system and its implant are advantageous in that the implant may be delivered and deployed at the target site via an antegrade percutaneous route (e.g., a trans-femoral or trans-jugular route) with the patient consciously sedated during the procedure. It is anticipated the implantation stage may take less than 60 minutes, and the implant and delivery system will have a cost substantially less expensive than prior cardiac valve repair systems. Finally, the regurgitation grade afforded by a cardiac valve repair completed via the implant 20 disclosed herein will be 2+ or lower. Accordingly, the cardiac repair system 10 is a significant improvement over prior art systems as it is atraumatic, materially less expensive and less time intensive, all while providing a significant improvement in the reduction of regurgitation.

I. Cardiac Valve Repair Implant

To begin a detailed discussion of the cardiac valve repair implant 20, reference is made to FIGS. 2-6, which are various views of an embodiment of the implant 20 when the implant is in an expanded state that exists when the implant is implanted in the cardiac valve to be repaired. As illustrated in these figures, the implant includes distal end 40 and a proximal end 45. The distal end 40 serves as the leading end of the implant 20 during implantation, as can be understood from FIG. 1A-1D.

As illustrated in FIGS. 2-6, the implant 20 further includes a central occluder 50, a frame 55 and a thin sheet 60 (also referred to herein as a thin layer 60) supported on the frame. The frame 55 extends proximally from a proximal end 65 of the central occluder 50. When in the expanded state, the frame 55 radiates laterally outwardly relative to a central longitudinal axis 70 (see FIG. 5) of the implant 20, and the thin sheet 60 forms an annular surface 62 supported on the expanded frame 55. The annular surface 62 has a distal radially inward edge 63 and a proximal radially outward edge 64. The distal radially inward edge 63 defines a central opening 66 in the thin sheet 60 and the implant 20. The proximal radially outward edge 64 forms the extreme proximal radially outward boundary of this embodiment of the implant when in the expanded state. The central longitudinal axis 70 passes through the extreme distal tip 75 of the central occluder 50 and a center point 80 (see FIG. 4) of the proximal end 65 of the central occluder. In light of the foregoing and in at least certain embodiments, the frame 55 is generally designed to sit on the floor of the atrium, to induce annular reduction, and to produce a neo-annulus.

Figure 10:
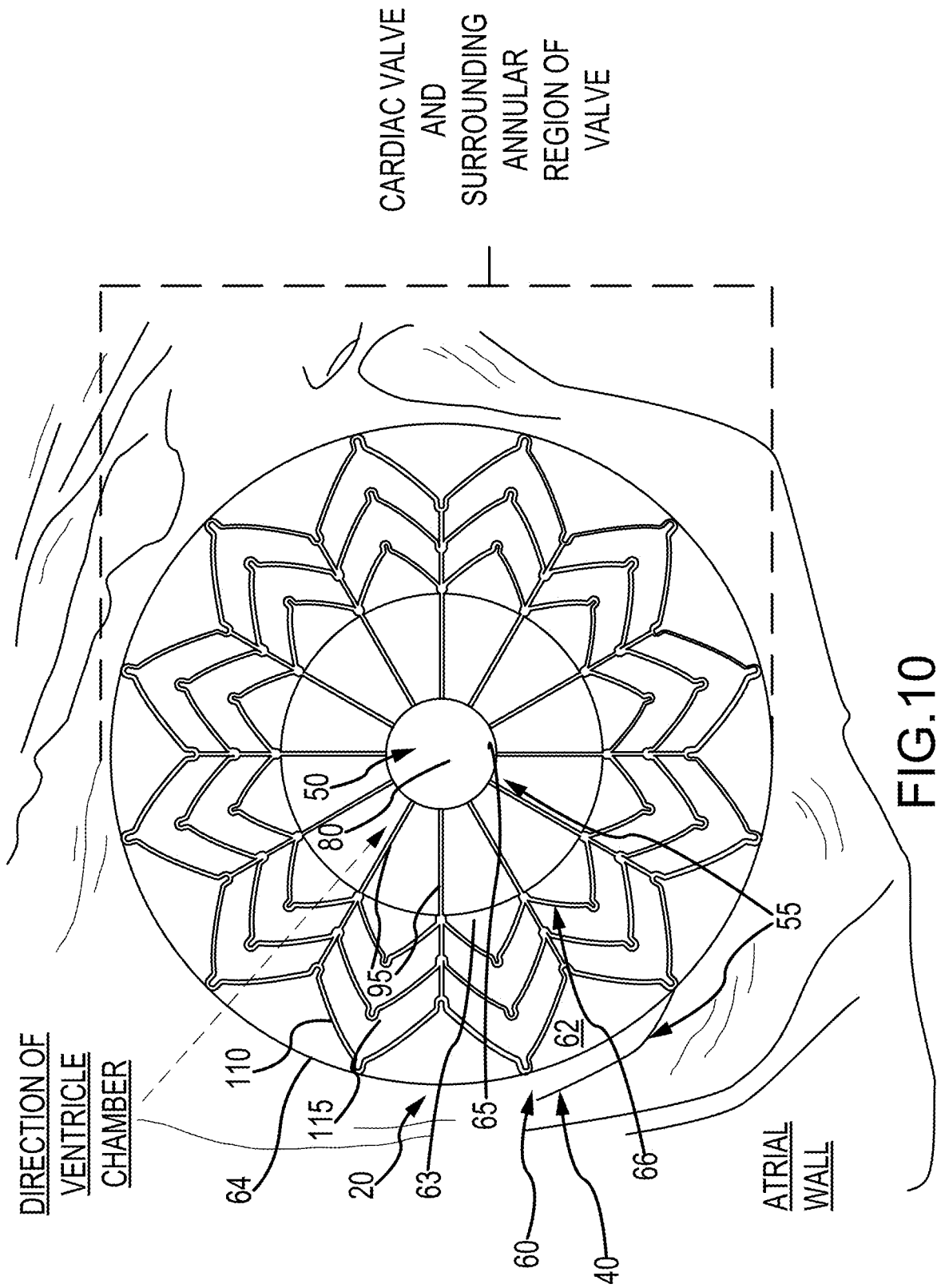
FIG. 10 is a view of the implantable cardiac valve repair implant implanted in a target cardiac valve, as viewed from an atrial position looking towards the valve and the ventricle chamber below.

As can be understood from FIGS. 2-6, in addition to being annular, the annular surface 62 may also be conical, or relatively so (e.g., parabolic), such that its proximal side, which faces the atrial chamber when the implant 20 is implanted in the target cardiac valve as depicted in FIG. 10, serves as a funnel arrangement distally leading from the atrial chamber towards the central opening 66 of the implant 20 and the valve opening distal the central opening 66. Similarly, the distal side of the annular surface 62 may also be conical to generally make mating surface contact with the semi-conical regions of the atrial wall surface and surrounding annular region of the target cardiac valve, as can be understood from FIG. 10.

Figure 6:
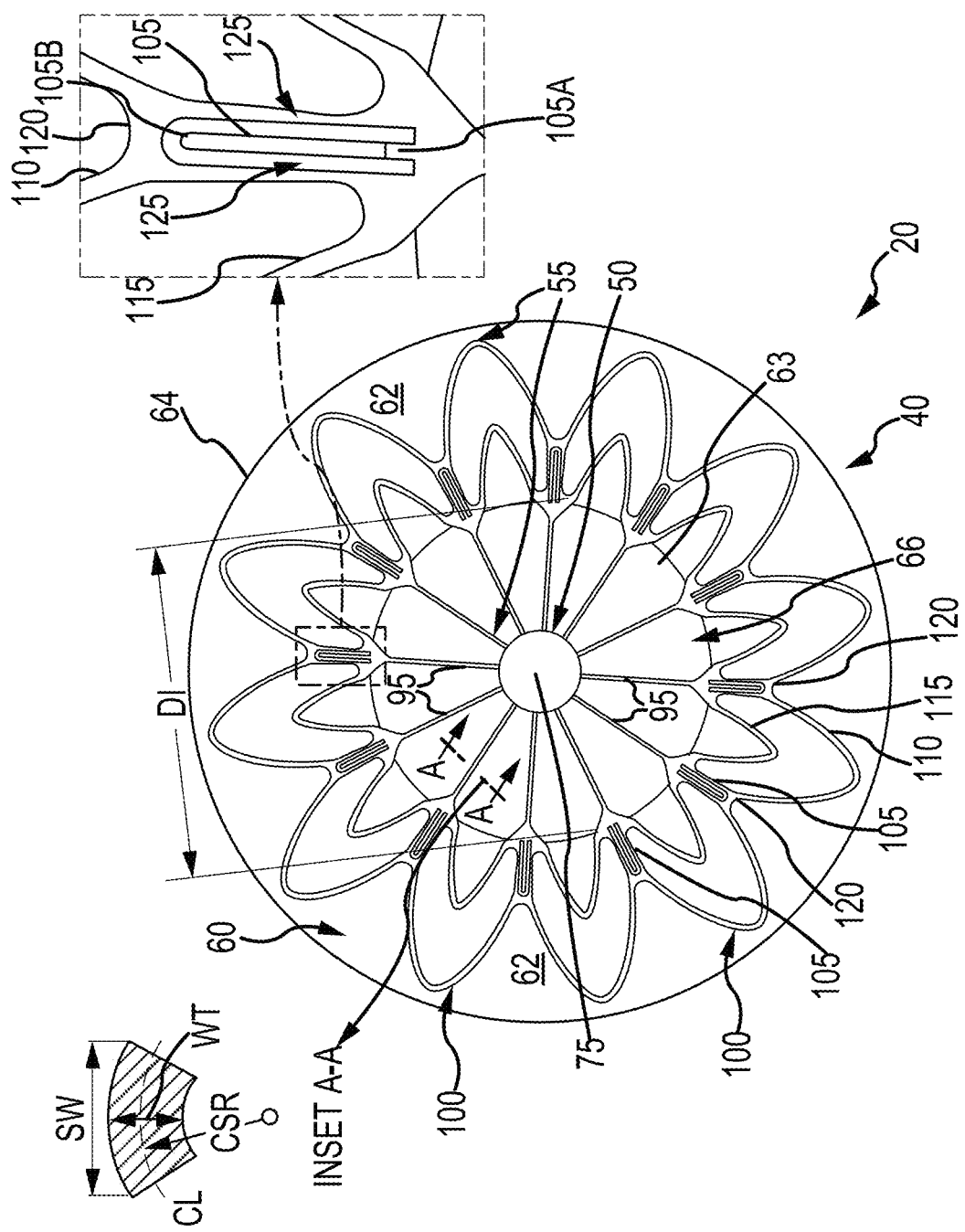
FIG. 6 is a distal plan view of the implantable cardiac valve repair implant in the expanded state.
Figure 7:
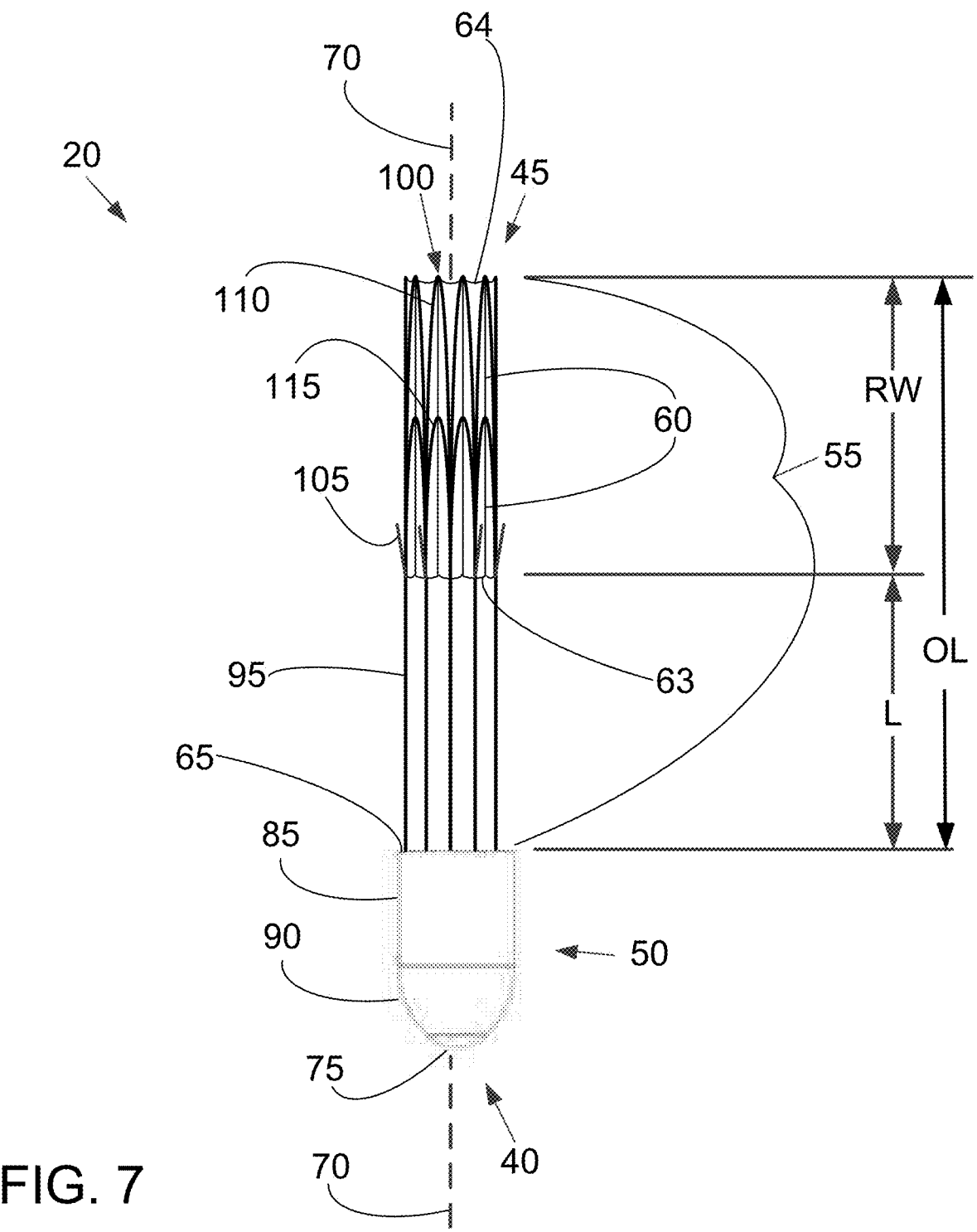
FIG. 7 is a side elevation view of the implantable cardiac valve repair implant in a collapsed state.

When in the collapsed state, as depicted in FIG. 7, which is a side view of the implant collapsed to allow its delivery to the target site via the tool 15, the frame 55 and thin sheet 60 collapse symmetrically about the central longitudinal axis 70. Thus, a comparison of the implant 20 in FIGS. 2-6 when in the expanded state to the implant 20 in FIG. 7 in the collapsed state indicates that the implant can transition from the collapsed state to the expanded state similar to an umbrella.

As can be understood from FIG. 9 and discussed in greater detail later in this Detailed Disclosure, during delivery, the implant 20 is maintained in the collapsed state of FIG. 7 by the tool 15 so as to allow the implant to be negotiated through the patient vascular system and into an atrial chamber of the heart for implantation of the implant within a target cardiac valve. For example, with the implant 20 maintained in the collapsed state by virtue of being confined within a tubular sheath 76 of the delivery tool 15, the implant may be delivered and deployed at the target site via an antegrade percutaneous route (e.g., an antegrade trans-femoral or trans-jugular route) with the patient consciously sedated during the procedure.

Upon being properly positioned in the target cardiac valve for repair, the physician actuates the tool 15 such that the tool no longer maintains the implant 20 in the collapsed state, as can be understood from FIG. 1A. Since the frame 55 of the implant 20 is biased to self-expand into the expanded state of FIGS. 2-6, the implant self-expands into the expanded state to anchor itself within the target cardiac valve and reduce regurgitation, as shown in FIG. 10.

Returning to FIGS. 2-6, it can be understood that the central occluder 50 may take the form of a bullet or conical shape. In doing so, the central occluder may have a cylindrical side 85 extending distally from the central occluder proximal end 65 and then transitioning to a bullnose 90 that distally extends to the central occluder extreme distal tip 75. Such a bullet or conical shape results in the central occluder 50 being atraumatic for delivery and implantation purposes. Further, such a shape facilitates the cylindrical side 85 of the central occluder substantially sealing against the cardiac valve leaflets, thereby materially reducing, if not eliminating, central regurgitation past the cardiac valve leaflets.

Without limitation and depending on the embodiment, the central occluder 50 may be formed from polytetrafluoroethylene (PTFE), polyether ether ketone (PEEK), acetal, silicone, nylon, polyethylene, polypropylene, polyethylene terephthalate (PET), polyurethane, or other thermoplastic elastomers. In certain embodiments, the material of the central occluder 50 may be angio- and/or echolucent.

In certain embodiments, the central occluder 50 may be filled with saline, a combination of saline with a radioopaque contrast agent, or other fluid. In such embodiments, the central occluder 50 may be delivered in a first configuration having a reduced diameter and then expanded into a second configuration having an increased diameter by introducing fluid into the central occluder 50 following delivery. The amount of saline delivered during implantation may be determined in real-time, for example, by monitoring a size of the central occluder 50, e.g., using an X-ray image, and/or by monitoring a reduction of regurgitation, e.g., using ultrasound imaging.

Figure 5:
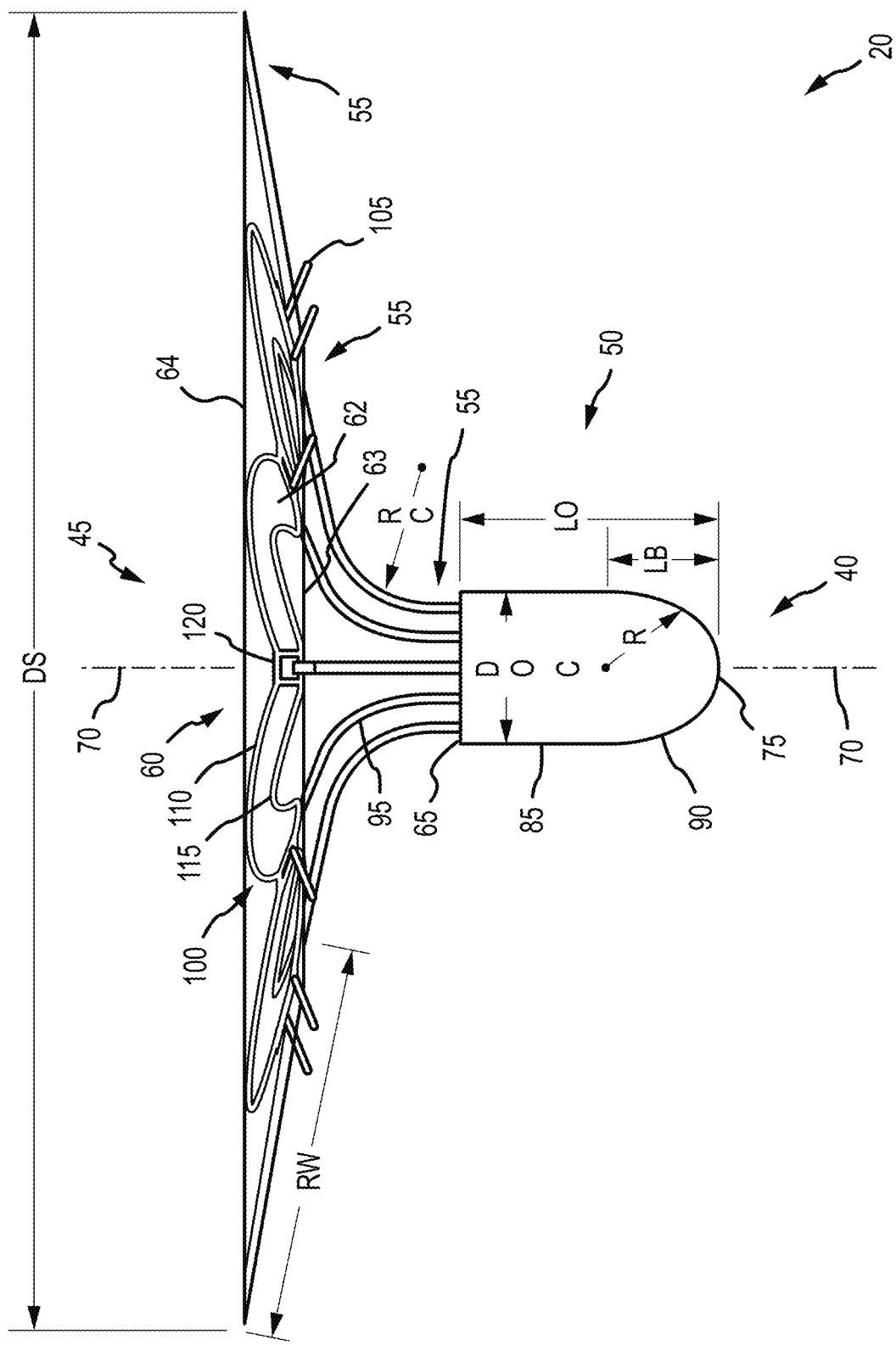
FIG. 5 is a side elevation view of the implantable cardiac valve repair implant in the expanded state.

In certain embodiments and without limitation, the central occluder 50 may be formed from a material having a durometer from and including 10 A to and including 100 D, from and including 10 D to and including 100 D, or from and including 40 D to and including 80 D. In one specific embodiment, the material of the central occluder 50 has a durometer of 80D. As indicated in FIG. 5, the central occluder may have an overall diameter DO that, in certain embodiments and without limitation, may be between approximately 5 millimeters (mm) and approximately 25 mm, between approximately 5 mm and approximately 15 mm, or between approximately 8 mm and approximately 12 mm. The central occluder 50 further has an overall length LO from its proximal end 65 to its extreme distal tip 75 that, in certain embodiments and without limitation, may be between approximately 5 mm and approximately 40 mm or between approximately 10 mm and approximately 20 mm. The bullnose 90 may have a length LB that, in certain embodiments and without limitation, may be between approximately 2.5 mm and approximately 12.5 mm, between approximately 2.5 mm and approximately 7.5 mm, or between approximately 4 mm and approximately 6 mm.

In certain embodiments and without limitation, the radius of curvature R of the bullnose 90 may be between approximately 2.5 mm and approximately 12.5 mm, between approximately 2.5 mm and approximately 7.5 mm, or between approximately 4 mm and approximately 6 mm. The general shape of the bullnose 90 may also vary across embodiments. For example, the bullnose 90 may have any of a parabolic profile, a conical profile, a spherical profile, or any other atraumatic profile. In other example embodiments, the bullnose 90 may have a trihedral, frustoconical shape, or other non-rounded shape. In certain example embodiments, the central occluder 50 may have a triangular or tri-lobe shape that provides surfaces for sealing against respective leaflets. In yet another example, the central occluder 50 may have a rounded double-concave shape. In still other embodiments, the central occluder 50 may be configured to allow distention of a distal portion of the frame 55, thereby facilitating reintervention (e.g., valve implantation). In yet other embodiments, the central occluder 50 may include a frame (e.g., inner struts) covered in a flexible material, such as, but not limited to expanded polytetrafluoroethylene (ePTFE), polyester fabric, or a similar material. In such embodiments, the flexible covering may allow the central occluder 50 to be compressed for delivery but to expand once positioned in the native valve to occlude and reduce regurgitation.

As can be understood from FIG. 5, in one embodiment, the central occluder 50 may have an overall diameter DO of approximately 10 mm, and its overall length LO may be approximately 16 mm. Additionally, the bullnose 90 may have an overall length LB of approximately 5 mm, and the radius of curvature of the bullnose 90 may or may not gradually transition over its length LB from proximal to distal. For example, the radius of curvature R may have a maximum value from approximately 2.5 mm to approximately 15 mm as measured from a center of curvature C to the distal tip 75 of the central occluder 50 but may transition to a radius of curvature R that is between approximately 2.5 mm and approximately 10 mm, but less than or equal to the maximum, at a location proximal the distal tip 75. In one embodiment, however, the bullnose 90 may have a constant radius of curvature of approximately 5 mm.

As can be understood from FIGS. 2-6, the thin sheet 60 is supported on the frame 55 and secured thereto. For example and without limitation, in certain embodiments the thin sheet 60 may be secured to the frame 55 by suturing the skirt against an inner surface and/or an outer surface of the frame 55. In other implementations, the thin sheet 60 may include a cuff or similar folded structure that is folded over an end of the frame 55. In still other implementations, the thin sheet 60 may be secured to the frame by sewing, welding, gluing/adhering, stapling, or any other suitable securement method or combination of securement methods. Depending on the embodiment, the thin sheet 60 may be on the distal side of the frame 55, the proximal side, or both such that the frame extends through and along the thin sheet. In one embodiment, the frame 55 is covered with a thin sheet 60 on the distal side of the frame where the frame contacts atrial tissue when the implant 20 is implanted in the target cardiac valve.

Depending on the embodiment, the thin sheet 60 may be formed of or include a woven or knit material or fabric that encourages tissue ingrowth. The porosity of the fabric of the thin sheet 60 assists in reducing commissural tricuspid regurgitation. Further reduction of commissural tricuspid regurgitation is provided by the angulation of the frame 55, which provides close contact with the commissures in a circumferential manner. For example, with the implant 20 implanted in the target cardiac valve, tissue in-growth into the fabric of the thin sheet 60 buttresses the myocardium, helping to keep the tissue from expanding further and reducing the potential of future regurgitation.

The fabric can be made from various methods, i.e. knitting, weaving, single or multiple layers. These fabrics can be laminated together with a polymer to make a composite structure, i.e. two pieces of knit (high porosity) with a polymer coating like silicone or urethane. Example materials for the woven or knit materials may include, without limitation, polyester, polypropylene, polyethylene, etc. The thin layer 60 may have a material thickness of between approximately 0.03 mm and approximately 1 mm, between approximately 0.05 mm and approximately 0.2 mm, or between approximately 0.07 mm and approximately 0.12 mm. In one example embodiment, the thickness of the thin layer 60 is approximately 0.2 mm. In another example embodiment, the thickness of the thin layer 60 is approximately 0.55 mm. In one embodiment, an additional textile layer may be added on the proximal side of the thin sheet 60 to create a smooth surface to minimize clot formation in an atrial chamber immediately adjacent the cardiac valve in which the implant 20 is implanted.

As indicated in FIGS. 5, 6 and 7, the thin sheet 60 has an outer diameter DS. In certain embodiments, the outer diameter DS may be between approximately 40 mm and approximately 80 mm, between approximately 50 mm and approximately 70 mm, or between approximately 55 mm and approximately 65 mm. The thin sheet 60 has a radial width RW. In certain embodiments, the radial width RW may be between approximately 10 mm and approximately 30 mm, between approximately 13 mm and approximately 23 mm, or between approximately 17 mm and approximately 19 mm. The thin sheet 60 has a central opening 66 with an inner diameter DI. In certain embodiments, the inner diameter DI may be between approximately 20 mm and approximately 60 mm, between approximately 25 mm and approximately 45 mm, or between approximately 28 mm and approximately 32 mm. For example, in one embodiment, the thin sheet 60 has an outer diameter DS of approximately 60 mm, a radial width RW of approximately 18.2 mm, and a central opening 66 with an inner diameter DI of approximately 30 mm. Due to its configuration, when the implant 20 is implanted in the target cardiac valve, the circumferential fabric of the thin sheet 60 covers a portion of the outer leaflet commissures to block leaks at the edges of the commissures.

As shown in FIGS. 2-6, the frame 55 includes spokes 95, arcuate petal portions 100 and protruding anchor members 105. The frame 55 may be made from a variety of super-elastic and/or shape memory materials, including, for example, nickel-titanium alloys (e.g., Nitinol), which may be laser cut from a tube or in the form of drawn wire. The features defined in the shape memory materials may be defined therein via various cutting methods known in the art, include laser, water jet, electrical discharge machining (EDM), stamping, etching, milling, etc.

In one embodiment, the frame 55 is made of super-elastic, shape memory nickel titanium alloy (e.g., Nitinol). Regardless of which shape memory material is employed, the shape memory aspects of the frame 55 allow the frame and, as a result, the implant 20 to self-bias from the collapsed state (see FIG. 7) to the expanded state (see FIGS. 2-6) when not physically maintained in the collapsed state by the delivery tool 15.

In various embodiments, the frame 55, central occluder 50 and the rest of the implant 20 remain implanted as a unit in the target cardiac valve. In other words, the implant 20 is implanted and remains so as configured in FIGS. 2-6.

There may be situations where it is desirable to remove the central occluder and then implant a replacement valve in the target cardiac valve. Accordingly, in alternate embodiments, the central occluder 50 and frame spokes or struts 95 may be removable after implantation, leaving the surrounding annular surface 62 of the implant in place, the annular surface 62 being formed by and including the frame arcuate petal portions 100 and the thin sheet 60 supported thereon. In such embodiments, a circumferential suture connection may exist between the spokes 95 and the rest of the frame 55 radially outward of the spokes 95. Thus, this circumferential suture connection may be cut and the central occluder 50 and its spokes 95 may be removed through a catheter, leaving the annular portion of the implant, which then acts as an "annuloplasty" frame.

As indicated in FIG. 7, when the implant 20 is in the collapsed state, the spokes 95 proximally extend from the proximal end 65 of the central occluder 50 to the arcuate petal portions 100. In doing so, the spokes 95 are substantially parallel with, and extend along and near to, the central longitudinal axis 70 of the implant 20. As can be understood from FIG. 7, when the implant is in the collapsed state, each spoke 95 has a length L from the central occluder proximal end 65 to a distal boundary of an arcuate petal portion 100. In certain embodiments, the length L may be between approximately 10 mm and approximately 40 mm or between approximately 15 mm and approximately 22 mm, with one embodiment having a length L of approximately 19 mm. As indicated in FIG. 7, the frame 55 in the collapsed state thus has an overall length OL that is the sum of the length L (shown in FIG. 7) and the radial width RW (shown in FIGS. 5 and 7), the candidate dimensions for the radial width RW being as discussed above with respect to FIG. 5.

As shown in FIGS. 2-6, when the implant 20 is in the expanded state, the spokes 95 proximally extend from the central occluder proximal end 65 and laterally radiate away from the central longitudinal axis 70 of the implant 20 to the arcuate petal portions 100. In doing so, the spokes 95 have a radius of curvature RC of between approximately 5 mm and approximately 20 mm, between approximately 10 mm and approximately 18 mm, or between approximately 15 mm and approximately 16 mm with one embodiment having a radius of curvature RC of approximately 15 mm, as can be understood from FIG. 5.

Depending on the embodiment, the frame 55 may include between approximately 3 and approximately 15 spokes 95. In certain embodiments, the number of spokes 95 and gaps therebetween may be selected to facilitate passage of other tools and devices past the frame 55. Embodiments may include spokes 95 with various cross-sectional shapes; however, in at least certain embodiments, spokes 95 have an annular sector cross-sectional shape, such as illustrated in Inset A-A of FIG. 6. In such embodiments, the cross-sectional shape of the spokes 95 may be defined by each of a strut width SW (defined as the maximum width of the spoke) and a wall thickness WT of the spokes 95. The spokes 95 may be further defined by a cross-sectional radius of curvature CSR as measured to a centerline CL of each spoke. In certain implementations, the wall thickness WT may be between approximately 0.2 mm and 0.8 mm, between approximately 0.3 mm and approximately 0.7 mm, or between approximately 0.4 mm and approximately 0.6 mm. In addition, in certain implementations, the spokes 95 may conform to certain spoke aspect ratios, which, in the context of the spokes 95 refers to the ratio of the wall thickness WT to the strut width SW. For example, and without limitation, embodiments may have a spoke aspect between 4:0.5 and 1:2, between 3:1 and 1:1.2, or between 2:1 and 1:1. In embodiments, the cross-sectional radios of curvature CSR may be between approximately 2 mm and approximately 6 mm, between approximately 3 mm and approximately 5 mm, or between approximately 3.5 mm and approximately 5 mm. In one particular embodiment, the frame 55 is made of Nitinol and the frame 55 has 12 spokes 95 with each spoke 95 having a wall thickness WT of approximately 0.46 mm, an aspect ratio of approximately 2:1 (resulting in a strut width SW of approximately 0.23 mm), and a cross-sectional radius of curvature CSR of approximately 5 mm. In certain embodiments, the spokes 95 may be arranged such that they extend distally from the frame 55 at an angle such that the thin sheet 60 occludes coaptation gaps. In certain embodiments of the present disclosure, each of the spokes 95 may be dimensionally identical; however, in other embodiments, one or more of the spokes 95 may differ in any of the various characteristics noted above.

As illustrated in FIGS. 2-6, each arcuate petal portion 100 is located between a pair of spokes 95 and forms a section of the circumference of a radially outward half of the expanded frame 55. As can be understood from FIG. 5, unlike the spokes 95, which are curved in the expanded state, the arcuate petal portions 100 in the expanded state are generally straight in a laterally radiating direction and have approximately the same radial width RW as that of the thin sheet 60. Each petal portion 100 has an outer arcuate member 110 and an inner arcuate member 115, both of which point radially outward. These arcuate members 110, 115 intersect at a junction portion 120 that extends from a respective spoke 95 and surrounds a protruding anchor member 105 that distally projects from a distal side of its junction portion 120.

Depending on the embodiment, the frame 55 may include different numbers of petal portions 100. For example, in certain example embodiments, the frame 55 may include between 3 and 18 petal portions 100, between 6 and 15 petal portions 100, or between 10 and 14 petal portions 100. In one embodiment, the frame 55 has 12 petal portions 100. Similarly, the frame 55 may include different numbers of protruding anchor members 105. For example, in certain example embodiments, the frame 55 may include between 6 and 60 protruding anchor members 105, between 12 and 36 protruding anchor members 105, or between 18 and 30 protruding anchor members 105. In one embodiment, the frame 55 has 24 protruding anchor members 105.

The frame 55 engages the atrial tissue via the protruding anchor members 105, which may be in the form of small barbs. The protruding anchor members 105 are designed to securely engage the atrial tissue without penetrating through the tissue or to the coronary vessels. Depending on the embodiment, the protruding anchor members or barbs 105 may be curved to slide before engaging tissue. There may be one row or multiple rows of retention barbs 105.

As indicated in the enlarged view of a junction portion 120 of FIG. 6, each protruding anchor member 105 is defined in the surrounding junction portion 120 via a slot 125 that extends around the protruding anchor member 105 such that the anchor member 105 is peninsular in the surrounding junction portion 120. A radially inward end 105A extends uninterrupted to the rest of the surrounding junction portion 120 and is opposite a radially outward free end 105B of the anchor member 105, the radially outward free end 105B forming a tip of the protruding anchor member 105. As can be understood from FIGS. 2, 3 and 5, the radially outward free end of the anchor member projects distally from the rest of the frame 55.

Depending on the embodiment, each protruding anchor member 105 may have a length of between approximately 0.5 mm and approximately 6 mm, between approximately 1 mm and 4 mm, or between approximately 1 mm and approximately 3 mm. Similar to the spokes 95, the protruding anchor members 105 may have various cross-sectional shapes. In at least certain embodiments, the protruding anchor members 105 have an annular sector cross-sectional shape, similar to that discussed above in the context of the spokes 95 and as illustrated in Inset A-A of FIG. 6 and which is referenced for purposes of the following discussion. Like the spokes 95, the cross-sectional shape of the protruding anchor members 105 may be defined by each of a strut width SW (defined as the maximum width of the spoke) and a wall thickness WT. The protruding anchor members 105 may be further defined by a cross-sectional radius of curvature CSR as measured to a centerline CL of each anchor member. In certain implementations, the wall thickness WT may be between approximately 0.2 mm and 0.8 mm, between approximately 0.3 mm and approximately 0.7 mm, or between approximately 0.4 mm and approximately 0.6 mm. In addition, in certain implementations, the protruding anchor members 105 may conform to certain aspect ratios between the wall thickness WT to the strut width SW. For example, and without limitation, protruding anchor members 105 according to certain embodiments may have an aspect between 4:0.5 and 1:2, between 3:1 and 1:1.2, or between 2:1 and 1:1. In certain embodiments, the cross-sectional radios of curvature CSR may be between approximately 2 mm and approximately 6 mm, between approximately 3 mm and approximately 5 mm, or between approximately 3.5 mm and approximately 5 mm. Each protruding anchor member 105 has a wall thickness WT of approximately 0.46 mm, an aspect ratio of approximately 2:1 (resulting in a strut width SW of approximately 0.23 mm), a cross-sectional radius of curvature CSR of approximately 5 mm, and a length of approximately 1.5 mm. In certain embodiments of the present disclosure, each of the protruding anchor members 105 may be dimensionally identical; however, in other embodiments, one or more of the protruding anchor members 105 may differ in any of the various characteristics noted above.

Figure 2:
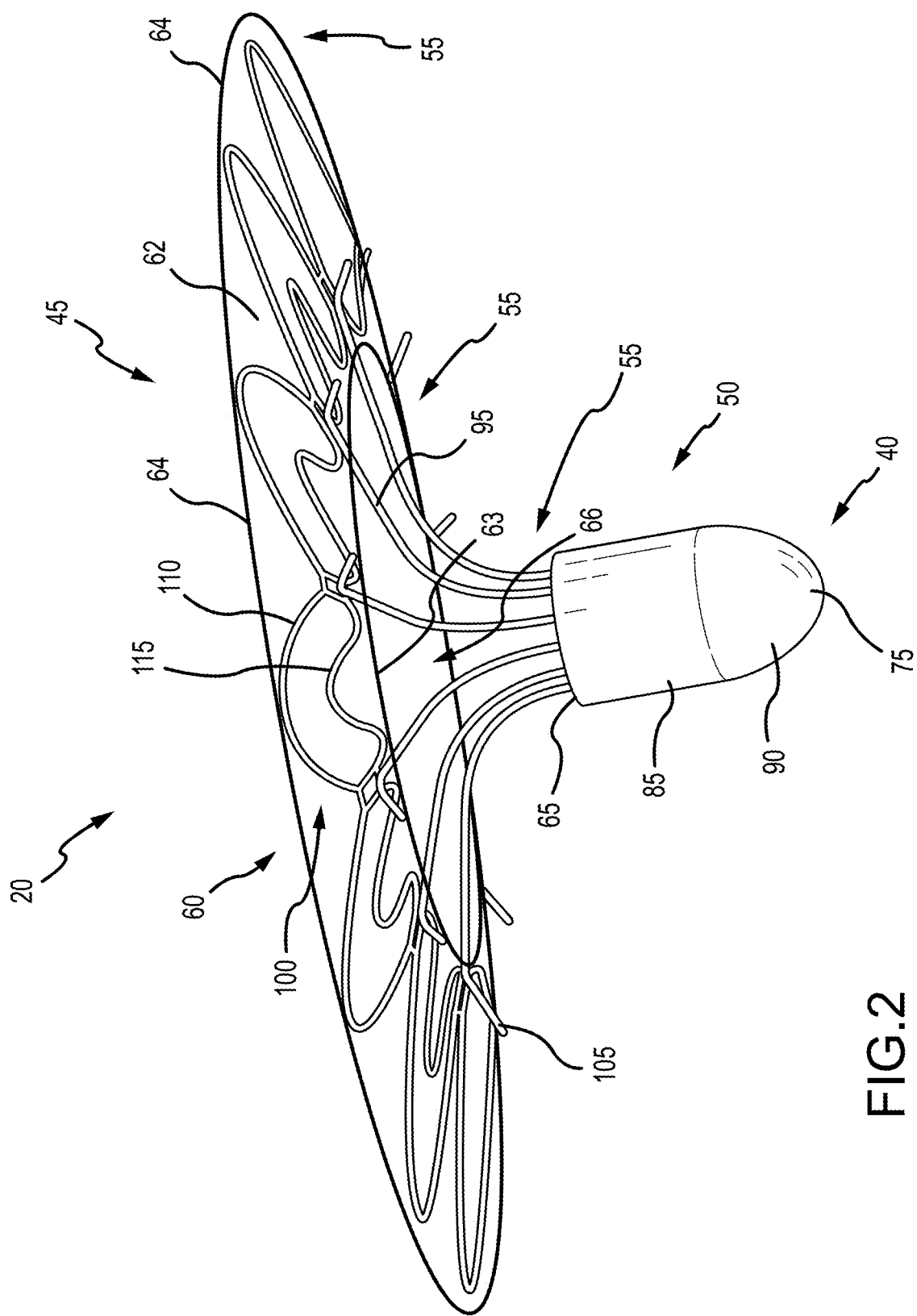
FIG. 2 is a perspective distal-side view of the implantable cardiac valve repair in an expanded state that is used when the implant is implanted in the cardiac valve.
Figure 3:
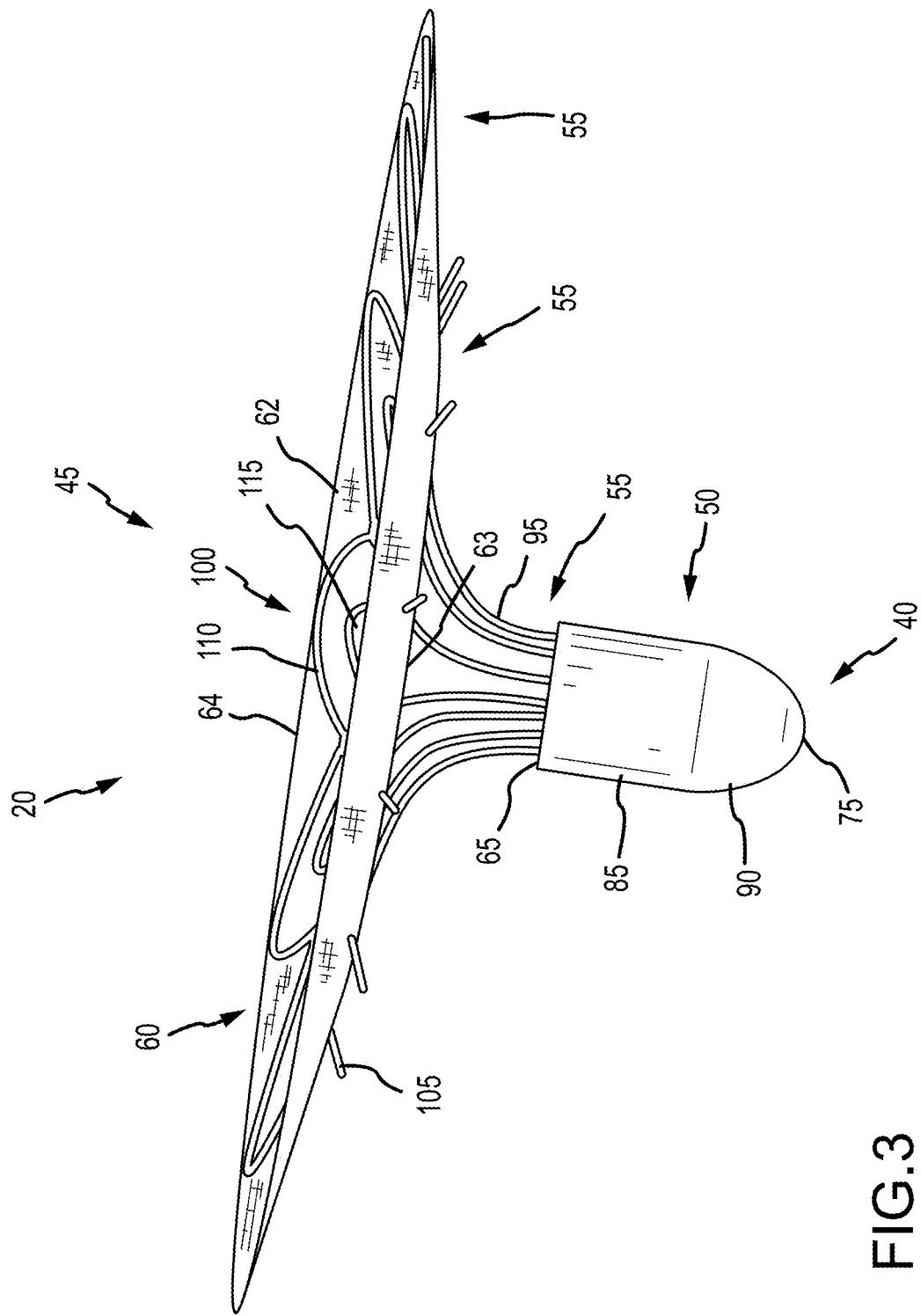
FIG. 3 is a perspective proximal-side view of the implantable cardiac valve repair implant in the expanded state.
Figure 4:
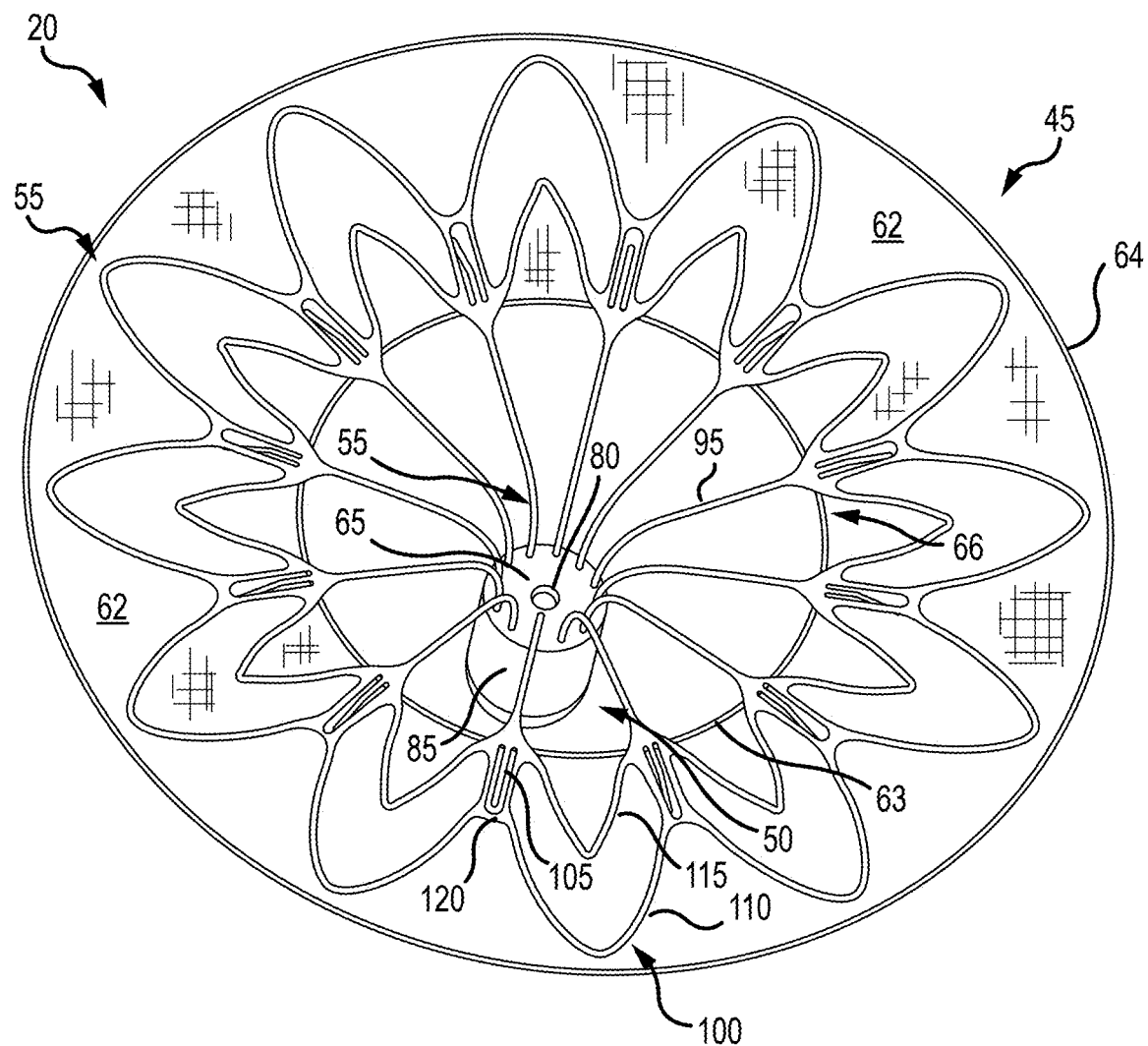
FIG. 4 is a perspective proximal-end view of the implantable cardiac valve repair implant in the expanded state.

In one embodiment, as can be understood from FIGS. 2, 3 and 5, the protruding anchor members or barbs 105 are oriented distally and radially outward. As a result, as the frame 55 is pushed towards the ventricle, the anchor members 105 slide along the atrial tissue. Ventricular pressure pushes the implant 20 towards the atrium, embedding the anchors or barbs 105 into the atrial tissue.

In an alternate embodiment, the anchors or barbs 105 are directionally reversed such that they project distally and radially inward. In this alternative embodiment, the delivery system over-expands the frame 55 during delivery and when the frame is released from the delivery system with the frame 55 in contact with tissue, the anchors or barbs 105 engage the atrial tissue as the frame contracts to its relaxed state.

II. Delivery Tool and Method of Implantation

As illustrated in FIGS. 1A-1D, the delivery tool 15 includes a proximal end 30, a distal end 25 opposite the proximal end, a control handle 35, a tubular sheath 76, and a catheter 77. The control handle 35 extends distally from the proximal end 30 and is used by a physician to manipulate the tool 15 in positioning the implant 20 at the target site and deploying the implant 20 within the target cardiac valve in need of repair. The sheath 76 and catheter 77 extend distally away from the control handle 35 towards the distal end 25 of the tool 15. The catheter 77 extends longitudinally through the sheath 76, the distal end 25 of the catheter 77 forming the distal end 25 of the tool 15. The sheath 76 is used to minimize tissue trauma while the catheter 77 and implant 20 are advanced to the implantation site. Thus, the delivery tool 15 is designed to deliver the implant 20 to the implantation site, position the implant in the target cardiac valve, and control the opening of the frame 55 of the implant 20, all in an atraumatic manner.

Figure 8:
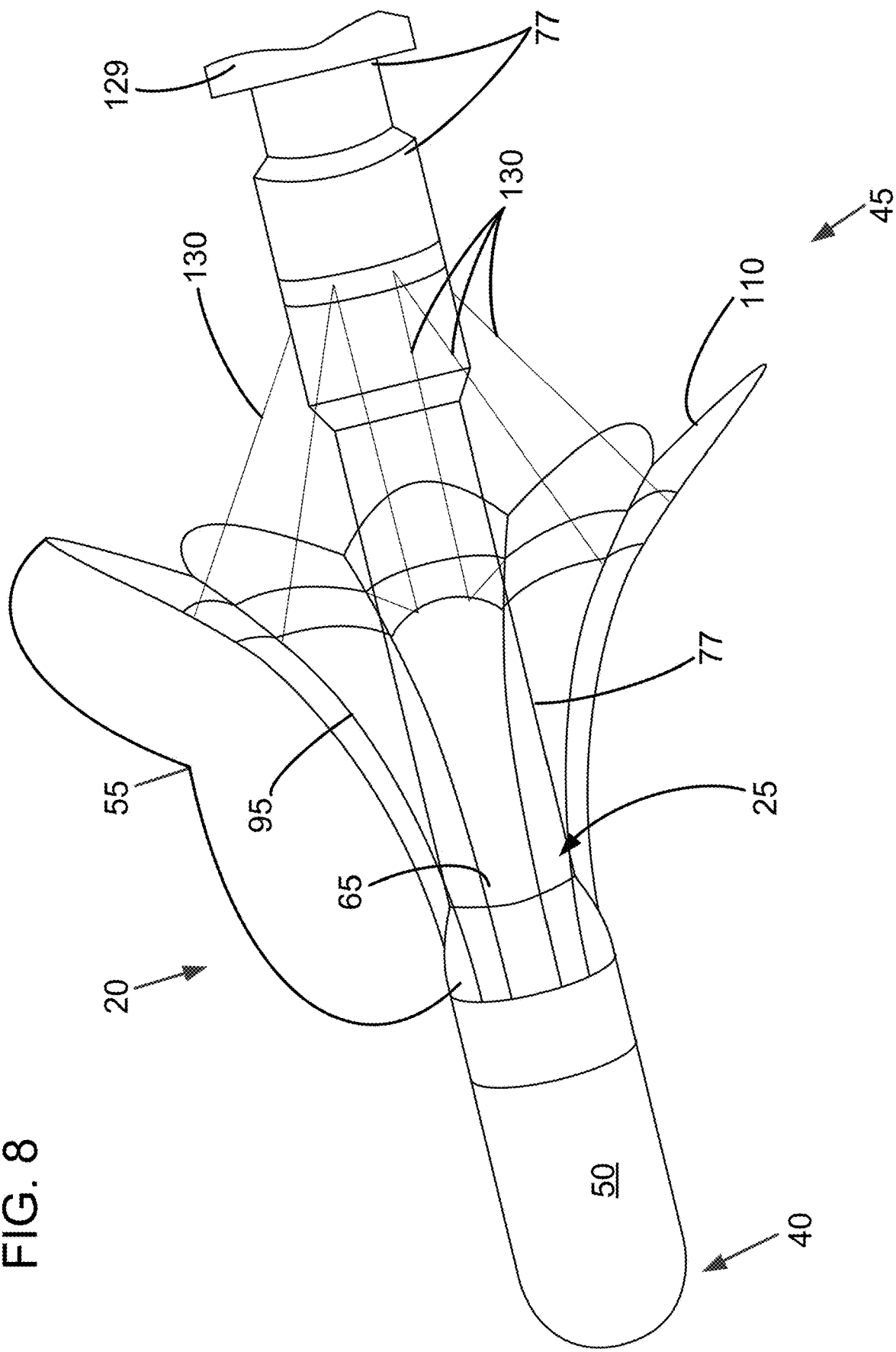
FIG. 8 is an enlarged view of the distal region of the cardiac repair system of FIG. 1A.

As depicted in FIG. 8, which is an enlarged view of the distal region of the cardiac repair system 10 of FIG. 1A, sutures 130 extend between a distal region of the catheter 77 and points of connection on the frame 55 of the implant 20. The sutures 130 further extend from the distal region of the catheter up into the handle 35 and, in one embodiment, may even extend out of the handle, as shown in FIG. 1A. Depending on the embodiment, the control sutures 130 could be replaced by cables or wire.

As can be understood from FIGS. 1A and 8, before the implant 20 is completely freed of the delivery tool 15, the sutures 130 can be manipulated via the handle 35 of the tool 15 to control the opening of the implant frame 55. Suture actuation may have one or two speeds, which may be in the form of a slow speed and/or a fast speed. The slower speed may be controlled by a spooling mechanism or a lead screw mechanism 135 within the handle. The fast speed may be controlled by a plunger style linear actuator 140 within the handle. The sutures 130 may be routed within the handle 35 to provide a 2-to-1 mechanical advantage to facilitate increased precision of control when deploying the implant 20.

The catheter 77 may employ steering via selective actuation (e.g., tension increase/decrease) of certain sutures to better control the position of the implant during deployment. This steering feature may be controlled at the handle 35.

Figure 9:
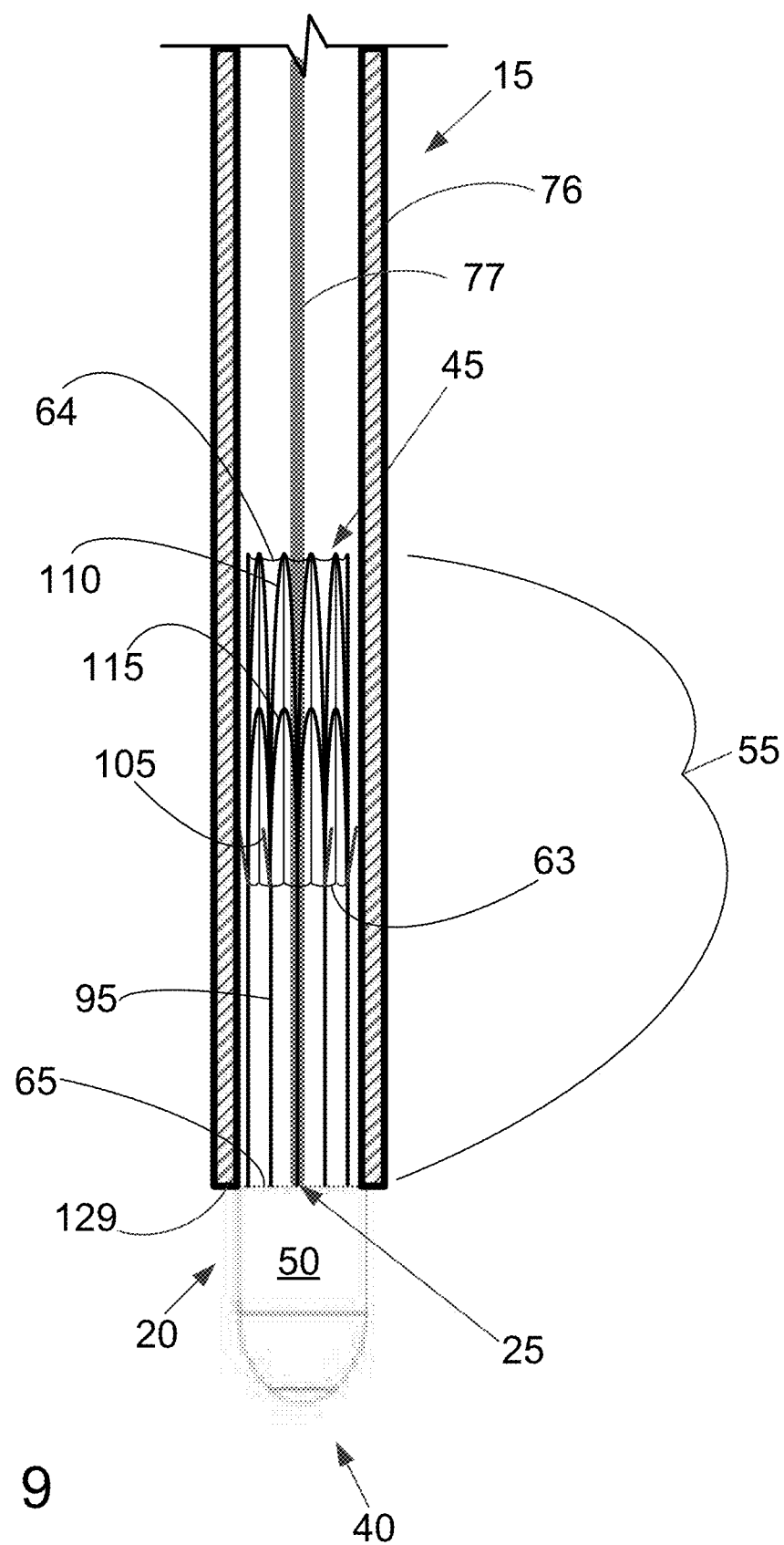
FIG. 9 is a side cross-sectional elevation view of a sheath of the delivery tool with the implantable cardiac valve repair implant maintained in the collapsed state by being confined within the sheath, the implant being coupled to a distal end of a catheter that extends through the sheath.

FIG. 9 is a side cross-sectional elevation view of the sheath 76 of the delivery tool 15 with the implantable cardiac valve repair implant 20 and distal region of the catheter 77 located therein. As can be understood from FIG. 9, during delivery the implant 20 is maintained in the collapsed state by being confined within the sheath 76, and the implant 20 is coupled to a distal end of a catheter 77 that extends through the sheath 76. The control sutures 130, while not shown in FIG. 9 for clarity purposes, would extend through the catheter 77 and/or the sheath 76, as can be understood from FIGS. 1A and 8.

With the implant 20 maintained in the collapsed state by virtue of being confined within the sheath 76 of the delivery tool 15, the implant may be delivered and deployed at the target site via an antegrade percutaneous route (e.g., a trans-femoral or trans-jugular route) with the patient consciously sedated during the procedure. A distal end 25 of the catheter 77 is coupled with the proximal end 65 of the central occluder 50 to maintain the implant 20 within the sheath 76 in the collapsed state until the physician decides to deploy the implant within the target cardiac valve.

Upon the implant being properly positioned in the atrium and beginning to approach the target cardiac valve for repair, the physician actuates the tool 15 to cause the catheter 77 to act as a plunger and/or stopper, thereby driving the collapsed implant 20 distally from the confines of the sheath 76 and/or allowing the sheath 76 to be withdrawn proximally from about the implant 20. Upon the collapsed implant 20 becoming exposed by action of exiting the distal end 129 of the sheath, the implant 20 self-biases into its expanded state, as depicted in FIGS. 2-6. However, as indicated in FIG. 8, despite having exited the sheath distal end 129 and assuming the expanded state, the proximal end 65 of the central occluder 50 of the implant 20 remains coupled to the catheter distal end 25 and the implant frame 55 is coupled to the sutures 130, thereby allowing the physician to use the delivery tool 15 to drive the implant into the target valve and manipulate the implant therein for implantation.

The configuration of the implant 20 facilitates delivery and implantation that is very easy and fast. The implant's ease of delivery is facilitated by it generally only requiring the user to approximately center the frame and push it into the valve.

Upon arrival of the implant 20 within the atrium and at the target cardiac valve, the physician simply uses the tool 15 to actuate the sutures 130 to allow the frame 55 to self-bias open over the atrial side of the target cardiac valve in a controlled manner. The catheter 77 of the tool 15 is then used to push the implant 20 towards the ventricle to engage the frame barbs 105 into the atrial tissue surrounding the target cardiac valve. The control sutures 130 can be used to collapse the frame 55 of the implant 20 to facilitate repositioning of the implant if necessary. Once the implant is fully implanted as desired by the physician, the exposed ends of the control sutures 130 are cut near their points of securement to the implant frame 55, and the catheter distal end 25 is released (e.g., unscrewed or otherwise decoupled) from the proximal end 65 of the central occluder 50. With the tool 15 so decoupled from the implanted implant, the tool can be withdrawn from the patient.

FIG. 10 is a view of the implant 20 implanted in a target cardiac valve, as viewed from an atrial position looking towards the valve and the ventricle chamber below. As depicted in FIG. 10, upon being implanted in the target cardiac valve, the implant anchors itself within the target cardiac valve and is configured to reduce regurgitation in the target cardiac valve. When implanted, the implant 20 is located on the atrial side of the target cardiac valve. The frame engages the atrial tissue via the small barbs 105. The thin sheet 60, which is supported on the frame 55, forms an annular surface 62 supported on the expanded frame 55. This annular surface 62 extends across the atrial tissue circumferentially around the circumference of the target cardiac valve. The central occluder 50 is suspended off the frame 55 and located in the middle of the valve orifice or opening. So positioned, the implant provides the following advantages and reduces regurgitation through multiple mechanisms-of-action.

First, the metal frame 55 supports a central occluder 50 that is positioned to block a central leak in the target cardiac valve, the central occluder thereby reducing central regurgitation through the target cardiac valve. Specifically, the central occluder may block part or all of the central regurgitation in the valve.

Second, the thin sheet 60 covering the frame 55 encourages ingrowth with the atrial and annular tissue surrounding the target cardiac valve. With such tissue ingrowth, the thin sheet and its supporting frame 55 can act as an annuloplasty ring to buttress the native tissue and reduce myocardial stretching that could increase regurgitation.

Third, the thin sheet 60 covering the frame 55 may overlap the edges of the leaflet commissures, reducing the possibility of commissural leak.

Finally, the frame 55 may be over-expanded before engaging the retention barbs 105 in the tissue. When the frame is allowed to relax, the frame 55 may reduce the valve orifice of the target cardiac valve and improve apposition of the valve leaflets, thereby reducing or eliminating regurgitation.

III. Steerable Delivery Tool

FIGS. 11A and 11B are plan and side elevation views, respectively, of an alternative valve repair system 1100 according to the present disclosure. Similar to valve repair systems previously discussed herein, the valve repair system 1100 is generally configured to deliver and deploy an implant 20 at a target site, which is generally in a cardiac valve requiring repair. Embodiments of the valve repair system 1100 may be used with, but are not limited to being used with, any implants discussed herein or that are otherwise consistent with this disclosure.

As shown in FIGS. 11A and 11B, the valve repair system 1100 includes a delivery tool 1115. The tool 1115 includes a proximal end 1130 opposite a tool distal end 1125. The delivery tool 1115 further includes a tubular sheath 1176, and a catheter 1177. A control handle 1135 extends distally from the proximal end 1130 and is used by a physician to manipulate the tool 1115 in positioning the implant 20 at the target site and deploying the implant 20 within the target cardiac valve in need of repair. The sheath 1176 and catheter 1177 extend distally away from the control handle 1135 towards the distal end 1125 of the tool 1115. The catheter 1177 extends longitudinally through the sheath 1176, the distal end 1125 of the catheter 1177 forming the distal end 1125 of the tool 1115. The sheath 1176 is used to minimize tissue trauma while the catheter 1177 and implant 20 are advanced to the implantation site. Thus, the delivery tool 1115 is designed to deliver the implant 20 to the implantation site, position the implant in the target cardiac valve, and control opening of the implant 20, all in an atraumatic manner.

Figure 11C:
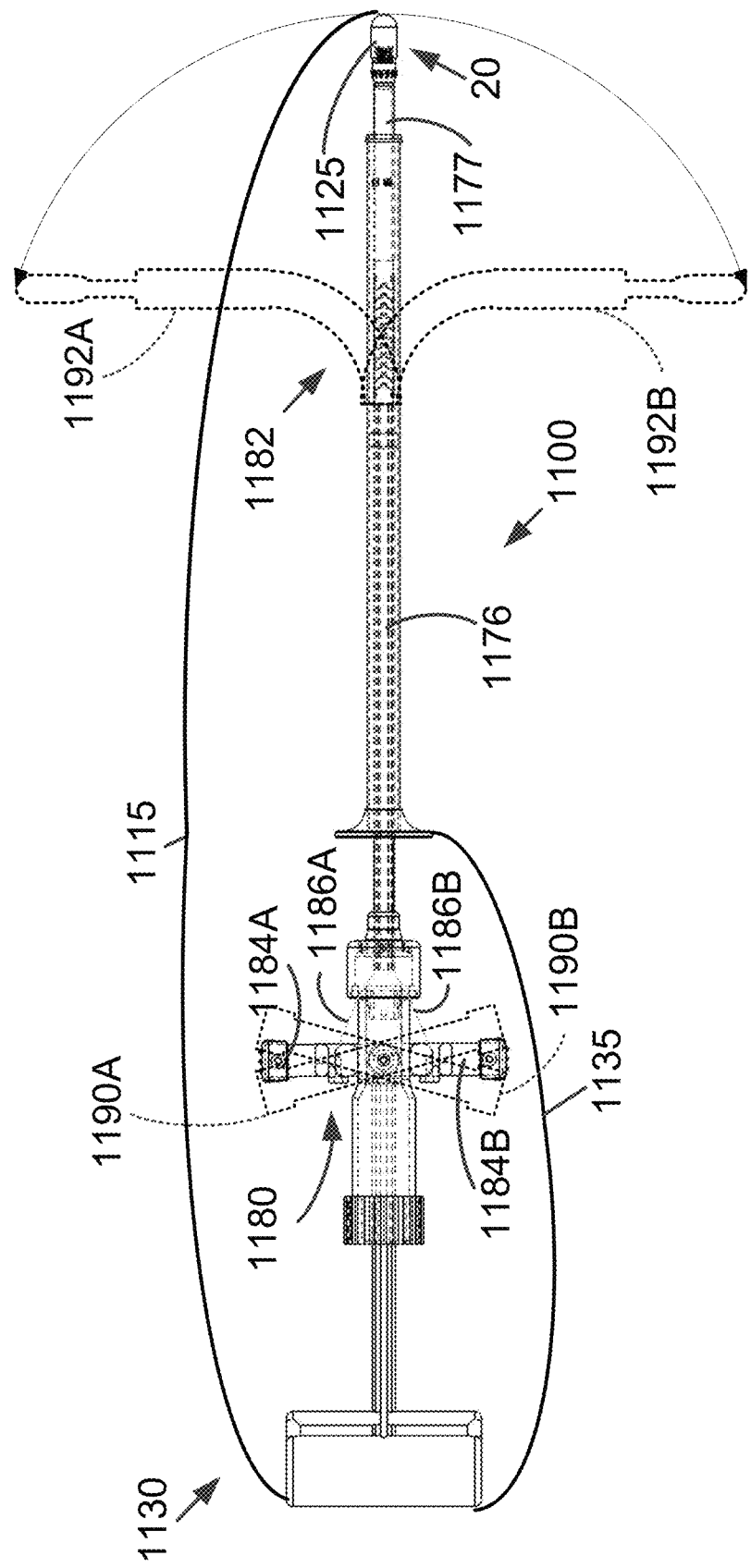

To facilitate delivery of the implant 20 to the implantation site, the catheter 1177 of the tool 1115 may be steerable. In the specific implementation illustrated in FIGS. 11A and 11B, for example, the control handle 1135 of the tool 1115 includes a bidirectional steering control 1180 that may be rotated to steer the distal end 1125 of the tool 1115. As illustrated in FIG. 11C, the steering control 1180 may be rotatable between two extents, illustrated by dashed outlines 1190A, 1190B, to steer the distal end 1125 between corresponding extents, illustrated by dashed outlines 1192A, 1192B. In the specific example illustrated, the steering control 1180 facilitates steering of the distal end 1125 across a range of motion of approximately 180 degrees. Stated differently, the steering control 1180 may rotate the distal end 1125 between a first position in which the distal end 1125 points in a first lateral direction and a second position in which the distal end points in a second lateral direction that is opposite the first lateral direction.

In certain embodiments, steering of the distal end 1125 is achieved by coupling the steering control 1180 to a steering segment 1182 disposed along the catheter 1177, distal the steering control 1180. More specifically, the steering control 1180 may include lateral members 1184A, 1184B, each of which is coupled to a respective side of a distal end of the steering segment 1182 by respective pull wires 1186A, 1186B. Accordingly, when the steering control 1180 is rotated, the corresponding pull wire is pulled and the steering segment 1182 is made to bend in the same direction. For example, referring to FIG. 11C, when the steering control 1180 is rotated counterclockwise with respect to the view of FIG. 11C, as illustrated by dashed outline 1190A, the lateral member 1184A pulls the pull wire 1186A, resulting in the distal end 1125 curling in a counterclockwise direction, as illustrated by dashed outline 1192A. Similarly, when the steering control 1180 is rotated clockwise with respect to the view of FIG. 11C, as illustrated by dashed outline 1190B, the lateral member 1184B pulls the pull wire 1186B, resulting in the distal end 1125 curling in a clockwise direction, as illustrated by dashed outline 1192B.

The steering segment 1182 may take various forms; but, in general, is a flexible and manipulable segment of the catheter 1177 or a separate sleeve or sheath coupled to the catheter 1177. In certain embodiments, for example, the steering segment 1182 may be a sleeve or a portion of the catheter 1177 that is formed from a flexible material. In other embodiments, the steering segment 1182 may be segmented or otherwise include slits, cutouts, or similar voids along its length to provide flexibility. In one specific implementation, the steering segment 1182 may have a helical shape. In still other embodiments, the steering segment 1182 may be a segment of the catheter 1177 having a reduced wall thickness. The foregoing are merely examples and other techniques for forming the steering segment 1182 that may be used are contemplated.

In certain embodiments, the pull wires 1186A, 1186B are run within an annular space defined between the sheath 1176 and the catheter 1177. Alternatively, the pull wires 1186A, 1186B may be run through a lumen defined within a wall of the catheter 1177, a wall of the sheath 1176, or a third annular body disposed along the distal length of the tool 1115. For example, the catheter 1177 or an additional tubular sheath disposed between the catheter 1177 and the sheath 1176 may be formed as a triple lumen extrusion including a central lumen and a pair of smaller lumens disposed on opposite sides of the central lumen and through which the pull wires 1186A, 1186B extend.

Although illustrated in FIG. 11C as having a 180-degree range of motion, embodiments of the present disclosure may be configured to have other ranges of motions. For example, certain embodiments may be configured to rotate the distal end 1125 through 360 degrees of rotation, e.g., from a first position in which the distal end 1125 points proximally on a first side of the tool 1115 to a second position in which the distal end 1125 also points proximally on a second side of the tool 1115 opposite the first side. In other embodiments, the distal end 1125 may have a reduced range of motion such as but not limited to 135 degrees, 90 degrees, 45 degrees, or 15 degrees. In addition, while the range of motion illustrated in FIG. 11C is illustrated as being substantially even in both directions, embodiments of the present disclosure may have ranges of motion that are uneven in different directions. For example, a tool with a 135-degree range of motion may travel 90 degrees in a first direction but only 45 degrees in a second direction opposite the first direction. Moreover, while the tool 1115 has a neutral position in which the catheter 1177 is substantially straight, the catheter 1177 may alternatively be configured to have a bias in a particular direction.

IV. Implant with Tension Control Line

Figure 12:
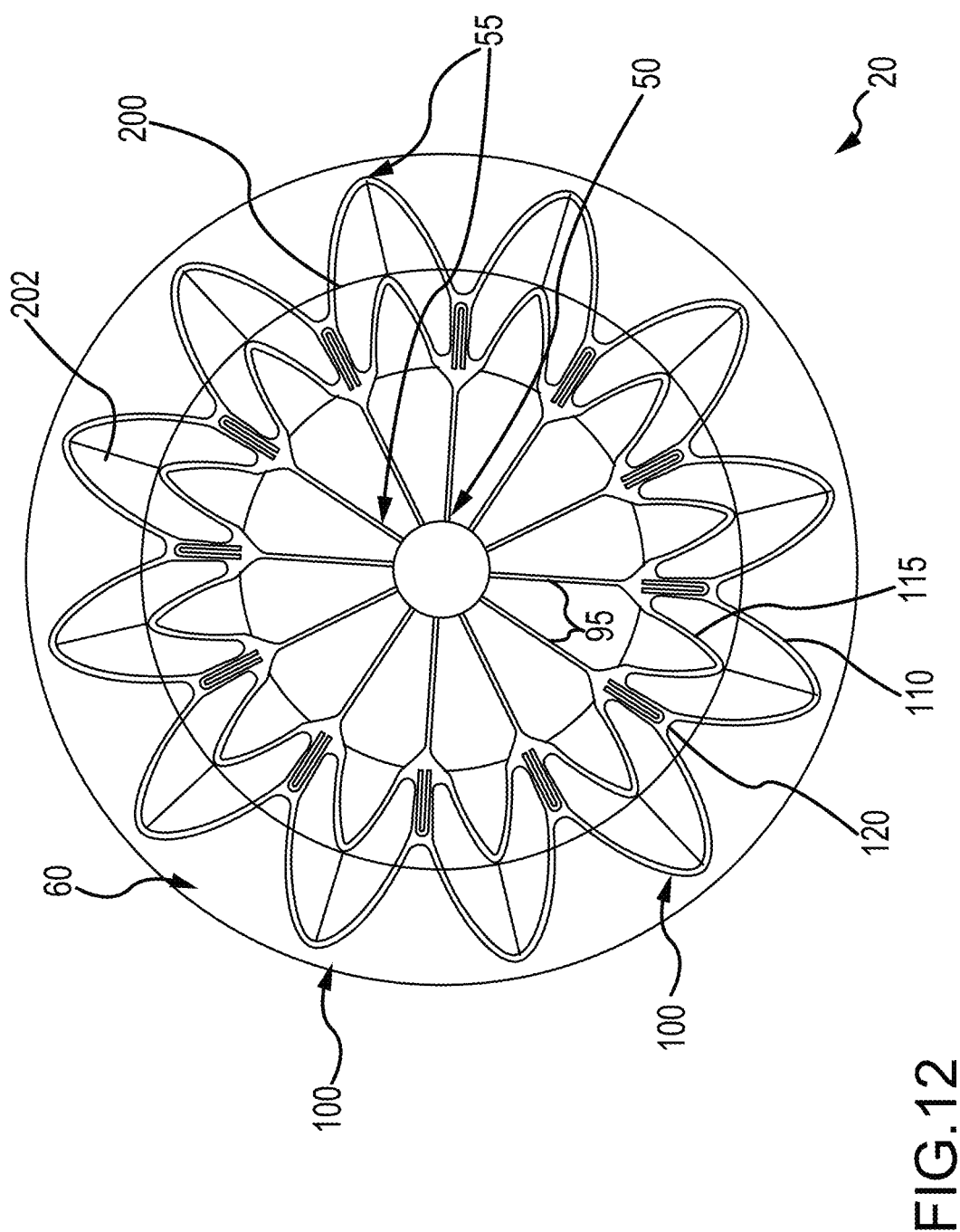
FIG. 12 is a distal plan view of an implantable cardiac valve repair implant in the expanded state and including a tension control line.

FIG. 12 is a distal plan view of the implant 20 in an expanded state and incorporating a tension control line 200. As previously discussed in the context of FIGS. 2-6, the implant 20 generally includes a central occluder 50, a frame 55 and a thin sheet 60 supported on the frame 55. Further details regarding the components and construction of the implant 20 and the frame 55 are provided above in the context of FIGS. 2-6.

As illustrated in FIG. 12, the tension control line 200 may be in the form of a wire, suture, cord, or similar elongate body coupled to the frame 55 and radially inward of the thin sheet 60 relative to the longitudinal axis 70 (shown in FIG. 5) of the implant 20. The tension control line 200 may form a loop extending around the frame 55 and may be formed from a single length of wire, suture, etc. In other implementations, the tension control line 200 may instead be formed from multiple discrete segments of wire, suture, etc., with each discrete segment coupled to the frame 55 and optionally coupled to adjacent segments of the control line 200.

During operation and, more specifically, during deployment of the implant 20, the tension control line 200 is releasably coupled to tension control members (e.g., tension control members 320 illustrated in FIGS. 13-22 and discussed below in further detail) of a delivery tool (e.g., delivery tool 300, similarly illustrated in FIGS. 13-22 and discussed below). The tension control members may be coupled to a handle or similar actuatable component of the delivery tool (such as the handle 35 of the tool 15 previously discussed), to vary tension applied to the tension control line 200 by the tension control members. For example, rotating the handle 35 in a first direction may cause the tension control members to translate proximally/retract, thereby increasing tension on the tension control line 200, while rotating the handle 35 in an opposite direction may cause the tension control members to translate distally/extend, thereby reducing tension on the tension control line 200. Stated differently, manipulating the handle 35 in a first direction generally stops expansion of and/or collapses the frame 55 of the implant 20 (e.g., to allow repositioning of the implant 20) while manipulating the handle 35 in a second direction generally stops collapse of the frame and/or expands the frame 55, whether by action of the handle 35 or as a result of a bias of the frame 55 to into the expanded configuration.

In general, the tension control line 200 is releasably retained by the tension control members at discrete locations along the length of the tension control line 200. The tension control line 200, however, extends across the frame 55 and is coupled to the frame 55 at multiple locations. As a result, even though tension modifications may be applied at the connection point between the tension control members and the tension control line 200, tension is distributed relatively evenly across the tension control line 200 and the frame 55, thereby providing even expansion and collapse of the frame 55 and improved control during deployment and placement of the implant 20.

In the implementation of FIG. 12, the tension control line 200 is coupled to (e.g., tied or adhered to) the inner arcuate members 115 of the frame 55. More generally, the tension control line 200 may be coupled to any suitable portion of the frame 55 such that the tension control line 200 substantially extends about the frame 55. For example, and without limitation, in other implementations of the present disclosure, the tension control line 200 may instead be fixed to spokes 95, outer arcuate members 110, or any other suitable portion of the petal portions 100 of the frame 55.

In certain implementations, the tension control line 200 may be additionally coupled to other locations of the frame 55 by additional control segments or linking structures. For example, FIG. 12 illustrates the tension control line 200 coupled to the inner arcuate members 115 of the frame 55. The tension control line 200 is further coupled to each of the outer arcuate members 110 by corresponding links, such as the link 202. Similar to the control line 200, the link 202 may be formed of wire, suture, or similar material and, in certain cases, may be formed of the same material as the control line 200. In operation, the link 202 helps to further distribute tension to the outer arcuate members 110 and, as a result, further improves control of expansion an collapse of the frame during deployment of the implant 20.

Although illustrated in FIG. 12 as coupling the tension control line 200 to the outer arcuate members 110, in other implementations, links may be used to couple the tension control line 200 to other elements of the frame 55 depending on how the tension control line 200 is configured. For example, in implementations in which the tension control line 200 is coupled to the outer arcuate members 110, links may be used to couple the tension control line 200 to the inner arcuate members 115.

V. Deployment of Implants with Tension Control Lines

As previously discussed, implants according to the present disclosure may include tension control lines for enhanced control during deployment and implantation. Such delivery and implantation may be further facilitated by corresponding delivery tools configured to modify and control tension applied to the tension control lines and to selectively release the implant when properly positioned.

Figure 13:
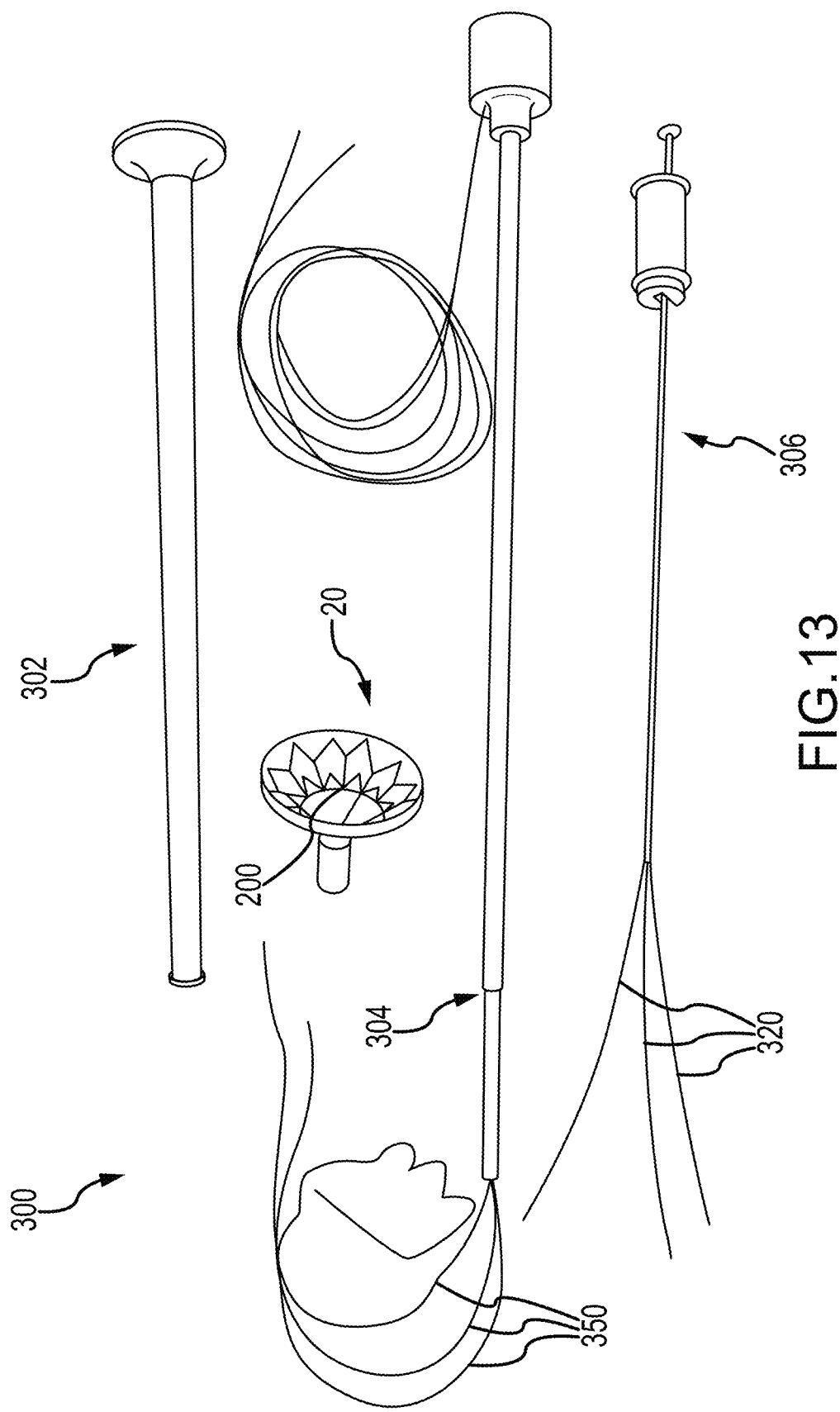
FIG. 13 is an illustration of an example implantable cardiac valve repair system in a disassembled configuration and including each of an implant and a delivery tool.

FIG. 13 is an illustration including a delivery tool 300 in accordance with the present disclosure in a disassembled state. As illustrated, the delivery tool 300 generally includes a sheath 302, a release catheter 304, and a tension control assembly 306. An implant 20 including a tension control line 200 is also pictured. The sheath 302 generally forms an exterior of the delivery tool 300 and houses the other components during insertion into the patient. More specifically, the release catheter 304 is generally disposed within the sheath 302 and the tension control assembly 306 is, in turn, disposed within the release catheter 304.

As described below in further detail, the tension control line 200 of the implant 20 is releasably coupled to the tension control assembly 306 by the release catheter 304 and is maintained in a collapsed state within the sheath 302 during initial insertion into the patient. During deployment, the release catheter 304 is distally extended from the sheath 302, thereby allowing the implant 20 to expand. Subsequent control of expansion and collapse of the implant 20 is facilitate by tension control members 320 extending from the tension control assembly 306, which are coupled to the tension control line 200 of the implant 20 by release lines 350 of the release catheter 304. Following location of the implant 20 within the patient, the release lines 350 are retracted to decouple the tension control members 320 from the tension control line 200, thereby releasing the implant 20.

Figure 14:
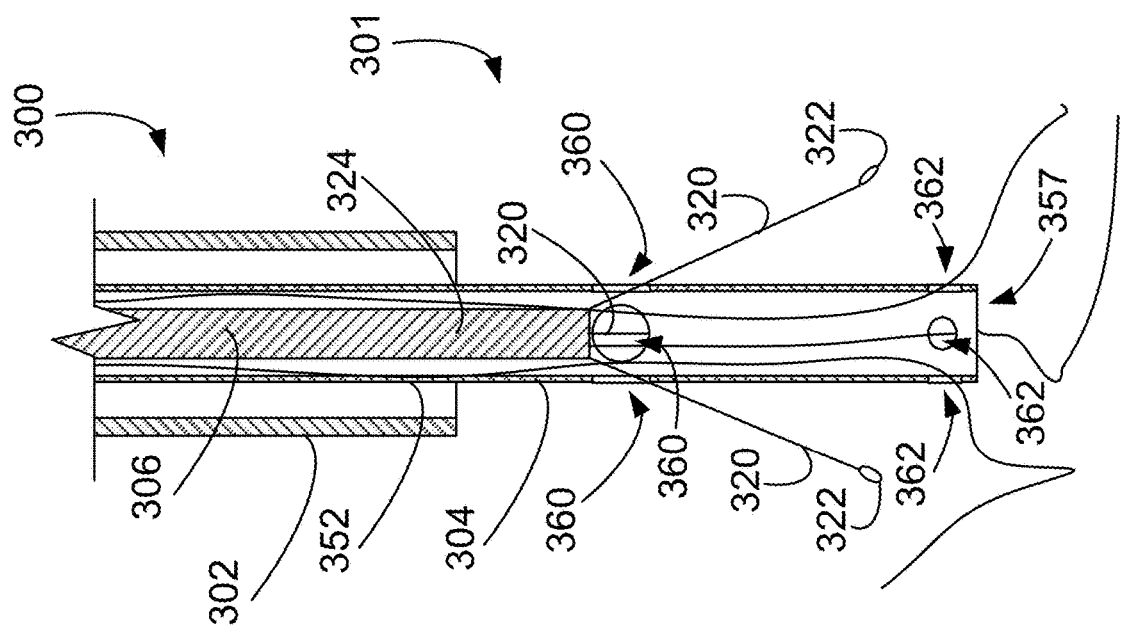
FIG. 14 is a side cross-sectional elevation view of a distal portion of the delivery tool of FIG. 13.

FIG. 14 is a cross-sectional view of a distal portion 301 of the delivery tool 300 in an assembled state and with each of the release catheter 304 and the tension control assembly 306 in an extended configuration for purposes of illustrating various elements of the delivery tool 300. FIG. is also a cross-sectional view of the distal portion 301 of the delivery tool 300 but further includes an implant 20 and illustrates the delivery tool 300 in a retracted state, such as would be the case during initial insertion of the delivery tool 300 into the patient. For purpose of illustrating coupling of the implant 20 to the release catheter 304, the frame 55 and associated components of the implant 20 are only partially illustrated in FIG. 15.

Figure 15:
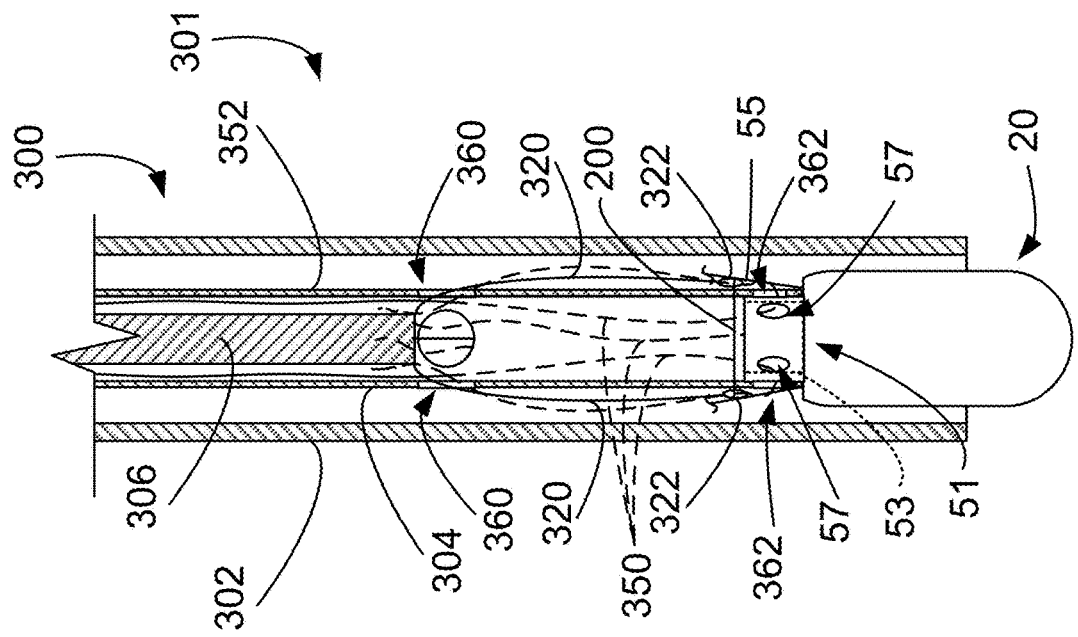
FIG. 15 is a side cross-sectional elevation view of a distal portion of the delivery tool of FIG. 13 coupled to the implant.
Figure 19:
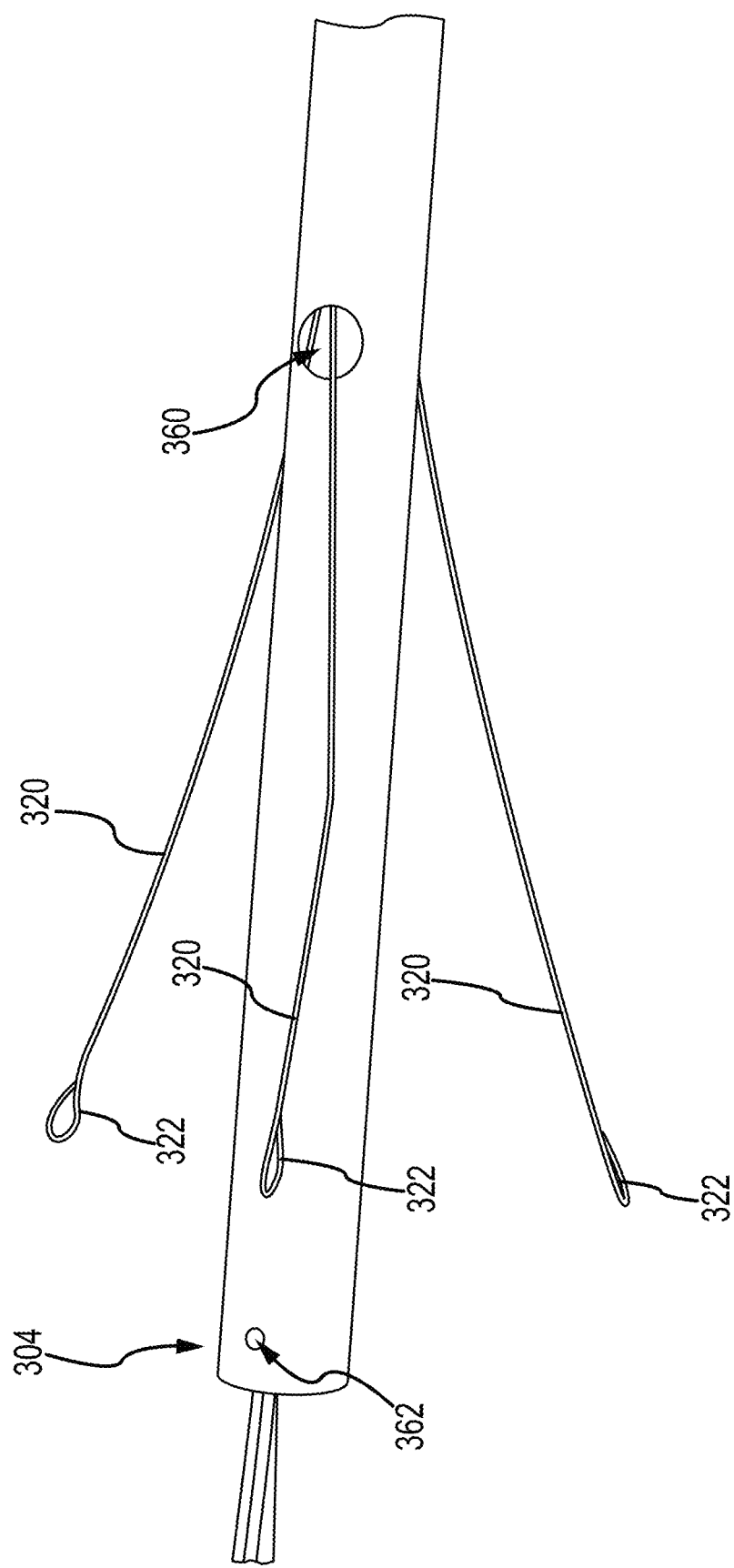
FIG. 19 is a plan view of the delivery tool illustrating protrusion of tension control members through a release catheter of the delivery tool.

As previously discussed, tension control assembly 306 generally includes tension control members 320 that are releasably coupled to the control line 200 of the implant 20. As illustrated in FIGS. 14 and 15, the tension control members 320 may be in the form of cables, control sutures, wires, or similar elongate structures that extend distally from a distal end of a tension control shaft 324. In at least certain implementations, the tension control members 320 may terminate in a loop (e.g., loop 322) or similar structure to facilitate coupling to the tension control members 320 to the tension control line 200 of the implant 20. FIG. 19 is an illustration of the tension control assembly 306 disposed within the release catheter 304 with the tension control members 320 extending distally out of a catheter body 352 of the release catheter 304.

The release catheter 304 includes release lines 350 disposed within and extending through the catheter body 352. The catheter body 352 further defines two sets of lateral holes for facilitating tensioning and release functionality of the delivery tool 300. More specifically, the catheter body 352 defines a set of proximal holes 360 and a set of distal holes 362. The catheter body 352 further defines a distal opening 357. As illustrated in FIGS. 14 and 19, the tension control assembly 306 is generally assembled with the release catheter 304 such that the tension control members 320 extend distally through the proximal holes 360.

Figure 16:
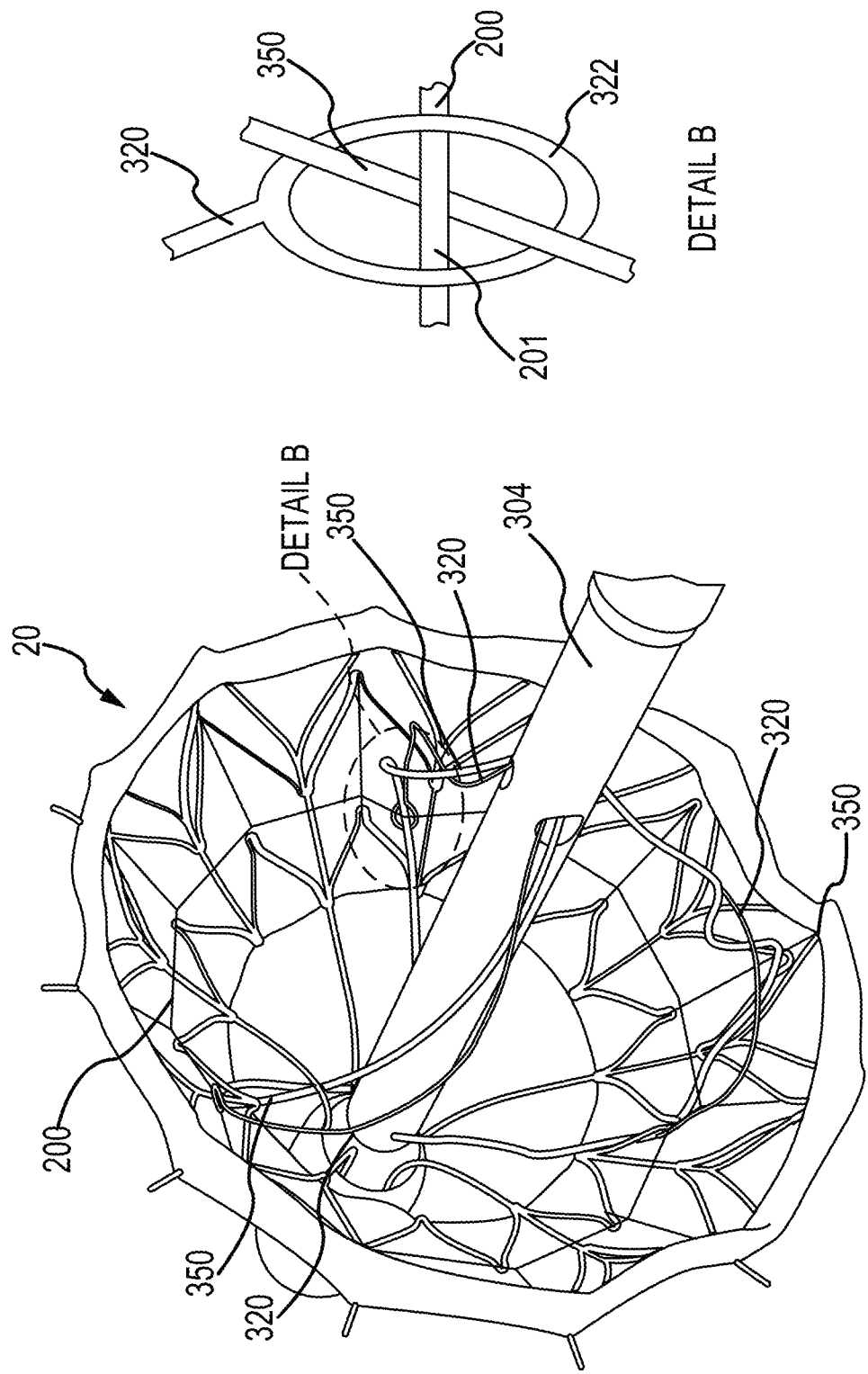
FIG. 16 is a distal perspective view of the implant coupled to the delivery tool and in an expanded state.
Figure 17:
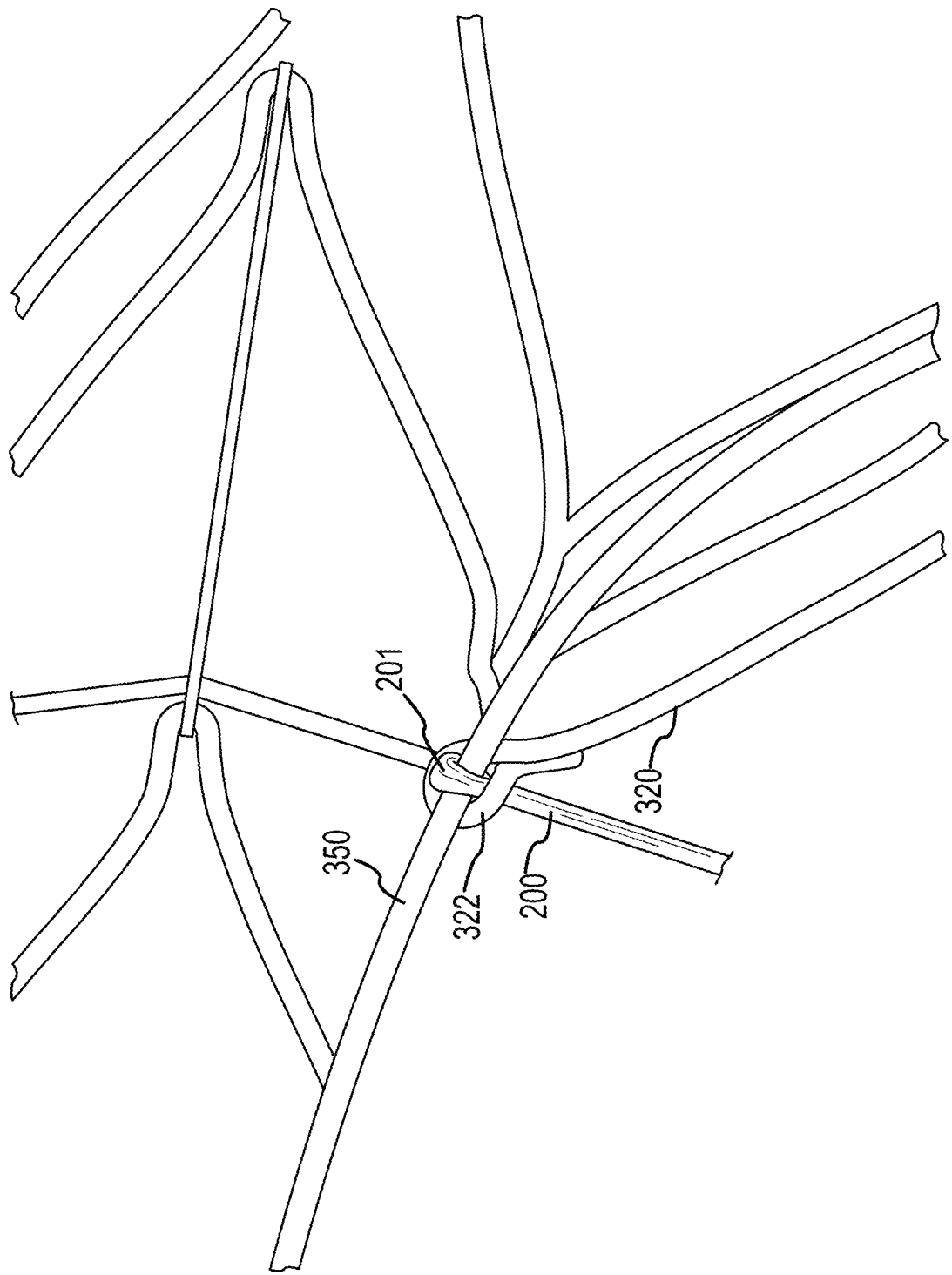
FIG. 17 is a detailed view of a connection between the delivery tool and the tension control line of the implant and, more specifically connection between a tension control member of the delivery tool and the control line of the implant using a release line of the delivery tool.
Figure 18:
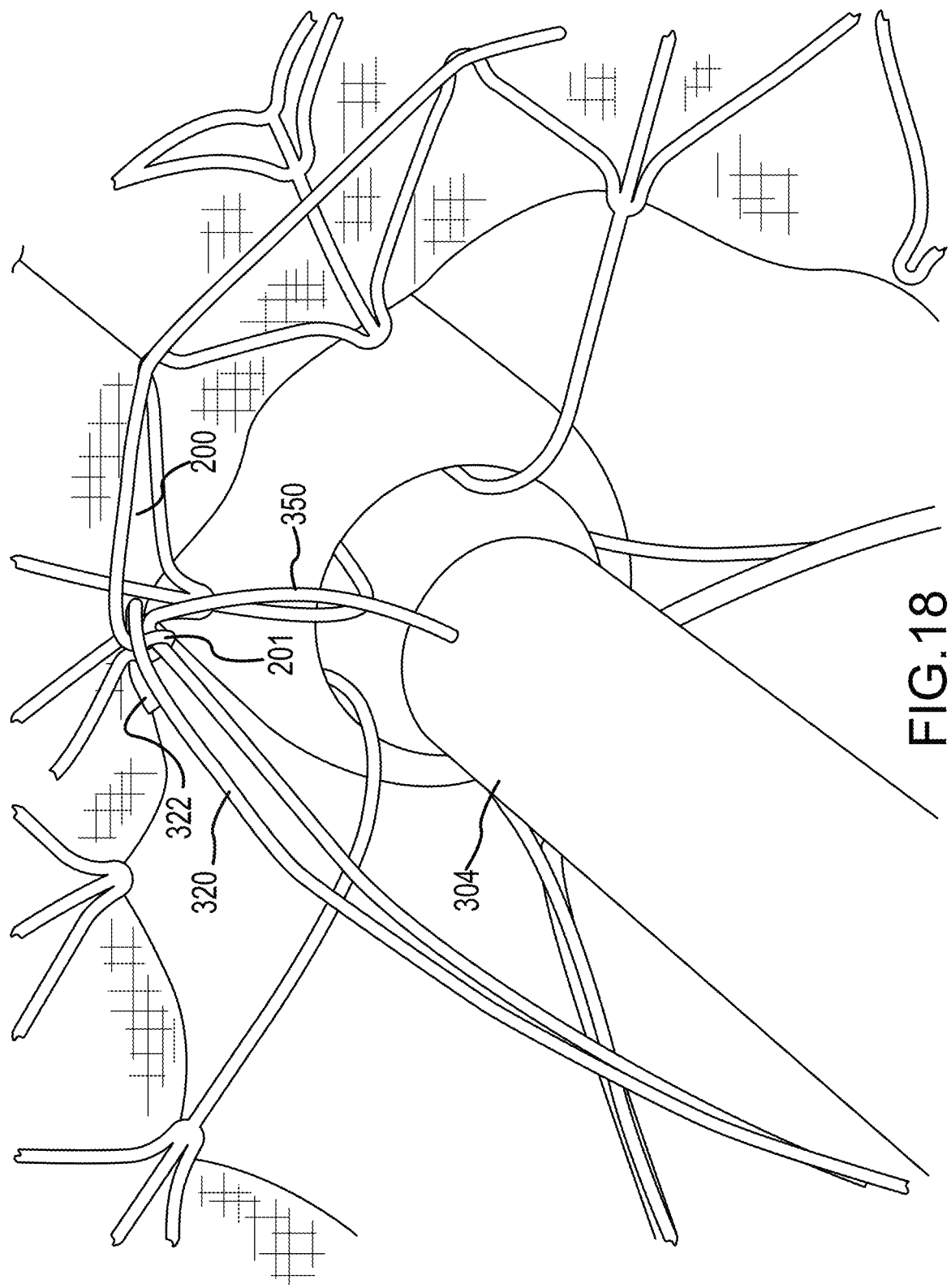
FIG. 18 is a second detailed view of a connection between the delivery tool and the tension control line of the implant.

The implant 20 is generally coupled to the delivery tool 300 by coupling the implant 20 to the tension control members 320 using the release lines 350. FIG. 16 is a proximal perspective view of the implant 20 coupled to the delivery tool 300 in an expanded state to illustrate such coupling. As illustrated in Detail B of FIG. 16, a loop 201 of the tension control line 200 is pulled through the loop 322 of the tension control member 320. The release line 350 is then passed through the loop 201 of the tension control line 200 and across the loop 322 of the tension control member 320, thereby retaining the loop 201 of the tension control line 200 through the loop 322 of the tension control member 320. To release the coupling between the control line 200 and the tension control member 320, the release line 350 is slid out of the loop 201, thereby enabling the loop 201 to pass through the loop 322 of the tension control member 320 and decoupling the tension control member 320 from the control line 200. Detailed illustrations of the loop 201 of the tension control line 200 coupled to the loop 322 of the tension control member 320 are provided in FIGS. 17 and 18.

Referring back to FIG. 15, routing of the release lines 350 generally includes routing the release lines 350 (shown in dashed lines for clarity and distinction over other illustrated elements) through the catheter body 352 to an exterior thereof, such as by passing the release lines 350 through the distal holes 362 of the catheter body 352. The release lines 350 may then be routed proximally to join the control line 200 to the tension control members 320, as noted above and as illustrated in FIGS. 16-18. The release lines 350 may then be routed proximally and back into the catheter body 352 through the proximal holes 360 where the release lines 350 may be retained, e.g., by friction, until the implant 20 is to be released.

As shown in FIG. 15, in at least certain implementations, the occluder 50 of the implant 20 may include a proximally extending annular protrusion 51 defining each of a proximally open annulus 53 and laterally extending holes 57 in communication with the annulus 53. In such implementations, the annular protrusion 51 may be disposed within the distal opening 357 (shown in FIG. 14) of the release catheter 304 during insertion and delivery to an implantation location and the release lines 350 may be further routed into the annulus 53 and through the holes 57 before being passed through the distal holes 362 of the catheter body 352.

Figure 20:
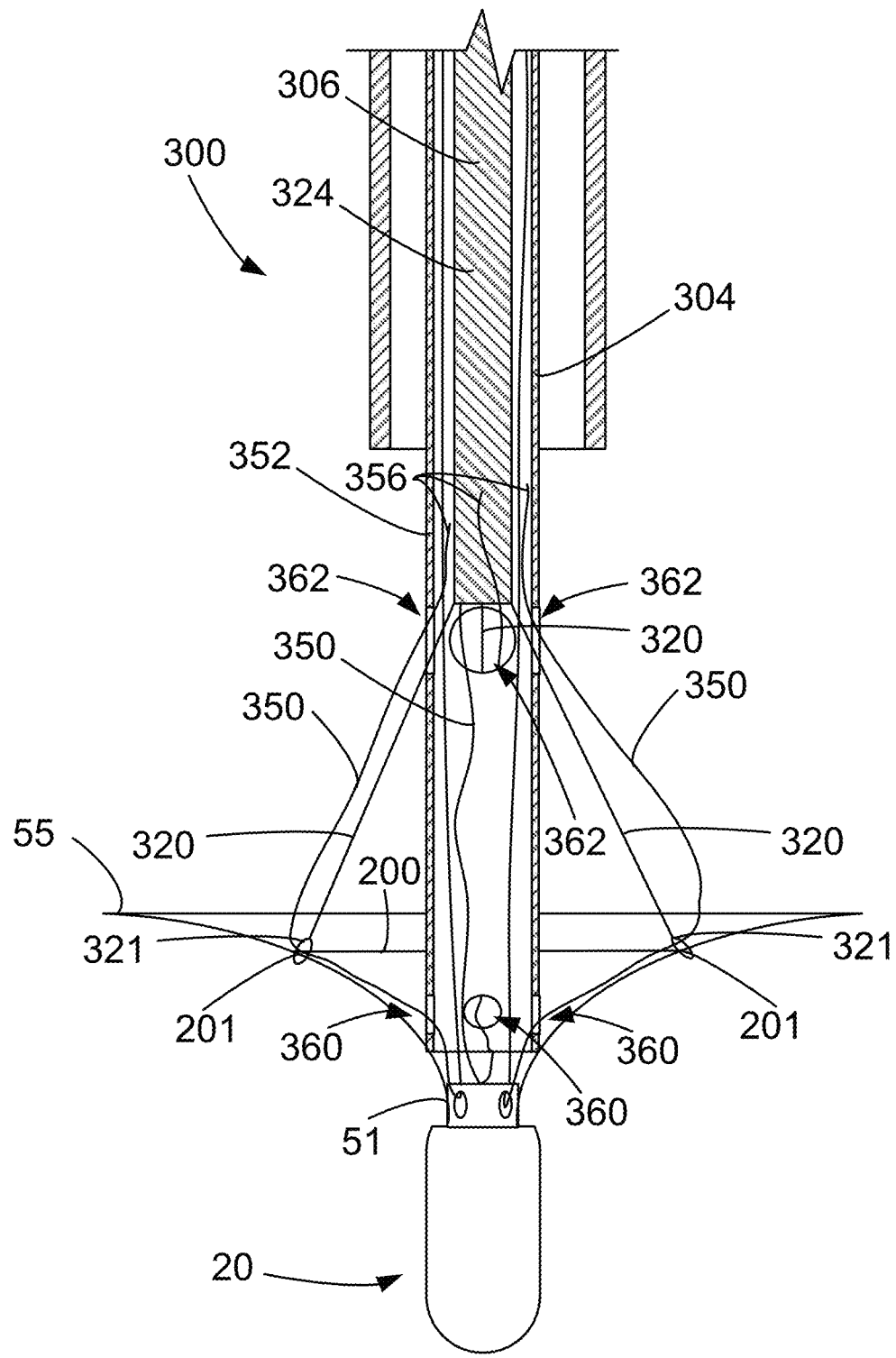
FIG. 20 is a side cross-sectional view of the delivery tool coupled to the implant with the implant in an expanded configuration.
Figure 21:
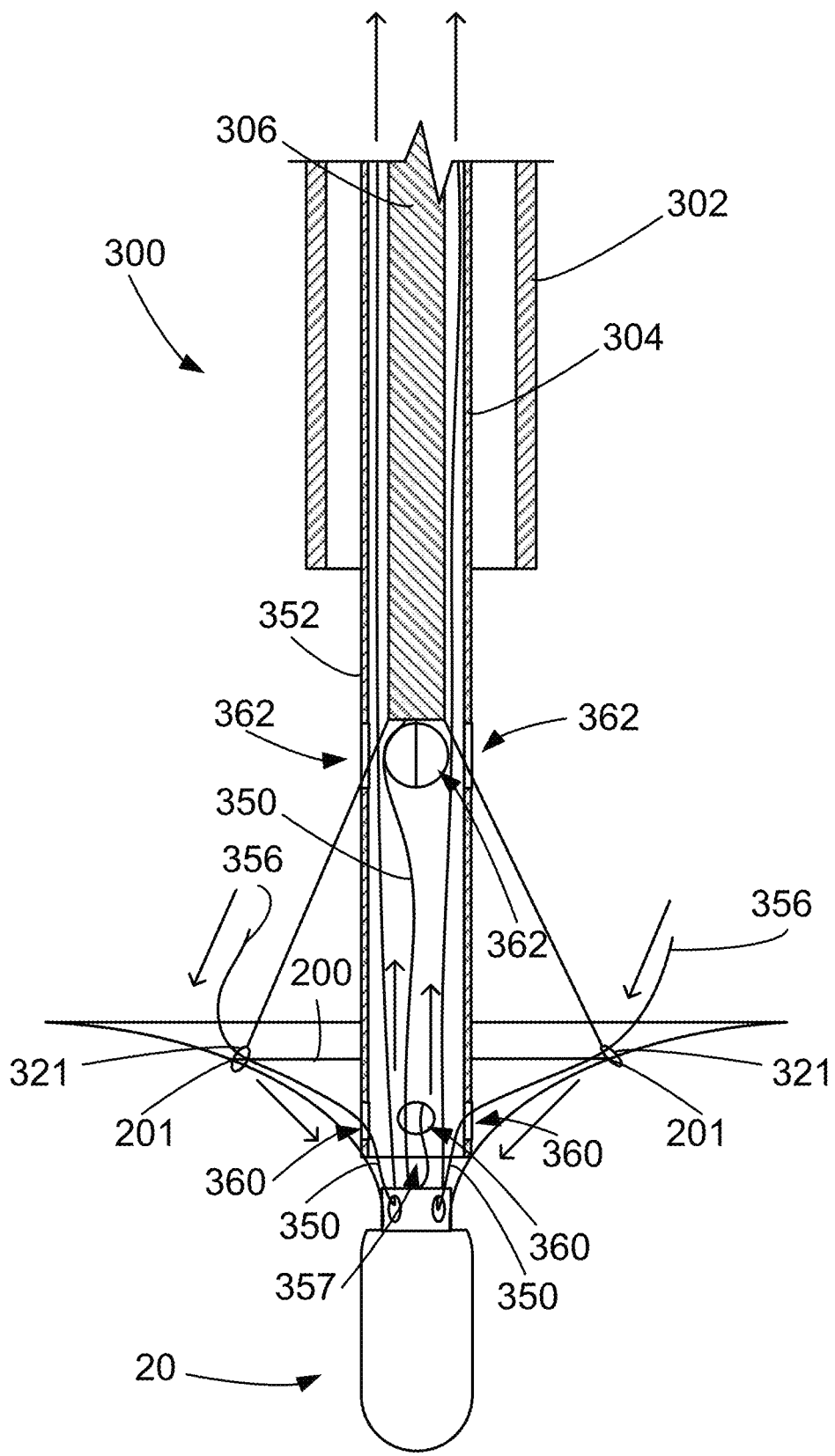
FIG. 21 is a side cross-sectional view of the delivery tool and the implant during release of the implant from the delivery tool.
Figure 22:
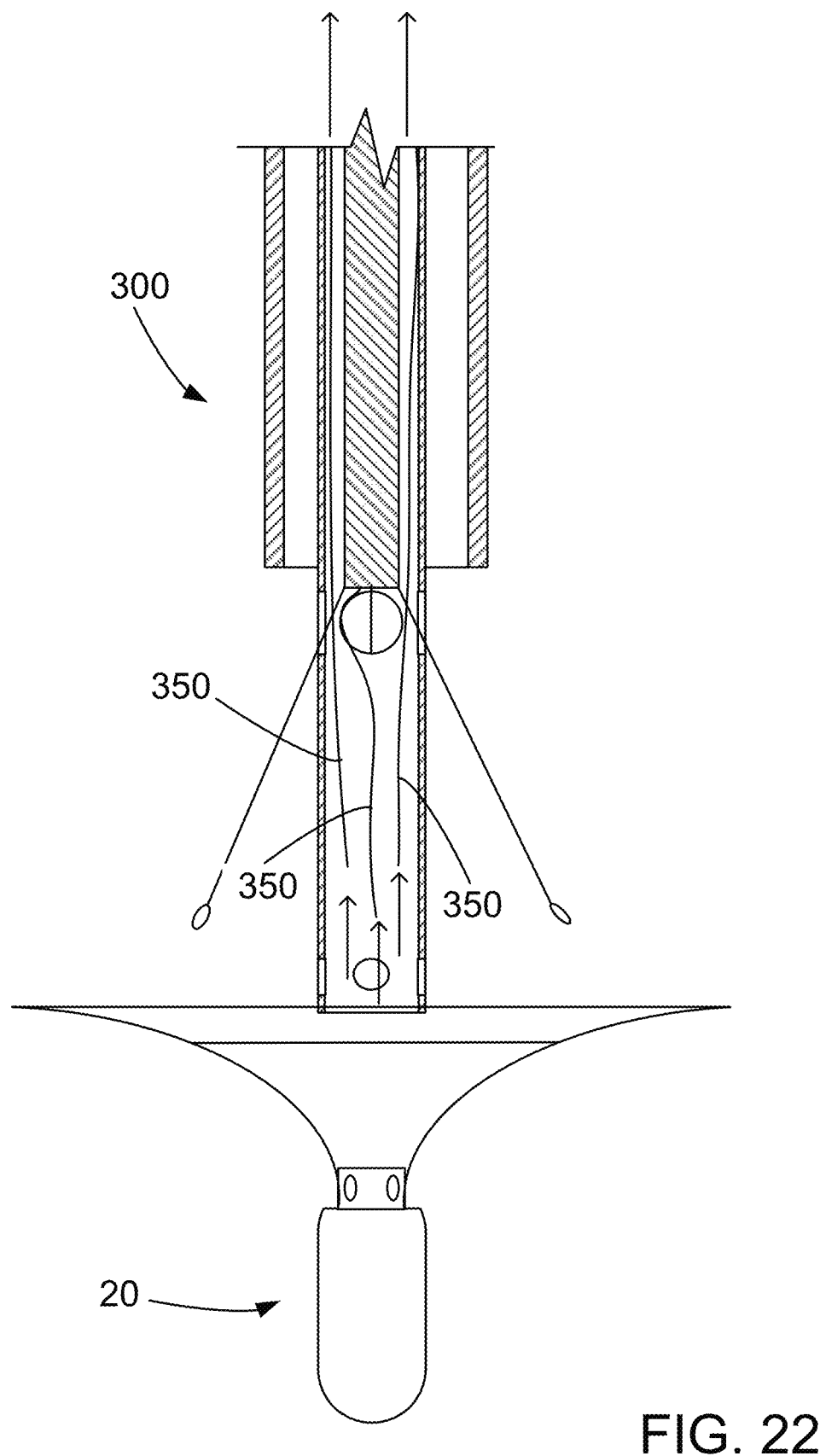
FIG. 22 is a side cross-sectional view of the delivery tool and the implant following release of the implant from the delivery tool.

FIGS. 20-22 illustrate the general process of releasing the implant 20 from the delivery tool 300. Referring first to FIG. 20, the delivery tool 300 and implant 20 are shown with the frame 55 of the implant 20 in an expanded configuration but still coupled to the delivery tool 300. More specifically, the implant 20 is coupled to the delivery tool 300 by virtue of the release lines 350 of the release catheter 304, each of which is routed, in order, through the catheter body 352, through the annular protrusion 51 of the implant 20, through one of the distal holes 362 of the catheter body 352, through one of the loops 201 of the tension control line 200 extending through a loop 321 of one of the tension control members 320, and back into the catheter body 352 through one of the proximal holes 360. As previously noted, in at least certain implementations, the ends 356 of the release lines 350 may be retained within the catheter body 352 by friction.

In the state illustrated in FIG. 20, the tension control shaft 324 of the tension control assembly 306 may be actuated (e.g., by translating and/or rotating the shaft or a handle assembly coupled to the shaft) to vary the tension applied to the frame 55 of the implant 20. By doing so, the frame 55 may be expanded and/or collapsed to facilitate placement of the implant 20 prior to release of the implant 20 from the delivery tool 300.

Referring next to FIG. 21, the delivery tool 300 and implant 20 are illustrated part way through release of the implant 20 from the delivery tool 300. In general, release of the implant 20 from the delivery tool 300 is performed by pulling the release lines 350 proximally through the catheter body 352. As illustrated and for each release line 350 and as indicated by the open arrows, such pulling causes the end 356 of the release line 350 to exit the catheter body 352 through one of the proximal holes 360, pass through one of the loops 201 of the tension control line 200 to release the loop 201 from a corresponding control member 320, pass through one of the distal holes 362 of the catheter body 352 and the annular protrusion 51 of the implant 20, and reenter the catheter body 352 through the distal opening 357 of the catheter body 352. As a result, pulling the release lines 350 decouples the implant from the delivery tool and allows removal of the delivery tool 300 with the implant 20 remaining in place, as shown in FIG. 22. Following release of the implant 20, each of the release catheter 304 and the tension control assembly 306 may be proximally retracted and/or proximally removed from the sheath 302.

Notably, the process of releasing the implant 20 from the delivery tool 300 by pulling the release lines 350 applies a net force on the implant 20 that expands the frame 55 and/or resists collapse of the frame 55. More specifically, as the release lines 350 are pulled to release the implant the release lines 350 apply a net distal force on the implant 20, thereby pressing the implant 20 into its current implantation location. Moreover, because such distal force is applied at the connection between the control line 200 and the tension control member 320 it acts to further expand or otherwise provide additional counterforce against collapse of the frame 55. In contrast, if a net proximal force were to be applied, the implant 20 may be pulled out of place and/or the frame 55 may undergo a partial collapse, each potentially leading to the implant 20 becoming dislodged or losing its orientation. Accordingly, by routing the release lines 350 as noted above, proper placement of the implant 20 is more easily controlled and more likely to be maintained following release of the implant 20.

VI. Multi-Part Occluder

Figure 23:
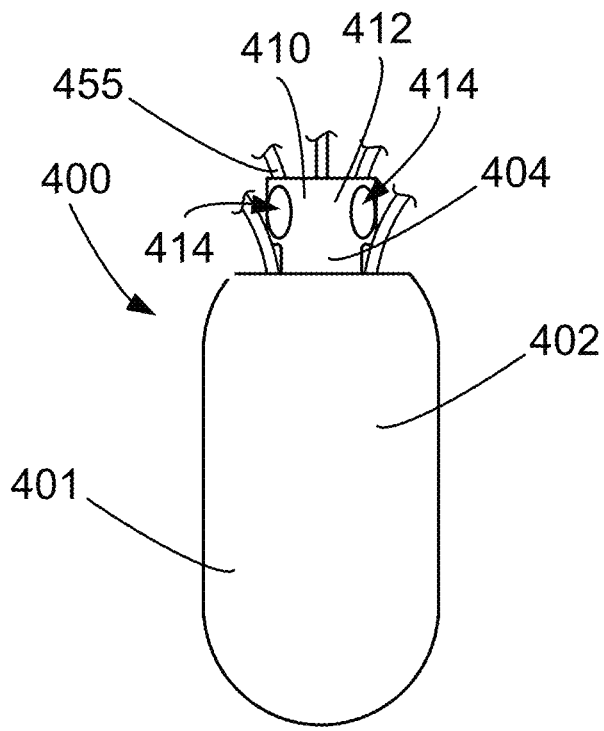
FIG. 23 is a side elevation view of a distal portion of an implant.
Figure 24:
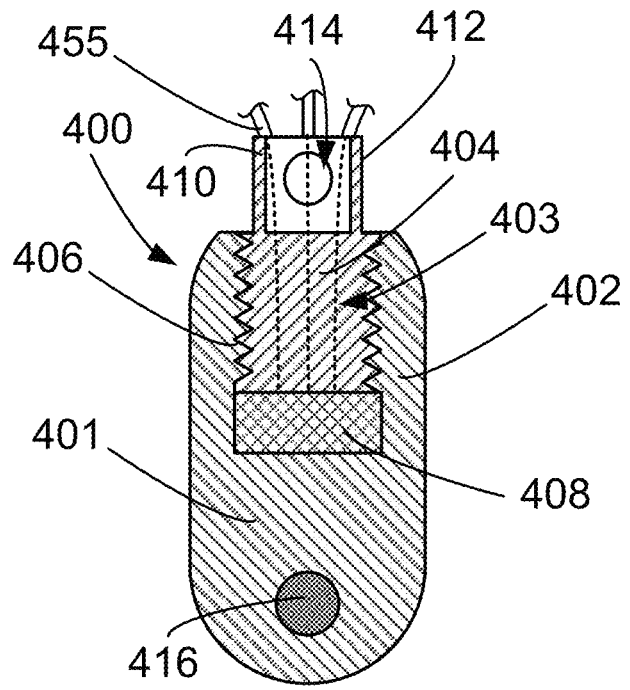
FIG. 24 is a side cross-sectional view of the distal portion of the implant of FIG. 23.

FIGS. 23 and 24 illustrate a distal portion of an example implant 400 that may be used in implementations of the present disclosure. More specifically, FIG. 23 is a side elevation view of the distal portion of the implant 400 while FIG. 24 is a cross-sectional view of the implant 400, each of which emphasize an occluder 401 of the implant 400.

As illustrated, the occluder 401 includes an occluder body 402 defining a cavity 403 within which an insert 404 is disposed. The insert 404 is coupled to the occluder body 402. In the specific implementation illustrated in FIGS. 23 and 24, the insert 404 is coupled to the occluder body 402 by a threaded connection 406; however, any suitable connection (e.g., adhesive, welding, etc.) may be used instead of a threaded connection.

The occluder 401 further includes a frame base 408 disposed within the cavity 403 of the occluder body 402 and distal the insert 404. The frame base 408 is coupled to a frame 455 of the implant 400 (shown in part and which may be substantially similar to other frames disclosed herein) which extends from the frame base 408 and exits proximally from the occluder body 402. The frame base 408 may be coupled to the occluder body 402 and/or may be maintained in place by the insert 404.

The insert 404 further includes a proximally extending annular protrusion 410. The annular protrusion 410 includes a sidewall 412 through which one or more laterally extending holes 414 may be defined. As previously discussed in the context of FIGS. 15 and 20-22, during use of systems disclosed herein, release lines of a delivery tool may be routed through the holes 414 to secure the implant 400 to a delivery tool and, more specifically, to a release catheter of a delivery tool.

The occluder 401 further includes a marker 416 disposed within the occluder body 402. In certain implementations, the marker 416 may be a radiopaque marker to facilitate fluoroscopic observation of the implant 400 during delivery and implantation. As shown, the marker 416 may be embedded within the occluder body 402, such as by molding the occluder body 402 about the marker 416. In other implementations, the cavity 403 may be shaped to receive the marker 416 in addition to the insert 404 and the frame base 408. In still other implementations, the marker 416 may be disposed on an exterior surface of the occluder body 402. Although illustrated as a spherical bead in FIG. 24, the marker 416 may have any suitable shape. Similarly, any suitable number of markers may be incorporated into the occluder body 402. In other implementations, the occluder body 402 may be formed from a material with radiopaque additives. In still other implementations, either or both of the frame base 408 and the insert 404 may be formed of radiopaque material or include one or more radiopaque markers.

VII. Skirted and Sheet-Based Occlusive Assemblies

As noted above, implementations of implants according to the present disclosure may include an occlusive body supported by a frame with a thin sheet supported by and extending around a proximal portion of the frame. When the implant is deployed within the heart to support function of a heart valve, the frame is supported by an annulus of the valve or by the walls of the atrium such that the occlusive body is disposed to interact with and seal against leaflets of the valve. In certain implementations, the thin sheet may be formed from a material that allows for tissue ingrowth such that, over time, the implant is retained more robustly within the heart. In addition to this structural function, the thin sheet may be configured to at least partially overlap one or more commissures of the valve leaflets to correct or reduce commissural regurgitation.

In addition to the outer thin sheet discussed above, implementations of this disclosure may alternatively or additionally include an inner sheet. For example, implants of the present disclosure may include an occlusive assembly that includes an occlusive body (such as the bullnose-style occluder or other occluders discussed above) and a sheet of material (generally referred to as a "skirt" or "inner sheet" herein) that extends from and circumferentially around the occlusive body. In such implementations, the inner sheet may be coupled to the occlusive body and/or portions of the implant frame extending from the occlusive body. In other implementations, the occlusive assembly may omit an occlusive body such that the inner sheet forms a cap-like structure on a distal end of the implant supported by and coupled to a distal portion of the frame. In such implants, the inner sheet may provide a sealing surface for the valve leaflets similar to that provided by the occlusive body. Like the outer sheet, the inner sheet may be formed of a material that promotes or allows tissue ingrowth to create a smooth layer of biological cells. The layer of biological cells may provide a barrier between the inner sheet and native valve leaflets to prevents wearing effects between the inner sheet and native valve leaflets. Alternatively, the inner sheet may be formed from a low friction material (such as PTFE or ePTFE) that resists cell in-growth to provide a smooth surface that prevents wearing effects between the inner sheet and native valve leaflets.

In certain implementations, either of the outer and inner sheets may have a multi-layered construction in which an internal pocket is defined between layers of sheet material. The pocket may contain an additional layer of fabric to serve as padding (e.g., a layer of PET, ePTFE, or other fabric). The pocket may also or alternatively contain a water-absorbing material, such as a hydrogel (e.g., sodium polyacrylate or polyvinyl alcohol) that expands following implantation. In any of the foregoing cases, the filling may form a pad. In implementations in which the inner sheet is formed to include an absorbing/expanding pocket, such pockets may generally pad or otherwise increase the distance between the occluding surface/sheet and the underlying frame of the implant, thereby preventing and padding contact between valve leaflets and the frame.

The foregoing aspects of this disclosure and related concepts are now discussed in further detail with reference to the figures.

Figure 25:
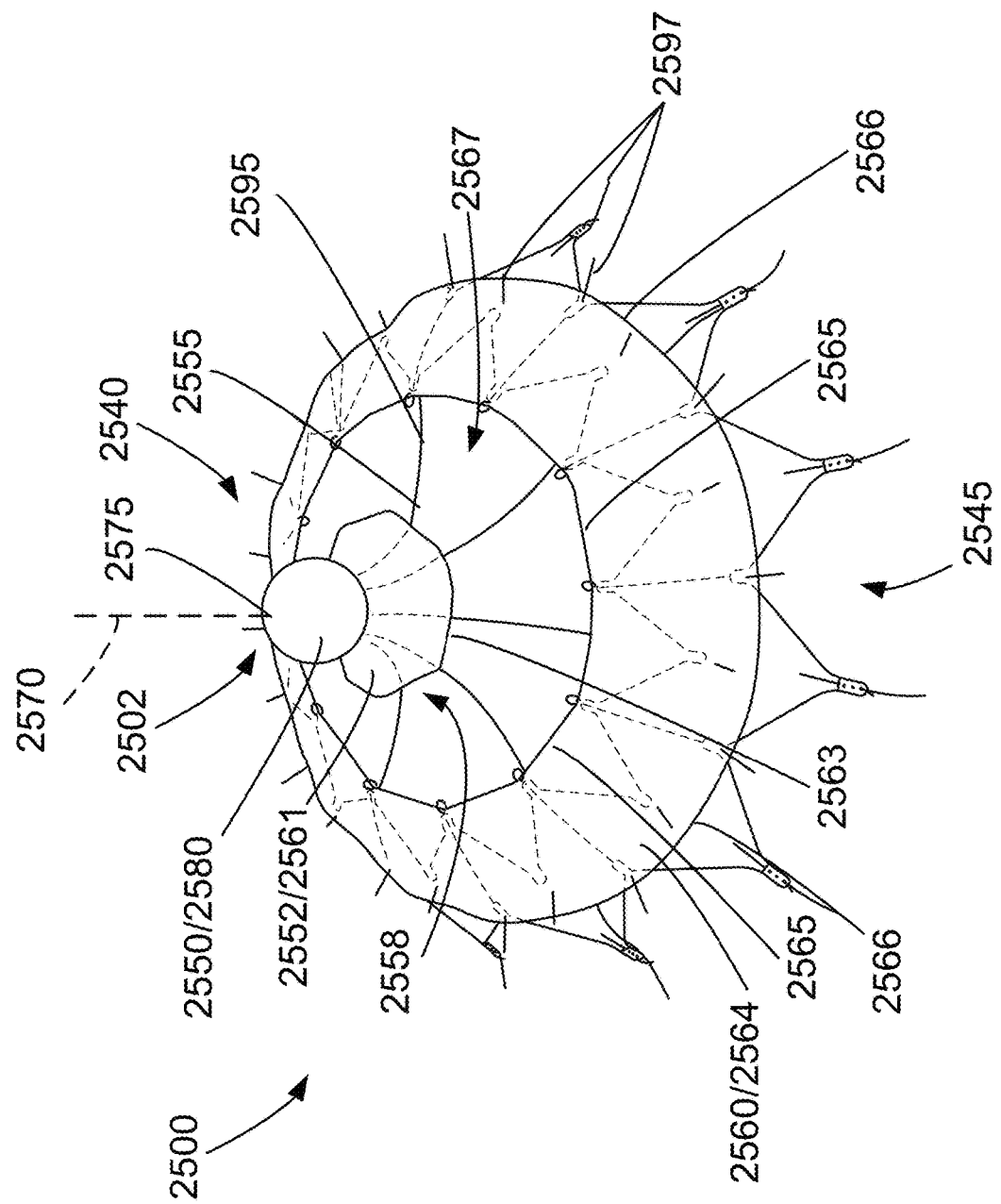
FIG. 25 is a perspective distal-end view of an implant including an occlusive assembly having an inner sheet.
Figure 26:
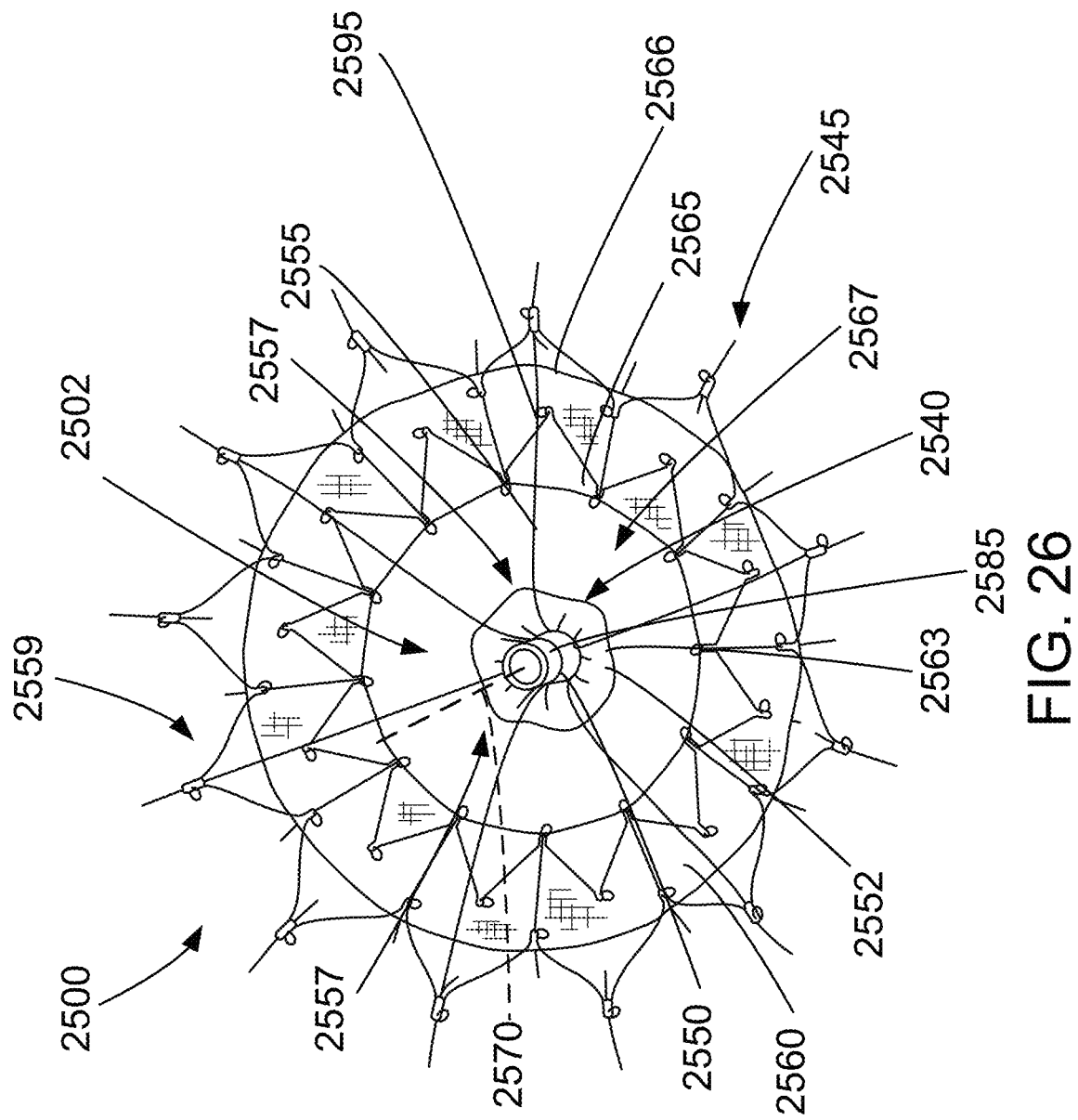
FIG. 26 is perspective proximal-end view of the implant of FIG. 25.

FIGS. 25 and 26 illustrate an example of an implant 2500 including a skirted occlusive assembly. Specifically, FIG. 25 is a perspective distal-side view of implant 2500 while FIG. 26 is a perspective proximal-side view of implant 2500. FIGS. 25 and 26 illustrate implant 2500 when implant 2500 is in an expanded state, such as exists when implant 2500 is implanted in a cardiac valve to be repaired. As illustrated in FIG. 25, implant 2500 includes a distal end 2540 and a proximal end 2545. Distal end 2540 serves as the leading end of implant 2500 during implantation.

Implant 2500 includes an occlusive assembly 2502 that includes a central occlusive body 2550 and an inner sheet 2552 extending about central occlusive body 2550. Implant 2500 further includes a frame 2555 and an outer sheet 2560 supported on frame 2555. In the implementation of FIGS. 25 and 26, frame 2555 extends proximally from central occlusive body 2550. When in the expanded state, the frame 2555 radiates laterally outwardly relative to a central longitudinal axis 2570 of implant 2500. In the expanded state, inner sheet 2552 forms a first annular surface 2561 and outer sheet 2560 forms a second annular surface 2564, each of which is supported on frame 2555.

First annular surface 2561 has a proximal radially outward edge 2563. Similarly, second annular surface 2564 has a distal radially inward edge 2565 and a proximal radially outward edge 2566. Proximal radially outward edge 2563 of first annular surface 2561 and distal radially inward edge 2565 of second annular surface 2564 define a central opening 2567 between inner sheet 2552 and outer sheet 2560. Proximal radially outward edge 2566 of outer sheet 2560 may form the extreme proximal radially outward boundary of the implant when in the expanded state; however, as shown in FIGS. 25 and 26, at least a portion of frame 2555 may extend beyond proximal radially outward edge 2566 of outer sheet 2560. Central longitudinal axis 2570 passes through the extreme distal tip 2575 of central occlusive body 2550. Considering the foregoing and in at least certain embodiments, frame 2555 is generally designed to sit on the floor of the atrium, to induce annular reduction, and to produce a neo-annulus.

In addition to being annular, either of first annular surface 2561 and second annular surface 2564 may also be conical, or relatively so (e.g., parabolic).

When implant 2500 is in the collapsed state, e.g., during delivery of implant 2500 to the target site via a corresponding tool (e.g., the tool 15 of FIG. 1A), frame 2555, inner sheet 2552, and outer sheet 2560 collapse symmetrically about the central longitudinal axis 2570. Thus, like implant 20 of FIGS. 2-6, implant 2500 can transition from the collapsed state to the expanded state like an umbrella. For example and as previously discussed herein in the context of implant 20, implant 2500 may be maintained in a collapsed state (similar to that illustrated in FIG. 7 for implant 20) by the tool so as to allow implant 2500 to be negotiated through the patient vascular system and into an atrial chamber of the heart for implantation of the implant within a target cardiac valve. For example, with implant 2500 maintained in the collapsed state by virtue of being confined within a tubular sheath 76 of the delivery tool 15, implant 2500 may be delivered and deployed at the target site via an antegrade percutaneous route (e.g., an antegrade trans-femoral or trans-jugular route) with the patient consciously sedated during the procedure. Upon being properly positioned in the target cardiac valve for repair, the physician may actuate tool 15 such that tool 15 no longer maintains implant 2500 in the collapsed. Since frame 2555 of implant 2500 is biased to self-expand, implant 2500 self-expands into the expanded state to anchor itself within the target cardiac valve and reduce regurgitation.

Central occlusive body 2550 may take on various forms and shapes. For example, as previously discussed in the context of implant 20, central occlusive body 2550 may have a bullet or conical shape. Additional details regarding such shapes are provided above. Another alternative shape for central occlusive body 2550 is a bulb and is illustrated in FIGS. 25 and 26. In such implementations, central occlusive body 2550 may include a distal bulb 2580 (shown in FIG. 25) with a cylindrical side 2585 (shown in FIG. 26) extending proximally therefrom. In certain implementations, distal bulb 2580 may have a spherical shape; but may alternatively have an ovoid or oblong shape. More generally, distal bulb 2580 may have a shape selected to be atraumatic during delivery and implantation purposes and that facilitates sealing of distal bulb 2580 against the cardiac valve leaflets to reduce or even eliminate central regurgitation past the cardiac valve leaflets.

In general, characteristics of central occlusive body 2550 may be similar to those of central occluder 50 of implant 20. For example, central occlusive body 2550 may be formed various materials, including angio- and/or echolucent materials, may be filled or fillable (e.g., with saline) and may have properties and dimensional characteristics like those of central occluder 50 discussed above.

Like thin sheet 60 of implant 20 being supported by frame 55, each of inner sheet 2552 and outer sheet 2560 is supported on frame 2555 and secured thereto. For example, and without limitation, inner sheet 2552 and/or outer sheet 2560 may be secured to frame 2555 by suturing the respective sheet against an inner surface and/or an outer surface of frame 2555. In other implementations, inner sheet 2552 or outer sheet 2560 may include a cuff or similar folded structure that is folded over an end of frame 2555. For example, as illustrated in FIG. 26, inner sheet 2552 is folded over and sutured against a distal frame portion 2558. More specifically, distal frame portion 2558 includes a circumferential arrangement of arcuate petal portions (e.g., arcuate petal portion 2557) extending distally from central occlusive body 2550. Inner sheet 2552 is then wrapped around a distal surface of distal frame portion 2558, folded over each arcuate petal portion 2557 and sutured in place such that inner sheet 2552 is secured to distal frame portion 2558.

Alternatively, each of inner sheet 2552 and outer sheet 2560 may be secured to frame 2555 by sewing, welding, gluing/adhering, stapling, or any other suitable securement method or combination of securement methods. Inner sheet 2552 and/or outer sheet 2560 may be on the distal side of frame 2555, the proximal side of frame 2555, or both such that the frame extends through and along inner sheet 2552 and/or outer sheet 2560. In at least one specific implementation, each of inner sheet 2552 and outer sheet 2560 are supported on a distal side of frame 2555 such that, when implanted, outer sheet 2560 contacts the tissue of the atrial floor while inner sheet 2552 is positioned to interact with and seal against the valve leaflets.

Depending on the particular implementation, inner sheet 2552 and/or outer sheet 2560 may be formed of or include a woven or knit material or fabric that encourages tissue ingrowth. Fabric for inner sheet 2552 and/or outer sheet 2560 may generally have any of the properties or characteristics discussed above with respect to thin sheet 60 of implant 20. Regarding outer sheet 2560, the porosity of the fabric may assist in reducing commissural tricuspid regurgitation. Further reduction of commissural tricuspid regurgitation may be provided by the angulation of frame 2555, which provides close contact between outer sheet 2560 and the commissures in a circumferential manner. For example, with the implant 2500 implanted in the target cardiac valve, tissue in-growth into the fabric of outer sheet 2560 buttresses the myocardium, helping to keep the tissue from expanding further and reducing the potential of future regurgitation. Regarding inner sheet 2552, the porosity of the fabric may assist in reducing central regurgitation by providing an expanded surface relative to central occlusive body 2550 alone against which the valve leaflets may seal. In at least certain implementations, inner sheet 2552 may be formed from PTFE, ePTFE, or a similar low-friction polymer to provide a smooth surface for the native leaflets to abut against.

Frame 2555 may include spokes 2595 from which various arcuate petal portions extend. For example, as discussed above, a distal portion of frame 2555 may include distal or inner arcuate petal portions, such as arcuate petal portion 2557, that support inner sheet 2552. Frame 2555 may further include outer arcuate petal portions, such as arcuate petal portion 2559 configured to support outer sheet 2560. The outer arcuate petal portions may be similar to or otherwise share characteristics and variations of petal portions 100 of implant 20, which are described above in further detail.

Frame 2555 may be made from a variety of super-elastic and/or shape memory materials, including, for example, nickel-titanium alloys (e.g., Nitinol), which may be laser cut from a tube or in the form of drawn wire. The features defined in the shape memory materials may be defined therein via various cutting methods known in the art, include laser, water jet, electrical discharge machining (EDM), stamping, etching, milling, etc.

Like central occluder 50 and frame spokes or struts 95 of implant 20, occlusive assembly 2502 and spokes 2595 may be removable after implantation, leaving second annular surface 2564 formed by outer sheet 2560 in place. In such embodiments, a circumferential suture connection may exist between spokes 2595 and the rest of frame 2555 radially outward of spokes 2595. Thus, this circumferential suture connection may be cut and occlusive assembly 2502 and spokes 2595 may be removed through a catheter, leaving the annular portion of the implant, which then acts as an "annuloplasty" frame.

Like spokes 95 of implant 20, spokes 2595 may proximally extend from central occlusive body 2550 to the outer arcuate petal portions. In certain implementations, spokes 2595 may extend substantially parallel with, and extend along and near to, central longitudinal axis 2570 of implant 2500. When implant 2500 is in the expanded state, spokes 2595 proximally extend from central occlusive body 2550 and laterally radiate away from central longitudinal axis 2570 to the outer arcuate petal portions. In general, spokes 2595 may be configured similar to and have characteristics to spokes of other frame embodiments discussed herein. For example, the dimensional characteristics and variations provided above with respect to frame 55 (and elements thereof) of implant 20 may be similarly applicable to frame 2555 and its components.

Outer arcuate petal portions, such as arcuate petal portion 2559 may be similar to petal portions 100 of implant 20, discussed above. Inner arcuate petal portions, such as arcuate petal portion 2557, may be located between a pair of spokes 2595. When in the expanded state, the inner arcuate petal portions may be straight or curved in a laterally radiating direction. In certain implementations, when curved, the radius of curvature of the inner arcuate petal portions may be like that of spokes 2595 or may differ from that of spokes 2595. Although illustrated as including only singular arcuate members, each inner arcuate petal portion 2557 may instead include multiple arcuate members, such as the inner and outer arcuate members of petal portions 100.

In different implementations, frame 2555 may include different numbers of inner arcuate petal portions. For example, in certain example embodiments, frame 2555 may include between 6 and 8, between 4 and 10, or between 2 and 12 inner acuate petal portions. In the specific implementation illustrated in FIGS. 25 and 26, for example, frame 2555 includes 6 inner arcuate petal portions.

Like frame 55, frame 2555 may engage the atrial tissue via the protruding anchor members 2597, which may be in the form of small barbs. Anchor members 2597 are designed to securely engage the atrial tissue without penetrating through the tissue or to the coronary vessels. Depending on the embodiment, the protruding anchor members or barbs 2597 may be curved to slide before engaging tissue and there may be one or more rows of protruding anchor members 2597. As shown in FIG. 25, for example, frame 2555 includes three offset rows of protruding anchor members 2597 with a distal and intermediate row extending through outer sheet 2560 and a proximal row projecting from a distal end of frame 2555. Further details and alternative configurations provided above with respect to protruding anchor members 105 are similarly applicable to anchor members 2597, including implementations in which anchor members 2597 are directionally reversed such that they project distally and radially inward.

Figure 27:
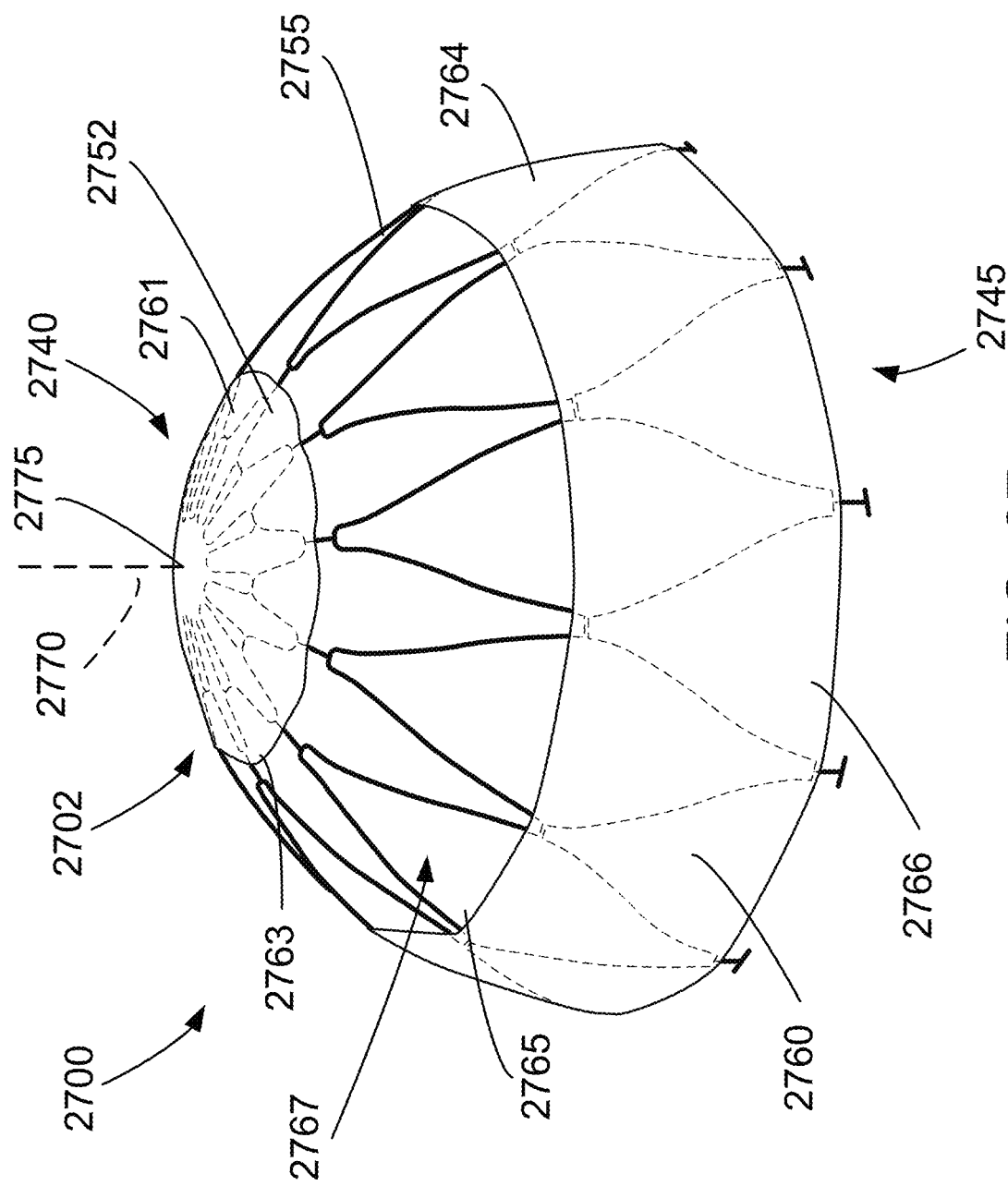
FIG. 27 is perspective distal-end view of a proximally concave implant.
Figure 28:
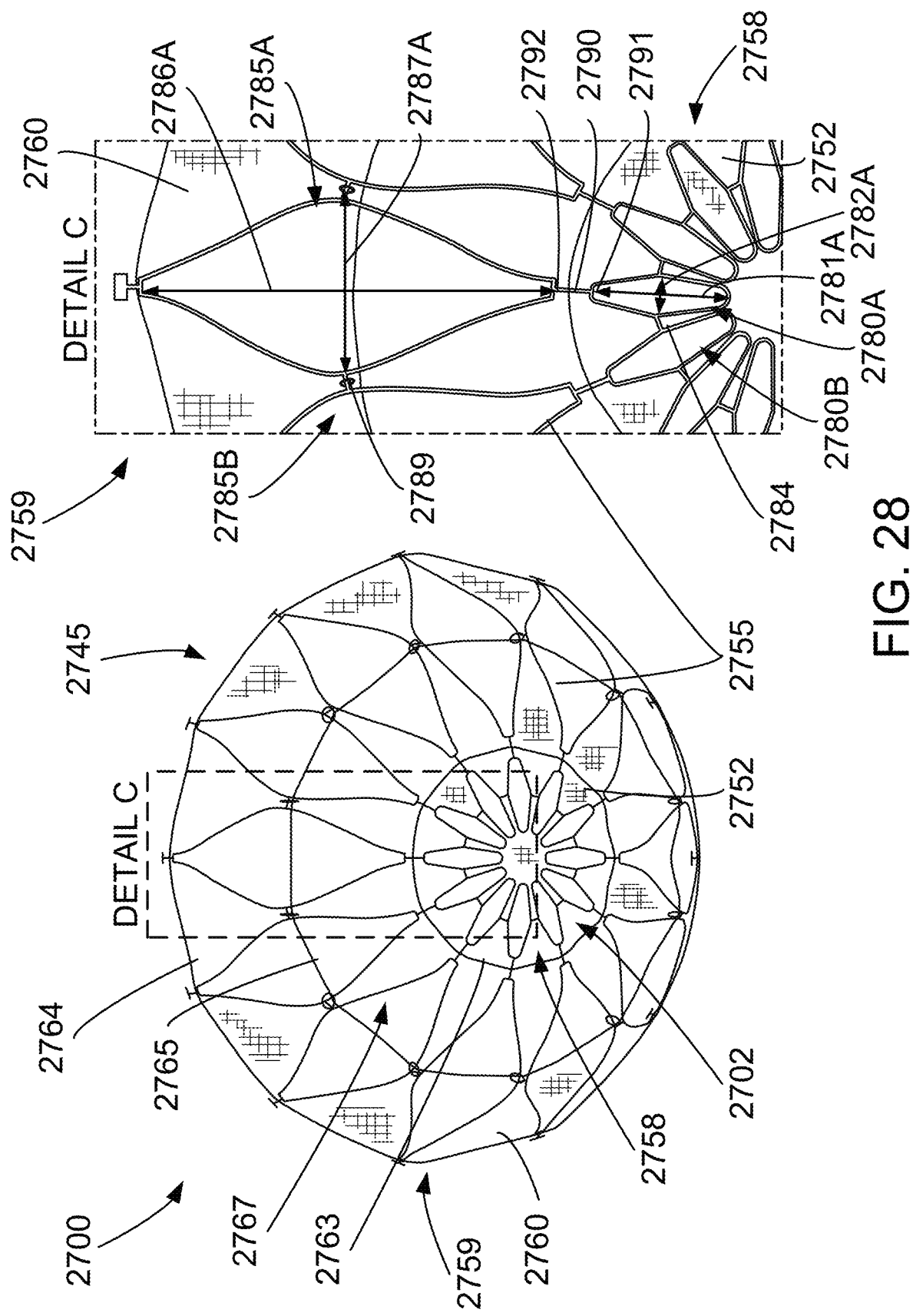
FIG. 28 is a perspective proximal-end view of the implant of FIG. 27.

FIGS. 27 and 28 illustrate another implant 2700 according to the present disclosure. Specifically, FIG. 27 is a perspective distal-side view of implant 2700 while FIG. 28 is a perspective proximal-side view of implant 2700. FIGS. 27 and 28 illustrate implant 2700 when implant 2700 is in an expanded state, such as exists when implant 2700 is implanted in a cardiac valve to be repaired. As illustrated in FIGS. 27 and 28, implant 2700 includes a distal end 2740 (indicated in FIG. 27) and a proximal end 2745. Distal end 2740 serves as the leading end of implant 2700 during implantation.

Implant 2700 includes an occlusive assembly 2702 disposed at distal end 2740. In contrast to occlusive assembly 2502 of implant 2500, occlusive assembly 2702 does not include an occlusive body. Rather, occlusion in occlusive assembly 2702 is provided entirely by an inner sheet 2752, which forms a cap-like structure disposed on distal end 2740. Like implant 2500, implant 2700 further includes a frame 2755 and an outer sheet 2760, with each of inner sheet 2752 and outer sheet 2760 supported on frame 2755. When in the expanded state, frame 2755 radiates laterally outwardly relative to a central longitudinal axis 2770 (indicated in FIG. 27) of implant 2500. In the expanded state, inner sheet 2752 forms a distal surface 2761 and outer sheet 2760 forms an annular surface 2764, each of which is supported on frame 2755.

Distal surface 2761 has a proximal radially outward edge 2763 while annular surface 2764 has a distal radially inward edge 2765 and a proximal radially outward edge 2766. Proximal radially outward edge 2763 of distal surface 2761 and distal radially inward edge 2765 of annular surface 2764 define a central opening 2767 between inner sheet 2752 and outer sheet 2760. Central longitudinal axis 2770 passes through an extreme distal tip 2775 of inner sheet 2752. Given the parabolic shape of frame 2755, implant 2700 may be configured to traverse at least partially up the atrial walls. However, in other implementations, frame 2755 may be configured such that implant 2700 is generally designed to sit on the floor of the atrium. In either case, implant 2700 may generally induce annular reduction and produce a neo-annulus.

Like implant 2500, implant 2700 may be transitioned into a collapsed state, such as during delivery of implant 2700 to the target site. When collapsed, frame 2755, inner sheet 2752, and outer sheet 2760 may collapse symmetrically about central longitudinal axis 2570. Thus, like implant 20 of FIGS. 2-6 and implant 2500, implant 2700 can transition from the collapsed state to the expanded state like an umbrella. Also, like frame 55 of implant 20 and central occlusive body 2550 of implant 2500, frame 2755 of implant 2700 may be biased to self-expand such that implant 2700 self-expands into the expanded state to anchor itself within the target cardiac valve.

Each of inner sheet 2752 and outer sheet 2760 is supported on frame 2755 and secured thereto using any suitable method. For example, and without limitation, inner sheet 2752 and/or outer sheet 2760 may be secured to frame 2755 by suturing, sewing, welding, gluing/adhering, stapling, or any other suitable securement method or combination of securement methods. In certain implementations, inner sheet 2752 or outer sheet 2760 may include a cuff or similar folded structure that is folded over a portion of frame 2755. In the specific implementation illustrated in FIG. 28, inner sheet 2752 is sutured or otherwise coupled to a distal frame portion 2758 of frame 2755 without such a cuff or fold.

Like sheets previously discussed herein, inner sheet 2752 and/or outer sheet 2760 may be on the distal side of frame 2755, the proximal side of frame 2755, or both such that the frame extends through and along inner sheet 2752 and/or outer sheet 2760. In at least one specific implementation, each of inner sheet 2752 and outer sheet 2760 are supported on a distal side of frame 2755 such that, when implanted, outer sheet 2760 contacts the tissue of the atrial floor and/or atrial wall while inner sheet 2752 is positioned to interact with and seal against the valve leaflets. Like previous embodiments discussed herein, inner sheet 2752 and/or outer sheet 2760 may be formed of or include a woven or knit material or fabric that encourages tissue ingrowth to provide the various advantageous discussed above.

Implementations of this disclosure are not limited to any sizes or dimensions and may be modified or customized to meet the needs of patients and specific applications. Nevertheless, in certain implementations, proximal radially outward edge 2763 of inner sheet 2752 may be from and including about 18 mm to and including about 28 mm. For example, in one specific implementation proximal radially outward edge 2763 may be 23 mm. Similarly, distal radially inward edge 2765 may be from and including about 35 mm to and including about 55 mm. For example, in one specific implementation, distal radially inward edge 2765 may be 44 mm. Finally, proximal radially outward edge 2766 may be from and including about 45 mm to and including about 65 mm. In one specific example, proximal radially outward edge 2766 may be 55 mm.

While implant 20 and implant 2500 each included respective frames that relied primarily on a spoke-based design, frame 2755 illustrates an example of a petal-based frame structure. Referring to FIG. 28, frame 2755 includes distal frame portion 2758, which supports inner sheet 2752, and a proximal frame portion 2759, which supports outer sheet 2760. In general, each of distal frame portion 2758 and proximal frame portion 2759 include a set of circumferentially distributed arcuate petal portions configured to collapse and expand as implant 2700 is similarly collapsed and expanded during delivery and implantation.

As shown in Detail C of FIG. 28, distal frame portion 2758 may include arcuate petal portions that may be ovate, diamond-shaped, or that have other elongate shape (e.g., generally diamond shaped albeit with rounded vertices or curved edges). Each such arcuate petal portion may be defined by respective major and minor axes. For example, as shown in Detail C, arcuate petal portion 2780A may have a major axis 2781A that extends in a substantially longitudinal direction and a minor axis 2782A that extends in a circumferential direction. In certain implementations, adjacent arcuate petal portions may be joined at or near the vertices along the minor axis, which are generally referred to as co-vertices. For example, and as indicated in FIG. 28, arcuate petal portion 2780A and arcuate petal portion 2780B are joined at a junction 2784 disposed distal the co-vertices of arcuate petal portion 2780A and arcuate petal portion 2780B.

Proximal frame portion 2759 may similarly include arcuate petal portions that may be ovate, diamond-shaped, or have another elongate shape. Each such arcuate petal portion may be defined by respective major and minor axes. For example, arcuate petal portion 2785A may have a major axis 2786A that extends in a substantially longitudinal direction and a minor axis 2787A that extends in a circumferential direction. In certain implementations, adjacent arcuate petal portions of proximal frame portion 2759 may be joined at or near the vertices along the minor axis (i.e., the co-vertices of the arcuate petal portions). For example, arcuate petal portion 2785A and arcuate petal portion 2785B are joined at a junction 2789 disposed at the corresponding co-vertices of arcuate petal portion 2785A and arcuate petal portion 2785B.

As further illustrated in FIG. 28, arcuate petal portions of distal frame portion 2758 may be joined to respective arcuate petal portions of proximal frame portion 2759. For example, arcuate petal portion 2780A is coupled to arcuate petal portion 2785A by a longitudinal member 2790 extending between a proximal vertex 2791 of arcuate petal portion 2780A and a distal vertex 2792 of arcuate petal portion 2785A.

Like previous frames discussed herein, frame 2755 may be made from a variety of super-elastic and/or shape memory materials, including, for example, nickel-titanium alloys (e.g., Nitinol), which may be laser cut from a tube or in the form of drawn wire. The features defined in the shape memory materials may be defined therein via various cutting methods known in the art, include laser, water jet, electrical discharge machining (EDM), stamping, etching, milling, etc.

Depending on the embodiment, frame 2755 may include different numbers of inner and/or outer arcuate petal portions. For example, in certain example embodiments, frame 2755 may include between 10 and 14, between 8 and 16, or between 6 and 18 inner and outer arcuate petal portions. In the specific implementation illustrated in FIGS. 27 and 28, for example, frame 2755 includes 12 each of inner and outer arcuate petal portions with each inner arcuate petal portion joined to a respective outer arcuate petal portion. In other implementations, the number of inner arcuate petal portions may differ from the number of outer arcuate petal portions. For example, frame 2755 may include twice as many inner arcuate petal portions as outer petal portions. Moreover, not every inner arcuate petal portion may be joined to a corresponding outer arcuate petal portion or vice versa regardless of whether the number of inner and outer arcuate petal portions matches. So, for example, in one implementation, an implant may include twice then number of inner arcuate petal portions as outer arcuate petal portions and every other inner arcuate petal portion may be joined to an outer arcuate petal portion. In another implementation, the number of inner and outer arcuate petal portions may be the same; however, joining may still only be between every other inner and outer arcuate petal portion.

As shown in FIGS. 27 and 28, each inner arcuate petal portion is uniform as is each outer arcuate petal portion. In other implementations, the inner and outer arcuate petal portions may vary in any direction. For example, the inner arcuate petal portions may alternate between arcuate petal portions having a first major axis dimension and arcuate petal portions have a second major axis dimension different than the first major axis dimension.

Other examples of alternative frame configurations are discussed below in the context of FIGS. 31-33.

Although not illustrated in FIGS. 27 and 28, frame 2755 may engage atrial tissue via protruding anchor members, like protruding anchor members 105 of implant 20 or protruding anchor members 2597 or implant 2500, discussed above.

VIII. Alternative Implant Frame Shapes

The overall shape of implants according to the present disclosure when in the expanded state may vary across implementations to address various needs of a patient. Among other things, implant shape may be varied to accommodate variations in patient anatomy and pathology. For example, in cases where a patient may have weakened valves or valves exhibiting reduced travel, an implant configuration in which an occlusive assembly is positioned deeper into the ventricle may be advantageous such that contact and sealing between the occlusive assembly and leaflet occurs earlier in the leaflet's travel. In contrast, a more planar or flat implant structure in which the sheets of the implant cover a greater proportion of the tricuspid valve structure may be more advantageous when commissural regurgitation is present despite substantially normal leaflet function. These and other considerations are described below in further detail.

Figure 29A:
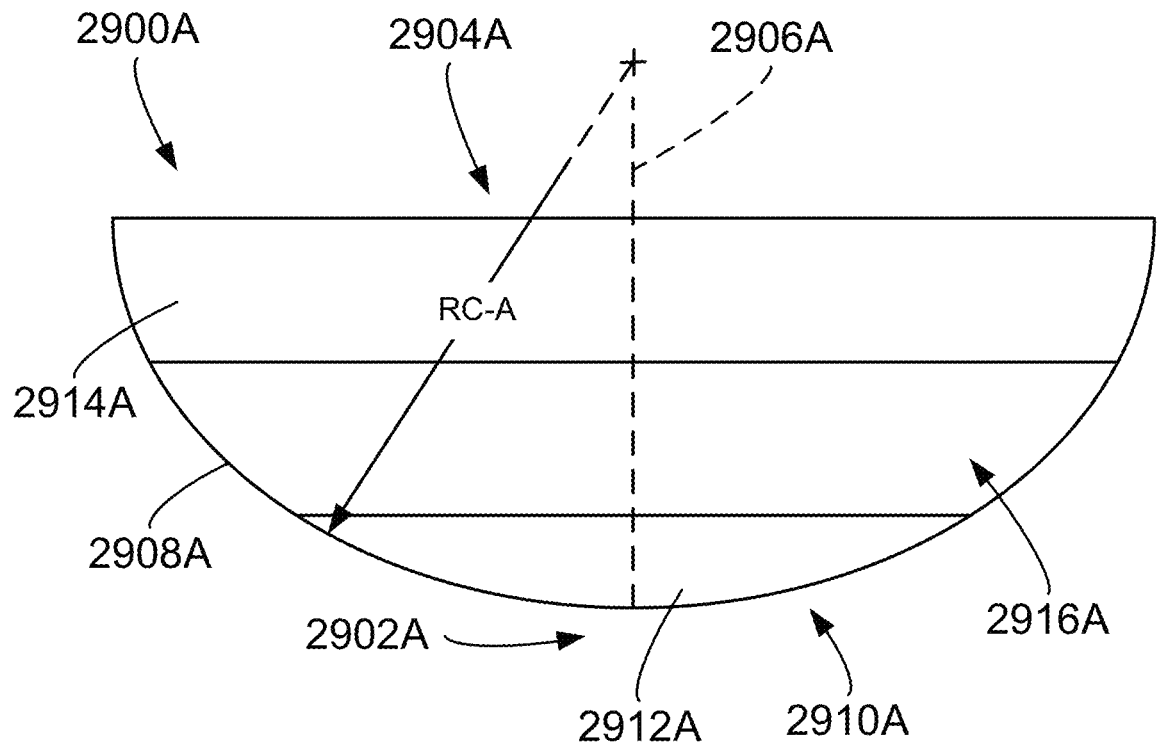
FIG. 29A is a simplified elevation view of a proximally concave implant.
Figure 29B:
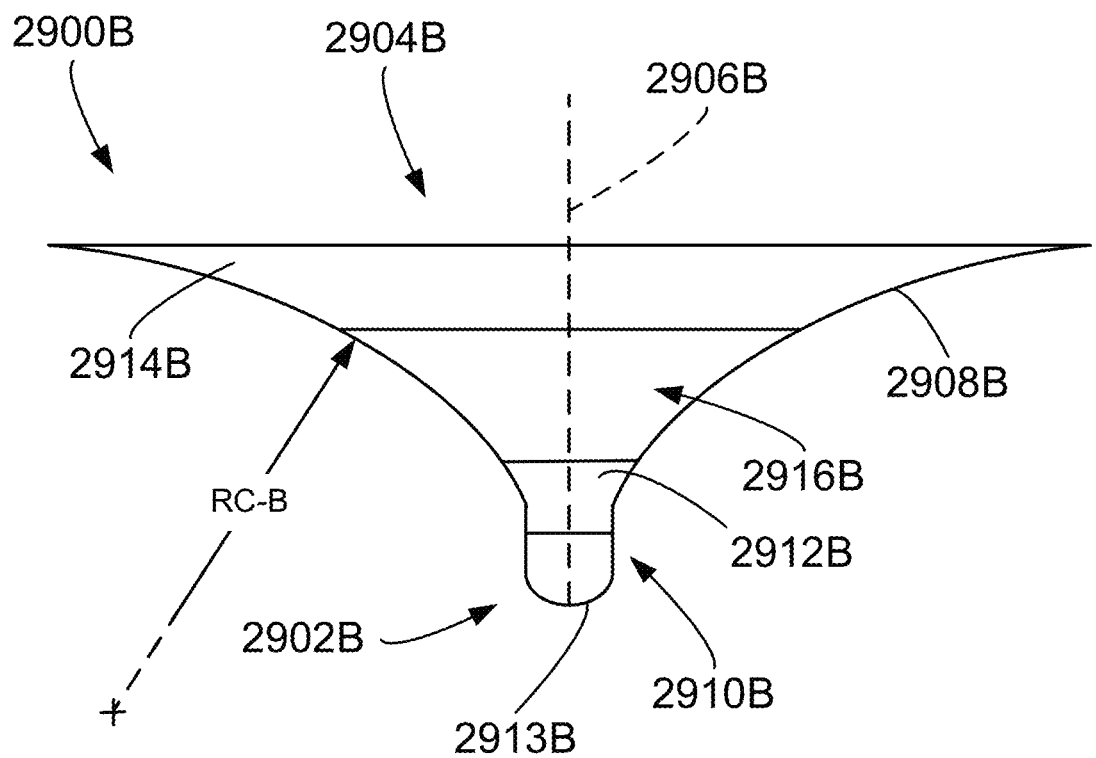
FIG. 29B is a simplified elevation view of a distally concave implant.
Figure 29C:
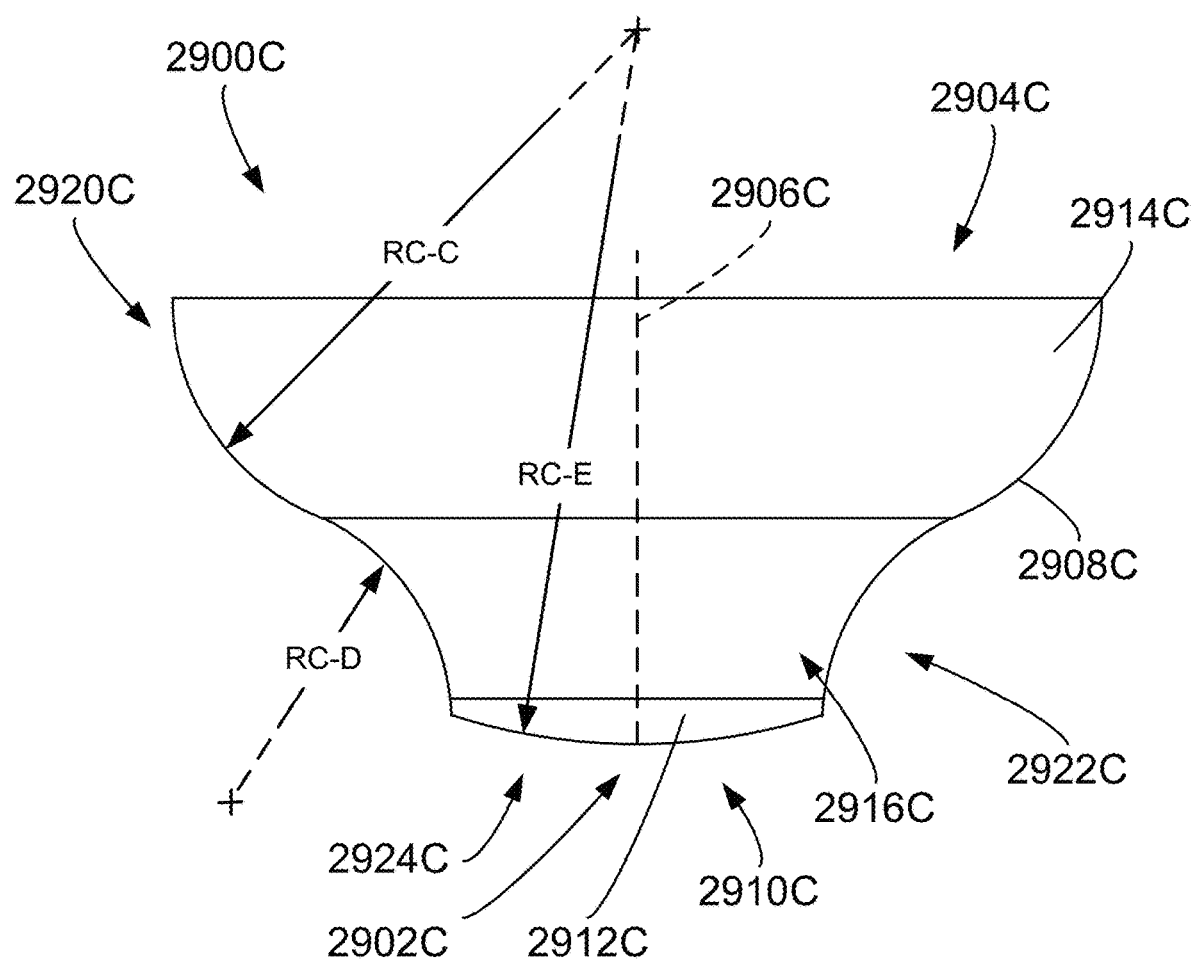
FIG. 29C is a simplified elevation view of an implant including a proximal portion having a proximally concave shape and a distal portion having a distally concave shape.

In one aspect, implants according to the present disclosure may vary in curvature when in the expanded state. Examples of varying curvature are provided in FIGS. 29A-29C. More specifically, FIG. 29A is an elevation view of an implant 2900A that has a proximally concave shape when deployed/expanded, FIG. 29B is an elevation view of an implant 2900B that has a distally concave shape when deployed/expanded, FIG. 29C is an elevation view of an implant 2900C including a proximally concave proximal portion and a distally concave distal portion. For clarity and simplicity, each of implant 2900A-2900C are shown in a simplified view in which overall shape is emphasized and certain elements of each implant are omitted. Accordingly, and unless stated otherwise, implants 2900A-2900C may generally include elements of and be in accordance with any other implementation discussed herein. For example, FIGS. 29A-29C generally omit details regarding the frames of the corresponding implants; however, it should be understood that such frames may be in accordance with any frame style disclosed herein.

Referring first to FIG. 29A, implant 2900A includes a distal end 2902A and a proximal end 2904A such that a longitudinal axis 2906A of implant 2900A extends between distal end 2902A and proximal end 2904A. Implant 2900A includes a frame 2908A that supports an occlusive assembly 2910A at distal end 2902A. As shown, occlusive assembly 2910A includes an inner sheet 2912A; however, in other implementations, occlusive assembly 2910A may include an occlusive body instead of or in addition to inner sheet 2912A. For example, occlusive assembly 2910A may include a bulb- or bullnose-shaped occluder about which inner sheet 2912A extends. Implant 2900A further includes an outer sheet 2914A supported on frame 2908A at proximal end 2904A such that an annular opening 2916A is defined between inner sheet 2912A and outer sheet 2914A.

FIG. 29A shows implant 2900 in the expanded state (e.g., following deployment). As shown, implant 2900A has a proximally concave shape defined by a radius of curvature (RC-A) such that implant 2900A has an overall bowl-like shape. Implant 2700 of FIGS. 27 and 28 is an example of a proximally concave implant according to this disclosure and is discussed above in further detail. Notably, while illustrated as being hemispherical, implant 2900A may alternatively have an ovoid or similar rounded but non-spherical shape.

RC-A may differ in implementations of this disclosure depending on the specific application and needs of the patient. For example, when the overall diameter of proximal end 2904A is held constant, RC-A generally controls the position of distal end 2902A and occlusive assembly 2910A relative to proximal end 2904A. More specifically, as RC-A increases, implant 2900A takes on a shallower geometry when in the expanded shape such that distal end 2902A is closer to the valve annulus following deployment. Conversely, as RC-A decreases, implant 2900A takes on a deeper shape such that distal end 2902A and occlusive assembly 2910A deploy further within the ventricle. As noted above, placement of occlusive assembly 2910A relative to the valve annulus determines how and when the valve leaflets contact and seal against occlusive assembly 2910A and, as a result, RC-A may be chosen to account for various needs and idiosyncrasies of a particular patient.

For example, the proximally concave/distally convex shape illustrated in FIG. 29A generally includes larger and more accessible gaps as compared to the distally concave/proximally convex design illustrated in FIG. 29B and discussed below in further detail. As a result, proximally concave implants according to the present disclosure may allow for easier and more accurate placement of other cardiac devices, such as pacemaker leads, though the implant. Proximally concave implants according to this disclosure may also be readily inverted. Such invertibility can facilitate removal of the implant at a later date as the implant can be funneled and pulled back into a retrieval catheter.

Regardless of concavity, implants according to this disclosure having frames formed of metal or other radiopaque materials may further facilitate placement of a pacemaker lead by being visible on fluoroscopy and providing a target for delivering the pacemaker lead. The frame of the implant may also provide constraints for the pacemaker lead to reduce movement of the lead following delivery and implantation. Among other things, such reinforcement of the lead may prevent or reduce the likelihood that the pacemaker lead may obstruct or otherwise interfere with movement of the valve leaflets.

Referring next to FIG. 29B, implant 2900B includes a distal end 2902B and a proximal end 2904B such that a longitudinal axis 2906B of implant 2900B extends between distal end 2902B and proximal end 2904B. FIG. 29B shows implant 2900B in the expanded state about longitudinal axis 2906B. Implant 2900B includes a frame 2908B that supports an occlusive assembly 2910B at distal end 2902B and that is shown including an inner sheet 2912B as well as an occlusive body 2913B. In other implementations, occlusive assembly 2910B may instead include only one of inner sheet 2912B and occlusive body 2913B. Implant 2900B further includes an outer sheet 2914B supported on frame 2908B at proximal end 2904B such that an annular opening 2916B is defined between inner sheet 2912B and outer sheet 2914B. When in the expanded state (e.g., following deployment) implant 2900B has a distally concave shape defined by a radius of curvature (RC-B) such that implant 2900B has an overall funnel-like shape. Examples of implants with a similar shape include implant 20 and implant 2500, discussed above in further detail.

Like RC-A of implant 2900A, RC-B of implant 2900B may differ in implementations of this disclosure depending on the specific application and needs of the patient. Among other things, the distally concave design of implant 2900B ensures that initial contact between the valve leaflets and implant 2900B is with occlusive assembly 2910B as opposed to a portion of frame 2908B, as may occur in the distally concave design of implant 2900A. More generally, the distally concave shape reduces the overall size of the implant portion within the ventricle, reducing the likelihood that the implant may obstruct or otherwise interfere with cardiac structures and their respective functions. For example, the distally concave shape reduces contact between the valve leaflets and the implant, thereby reducing the likelihood that the implant will interfere with or otherwise impede travel of the leaflets. As another example, the distally convex shape may reduce the likelihood that the implant will interfere with or obstruct the coronary sinus or similar vessels of the heart.

Implant 2900C includes a distal end 2902C and a proximal end 2904C such that a longitudinal axis 2906C of implant 2900B extends between distal end 2902C and proximal end 2904C. FIG. 29C shows implant 2900C in the expanded state about longitudinal axis 2906C. Implant 2900C includes a frame 2908C that supports an occlusive assembly 2910C at distal end 2902C and that is shown including an inner sheet 2912C. In other implementations, occlusive assembly 2910C may further or alternatively include an occlusive body. Implant 2900C also includes an outer sheet 2914C supported on frame 2908C at proximal end 2904C such that an annular opening 2916C is defined between inner sheet 2912C and outer sheet 2914C.

Implant 2900C includes both proximally and distally concave portions. More specifically, 2900C includes proximal portion 2920C that has a proximally concave shape. Implant 2900C transitions into a distal portion 2922C that has a distally concave shape. In the implementation illustrated in FIG. 29C, distal portion 2922C further transitions into a proximally concave cap portion 2924C that includes occlusive assembly 2910C and, more specifically, inner sheet 2912C. In other implementations, distal portion 2922C may instead terminate in an occlusive body, such as central occluder 50 of implant 20 or central occlusive body 2550 of implant 2500.

When in the expanded state (e.g., following deployment) the shape of implant 2900C may be defined by at least two radii of curvature. More specifically, the shape of implant 2900C may be defined by a radius of curvature (RC-C) corresponding to proximal portion 2920C (i.e., the proximally concave portion of implant 2900C) and a radius of curvature (RC-D) corresponding to the distal portion 2922C (i.e., the distally concave portion of implant 2900C). To the extent an implementation of this disclosure further includes proximally concave cap portion 2924C, implant 2900C may be further defined by a radius of curvature (RC-E) corresponding to proximally concave cap portion 2924C. In certain implementations, RC-E and RC-C may be the same; however RC-E and RC-C may also differ such that proximally concave cap portion 2924C may have a more or less pronounced curvature than proximal portion 2920C.

Figure 30A:
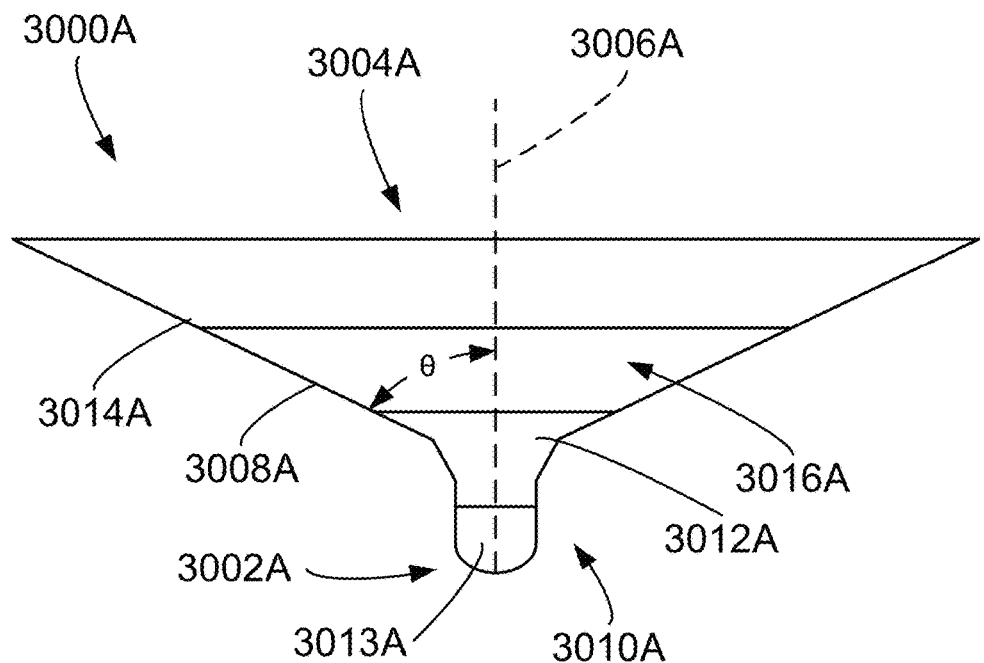
FIG. 30A is a simplified elevation view of a frustoconical implant.
Figure 30B:
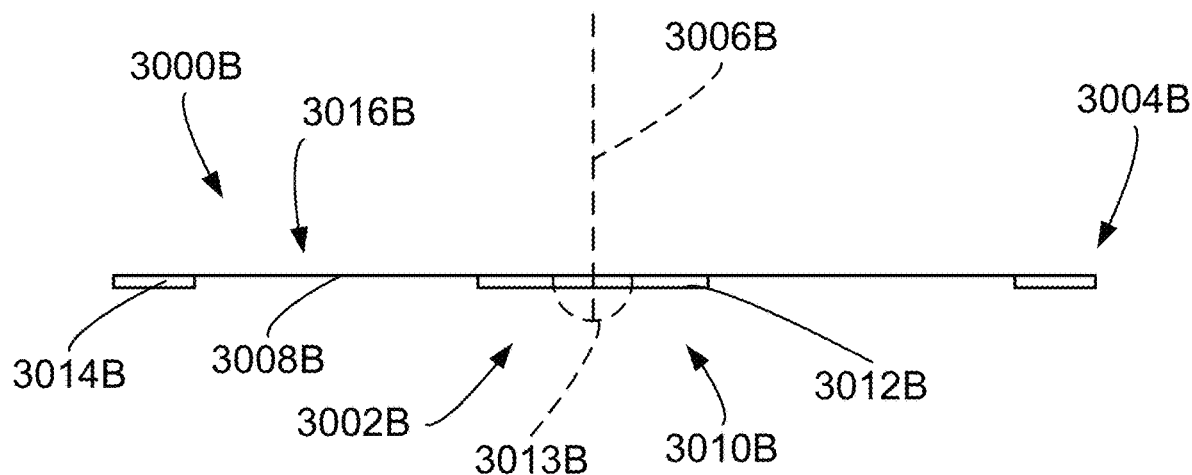
FIG. 30B is a simplified elevation view of a planar implant.

While each of implant 2900A, implant 2900B, and implant 2900C have an overall curved shape, implants according to this disclosure may also have non-curved shapes when deployed. Examples of such non-curved implants are provided in FIGS. 30A and 30B. More specifically, FIG. 30A is an elevation view of an implant 3000A having a conical shape when deployed while FIG. 30B is an elevation view of an implant 3000B having a flat or planar shape when deployed. Like FIGS. 29A and 29B, for clarity and simplicity, each of implant 3000A and implant 3000B are shown in a simplified view in which overall shape is emphasized and certain elements of each implant are omitted. Accordingly, and unless stated otherwise, implant 3000A and implant 3000B may generally include elements of and be in accordance with any other implementation discussed herein.

Referring to FIG. 30A, implant 3000A includes a distal end 3002A and a proximal end 3004A such that a longitudinal axis 3006A of implant 3000A extends between distal end 3002A and proximal end 3004A. Implant 3000A includes a frame 3008A that supports an occlusive assembly 3010A at distal end 3002A. As shown, occlusive assembly 3010A includes an inner sheet 3012A and an occlusive body 3013A. In other implementations, occlusive assembly 3010A may instead include only one of inner sheet 3012A and occlusive body 3013A. Implant 3000A further includes an outer sheet 3014A supported on a proximal portion of frame 3008A such that an annular opening 3016A is defined between inner sheet 3012A and outer sheet 3014A.

FIG. 30A shows implant 3000 in the expanded state (e.g., following deployment). As shown and in contrast to the curved funnel shape of implant 2900B, implant 3000A has a straight-sided funnel shape. Stated differently, when deployed, implant 3000A has a distally expanding conical or frustoconical shape.

Like implant 2900A and implant 2900B, implant 3000A may be modified to vary the degree to which occlusive assembly 3010A enters the ventricle when implant 3000A is deployed within the heart. For example, the general shape of implant 3000B may be determined by an angle θ, which may be defined as the angle between the sides of frame 3008A and longitudinal axis 3006A of implant 3000A when implant 3000A is in the expanded/deployed state. Assuming other dimensions of implant 3000A (e.g., maximum diameter at proximal end 3004A) remain substantially constant, varying θ changes overall length of implant 3000A when expanded and, as a result, the depth of occlusive assembly 3010A within the ventricle. More specifically, reducing θ increases the overall length of implant 3000A and the depth of occlusive assembly 3010A within the ventricle when implant 3000A is deployed. Conversely, increasing θ reduces the overall length of implant 3000A when deployed (e.g., results in implant 3000A being more planar in the expanded state) and the depth of occlusive assembly 3010A within the ventricle.

Referring next to FIG. 30B, implant 3000B expands into a flat or planar shape when deployed. Implant 3000B includes a radially inward portion 3002B and a radially outward portion 3004B relative to a longitudinal axis 3006B. When in the collapsed state (e.g., when implant 3000B is collapsed about longitudinal axis 3006B during delivery), radially inward portion 3002B forms a distal or leading end of implant 3000B while radially outward portion 3004B forms a proximal end of implant 3000B. Like other implants disclosed herein, implant 3000B includes a frame 3008B that supports an occlusive assembly 3010B at radially inward portion 3002B. As shown, occlusive assembly 3010B includes an inner sheet 3012B. In other implementations, occlusive assembly 3010B may further or alternatively include an occlusive body 3013B, which FIG. 30B shows in dashed lines. Implant 3000B further includes an outer sheet 3014B supported on a proximal portion of frame 3008B such that an annular opening 3016B is defined between inner sheet 3012A and outer sheet 3014B.

Planar implants, such as implant 3000B, may be particularly advantageous in cases where regurgitation results despite substantially normal valve leaflet travel. When deployed, implant 3000B may be positioned along the floor of the atrium across the valve annulus with occlusive assembly 3010B centrally located or approximately centrally located. In implementations in which occlusive assembly 3010B includes occlusive body 3013B, occlusive body 3013B may project into the valve annulus or across the valve annulus into the ventricle, depending on its size and shape. When the valve is in the closed position and with implant 3000B properly positioned, the valve leaflets contact and seal against occlusive assembly 3010B. In this position, portions of occlusive assembly 3010B, such as inner sheet 3012B, may extend over the leaflets and, in particular, the commissures between the leaflets. By doing so, inner sheet 3012B provides an additional and expanded sealing surface for the leaflets and may cover at least a portion of commissural gaps that may be present, thereby reducing regurgitation. In addition to inner sheet 3012B, additional regurgitation reduction may be provided by outer sheet 3014B, which may similarly seal against the leaflets and cover commissural gaps that may be present toward the outward edge of the valve annulus.

IX. Alternative Frame Configurations

As previously discussed, implants according to the present disclosure include a frame configured to support a distal occlusive assembly. The frame may further support or otherwise be coupled to one or more thin sheets or similar structures. In certain implementations such sheets may include a proximal or outer sheet configured to contact the atrial floor and/or a distal or inner sheet included in the occlusive assembly (e.g., as a "skirt" extending circumferentially around an occlusive body of the occlusive assembly).

In addition to providing structural integrity, frames of implants according to this disclosure are configured to be expandable about a longitudinal axis of the implant. More specifically, frames of implants according to the present disclosure are configured to transition between a collapsed state and an expanded state. The collapsed state may correspond, for example, to a state of the implant during delivery using a delivery tool, such as tool 15 (shown in FIG. 1A), tool 1115 (shown in FIGS. 11A-11B), or delivery tool 300 (shown in FIG. 13), each of which is discussed above in detail. In contrast, the expanded state may correspond to a state of the implant following delivery and deployment within a patient heart. Implant frames according to this disclosure may be biased into the expanded state such that the implant transitions into the expanded state absent resistance provided by a delivery tool. For example, and with reference to FIG. 16, tension control members 320 of the delivery tool may be coupled to a tension control line 200 of the implant such that by applying tension to the tension control members 320, a user may resist expansion of the implant. In certain implementations, a user may apply sufficient tension to collapse the implant (e.g., to transition the implant from the expanded state to the collapsed state).

This disclosure previously described various example frame styles. For example, FIGS. 2-8 and 12 include a first style of frame for a distally concave implant in which radially extending spokes support arcuate petal portions circumferentially distributed about a central occluder. FIGS. 25 and 26 illustrate a similar frame style albeit with the further inclusion of inner arcuate petal portions configured to support an inner sheet. FIGS. 27 and 28 introduce the concept of a proximally concave frame formed by joining an inner/distal set of circumferentially distributed arcuate petals to an outer/proximal set of circumferentially distributed arcuate petals. FIGS. 29A-30B expand on these general frame styles by providing additional examples of overall frame shapes and configurations.

Figure 31:
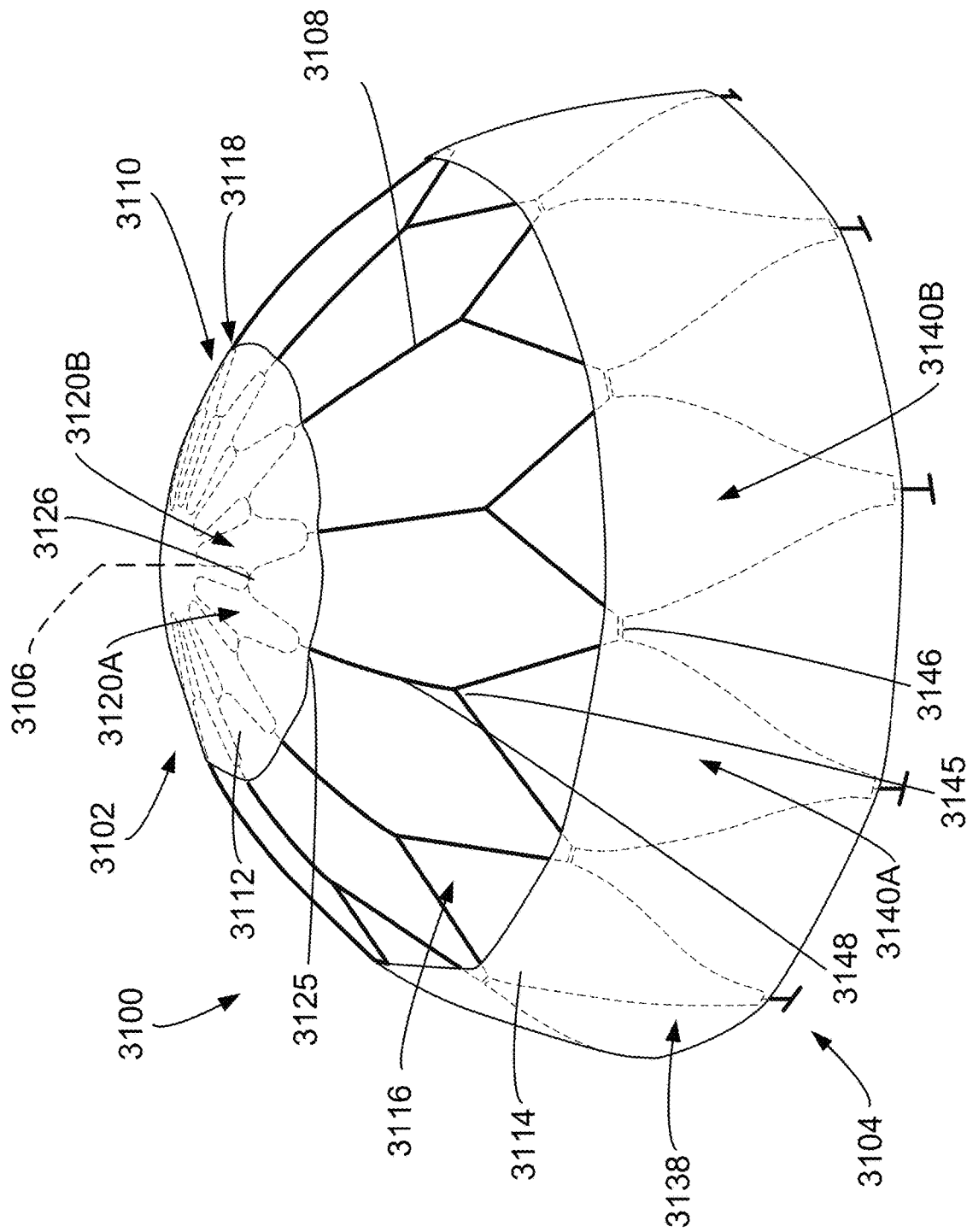
FIG. 31 is a perspective distal-end view of an implant having a frame including arcuate petal portions connected by elongate longitudinal members.
Figure 32:
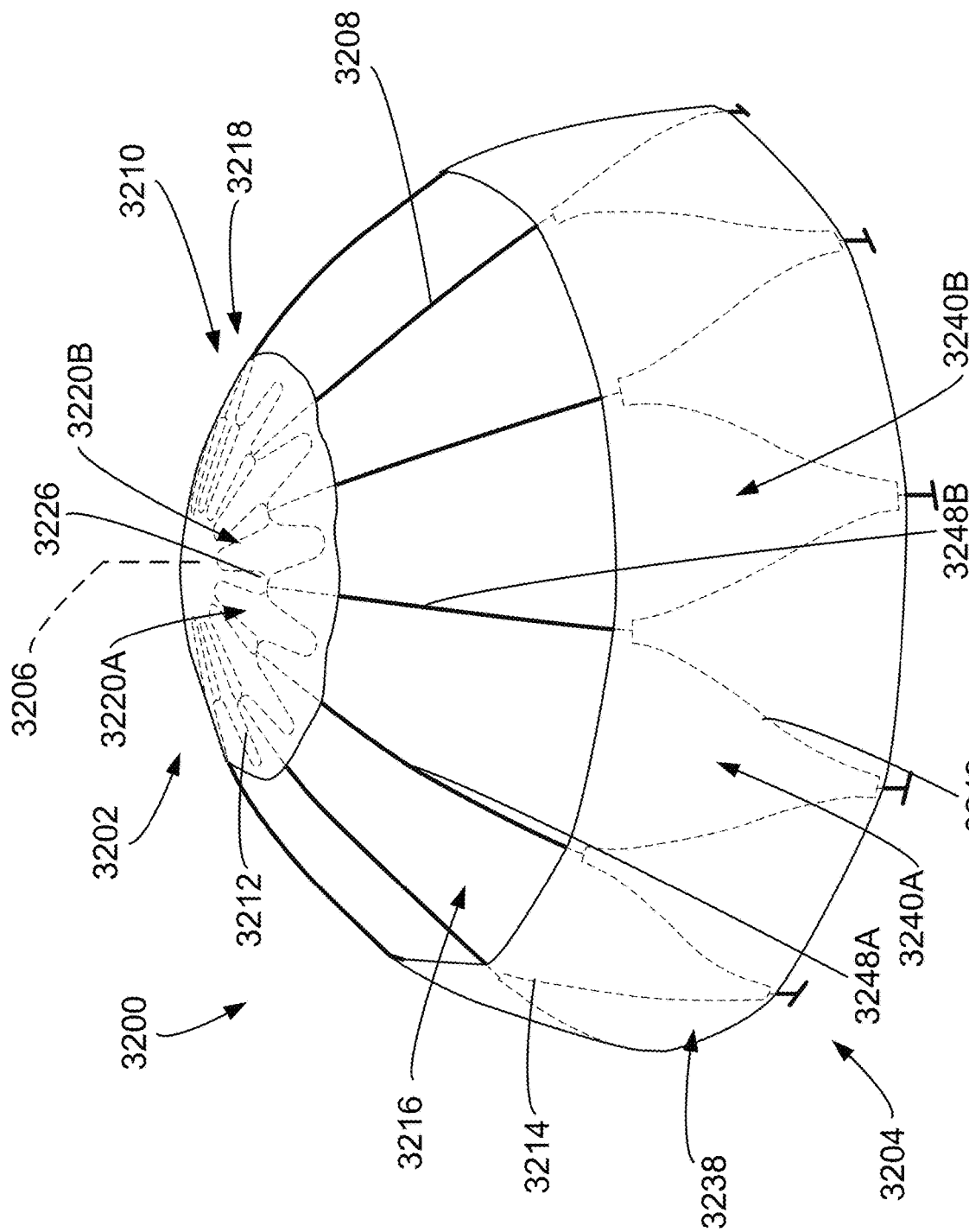
FIG. 32 is a distal-end view of an implant having a frame including distally open arcuate petal portions.
Figure 33:
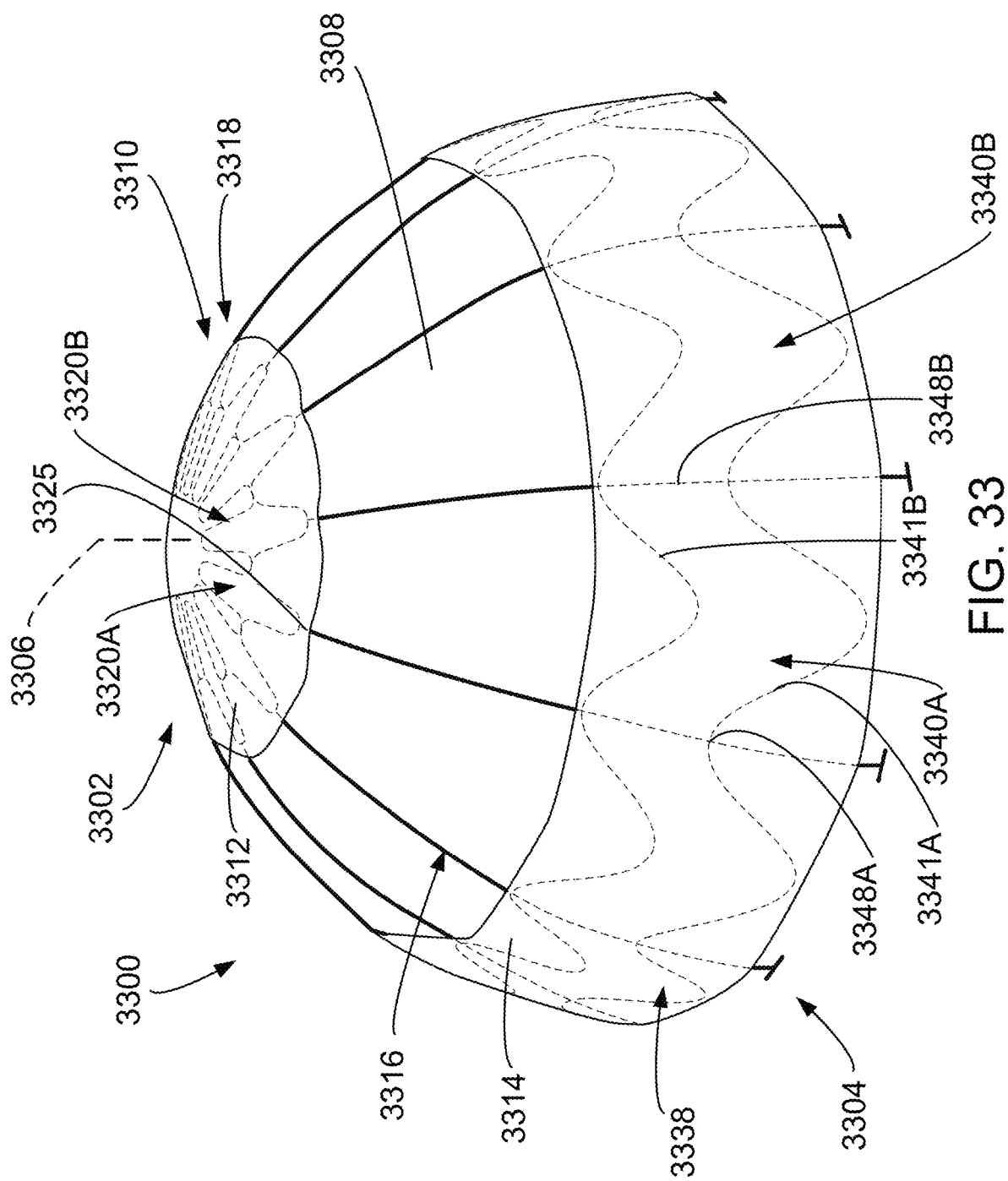
FIG. 33 is a distal-end view of an implant having arcuate petal portions formed by arcuate members extending between longitudinal members.

To further illustrate the scope of frames contemplated by this disclosure, FIGS. 31-33 provide additional examples of frame styles that may be used in implants according to the present disclosure. Notably, while each of FIGS. 31-33 describe the alternative frame styles as applied to a proximally concave implant (similar to implant 2700 of FIGS. 27 and 28), the concepts and structures illustrated in FIGS. 31-33 may be applied to implants having distally concave, frustoconical, planar, or other overall shapes. Notably, FIGS. 31-33 omit certain features of the illustrated implants for purposes of clarity. For example, each of FIGS. 31-33 omit a backside of the depicted implants (relative to the illustrated perspective) to more clearly illustrate the structure and configuration of the frames of the implants.

FIG. 31 illustrates an implant 3100 having a first alternative frame configuration. Implant 3100 includes a distal end 3102 and a proximal end 3104 such that a longitudinal axis 3106 of implant 3100 extends between distal end 3102 and proximal end 3104. Implant 3100 includes a frame 3108 that supports an occlusive assembly 3110 at distal end 3102. As shown, occlusive assembly 3110 includes an inner sheet 3112; however, in other implementations, occlusive assembly 3110 may include an occlusive body instead of or in addition to inner sheet 3112. Implant 3100 further includes an outer sheet 3114 supported on a proximal portion of frame 3108 such that an annular opening 3116 is defined between inner sheet 3112 and outer sheet 3114.

Similar to frame 2755 of implant 2700, frame 3108 of implant 3100 includes a distal frame portion 3118 including a first set of circumferentially distributed arcuate petal portions, such as arcuate petal portion 3120A and arcuate petal portion 3120B, and a proximal frame portion 3138 including a second set of circumferentially distributed arcuate petal portions, such as arcuate petal portion 3140A and arcuate petal portion 3140B. As described in the context of FIGS. 27 and 28, above, arcuate petals portions according to this disclosure may be ovate, diamond-shaped, or have any similar elongate shape (e.g., generally diamond shaped albeit with rounded vertices or curved edges). More generally, arcuate petal portions according to this disclosure may have any suitable shape that enables collapsing and expanding of the frame and other functionality described herein (e.g., support of fabric sheets, such as inner sheet 3112 and outer sheet 3114).

As shown in FIG. 31, adjacent arcuate petal portions of distal frame portion 3118 may be joined at or near their respective co-vertices. For example, arcuate petal portion 3120A and arcuate petal portion 3120B are joined at a junction 3126 disposed at the corresponding co-vertices of arcuate petal portion 3120A and arcuate petal portion 3120B. Adjacent arcuate petal portions of proximal frame portion 3138 likewise may be joined at or near their respective co-vertices. For example, arcuate petal portion 3140A and arcuate petal portion 3140B are joined at a junction 3146 disposed at the corresponding co-vertices of arcuate petal portion 3140A and arcuate petal portion 3140B Arcuate petal portions of distal frame portion 3118 may be joined to respective arcuate petal portions of proximal frame portion 3138. For example, arcuate petal portion 3120A is coupled to arcuate petal portion 3140A by a longitudinal member 3148 extending between a proximal vertex 3125 of arcuate petal portion 3120A and a distal vertex 3145 of arcuate petal portion 3140A.

As illustrated in FIG. 31, longitudinal member 3148 extending between arcuate petal portion 3120A and arcuate petal portion 3140A is substantially longer than longitudinal member 2790 extending between arcuate petal portion 2780A and arcuate petal portion 2785A of implant 2700 (shown in FIG. 28).

Although FIG. 31 illustrates longitudinal members (e.g., longitudinal member 3148) as extending between the proximal vertices of the first set of arcuate petal portions and the distal vertices of the second set of arcuate petal portions, in other implementations, longitudinal members may extend between other locations of frame 3108. For example, in certain implementations, longitudinal members may be offset from the arcuate petal portions such that the longitudinal members extend between the circumferential junctions of the arcuate petal portions. So, for example and with reference to FIG. 31, longitudinal members may extend between the junctions of the first set of arcuate petal portions (e.g., junction 3126) and the junctions of the second set of arcuate petal portions (e.g., junction 3146). In other implementations, the first set of arcuate petal portions can be rotationally offset from the second set of arcuate petal portions such that the junctions of one set align with the vertices of the other set. In such implementations, longitudinal members may extend between the junctions of one set and the vertices of the other. So, for example, longitudinal members may extend between junctions of the first set of arcuate petal portions (e.g., junction 3126) and the distal vertices of the second set of arcuate petal portions (e.g., distal vertex 3145). Alternatively, longitudinal members may extend between the proximal vertices of the first set of arcuate petal portions (e.g., proximal vertex 3125) and the junctions of the second set of arcuate petal portions (e.g., junction 3146).

In implementations of the present disclosure, either of the inner sheet or the outer sheet may define one or more internal pockets. For example, in certain implementations, the sheet may include two or more layers stitched or otherwise coupled together to form internal pockets between adjacent layers. In one implementation, the adjacent layers may include a first layer disposed on a proximal or inner surface of the implant frame and a second layer disposed on a distal or outer surface of the implant frame such that the frame also extends between the layers. In other implementations, the layers forming the internal pockets may be disposed entirely on the proximal/inner surface of the frame or the distal/outer surface of the frame. Pockets formed in this way may be filled, such as with additional layers of fabric, batting, or a water-absorbing material, such as a hydrogel. In such cases, the filling generally forms a pad that may increase the distance between the occluding surface/sheet and the underlying frame of the implant, thereby preventing and padding contact between valve leaflets and the frame.

FIG. 32 illustrates an implant 3200 with another alternative frame configuration. Implant 3200 includes a distal end 3202 and a proximal end 3204 such that a longitudinal axis 3206 of implant 3200 extends between distal end 3202 and proximal end 3204. Implant 3200 includes a frame 3208 that supports an occlusive assembly 3210 at distal end 3202. As shown, occlusive assembly 3210 includes an inner sheet 3212; however, in other implementations, occlusive assembly 3210 may include an occlusive body instead of or in addition to inner sheet 3212. Implant 3200 further includes an outer sheet 3214 supported on a proximal portion of frame 3208 such that an annular opening 3216 is defined between inner sheet 3212 and outer sheet 3214.

Frame 3208 of implant 3200 includes a distal frame portion 3218 including a first set of circumferentially distributed arcuate petal portions, such as arcuate petal portion 3220A and arcuate petal portion 3220B, and a proximal frame portion 3238 including a second set of circumferentially distributed arcuate petal portions, such as arcuate petal portion 3240A and arcuate petal portion 3240B.

The first or inner set of arcuate petal portions of implant 3200 are shown as being substantially similar to those of implant 3100. The second set arcuate petal portions of implant 3200, on the other hand, have a distally open shape in contrast to the ovate shape of implant 3100. More specifically, each arcuate petal portion of the second set of arcuate petal portions is formed by a pair of longitudinal members and an arcuate frame portion. For example, arcuate petal portion 3240A is formed by a longitudinal member 3248A, a longitudinal member 3248B, and an arcuate frame portion 3249, which extends between longitudinal member 3248A and longitudinal member 3248B. As illustrated, each longitudinal member extends from a respective junction of the first set of arcuate petal portions. For example, longitudinal member 3248A extends from a junction 3226 between arcuate petal portion 3220A and arcuate petal portion 3220B. Like noted above with respect to implant 3100, the first and second set of arcuate petal portions of implant 3200 may be rotationally offset from the configuration illustrated in FIG. 32 such that the longitudinal members instead extend from proximal vertices (e.g., proximal vertex 3125) of the first set of arcuate petal portions.

FIG. 33 illustrates an implant 3300 having yet another alternative frame configuration. Implant 3300 includes a distal end 3302 and a proximal end 3304 such that a longitudinal axis 3306 of implant 3300 extends between distal end 3302 and proximal end 3304. Implant 3300 includes a frame 3308 that supports an occlusive assembly 3310 at distal end 3302. As shown, occlusive assembly 3310 includes an inner sheet 3312; however, in other implementations, occlusive assembly 3310 may include an occlusive body instead of or in addition to inner sheet 3312. Implant 3300 further includes an outer sheet 3314 supported on a proximal portion of frame 3308 such that an annular opening 3316 is defined between inner sheet 3312 and outer sheet 3314.

Frame 3308 of implant 3300 includes a distal frame portion 3318 including a set of circumferentially distributed arcuate petal portions, such as arcuate petal portion 3320A and arcuate petal portion 3320B. Frame 3308 further includes a proximal frame portion 3338 including a second set of circumferentially distributed arcuate petal portions, such as arcuate petal portion 3340A and arcuate petal portion 3340B.

As shown in FIG. 33, the first or inner set of arcuate petal portions of implant 3300 are shown as being substantially like those of implant 3100. However, in contrast to implant 3100, each arcuate petal portion of the second set of arcuate petal portions of implant 3300 is formed by arcuate frame members extending between longitudinal members. For example, arcuate petal portion 3340A is formed by arcuate frame member 3341A and arcuate frame member 3341B, which extend between longitudinal member 3348A and longitudinal member 3348B.

As shown in FIG. 33, longitudinal member 3348A and longitudinal member 3348B extend from respective junctions of the first set of arcuate petal portions. For example, longitudinal member 3348A extends from a junction formed between arcuate petal portion 3320A and arcuate petal portion 3320B. Like noted above with respect to implant 3100, the first and second set of arcuate petal portions of implant 3300 may be rotationally offset from the configuration illustrated in FIG. 33 such that the longitudinal members instead extend from proximal vertices (e.g., proximal vertex 3325) of the first set of arcuate petal portions.

In the implementation shown, arcuate frame member 3341A is proximal and arcuate frame member 3341B and each of arcuate frame member 3341A and arcuate frame member 3341B are distally concave. In other implementations, one or both of arcuate frame member 3341A and arcuate frame member 3341B may be proximally concave. Also, in other implementations, the combination of arcuate frame member 3341A and arcuate frame member 3341B may be replaced with a single arcuate frame member or supplemented with any suitable number of additional arcuate frame members. Moreover, the number of arcuate frame members may vary between arcuate petal portions. So, for example, certain arcuate petal portions may include no or only a single arcuate frame member while others may include two or more.

As previously discussed herein, implants according to this disclosure are capable of transitioning between an expanded state (e.g., when implanted) and a collapsed state (e.g., during delivery). The transition from collapsed state into the expanded state causes a proximal portion of the frame of the implant to travel radially outward away from the central longitudinal axis of the implant. The transition into the expanded state may also include a longitudinal shift of the proximal portion of the frame. As a result, as the implant expands, it extends radially outward but reduces in length along the longitudinal axis.

The presence, size, and quantity of arcuate petal portions contributes to the overall length of the implant when in the collapsed state. When an arcuate petal portion is collapsed (e.g., when the implant is in the collapsed state), the arcuate petal portion undergoes each of circumferential compression and longitudinal elongation. As a result, a first implant with more and/or larger arcuate petal portions than a second implant will typically have a longer collapsed length than the second implant even when the first and second implants have the same overall dimensions when in their respective expanded states.

The relationship between collapsed length and arcuate petal portion characteristics may be leveraged to design implants for specific applications. For example, if a surgeon anticipates that delivery and implantation may be challenging, a first implant having a frame with more and/or longer longitudinal members may be selected over a second implant having a frame with more and/or larger arcuate petal portions due to the first implant having a shorter and more maneuverable length when in the collapsed state (i.e., during delivery). In contrast, if additional devices (e.g., pacemaker leads) are to be subsequently implanted in the patient, the surgeon may opt for the second implant due to the size, shape, and positioning of the openings defined by the arcuate petal portions providing additional options and flexibility for delivery and support of the additional devices.

As another example, designs with a higher proportion of longitudinal members tend to exert less radial force when transitioning between from the collapsed state to the expanded state and may generally exhibit lower radial rigidity. Accordingly, an implant frame with a higher proportion of longitudinal members and a lower proportion of arcuate petal portions (or similar expanding structures) may be selected in implementations in which cardiac tissue may be damaged by higher radial forces or that may require the implant to conform to more complex geometry within the heart.

Figure 34:
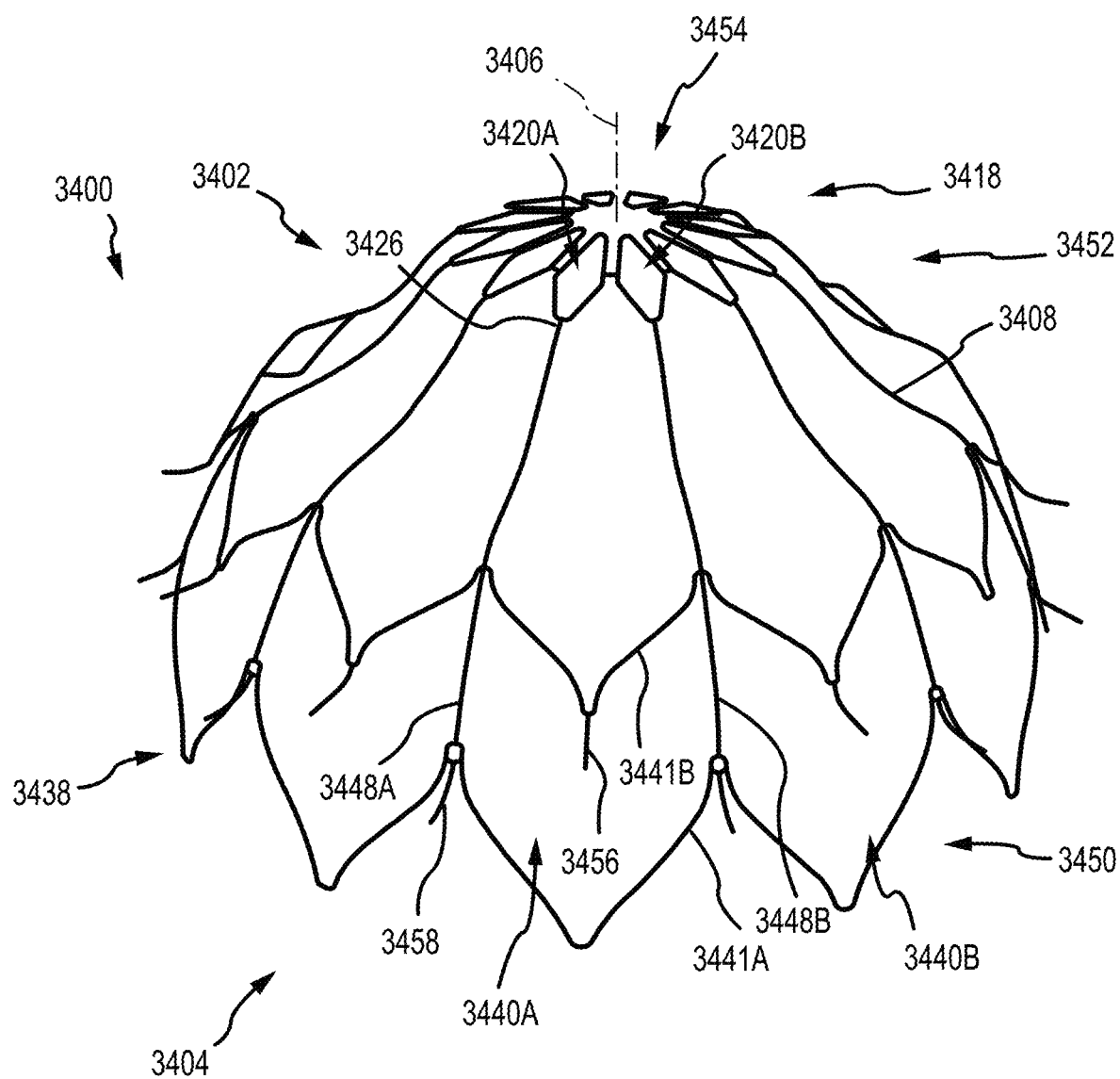
FIG. 34 is a distal-end view of an implant having arcuate petal portions formed by arcuate members extending between longitudinal members and having an overall shape that includes a proximal portion having a proximally concave shape and a distal portion having a distally concave shape.

FIGS. 31-33 illustrate alternative frame configurations according to this disclosure and are limited to proximally concave designs. The frame configuration may nevertheless be readily adapted to other implant shapes including, but not limited to, implants having overall shapes that are distally concave, frustoconical, planar, or include combinations of different concavities. FIGS. 34-35B, for example, illustrate certain frame alternatives implemented in implants having a combination of a proximally concave distally concave distal portions.

FIG. 34 illustrates an implant 3400 having a frame configuration similar to that of implant 3300 of FIG. 33. Implant 3400 includes a distal end 3402 and a proximal end 3404 such that a longitudinal axis 3406 of implant 3400 extends between distal end 3402 and proximal end 3404. Implant 3400 includes a frame 3408 that may support an occlusive assembly at distal end 3302. FIG. 34 omits the occlusive assembly to show the various features and configuration of frame 3408 more clearly. Like other implementations discussed herein, when included, the occlusive assembly may include an occlusive body and/or an inner sheet. Implant 3400 may also include an outer sheet (not shown in FIG. 34) supported on a proximal portion of frame 3408 such that an annular opening is defined between the inner sheet/occlusive assembly and the outer sheet.

Frame 3408 of implant 3400 includes a distal frame portion 3418 including a set of circumferentially distributed arcuate petal portions, such as arcuate petal portion 3420A and arcuate petal portion 3420B. Frame 3408 further includes a proximal frame portion 3438 including a second set of circumferentially distributed arcuate petal portions, such as arcuate petal portion 3440A and arcuate petal portion 3440B. Each arcuate petal portion of the second set of arcuate petal portions of implant 3400 is formed by arcuate frame members extending between longitudinal members. For example, arcuate petal portion 3440A is formed by arcuate frame member 3441A and arcuate frame member 3441B, which extend between longitudinal member 3448A and longitudinal member 3448B. Longitudinal member 3348A and longitudinal member 3348B extend from respective proximal tips of arcuate petal portions of the first set of arcuate petal portions, e.g., longitudinal member 3448A extends from a proximal tip 3426 of arcuate petal portion 3420A.

In contrast to implant 3300 of FIG. 33, which has a proximally concave shape, implant 3400 of FIG. 34 has varying concavity, like implant 2900C of FIG. 29C. More specifically, implant 3400 includes each of a proximal portion 3450 that is proximally concave, a distal portion 3452 that is distally concave, and a cap portion 3454 that is proximally concave.

Implant 3400 further includes circumferentially distributed anchor members, such as anchor member 3456 and anchor member 3458. Anchor member 3456 is part of a first set of anchor members that extend radially outward from a proximal tip of a respective arcuate frame member. Specifically, each anchor member of the first set of anchor members extends from a proximal tip of the distal frame member of each arcuate petal portion. So, for example, anchor member 3456 extends from the proximal tip of arcuate frame member 3441B. Anchor member 3458, on the other hand, is part of a second set of anchor members that extend radially outward from junctions between arcuate tip members and longitudinal members. Specifically, each anchor member of the second set of anchor members extends from a respective junction between the proximal frame member of each arcuate petal portion and each longitudinal member. So, for example, anchor member 3458 extends from the junction between arcuate frame member 3441A and longitudinal member 3348A. In other implementations, anchor members may alternatively or additional be disposed at other locations of the frame including, but not limited, to the proximal tip of the proximal arcuate frame member (e.g., arcuate frame member 3441A) and the junctions formed between the distal arcuate frame members and the longitudinal members.

Figure 35A:
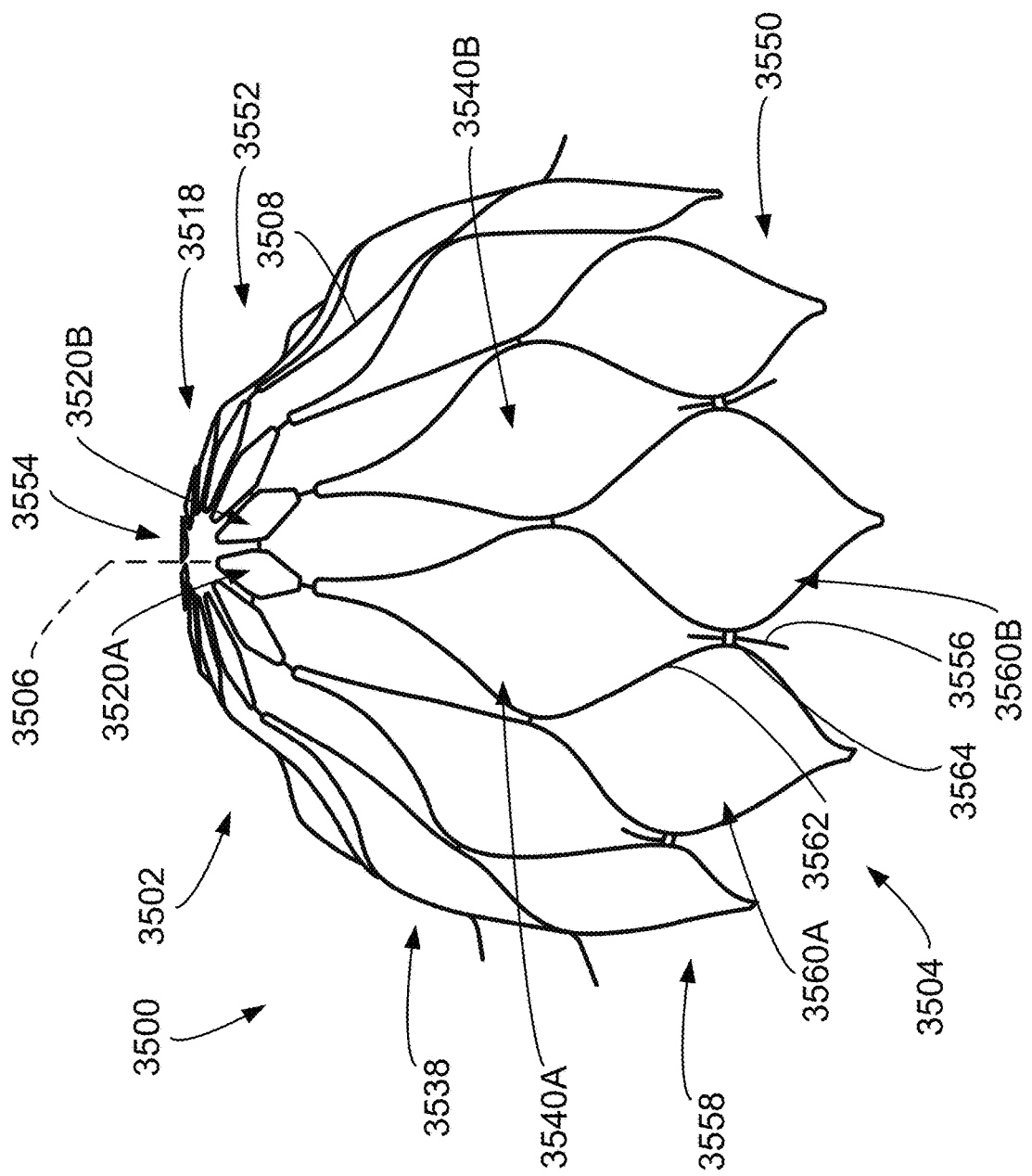
FIG. 35A is a first distal-end view of an implant having arcuate petal portions formed by arcuate members extending between longitudinal members and having an overall shape that includes a proximal portion having a proximally concave shape and a distal portion having a distally concave shape.

FIGS. 35A and 35B illustrate another implant 3500 having an overall shape with varying concavities. Implant 3500 includes a distal end 3502 and a proximal end 3504 such that a longitudinal axis 3506 of implant 3500 extends between distal end 3502 and proximal end 3504. Implant 3500 includes a frame 3508 that may support an occlusive assembly 3510 at distal end 3302. FIG. 35A omits the occlusive assembly to show the various features and configuration of frame 3508 more clearly while; however, FIG. 35B includes occlusive assembly 3510. Like other implementations discussed herein, occlusive assembly 3510 includes an inner sheet 3512 but may alternatively or additionally include an occlusive body. Implant 3500 may also include an outer sheet 3514 (also shown in FIG. 35B), which is supported on a proximal portion of frame 3508 such that an annular opening 3516 is defined between inner sheet 3512 and outer sheet 3514.

Frame 3508 of implant 3500 includes a distal frame portion 3518 including a set of circumferentially distributed arcuate petal portions, such as arcuate petal portion 3520A and arcuate petal portion 3520B (each labelled in FIG. 35A). Frame 3508 further includes an intermediate frame portion 3538 including a second set of circumferentially distributed arcuate petal portions, such as arcuate petal portion 3540A and arcuate petal portion 3540B (each labelled in FIG. 35A) and a proximal frame portion 3558 including a third set of circumferentially distributed arcuate petal portions, such as arcuate petal portion 3560A and arcuate petal portion 3560B (each labelled in FIG. As most clearly seen in FIG. 35A, the first and second set of arcuate petal portions are aligned to facilitate joining of each arcuate petal portion of the first set of arcuate petal portions to a respective arcuate petal portion of the second set of petal portions. For example, a proximal tip of arcuate petal portion 3520A is joined to a distal tip of arcuate petal portion 3540A. In contrast, the second and third sets of arcuate petal portions are rotationally offset and longitudinally overlap each other. For example, arcuate petal portion 3540A is rotationally offset from and longitudinally overlaps arcuate petal portion 3560A. Adjacent arcuate petal portions of the second set and the third set may also share common frame elements. For example, arcuate petal portion 3540A and arcuate petal portion 3560A each include frame element 3562.

Like implant 3400 of FIG. 34 and implant 2900C of FIG. 29C, implant 3500 of FIGS. 35A and 35B has varying concavity. More specifically, implant 3500 includes each of a proximal portion 3550 that is proximally concave, a distal portion 3552 that is distally concave, and a cap portion 3554 that is proximally concave.

Also, like implant 3400, implant 3500 includes circumferentially distributed anchor members, such as anchor member 3556. Anchor member 3556 is part of a set of anchor members that extend radially outward from each junction between adjacent arcuate petal portions of the third set of arcuate petal portions. So, for example, anchor member 3556 extends from a junction 3564 between arcuate petal portion 3560A and arcuate petal portion 3560B. In other implementations, anchor members may alternatively or additional be disposed at other locations of the frame including, but not limited, junctions between adjacent arcuate petal portions of the second set of arcuate petal portions and the proximal tips of the arcuate petal portions of the third set of arcuate petal portions.

Implementations of this disclosure corresponding to implant 3500 are not limited to any sizes or dimensions and may be modified or customized to meet the needs of patients and specific applications. Nevertheless, in certain implementations, a proximal radially outward edge 3563 of inner sheet 3512 may be from and including about 16 mm to and including about 30 mm. For example, in one specific implementation proximal radially outward edge 3563 may be 24 mm. Similarly, a distal radially inward edge 3565 of outer sheet 3514 may be from and including about 35 mm to and including about 55 mm. For example, in one specific implementation, proximal radially outward edge 3563 may be 42 mm. A proximal radially outward edge 3566 of implant 3500 may be from and including about 42 mm to and including about 68 mm. In one specific example, proximal radially outward edge 3566 may be 56 mm. In implementations in which implant 3500 includes anchor members, such as anchor member 3556, at least a portion of the anchor members may be distributed around a common circumference 3567 of implant 3500. Although the diameter of common circumference 3567 may vary, in at least certain implementations, common circumference 3567 may have a diameter from and including about 42 mm to and including about 68 mm. For example, common circumference 3567 may have a diameter of 54 mm. As a final example, the overall height of implant 3500 in the expanded state may vary; however, in at least certain implementations, the overall height of implant 3500 may be from and including about 26 mm to and including about 48 mm and, in one specific implementation, may be 36 mm.

While only a select few implementations of this disclosure are shown or described as including anchor members (e.g., protruding anchor members 105 of frame 55), such anchor members may be added to or otherwise included in any implant design discussed herein. Similarly, while this disclosure discusses control of implant expansion by a tension control line in the context of FIGS. 12-22, such functionality may be adapted to and included in any other implant discussed herein.

X. Alternative Delivery Tool Configuration

Figure 36:
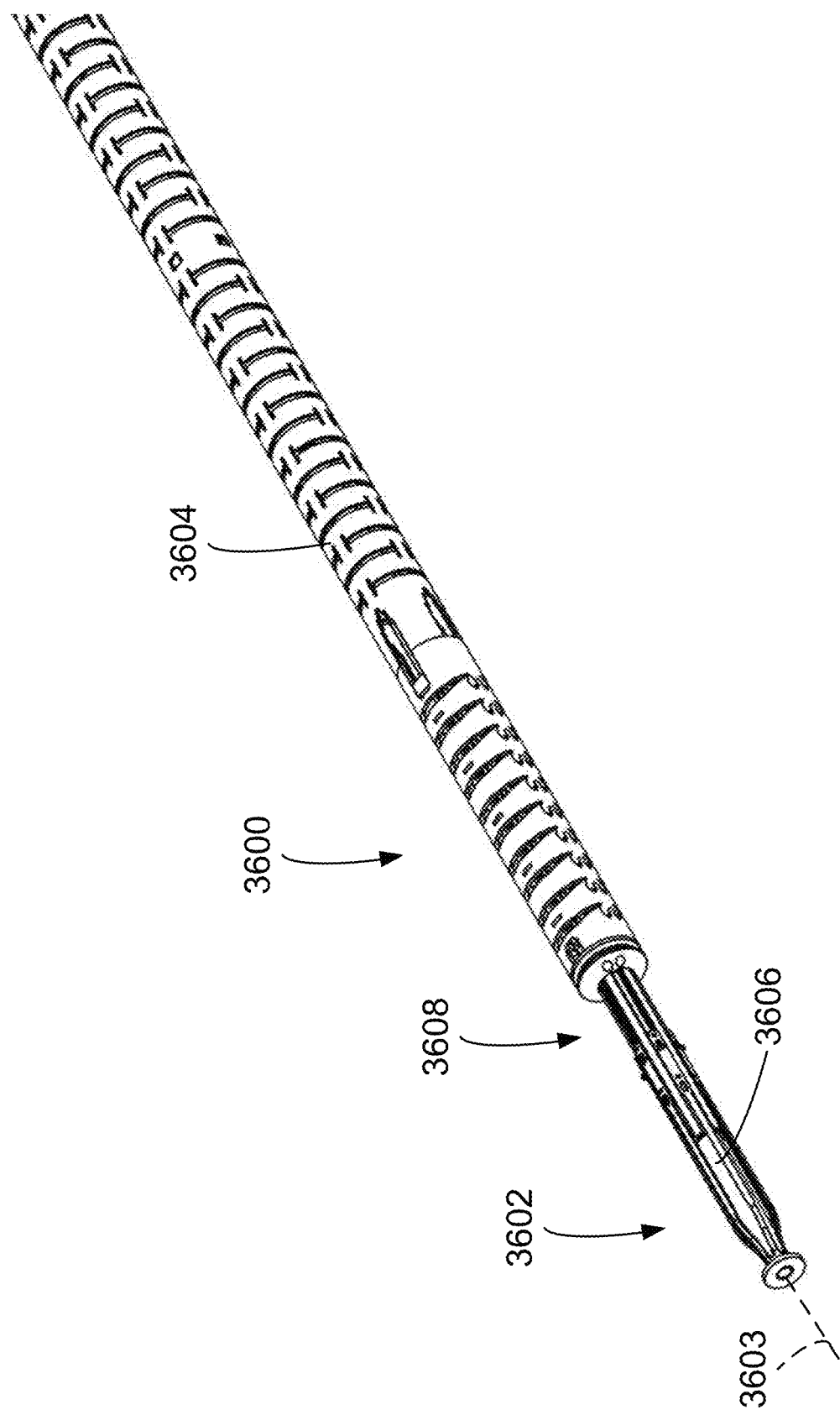
FIG. 36 is a distal-end view of an alternative delivery device according to the present disclosure in a collapsed state.
Figure 37:
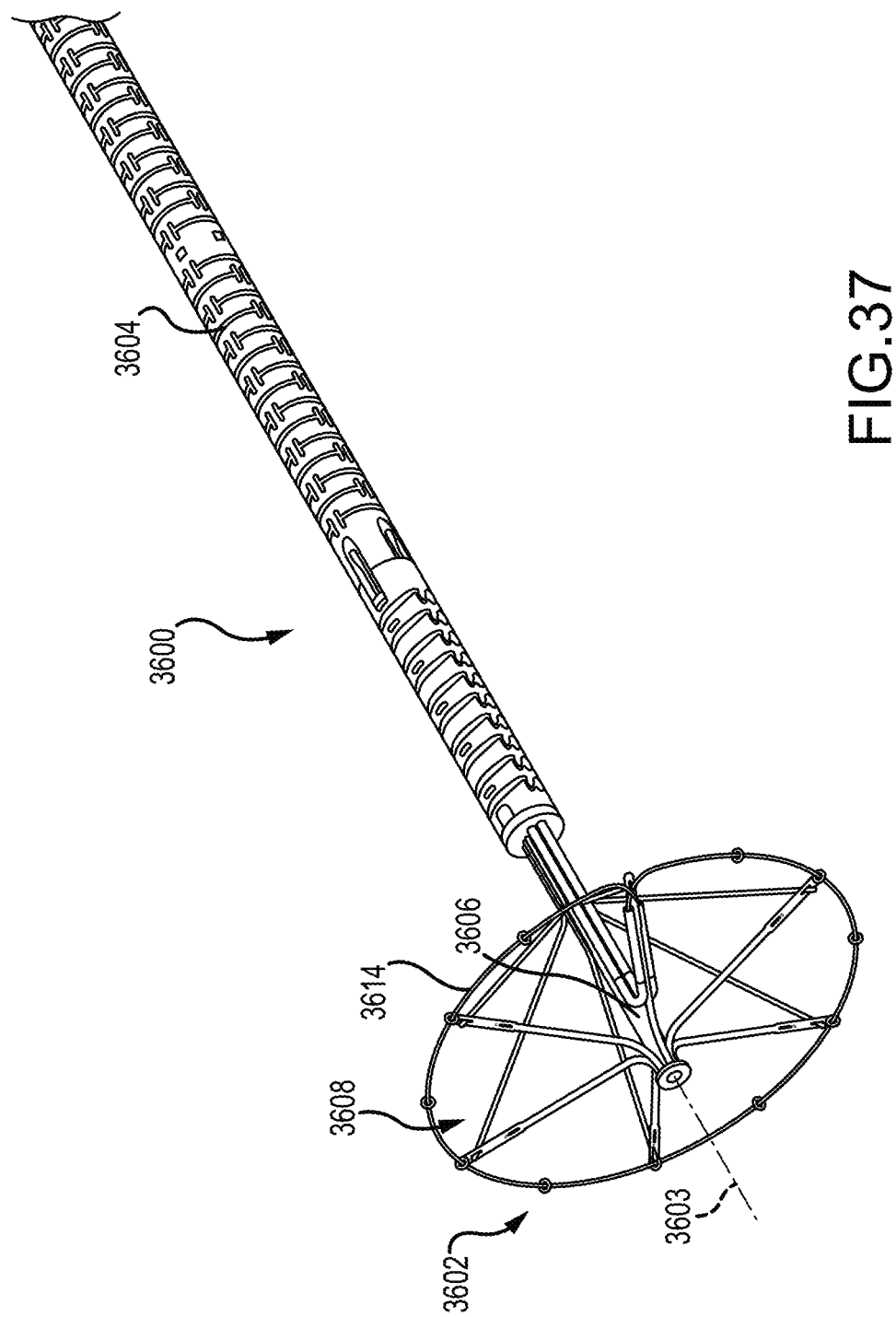
FIG. 37 is a distal-end view of the delivery device of FIG. 36 in an expanded state.
Figure 38:
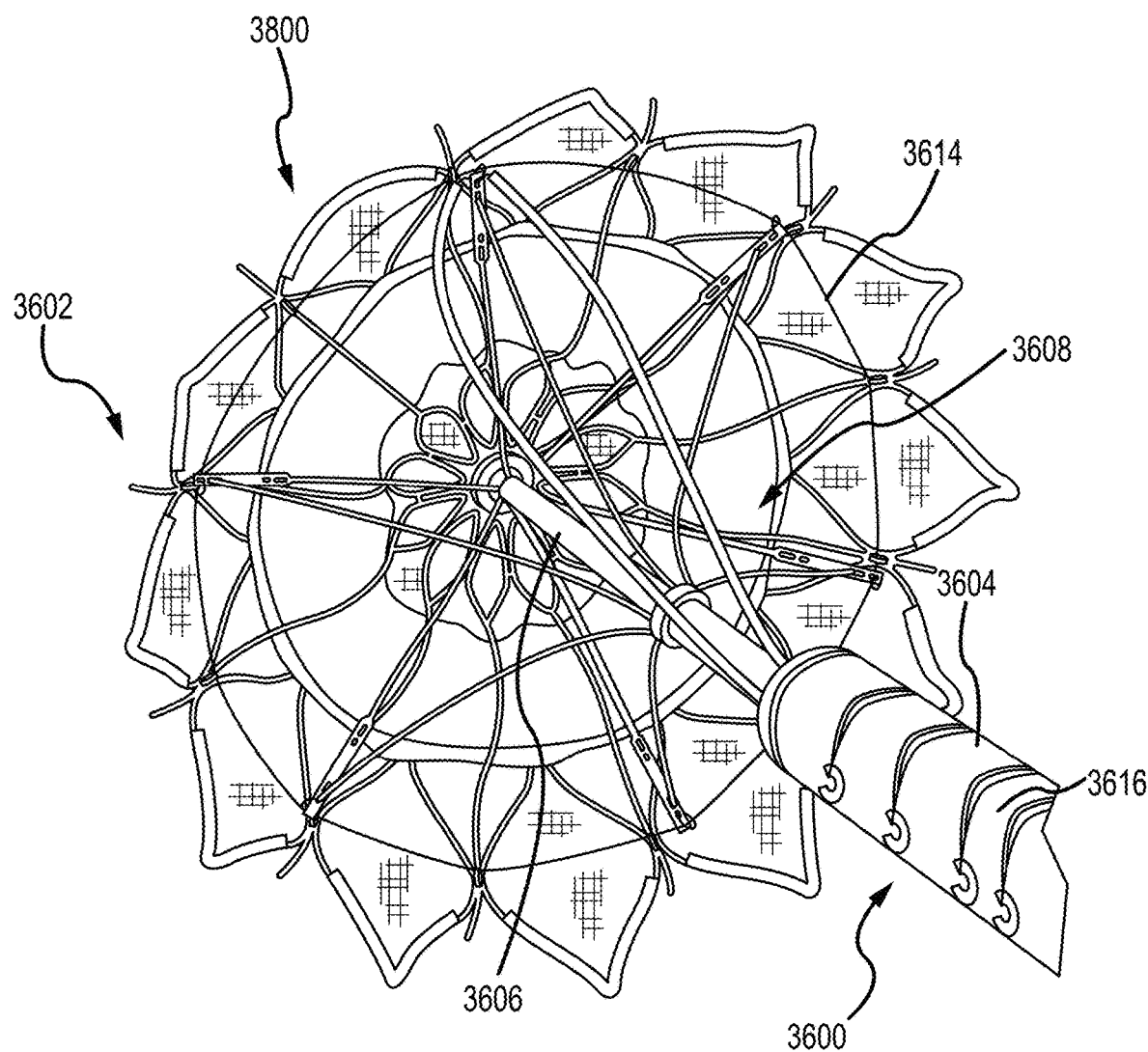
FIG. 38 is a proximal view of a distal end of the delivery device of FIG. 36 including a valve repair implant coupled to the distal end of the delivery device.

FIGS. 36-38 illustrate a delivery device 3600 according to an alternative implementation of the present disclosure. More specifically, FIGS. 36 and 37 are schematic illustrations of a distal portion 3602 of delivery device 3600 in a collapsed and expanded state, respectively, and with a valve repair implant omitted for clarity. FIG. 38 is an illustration of delivery device 3600 and, in particular, a proximal view of distal portion 3602 including a valve repair implant 3800 coupled to delivery device 3600. Delivery device 3600 includes multiple variations on features previously discussed in this disclosure, each of which is described below in further detail. Notably, while delivery device 3600 incorporates multiple features that differ from previously disclosed implementations, each feature should be considered independent and, as a result, may be readily adapted for inclusion in other implementations included in this disclosure.

As shown in FIGS. 36-38, delivery device 3600 includes a delivery catheter 3604 and an extension member 3606 extending from distal portion 3602. In certain implementations and as discussed below in further detail, extension member 3606 may be selectively extended and retracted from delivery catheter 3604 during deployment of valve repair implant 3800.

During deployment and implantation of valve repair implant 3800, valve repair implant 3800 is releasably coupled to a control arm assembly 3608 of delivery device 3600. As described below in further detail, the control arm assembly can be manipulated to expand laterally or collapse medially relative to a longitudinal axis 3603 of delivery device 3600. Due to the coupling of the control arm assembly 3608 to valve repair implant 3800, such expansion and collapse of the control arm assembly 3608 results in corresponding expansion and collapse of valve repair implant 3800.

During delivery and deployment of valve repair implant 3800, valve repair implant 3800 may be coupled to delivery device 3600 by a cinch line 3614 (shown in FIGS. 37 and 38). As illustrated, cinch line 3614 forms a loop that extends distally from delivery catheter 3604 and routes through loops, rings, apertures, or similar features of each of the control arm assembly 3608 and valve repair implant 3800 to couple valve repair implant 3800 to the control arm assembly 3608. In addition to coupling valve repair implant 3800 to delivery device 3600, cinch line 3614 facilitates accurate control of expansion and collapse of valve repair implant 3800 during deployment and implantation. In particular, cinch line 3614 may be selectively tensioned during to encourage uniform expansion and collapse of valve repair implant 3800.

FIGS. 39-44 are detailed views of distal portion 3602 of delivery device 3600 with various components of delivery device 3600 selectively removed to further illustrate the construction and functionality of delivery device 3600. FIGS. 39-44 are intended to introduce the various internal components of delivery device 3600, many of which will be discussed in further detail in later sections of this disclosure.

Figure 39:
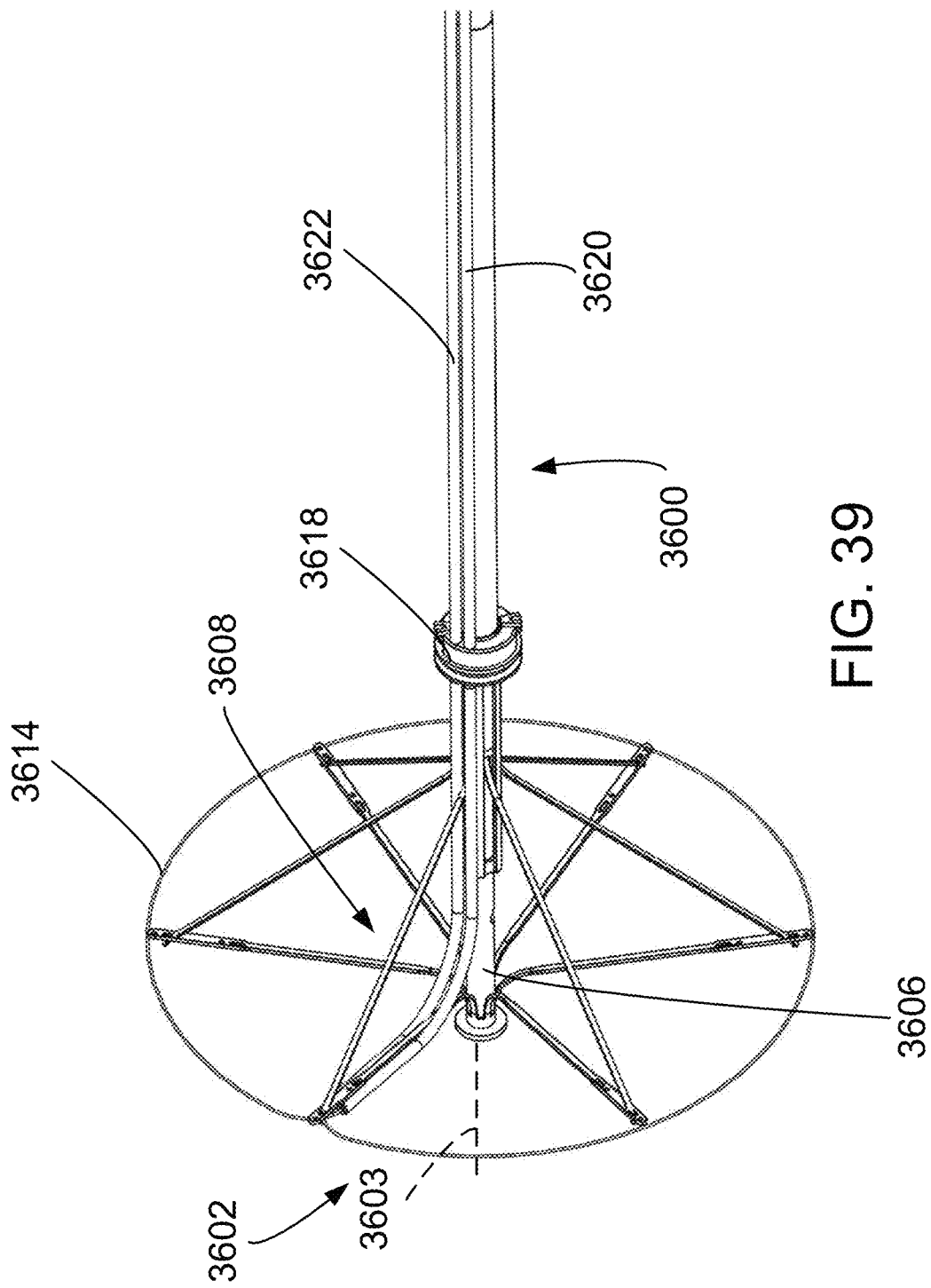
FIGS. 39-44 are side views of the delivery device of FIG. 36 with various components removed to illustrate the internal construction of the delivery device.

FIG. 39 shows delivery device 3600 with delivery catheter 3604 and a sheath 3616 (shown in FIG. 38) removed. As shown, in at least certain implementations, delivery catheter 3604 may be capped with a tip or a collar 3618 through which various components of delivery device 3600 may extend. For example, each of extension member 3606 and control arm assemblies (e.g., control arm assembly 3608) extend through collar 3618, which supports and maintains relative positioning of components of delivery device 3600, such as extension member 3606 and control arm assembly 3608.

FIG. 39 further includes a cinch line tube 3620 and a cinch line tube 3622, each of which extends through delivery catheter 3604 to guide and protect cinch line 3614. In certain implementations, cinch line tube 3620 and cinch line tube 3622 may be coiled tubes and may be coupled to or otherwise supported by control arm assembly 3608 such that as control arm assembly 3608 expands and collapses, cinch line tube 3620 and cinch line tube 3622 extend and retract from delivery catheter 3604. Alternatively, cinch line tube 3620 and cinch line tube 3622 may be fixed and extend from delivery catheter 3604. In still other implementations, cinch line tube 3620 and cinch line tube 3622 may be selectively extended and retracted by a corresponding control of a control assembly disposed on a proximal end of delivery catheter 3604.

Figure 40:
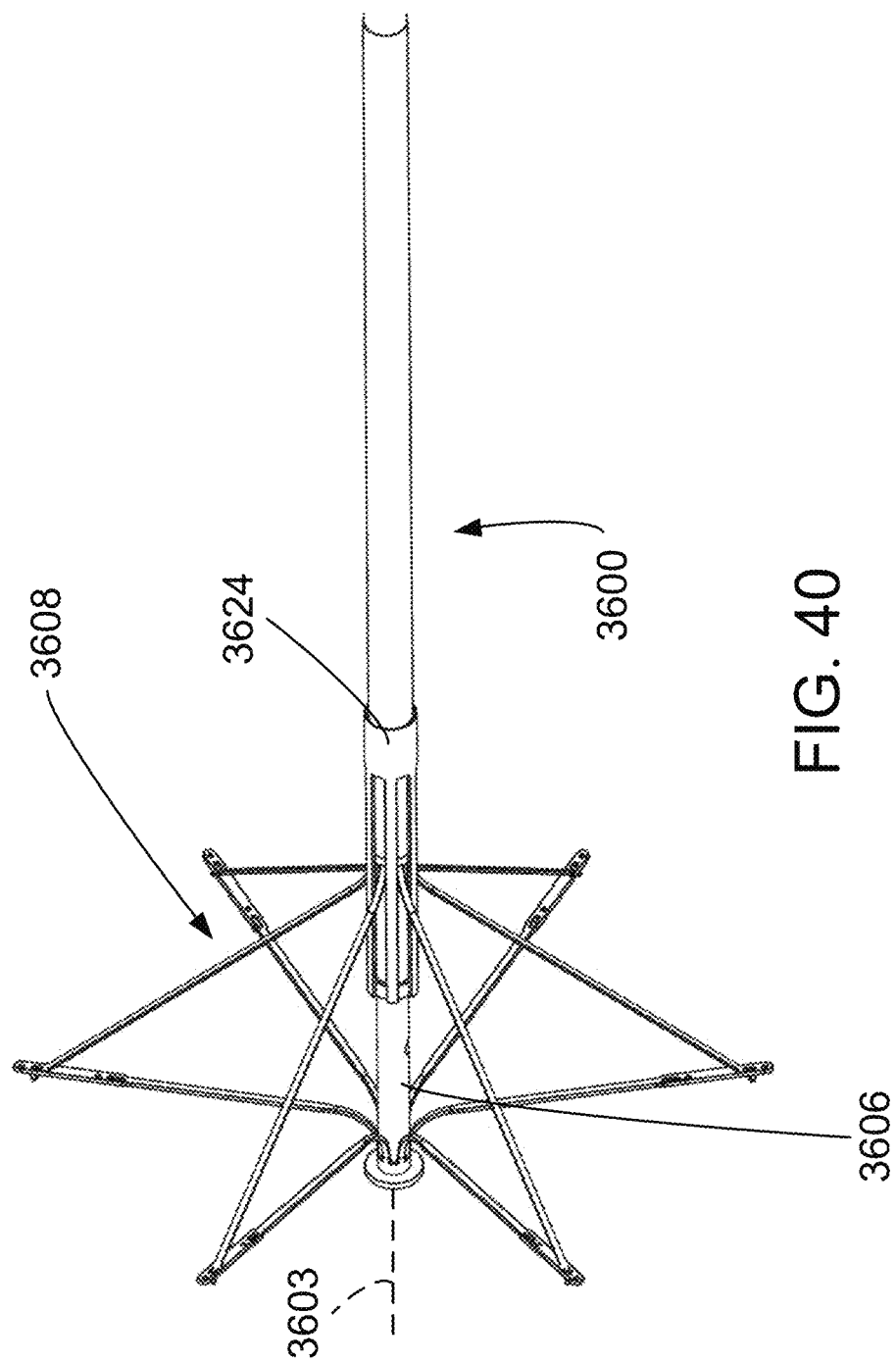

FIG. 40 illustrates delivery device 3600 with cinch line 3614, cinch line tube 3620, cinch line tube 3622, and collar 3618 removed. As shown, delivery device 3600 may include a support member 3624, which may be coupled to or otherwise extend from collar 3618. Support member 3624 may have a cage-like structure that supports and allows longitudinal translation of extension member 3606. Support member 3624 may further include multiple apertures through which control arm pairs of control arm assembly 3608 may extend.

Figure 41:
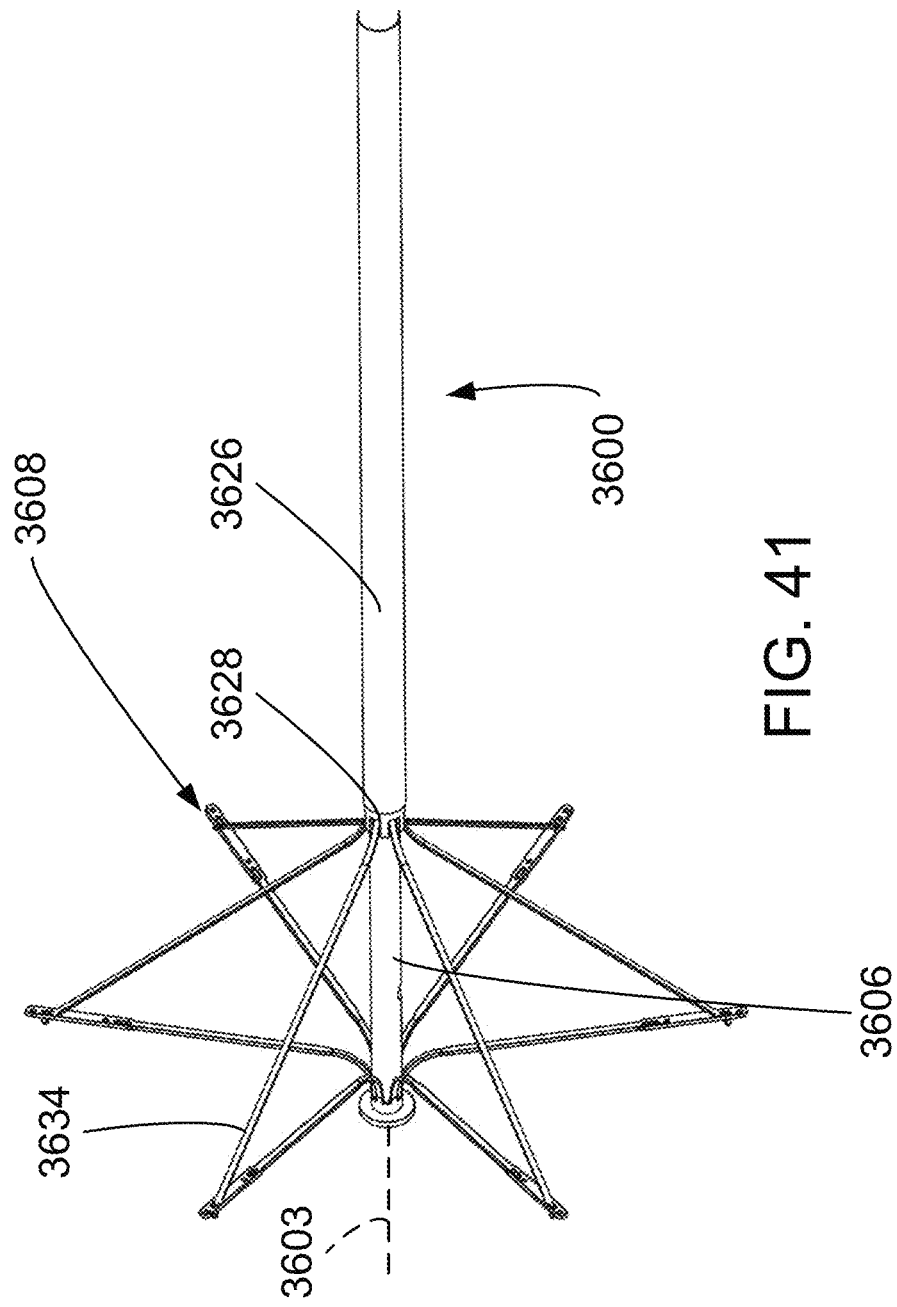

FIG. 41 illustrates delivery device 3600 with support member 3624 removed. As shown, delivery device 3600 may include a distal tube 3626 within which a proximal portion of control arm assembly 3608 is translatable to selectively expand and collapse control arm assembly 3608. In certain implementations, distal tube 3626 may terminate or be capped with a diverter 3628, which directs proximal arms (such as proximal arm 3634) of control arm assembly 3608 in an at least partially lateral/medial direction relative to longitudinal axis 3603 of delivery device 3600 to facilitate expansion and collapse of control arm assembly 3608. In addition to or as an alternative to diverter 3628, proximal control arms of control arm assembly 3608 may instead be outwardly curved or otherwise biased into an outwardly curved shape to facilitate expansion and collapse of control arm assembly 3608.

Figure 42:
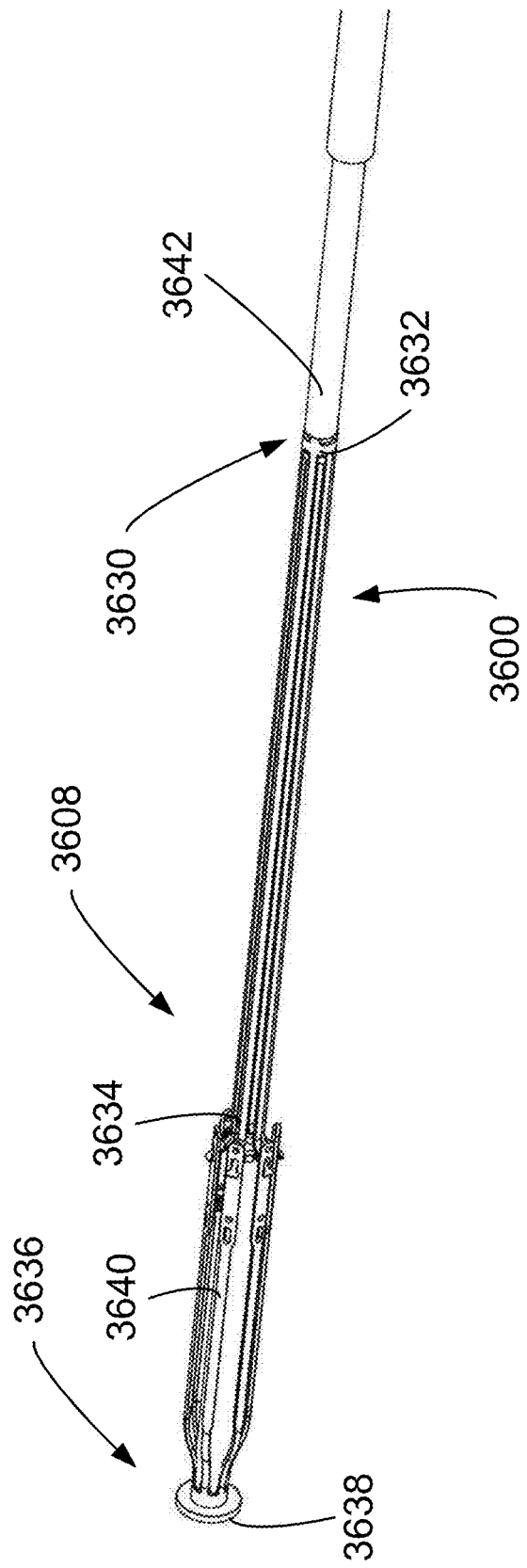
Figure 43:
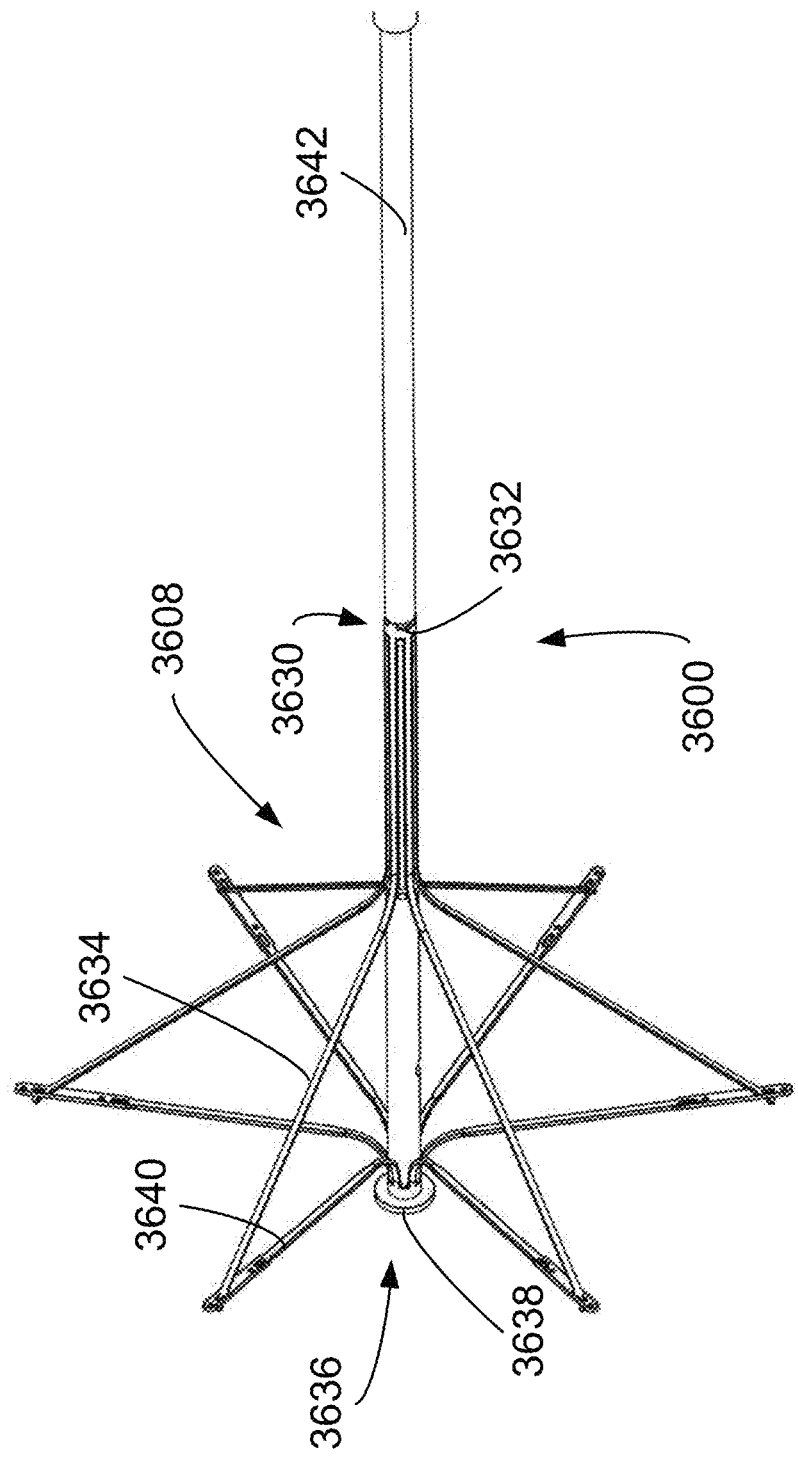

FIGS. 42 and 43 illustrate delivery device 3600 with distal tube 3626 removed. In particular, FIG. 42 illustrates delivery device 3600 with control arm assembly 3608 in a collapsed state while FIG. 43 illustrates delivery device 3600 with control arm assembly 3608 in an expanded state.

As shown, control arm assembly 3608 may include a proximal portion 3630 including a proximal collar 3632 from which multiple proximal arms (e.g., proximal arm 3634) extend. Delivery device 3600 further includes a distal cap 3638 from which multiple distal arms (e.g., distal arm 3640) of control arm assembly 3608 extend. As described in further detail later in this disclosure, each of the distal arms forms a control arm pair with a respective one of the proximal arms and each control arm pair may be moved between an expanded and collapsed state by actuating control arm assembly 3608. In the specific implementation shown in FIGS. 42 and 43, actuation of control arm assembly 3608 includes proximally driving or distally retracting proximal portion 3630 using a control arm shaft 3642, which may be coupled to a control assembly of delivery device 3600, the control assembly including suitable controls for selectively translating control arm shaft 3642.

Figure 44:
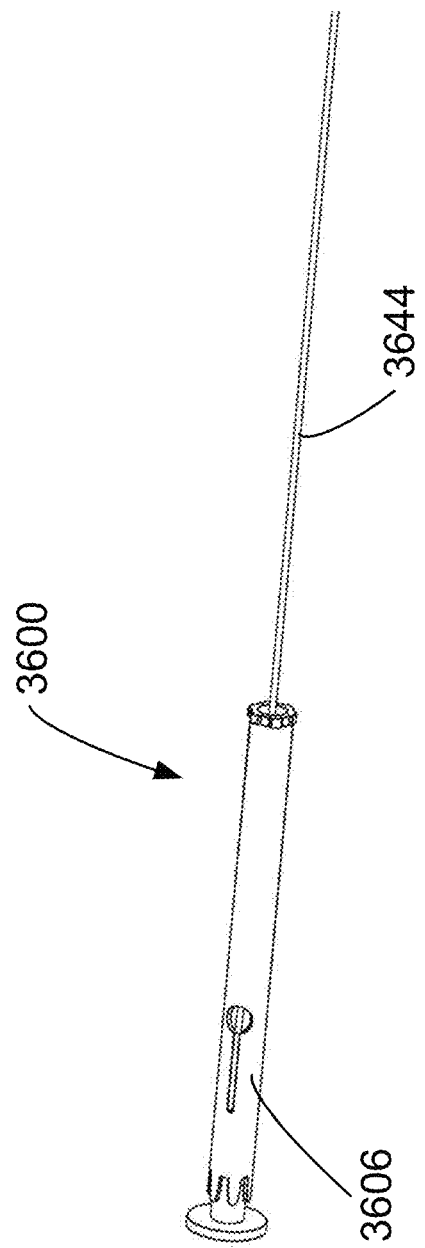

FIG. 44 illustrates delivery device 3600 with control arm assembly 3608 removed. As shown, delivery device 3600 may include an extension member control rod 3644 that extends through delivery catheter 3604 and couples to extension member 3606 to facilitate extension and retraction of extension member 3606 relative to delivery catheter 3604. In at least some implementations, a proximal end of extension member control rod 3644 may be coupled to a control assembly at a proximal end of delivery catheter 3604, the control assembly including a control element for selectively translating extension member control rod 3644.

With the foregoing in mind for context, the following sections of this disclosure will describe certain features of delivery device 3600 in additional detail.

XI. Multi-Directional Steering

As discussed in the context of FIGS. 11A-11C, implementations of the present disclosure may include a steerable delivery catheter. For example, valve repair system 1100 illustrated in FIGS. 11A-11C includes catheter 1177, which may be inserted into a patient via sheath 1176 and subsequently steered using steering control 1180. More specifically, catheter 1177 is illustrated and discussed as being steerable along a single plane between two extents, generally illustrated by dashed outlines 1192A and dashed outlines 1192B. Accordingly, the implementation illustrated in FIGS. 11A-11C provides a single degree of freedom for steering catheter 1177.

Other implementations of this disclosure may include an alternative delivery catheter configuration that provides multiple degrees of freedom. For example, delivery tools according to this disclosure may be divided into multiple segments, each of which may be steerable along one or more planes. Such increased maneuverability facilitates navigation of the delivery tool to an implant location and final placement of the valve repair implant, among other benefits, ultimately resulting in faster, more efficient, and more accurate implantation procedures.

Figure 45A:
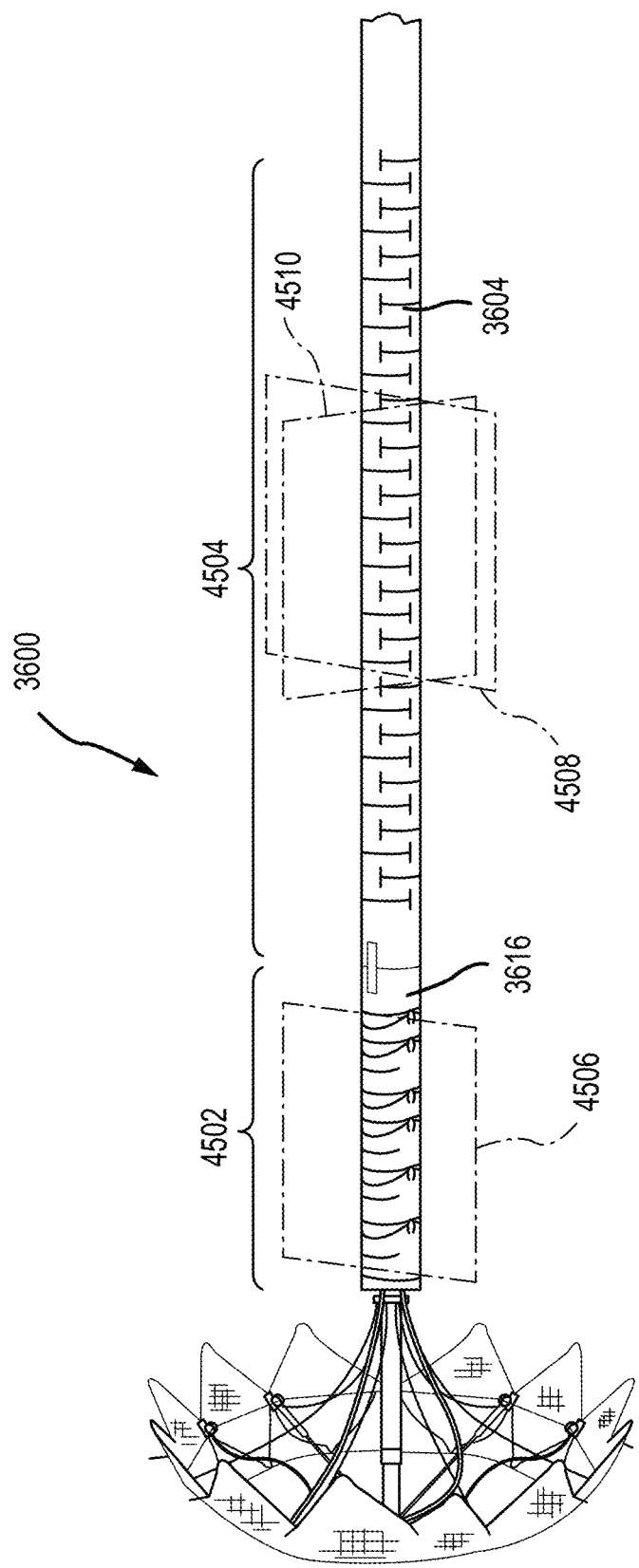
FIG. 45A is a side view of a distal end of the delivery device of FIG. 36 illustrating steerable sections of the delivery device.

FIG. 45A is a side view of delivery device 3600 with an external sheath removed and implant 3800 in a deployed and expanded configuration. Delivery device 3600 includes delivery catheter 3604, which, in certain implementations, may be a steerable catheter. For example, delivery device 3600 includes each of a distal steerable section 4502 and a proximal steerable section 4504, each of which may steered independently from a control assembly (not shown) coupled to a proximal end of delivery catheter 3604.

Like the distal portion of catheter 1177 of valve repair system 1100, distal steerable section 4502 may be configured to bend along a plane 4506. For example, the control assembly coupled to delivery catheter 3604 may include a knob, lever, arm, or similar control element attached to distal steerable section 4502 by a cable, wire, or similar control line such that manipulating the control element bends distal steerable section 4502 across a range of motion along plane 4506. Although the amount and range of bending may vary, in at least certain implementations, distal steerable section 4502 may be configured to have a minimum bend radius along plane 4506 from and including about 10 mm to and including about 20 mm and in one specific implementation may have a minimum bending radius of about 15 mm. Also, in addition to including control elements adapted to steer distal steerable section 4502, the control assembly may further include a mechanism (e.g., a knob, slide, button, etc.) for locking the angle of distal steerable section 4502.

Proximal steerable section 4504 may be configured to bend along a plane 4508 that is coplanar to plane 4506 when delivery device 3600 is in a neutral/straight configuration. In at least some implementations, proximal steerable section 4504 may also be independently steerable along a second plane, such as plane 4510. As illustrated, in at least certain implementations, plane 4510 may be orthogonal to plane 4508. To achieve steering of proximal steerable section 4504, the control assembly coupled to delivery catheter 3604 may include a respective knob, lever, arm, or similar control element for each degree of freedom of proximal steerable section 4504. Each such control element may in turn be attached to proximal steerable section 4504 by a cable, wire, or similar control line such that manipulating the control element bends proximal steerable section 4504 along the corresponding plane. Although the amount and range of bending may vary, in at least certain implementations, proximal steerable section 4504 may be configured to independently bend across each of plane 4508 and plane 4510 and to have a minimum bend radius along each plane from and including about 20 mm to and including about 30 mm and in one specific implementation may have a minimum bending radius of about 25 mm. The control assembly may further include respective mechanisms (e.g., knobs, slides, buttons, etc.) for locking each of the steering controls for the proximal steerable section 4504.

Figure 45B:
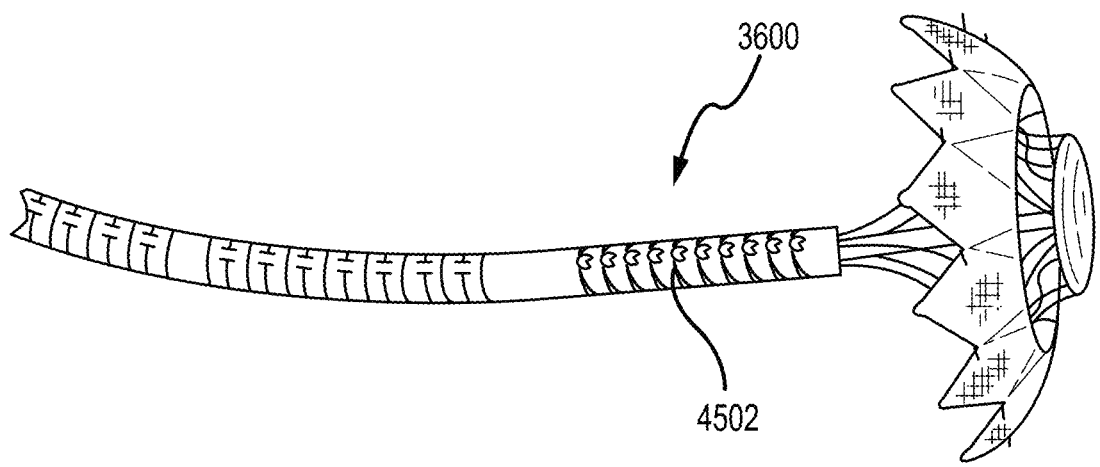
FIGS. 45B and 45C are illustrations of the delivery device of FIG. 36 illustrating steering of a distal steering section of the delivery device.
Figure 45C:
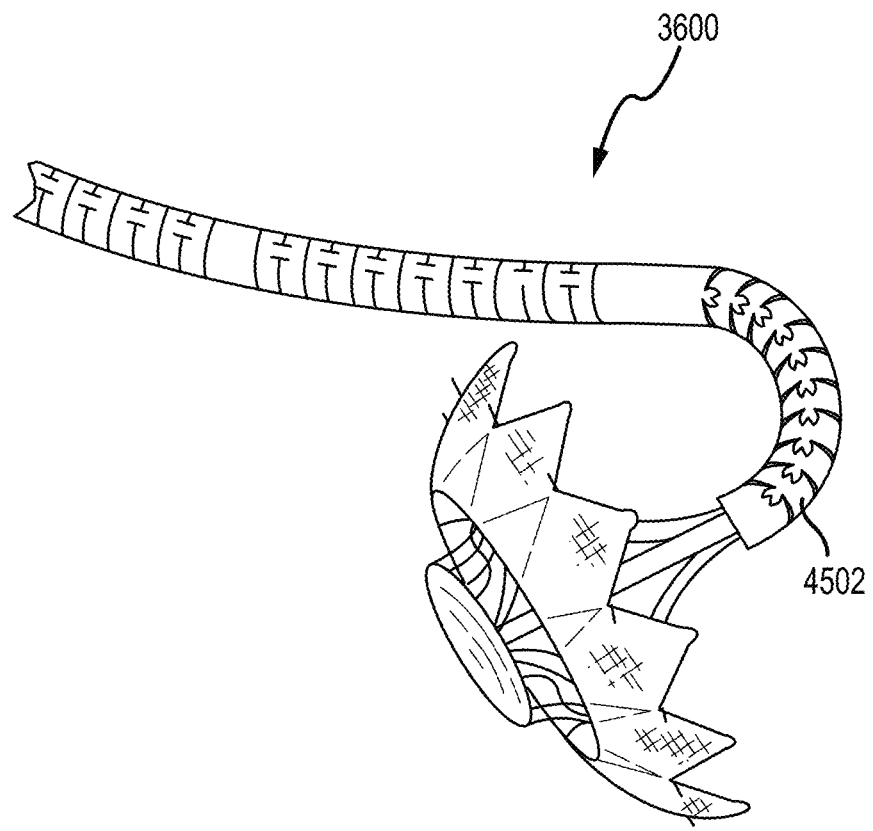

FIGS. 45B-45H further illustrate steering of delivery device 3600. First, FIGS. 45B and 45C illustrate steering of distal steerable section 4502 of delivery device 3600. More specifically, FIG. illustrates distal steerable section 4502 in a substantial neutral position while FIG. 45C illustrates steering of distal steerable section 4502 to a first extent along plane 4506 (shown in FIG. 45A). As shown in FIG. 45B, in at least certain implementations, distal steerable section 4502 may be steerable along plane 4506 by approximately 135 degrees; however, this disclosure is not limited to any specific bending angle of distal steerable section 4502. For example, in certain implementations, distal steerable section 4502 may be configured to bend up to 180 degrees or more in a given direction. Moreover, while FIG. 45C illustrates steering of distal steerable section 4502 in a first direction, in implementations of this disclosure, distal steerable section 4502 may be bidirectionally steerable from the neutral state shown in FIG. 45B. In at least certain implementations, distal steerable section 4502 may be steerable through approximately 360 degrees of bending along plane 4506.

In implementations in which delivery device 3600 is used for delivery of implants for tricuspid valve repair, for example, steering of distal steerable section 4502 as illustrated in FIGS. 45B and 45C may be particularly useful in achieving orthogonality between a longitudinal axis of the implant being and/or distal steerable section 4502 and the valve annulus. More specifically, during delivery of the implant to the right atrium, a clinician generally directs delivery device 3600 into the right atrium via the inferior vena cava with delivery device 3600 in the neutral state illustrated in FIG. 45B. Following entry into the right atrium, the clinician may steer distal steerable section 4502 to achieve and maintain substantial orthogonality of distal steerable section 4502 and the implant with the tricuspid valve annulus until delivery of the implant is complete.

While the specific bending radius of distal steerable section 4502 may vary based on the size and configuration of delivery device 3600, in at least certain implementations, distal steerable section 4502 may be configured to have a minimum bending radius of approximately 12.5 mm. Nevertheless, this disclosure contemplates that the overall size of delivery device 3600 and the bending radius of distal steerable section 4502 may be varied based on patient anatomy and other considerations.

Figure 45D:
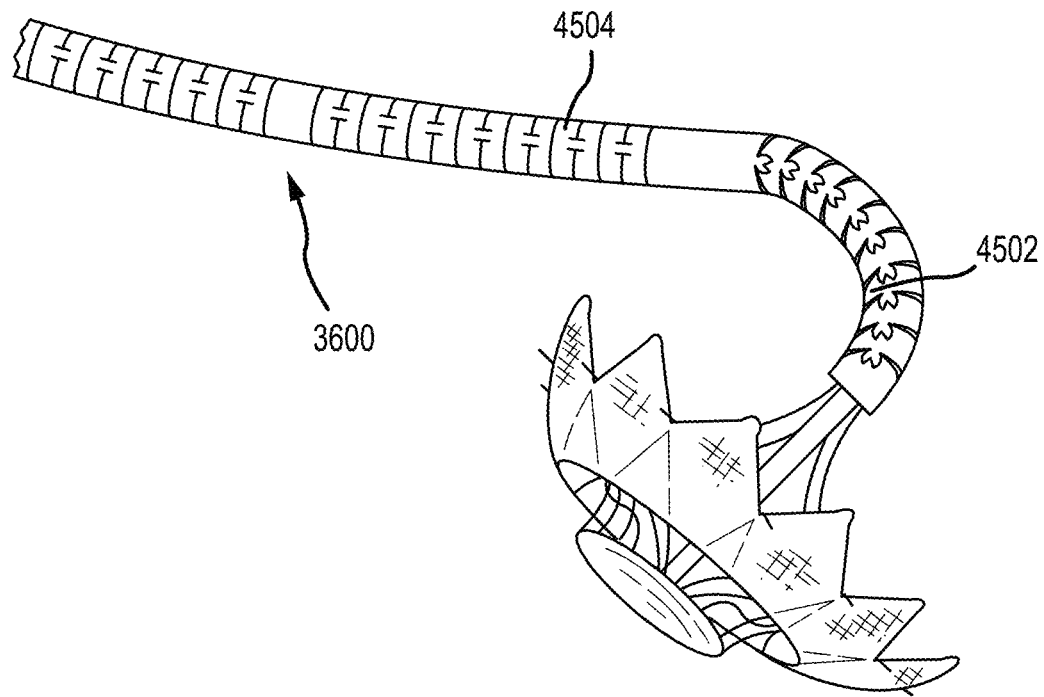
FIGS. 45D and 45E are illustrations of the delivery device of FIG. 36 illustrating steering of a proximal steering section of the delivery device along a first plane.
Figure 45E:
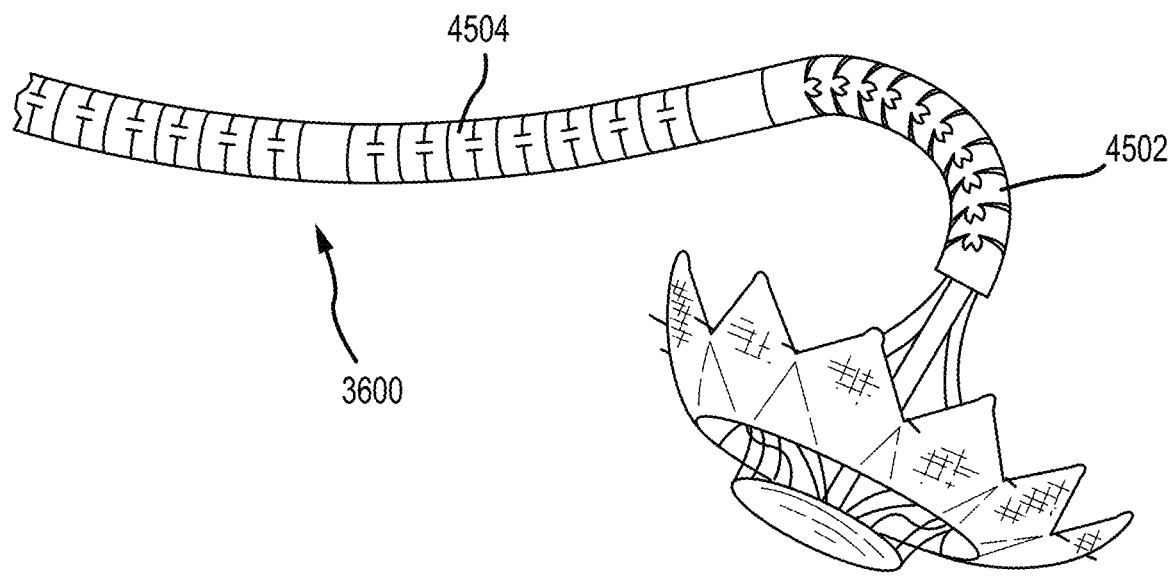

FIGS. 45D and 45E illustrate steering of proximal steerable section 4504 of delivery device 3600. More specifically, FIG. 45D illustrates proximal steerable section 4504 in a substantial neutral position while FIG. 45E illustrates proximal steerable section 4504 following bending along plane 4508 (shown in FIG. 45A). As shown in FIG. 45A, plane 4506 and plane 4508 are coplanar when delivery device 3600 is in a neutral state.

FIG. 45E illustrates how, in at least certain implementations, proximal steerable section 4504 may be steerable along plane 4508 by approximately 45 degrees; however, this disclosure is not limited to any specific bending angle of proximal steerable section 4504 along plane 4508. For example, in certain implementations, proximal steerable section 4504 may be configured to bend up to 60 degrees or more in a given direction along plane 4508. Also, similar to distal steerable section 4502, proximal steerable section 4504 may be bidirectionally steerable along plane 4508. In certain implementations, the bending radius of proximal steerable section 4504 along plane 4508 may be from and including about 5 cm to and including about 7 cm, for example approximately 6 cm; however, this disclosure is not limited to any particular bending radius for proximal steerable section 4504 along plane 4508.

Referring again to procedures for delivery of implants for tricuspid valve repair, steering of proximal steerable section 4504 along plane 4508 may be particularly useful in controlling the height/insertion of the implant and distal steerable section 4502 relative to the valve annulus and for maximizing use of the atrial volume to properly align the implant with the valve annulus. For example, when delivery device 3600 enters the right atrium via the inferior vena cava, distal steerable section 4502 may be oriented such that proximal steerable section 4504 and/or distal steerable section 4502 extend in a partially lateral direction toward the atrial septum. In certain cases, such an orientation can limit the range of motion of distal steerable section 4502 and, as a result, the ability of the clinician to align distal steerable section 4502 with the valve annulus by steering distal steerable section 4502 alone. To increase the range of motion of distal steerable section 4502, proximal steerable section 4504 may be steered as shown in FIG. 45E such that proximal steerable section 4504 is maintained near or along the medial surface of the right atrium, thereby increasing the volume of the right atrium available within which distal steerable section 4502 may be steered and manipulated.

Figure 45F:
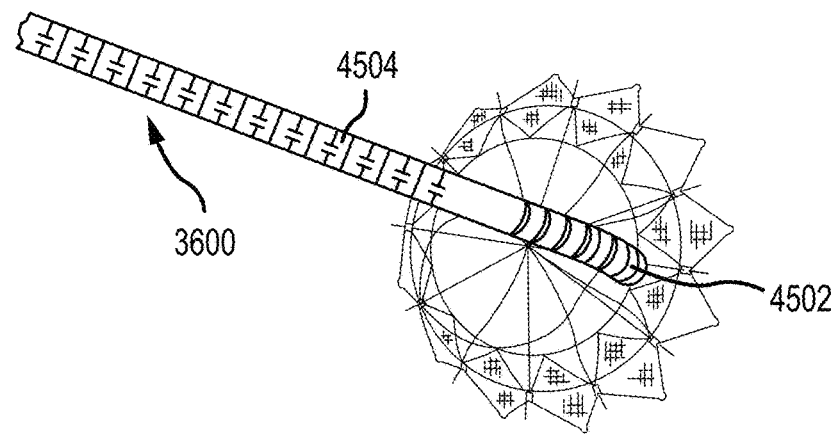
FIGS. 45F-45H are illustrations of the delivery device of FIG. 36 illustrating steering of the proximal steering section along a second plane, orthogonal to the first plane.
Figure 45G:
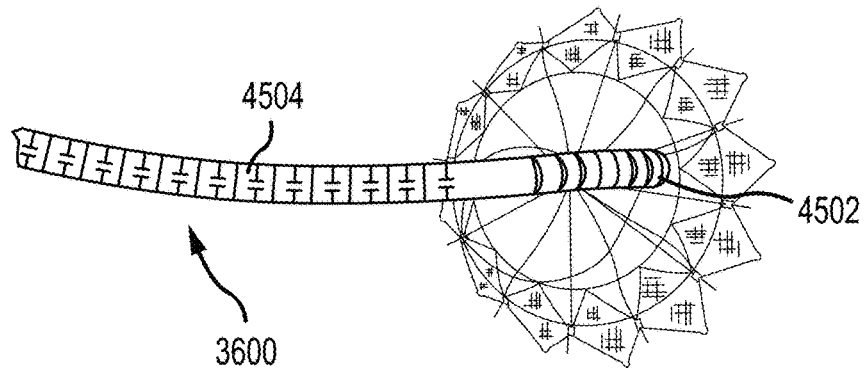
Figure 45H:
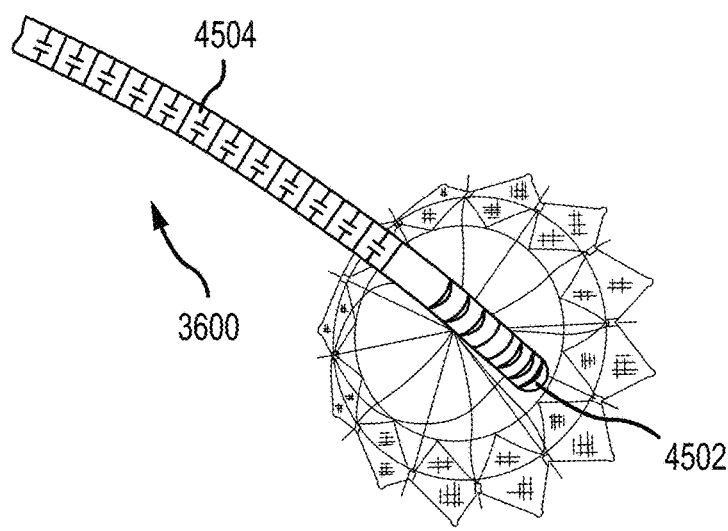

Finally, FIGS. 45F-45H illustrate steering of proximal steerable section 4504 of delivery device 3600. More specifically, FIG. 45F illustrates proximal steerable section 4504 in a substantial neutral position while FIG. 45G illustrates proximal steerable section 4504 following bending along plane 4510 (shown in FIG. 45A). As shown in FIG. 45A, plane 4510 is orthogonal to each of plane 4506 and plane 4508 are coplanar when delivery device 3600 is in a neutral state.

FIG. 45G illustrates proximal steerable section 4504 bent along plane 4510 in a first direction from the neutral state illustrated in FIG. 45F while FIG. 45H illustrates proximal steerable section 4504 bent along plane 4510 in a second direction from the neutral state and opposite the first direction. In the specific implementation illustrated in FIG. 45F-45H, bending of proximal steerable section 4504 along plane 4510 is up to approximately 30 degrees in either direction; however, this disclosure is not limited to any specific bending angle of proximal steerable section 4504 along plane 4508. More generally, in certain implementations, proximal steerable section 4504 may be configured to bend up to about 60 degrees or more in one or both directions relative to neutral along plane 4510.

When in use for delivering implants for tricuspid valve repair, steering of proximal steerable section 4504 along plane 4510 may be particularly useful to control offset of the implant relative to the tricuspid valve annulus. After a clinician has successfully positioned an implant using delivery device 3600, the clinician may generally align the implant to be orthogonal to the annulus of the tricuspid valve by steering each of the distal steerable section 4502 along plane 4506 and proximal steerable section 4504 along plane 4508. Despite being orthogonally oriented, the implant may nevertheless be misaligned with the valve annulus. For example, a longitudinal axis of the implant being offset relative to the longitudinal axis of the valve annulus. In such instances, steering of proximal steerable section 4504 along plane 4510 may be used to reposition the implant to reduce the offset while maintain orthogonality of the implant relative to the valve annulus.

FIGS. 46-49 are illustrations of a portion of a steering control assembly 4600 for delivery device 3600 and, in particular, a portion of steering control assembly 4600 including steering controls. As previously noted, steering control assembly 4600 may be coupled to a proximal end of delivery catheter 3604.

Figure 46:
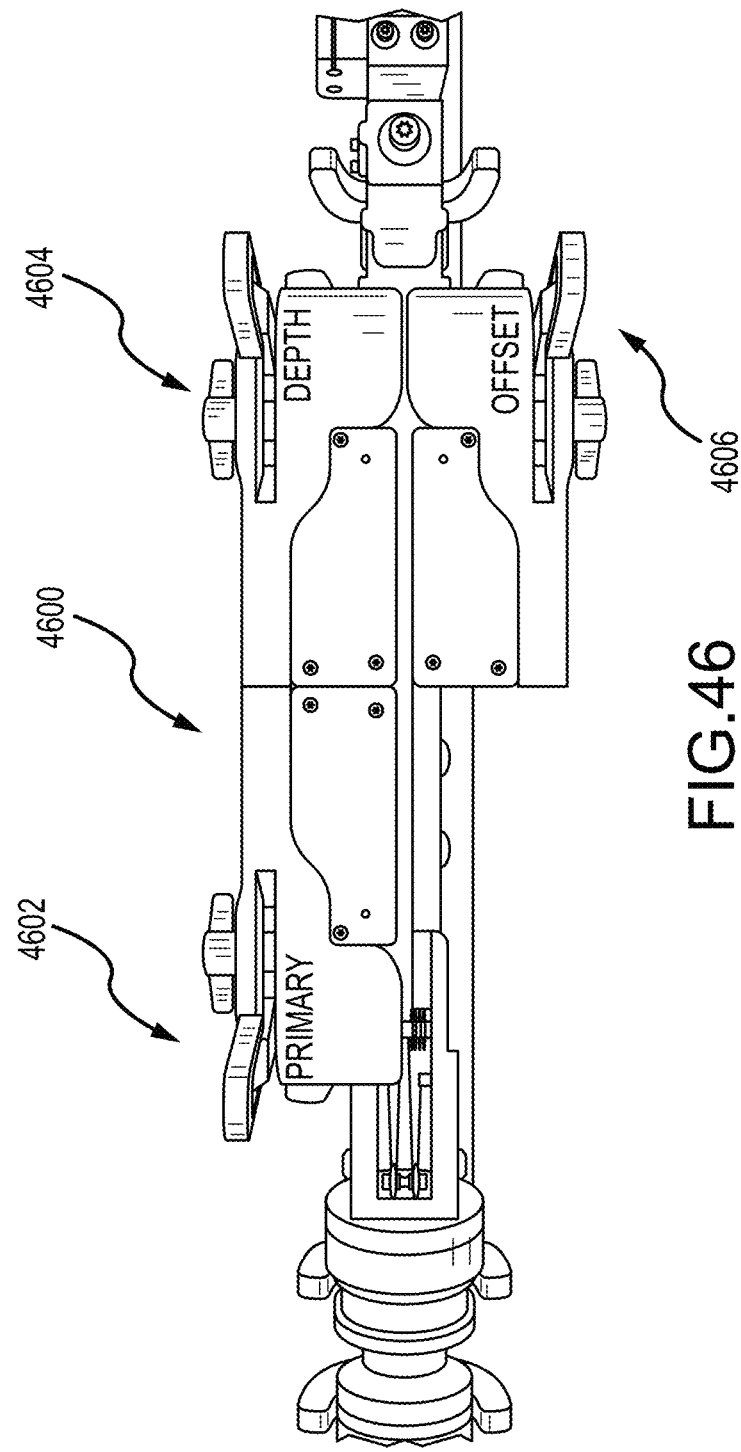
FIG. 46 is an illustration of a control assembly for steering the delivery device of FIG. 36.

FIG. 46 is an elevation view of steering control assembly 4600, which includes a first steering portion 4602, a second steering portion 4604, and a third steering portion 4606. The functions of each steering portion are described below in further detail; however, in the specific implementation illustrated in FIGS. 46-49, the first, second, and third steering portions generally correspond to a "primary" steering mechanism, a "depth" steering mechanism, and an "offset" steering mechanism, as labelled in the figures and as described below in further detail.

Figure 47:
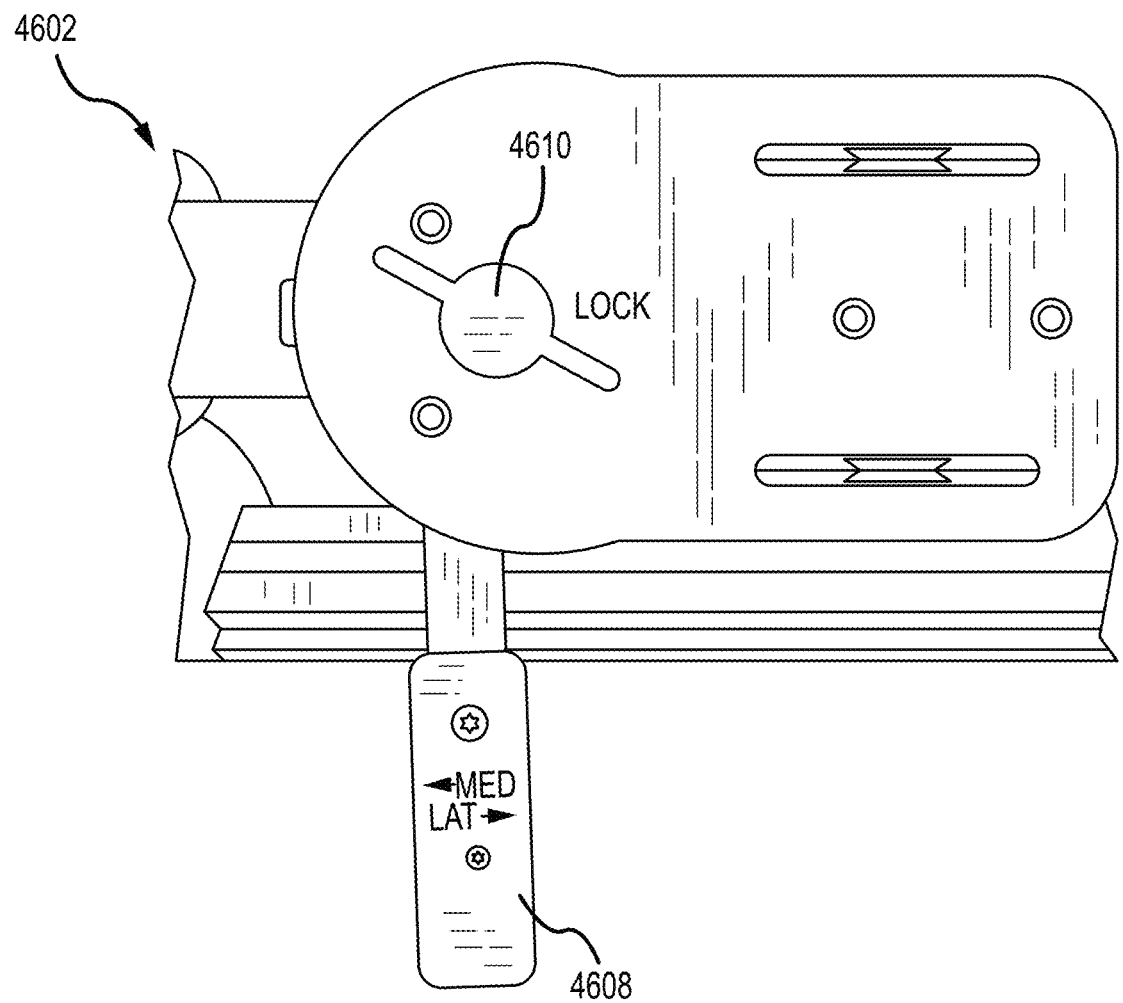
FIGS. 47-49 are detailed views of specific steering controls of the control assembly of FIG. 46.

FIG. 47 is a detailed view of first steering portion 4602, which is also referred to in this disclosure as the primary steering mechanism. When used in conjunction with delivery device 3600, first steering portion 4602 may control steering/bending of distal steerable section 4502 along plane 4506. In at least certain implementations, such movement corresponds to medial and lateral steering movement at the distal end of delivery catheter 3604. As illustrated in FIG. 47, first steering portion 4602 may include a steering lever 4608 or that can be manipulated to steer distal steerable section 4502 and a locking knob 4610 for locking the position of steering lever 4608 and, as a result, the direction of distal steerable section 4502 across plane 4506.

Figure 48:
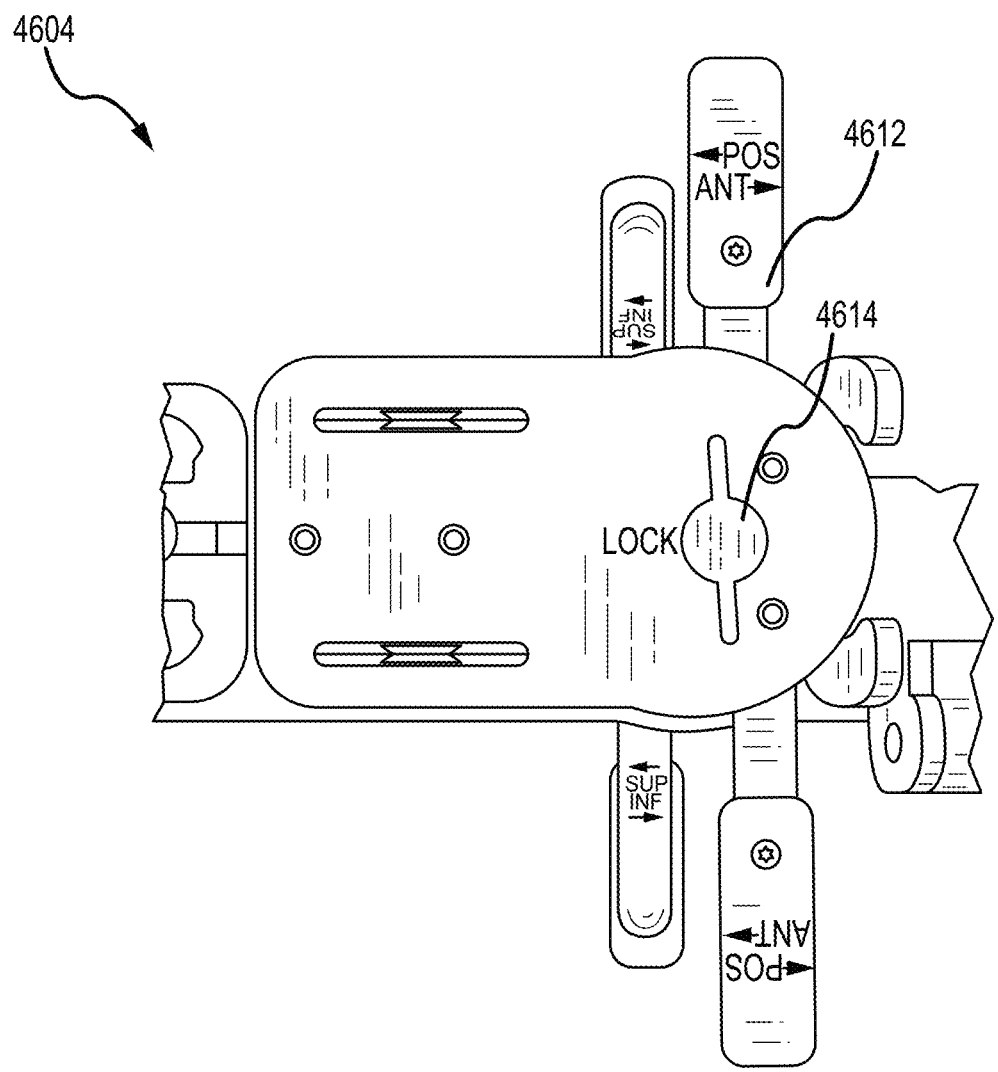

FIG. 48 is a detailed view of second steering portion 4604, which is also referred to in this disclosure as the depth steering mechanism. When used in conjunction with delivery device 3600, second steering portion 4604 may control steering/bending of proximal steerable section 4504 along plane 4508, which is coplanar to plane 4506 (i.e., the plane of movement for distal steerable section 4502) when delivery catheter 3604 is in a neutral configuration. In at least certain implementations, such movement corresponds to superior and inferior steering movement at the distal end of delivery catheter 3604. As illustrated in FIG. 48, second steering portion 4604 may include a steering lever 4612 that can be manipulated to steer proximal steerable section 4504 and a locking knob 4614 for locking the position of steering lever 4612 and, as a result, the direction of proximal steerable section 4504 across plane 4508.

Figure 49:
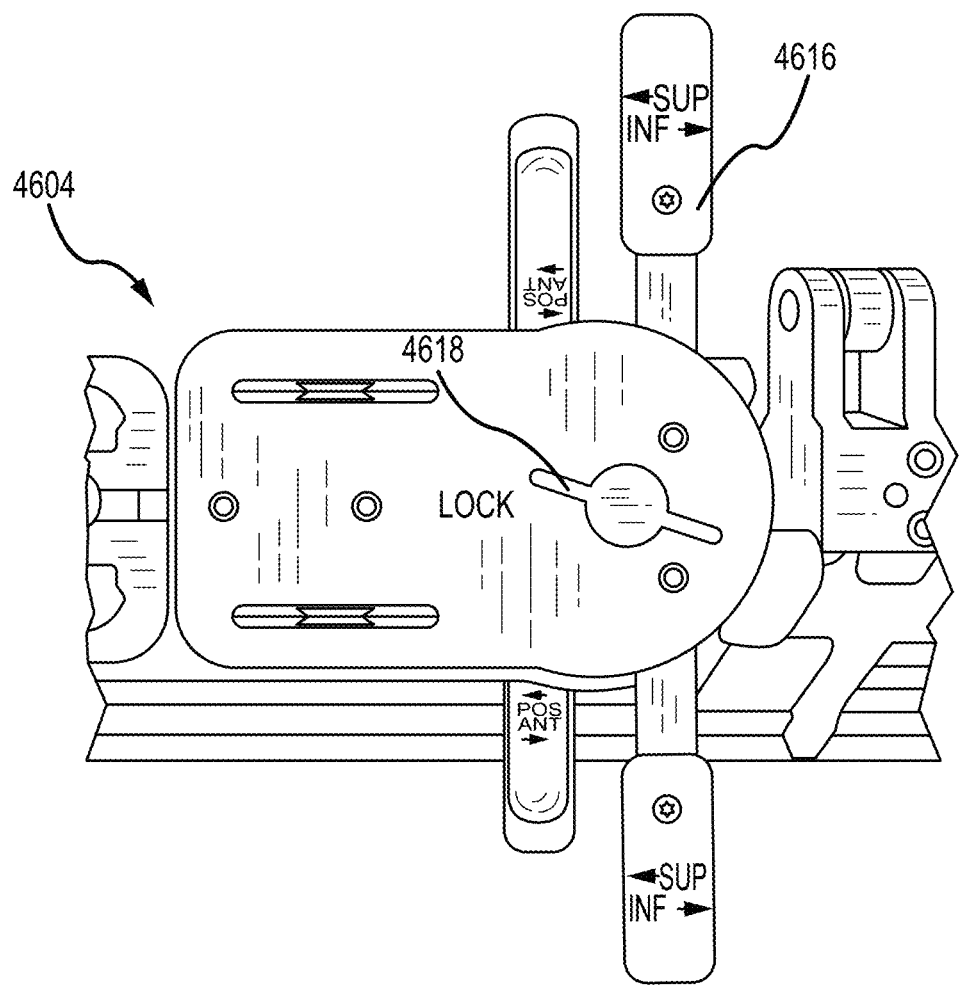

FIG. 49 is a detailed view of third steering portion 4606, which is also referred to in this disclosure as the offset steering mechanism. When used in conjunction with delivery device 3600, third steering portion 4606 may control steering/bending of proximal steerable section 4504 along plane 4510, which is orthogonal to plane 4508. In at least certain implementations, such movement corresponds to posterior and anterior steering movement at the distal end of delivery catheter 3604. As illustrated in FIG. 49, first steering portion 4602 may include a steering lever 4616 that can be manipulated to steer proximal steerable section 4504 and a locking knob 4618 for locking the position of steering lever 4616 and, as a result, the direction of proximal steerable section 4504 across plane 4510.

Steering control assembly 4600 is merely as an example implementation of a control assembly that may be used in conjunction with delivery device 3600 and other delivery devices according to this disclosure. Among other things, the number of steerable sections, the directions and degrees of freedom for each steerable section, the range and direction of each steerable section, and other aspects of steering control assembly 4600 and its functionality may vary. The construction and arrangement of steering control assembly 4600 as illustrated in FIGS. 46-49 are also non-limiting and other arrangement of control assembly components are fully considered within the scope of this disclosure.

XII. Extendable Sheath

Figure 50:
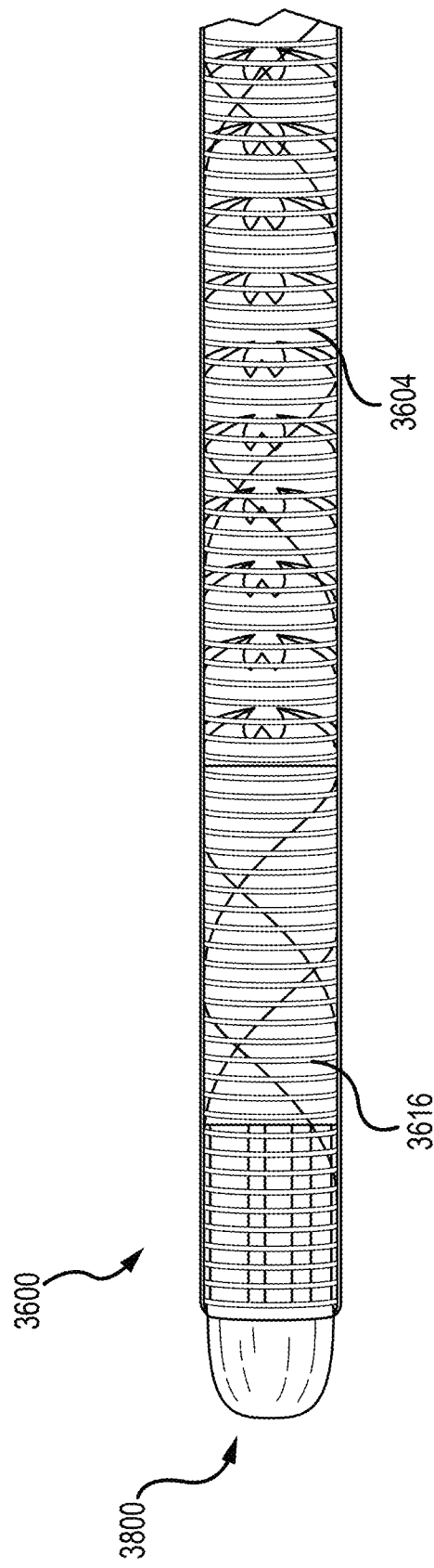
FIG. 50 is an illustration of a delivery device according to this disclosure with an implant coupled to a distal end and a sheath extended over the implant.

During delivery of valve repair implant 3800, implant 3800 is coupled to a distal end of delivery device 3600 and, more specifically to a distal end of delivery catheter 3604 of delivery device 3600. To maintain implant 3800 in a collapsed state and to facilitate navigation of delivery device 3600 and implant 3800 to an implantation location, delivery device 3600 may include a sheath that extends along an exterior surface of delivery catheter 3604. FIG. 50, for example, is an illustration of delivery device 3600 including a sheath 3616 disposed over delivery catheter 3604 and implant 3800.

In at least certain implementations, sheath 3616 is translatable relative to delivery catheter 3604. For example, sheath 3616 may be translatable from an extended configuration to a retracted configuration. In the extended configuration, sheath 3616 may extend sufficiently beyond a distal end of delivery catheter 3604 to cover and at least partially contain implant 3800. Following delivery of implant 3800 to an implantation region (e.g., into the atrium), sheath 3616 may be retracted, thereby permitting deployment of implant 3800. In at least certain implementations, sheath 3616 may also be configured to be distally re-extended following deployment and release of implant 3800. Among other things, such re-extension of sheath 3616 enables sheathing of the distal portion of delivery device 3600 for retraction and removal from the patient.

Figure 51:
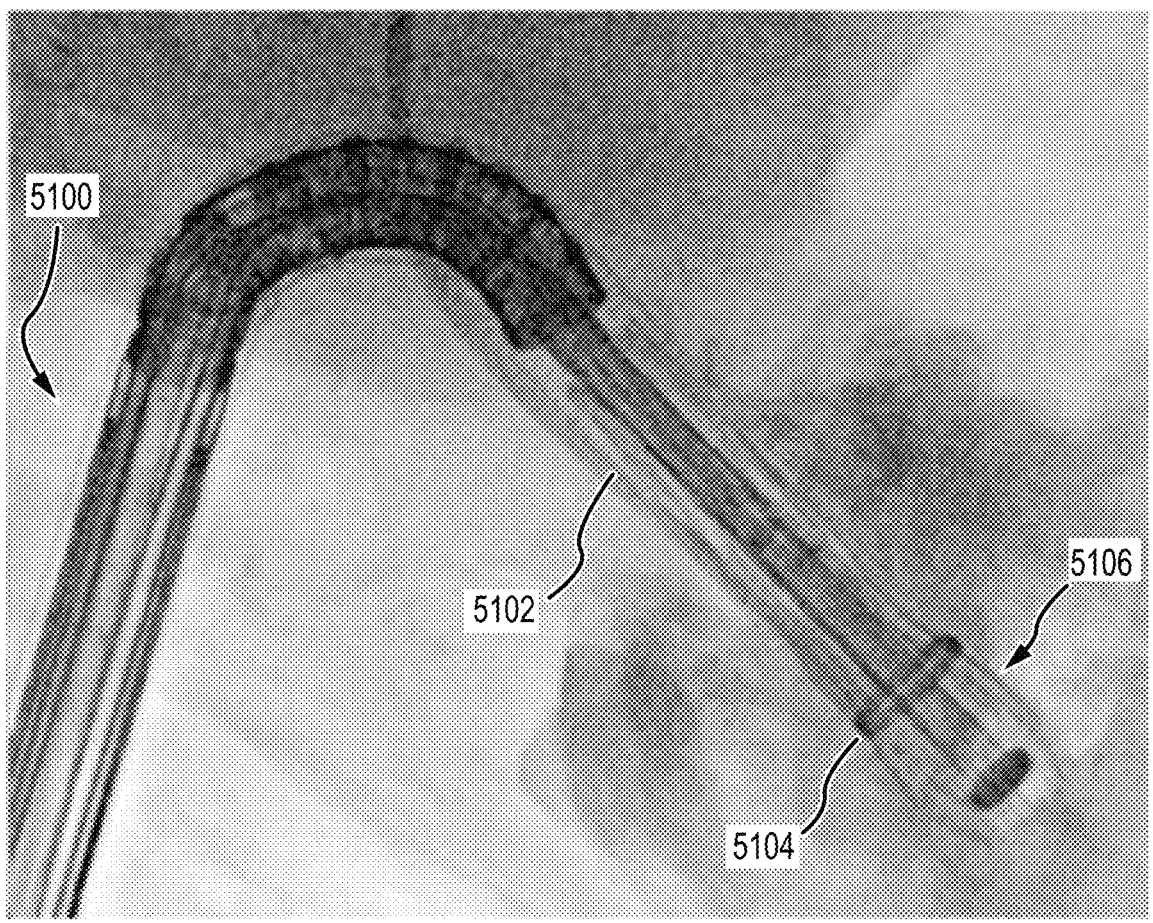
FIG. 51 is a radiographic image of a delivery device according to this disclosure including a sheath with an embedded radiopaque marker.

In at least certain implementations, sheath 3616 may include one or more embedded radiopaque markers. For example, FIG. 51 is a radiographic image of a delivery tool 5100 according to this disclosure. As shown, delivery tool 5100 includes a sheath 5102, which further includes a radiopaque marker in the form of a band 5104 (although other radiopaque markers, such as beads, strips, coils, and the like are also contemplated) that is embedded within a distal portion 5106 of sheath 5102.

Figure 52:
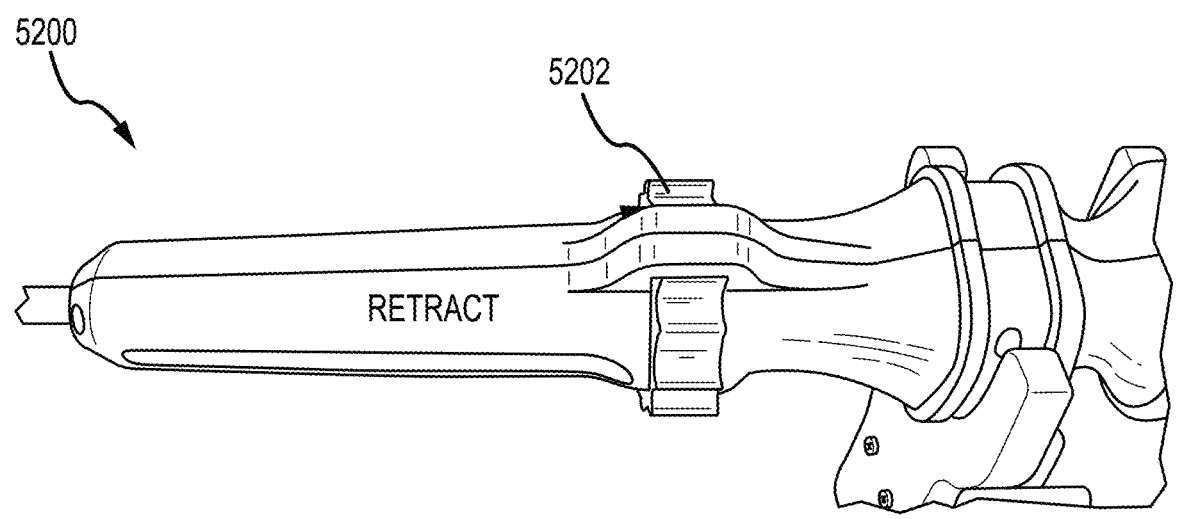
FIGS. 52 and 53 are detailed views of a control assembly for selectively extending and retracting a sheath of the delivery device of FIG. 36.
Figure 53:
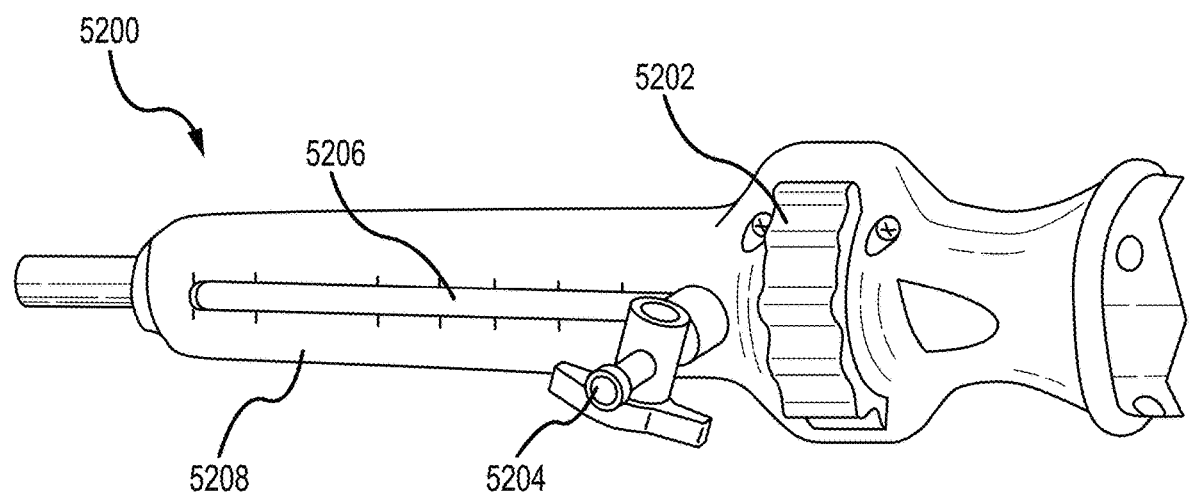

FIGS. 52 and 53 are illustrations of a portion of a sheath control assembly 5200 illustrating an example implementation of sheath controls that may be used in conjunction with delivery device 3600. Sheath control assembly 5200 includes a knob 5202 which can be rotated to extend and retract sheath 3616; however, knob 5202 may be substituted with a lever, slide, or similar control element in other implementations. As shown in FIG. 53, sheath control assembly 5200 may further include a flush port 5204 in communication with an internal volume of sheath 3616 to facilitate flushing of sheath 3616. Sheath control assembly 5200 may further include a window 5206 and indicators 5208 or similar markings to communicate the position of sheath 3616. For example, a proximal end of sheath 3616 may be visible through window 5206 and indicators 5208 may be in the form of lines, grooves, marks, etc. disposed adjacent window 5206 with which the proximal end of sheath 3616 may align to indicate the position of sheath 3616.

In at least certain implementations, sheath 3616 and sheath control assembly 5200 may be configured to permit from and including about 5 cm to and including about 12 cm of travel. For example, in at least one implementation, sheath 3616 may be retractable up to 8 cm from a fully extended configuration. As shown, sheath control assembly 5200 does not include a locking mechanism for locking the position of sheath 3616; however, in other implementations, sheath control assembly 5200 may include a locking mechanism (e.g., a knob, clamp, pin, etc.) for locking the position of sheath 3616, e.g., by positively engaging a portion of sheath 3616 within sheath control assembly 5200 or by preventing manipulation of the control element of sheath control assembly 5200 for extending and retracting sheath 3616.

XIII. Implant Extension and Retraction

During delivery of implant 3800, implant 3800 is maintained in a collapsed configuration and may also be at least partially covered by sheath 3616. Implant 3800 may also be partially or entirely disposed within delivery catheter 3604 during delivery. Accordingly, following delivery into the patient heart and prior to final placement, implant 3800 may need to be deployed from delivery catheter 3604. In addition to retracting sheath 3616, deployment of implant 3800 may include distally extending implant 3800 from delivery catheter 3604. Once clear of delivery catheter 3604 and sheath 3616, implant 3800 may be selectively expanded, collapsed, and located for implantation.

Due to the shape and construction of implant 3800, the total length of implant 3800 when collapsed may be substantially longer than the total length of implant 3800 when expanded. To facilitate improved location and implantation of implant 3800, delivery devices according to this disclosure may include a mechanism for extending implant 3800 from delivery catheter 3604 to a first extent for deployment. Following deployment, the mechanism may enable at least partial de-extension/retraction of implant 3800 to reduce the overall combined length of distal portion 3602 of delivery device 3600 and implant 3800. Given the confined space of the atria, such reduction in the combined length of delivery device 3600 and implant 3800 can provide substantially increased maneuverability and control of delivery device 3600 and implant 3800, leading to faster and more accurate implant placement.

In certain implementations, extension and de-extension/retraction of implant 3800 relative to delivery catheter 3604 may be achieved by extending and retracting extension member 3606 relative to delivery catheter 3604. As discussed in the context of FIGS. 36-38, extension member 3606 extends distally from delivery catheter 3604 and supports the distal control arms of the control arm assemblies. During delivery, implant 3800 is attached to delivery device 3600 by coupling implant 3800 to the control arm assemblies. Accordingly, given that the control arm assemblies are coupled to extension member 3606, extension and retraction of extension member 3606 relative to delivery catheter 3604 also results in extension and retraction of implant 3800 relative to delivery catheter 3604 when implant 3800 is attached to delivery device 3600.

Figure 54B:
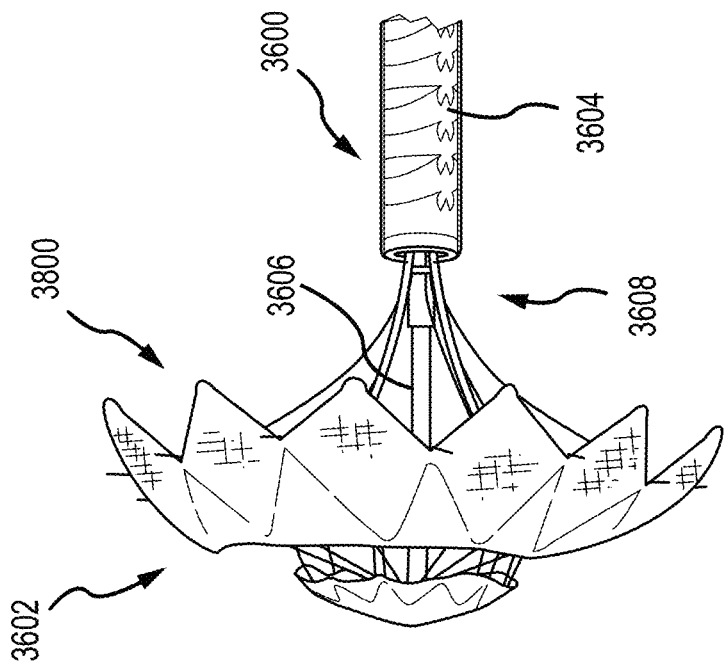
FIGS. 54A and 54B are illustrations of the distal end of the delivery device of FIG. 36 including a deployed implant in a fully extended and a de-extended/retracted configuration, respectively.
Figure 54A:
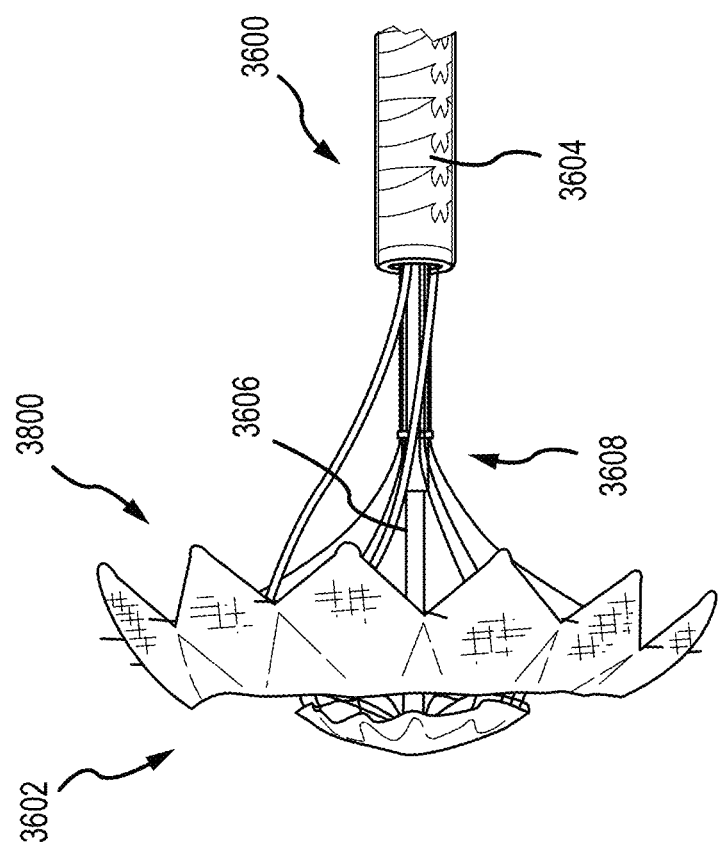

FIGS. 54A and 54B are illustrations of delivery device 3600 with implant 3800 attached. Specifically, FIG. 54A illustrates delivery device 3600 and implant 3800 in a fully extended configuration. As previously noted, the fully extended configuration may be used to facilitate initial deployment of implant 3800, e.g., by fully clearing implant 3800 from sheath 3616 (not shown) and delivery catheter 3604. To achieve the fully extended configuration, following navigation of distal portion 3602 of delivery device 3600 and implant 3800 into the atrium, delivery device 3600 may be actuated to distally extend extension member 3606 relative to delivery catheter 3604, thereby enabling deployment and expansion of implant 3800. Following deployment and expansion, extension member 3606 may be at least partially retracted relative to delivery catheter 3604, resulting in the retracted/de-extended configuration of FIG. 45B. In at least certain implementations, extension member 3606 may be configured to undergo from and including about 15 mm to and including about 25 mm of travel relative to delivery catheter 3604 with possible retraction/de-extension from and including about 50% to and including about 80% of the total travel distance of extension member 3606. For example, in one specific implementation, extension member 3606 may be configured to have approximately 20 mm of total travel with at least 12 mm of retraction/de-extension available following deployment of implant 3800.

Figure 55:
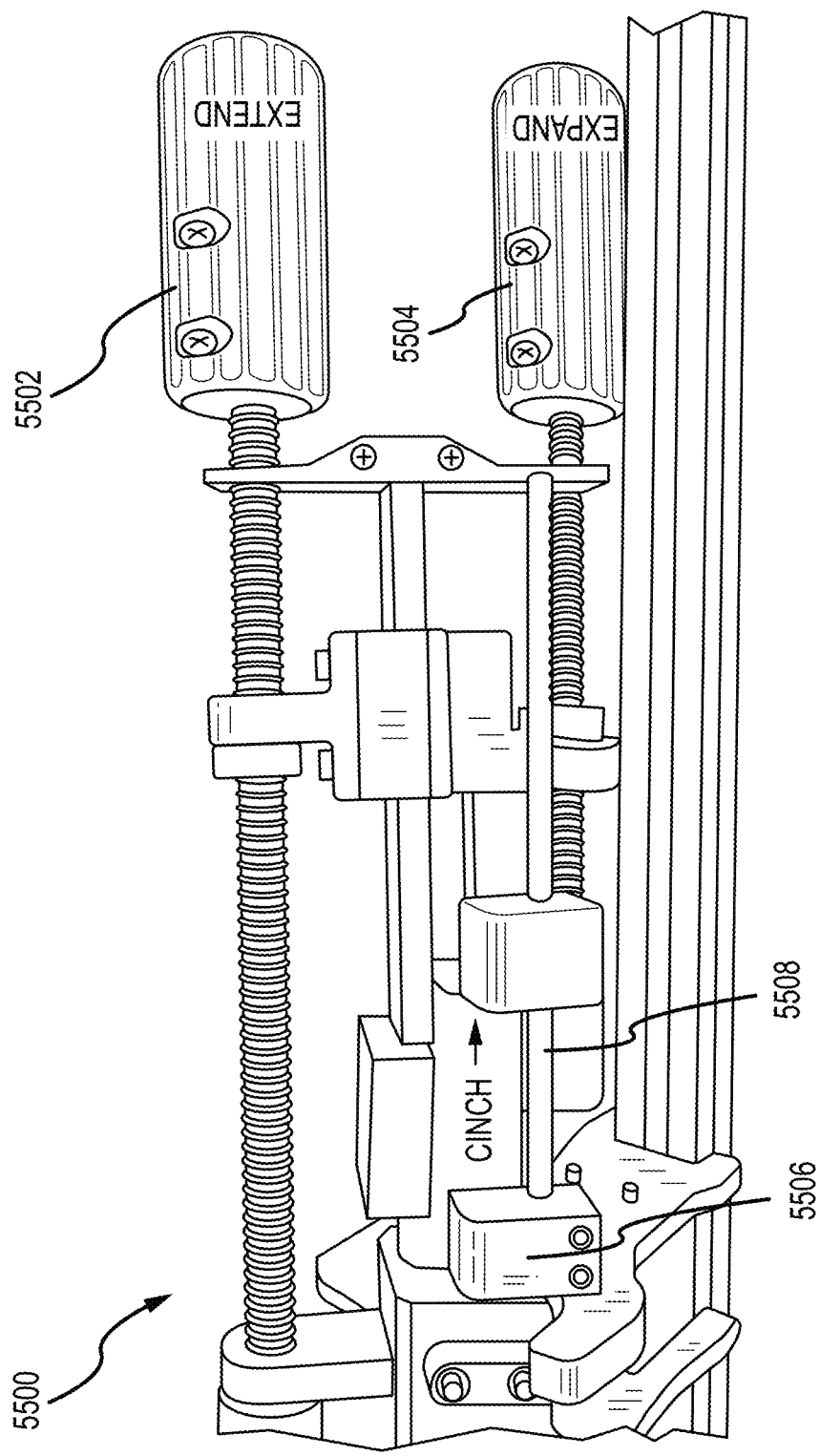
FIG. 55 is an illustration of a control assembly for use with the delivery device of FIG. 36, the control assembly including controls for each of extending/retracting an extension member, expanding and collapsing a control arm assembly, and controlling tension of a cinch line.

FIG. 55 is an illustration of a portion of a deployment control assembly 5500 illustrating an example implementation of extension/de-extension controls that may be used in conjunction with delivery device 3600. Deployment control assembly 5500 includes an extension handle 5502 which can be rotated to extend and retract extension member 3606; however, extension handle 5502 may be substituted with a lever, slide, knob, or similar control element in other implementations.

XIV. Control Arm Assembly and Cinch Line Routing

As previously discussed, control arm assembly 3608 enables selective expansion and collapse of implant 3800 during deployment and implantation of implant 3800. To do so, control arm assembly 3608 includes multiple control arm pairs with each control arm pair including a proximal arm and a distal arm. Each proximal arm is shaped, biased, diverted, or otherwise configured such that when the proximal arm extends distally from delivery catheter 3604 the proximal at least partially extends in a lateral/medial direction relative to longitudinal axis 3603 of delivery device 3600. A distal portion of each proximal arm is coupled to a proximal portion of its respective distal arm such that the distal arm similarly extends in a lateral/medial direction based on the degree of extension of the proximal arm. The distal arm generally provides support and stability to the proximal arm; however, in certain implementations, the proximal portion of the distal arm may also include a ring, a loop, an aperture, or similar feature through which cinch line 3614 may pass to couple implant 3800 to delivery device 3600.

Figure 56:
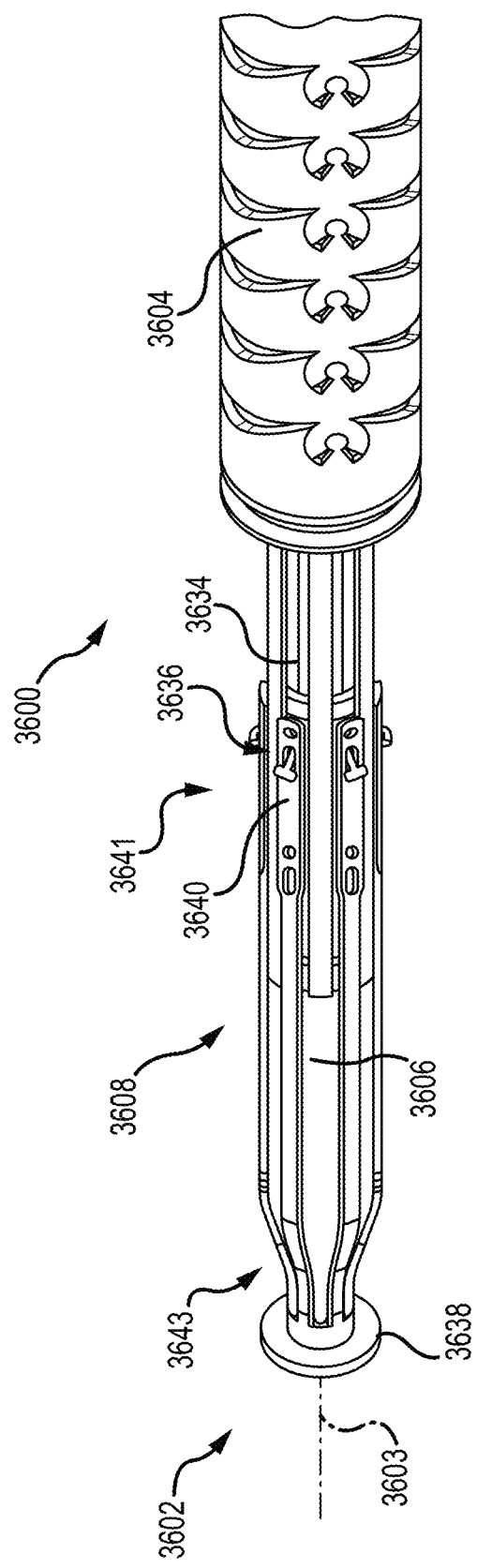
FIG. 56 is a side view of a distal portion of the delivery device of FIG. 36 with a control arm assembly in a collapsed state.
Figure 57:
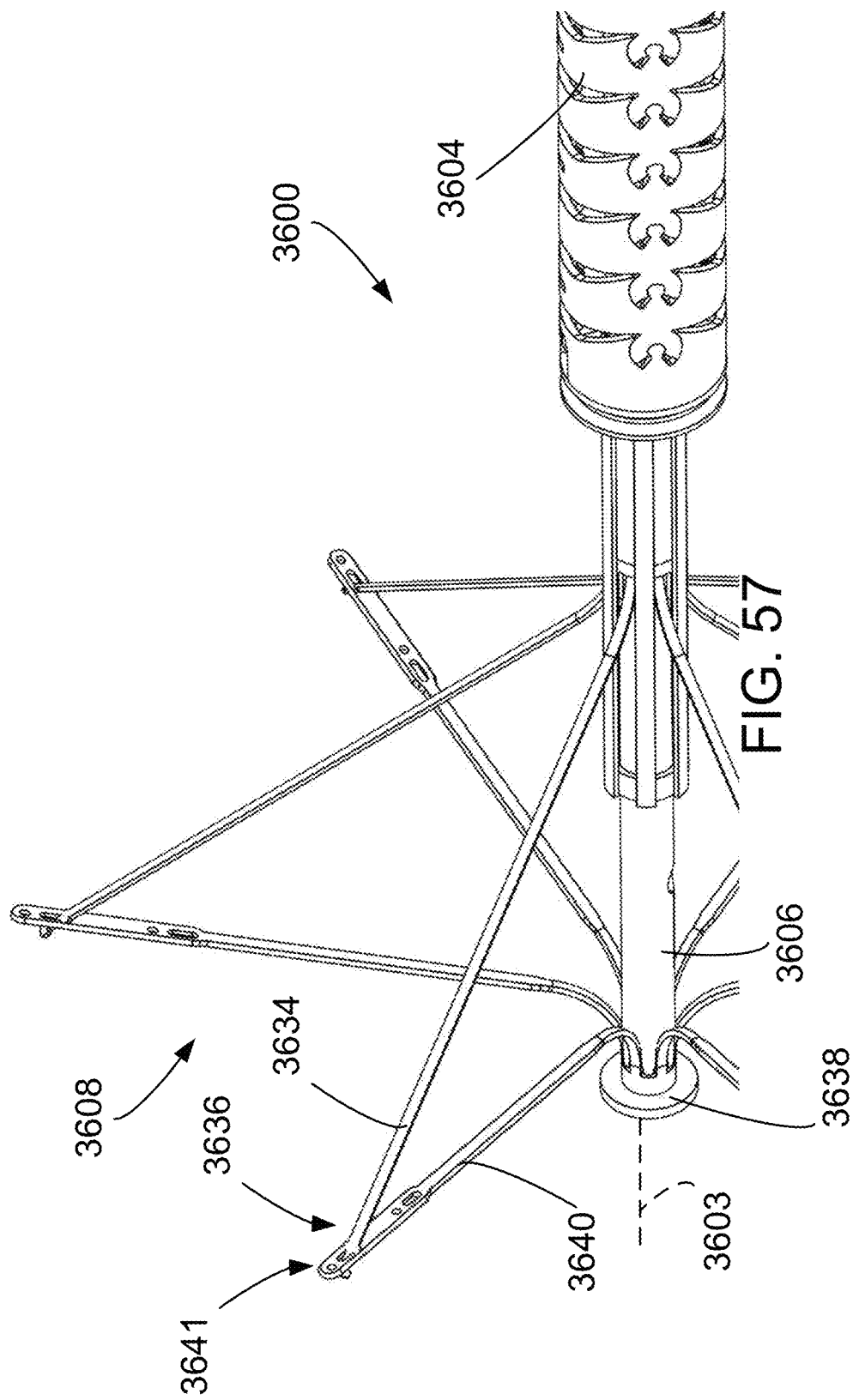
FIG. 57 is a detailed side view of a distal portion of the delivery device of FIG. 36 with the control arm assembly in an expanded state.

FIGS. 56 and 57 illustrate distal portion 3602 of delivery device 3600 with control arm assembly 3608 in a collapsed and expanded state, respectively. The following discussion describes operation of control arm assembly 3608 by referring primarily to proximal arm 3634 and distal arm 3640. Such references are intended for clarity and conciseness only. Unless otherwise specified, references to proximal arm 3634 and distal arm 3640 should be considered to apply generally to the other proximal and distal arms of control arm assembly 3608.

As illustrated in FIG. 56, when in the collapsed state, proximal arm 3634 and distal arm 3640 lie substantially flat and parallel to longitudinal axis 3603 of delivery device 3600. As control arm assembly 3608 is expanded, e.g., by pushing proximal portion 3630 of control arm assembly 3608 with control arm shaft 3642 as discussed in the context of FIGS. 42 and 43, distal portion 3636 of proximal arm 3634 travels in a partially lateral direction. In certain implementations, lateral travel of distal portion 3636 results from proximal arm 3634 having a shape or being biased in an outwardly curved direction. Alternatively, or in addition, delivery device 3600 may include a diverter or similar structural element (such as diverter 3628 illustrated in FIG. 41) that directs proximal arm 3634 in a lateral direction as proximal arm 3634 extends from delivery catheter 3604, as shown in FIG. 57.

Due to the coupling of distal portion 3636 of proximal arm 3634 with a proximal portion 3641 of distal arm 3640, extension of proximal arm 3634 from delivery catheter 3604 applies a lateral force to proximal portion 3641 of distal arm 3640. In the implementation shown in FIGS. 56 and 57, a distal portion 3643 of distal arm 3640 is fixed to distal cap 3638 of extension member 3606. Accordingly, as a lateral force is applied to proximal portion 3641 of distal arm 3640, distal portion 3643 of distal arm 3640 bends outwardly. In other implementations, distal arm 3640 may instead be coupled to distal cap 3638 by a hinge or similar movable joint that permits lateral movement of proximal portion 3641 of distal arm 3640 without substantial bending.

Collapse of control arm assembly 3608 may be achieved by retracting proximal portion 3630 of control arm assembly 3608, which in turn causes retraction of proximal arm 3634 into delivery catheter 3604. Due again to the coupling of distal portion 3636 of proximal arm 3634 with a proximal portion 3641 of distal arm 3640, retraction of proximal arm 3634 into delivery catheter 3604 applies a medial force to proximal portion 3641 or distal arm 3640, thereby causing distal arm 3640 to return to a collapsed configuration.

Figure 58:
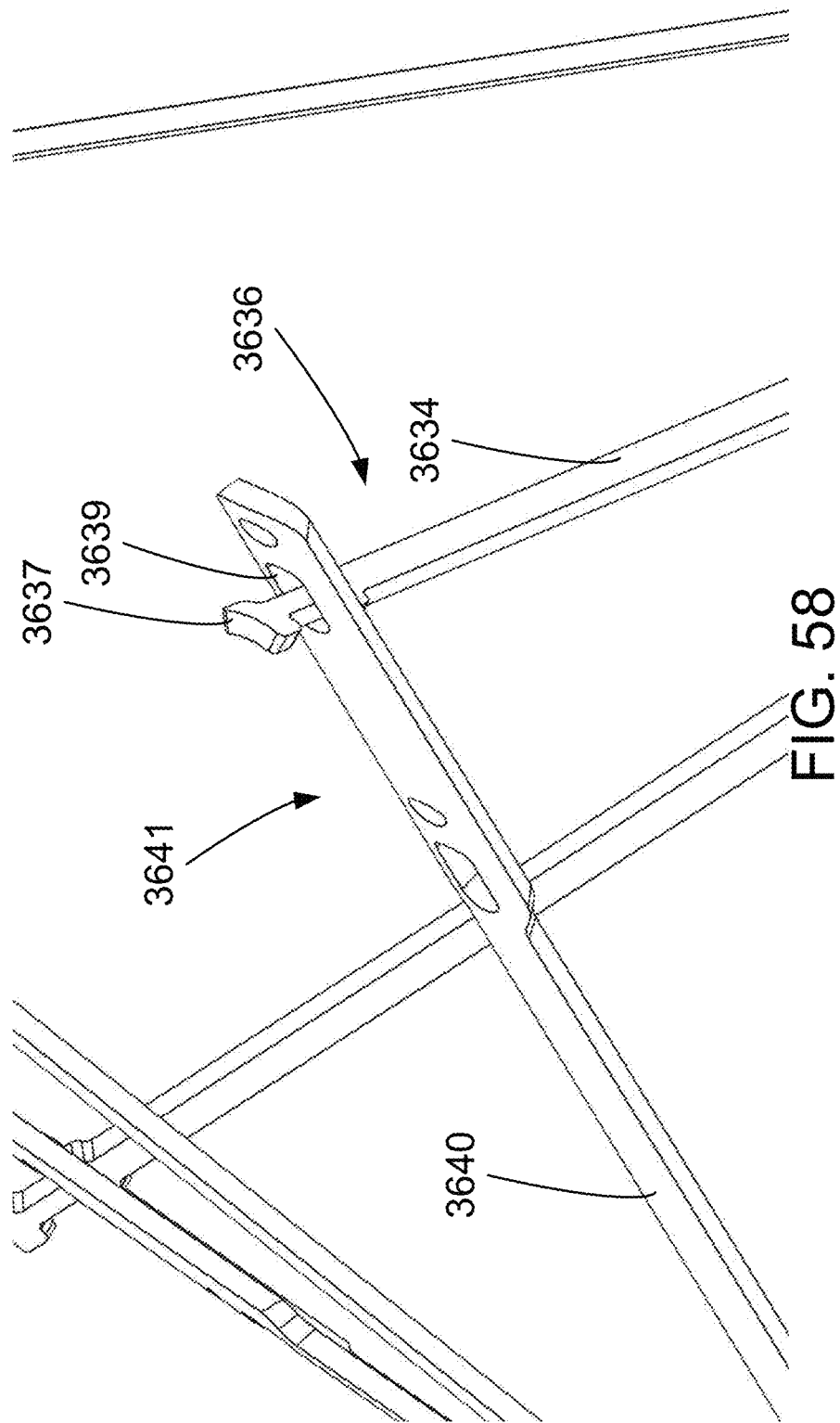
FIG. 58 is a detailed view of the delivery device showing coupling of a proximal and distal arm of the control arm assembly.

FIG. 58 illustrates an example coupling arrangement of proximal arm 3634 with distal arm 3640 in further detail. As illustrated, distal portion 3636 of proximal arm 3634 may include a first feature, e.g., a protrusion 3637, shaped to be inserted into and retained by a second feature, e.g., an aperture 3639 of distal arm 3640. For example, FIG. 58 shows protrusion 3637 as being T-, dogbone-, or barbell-shaped and aperture 3639 as an ovate slot. Accordingly, protrusion 3637 may be rotated 90 degrees, inserted through aperture 3639, and unrotated to cause protrusion 3637 to be retained by aperture 3639 and coupling distal portion 3636 to distal arm 3640. In other implementations, the protrusion and aperture may be reversed such that a protrusion of distal arm 3640 extends through and is retained by an aperture of proximal arm 3634. This disclosure contemplates other coupling arrangements of proximal arm 3634 with distal arm 3640 and notes that any coupling that permits the necessary movement of proximal arm 3634 relative to distal arm 3640 for expansion of control arm assembly 3608 may be used instead of the specific coupling arrangement illustrated in FIG. 58.

Figure 59:
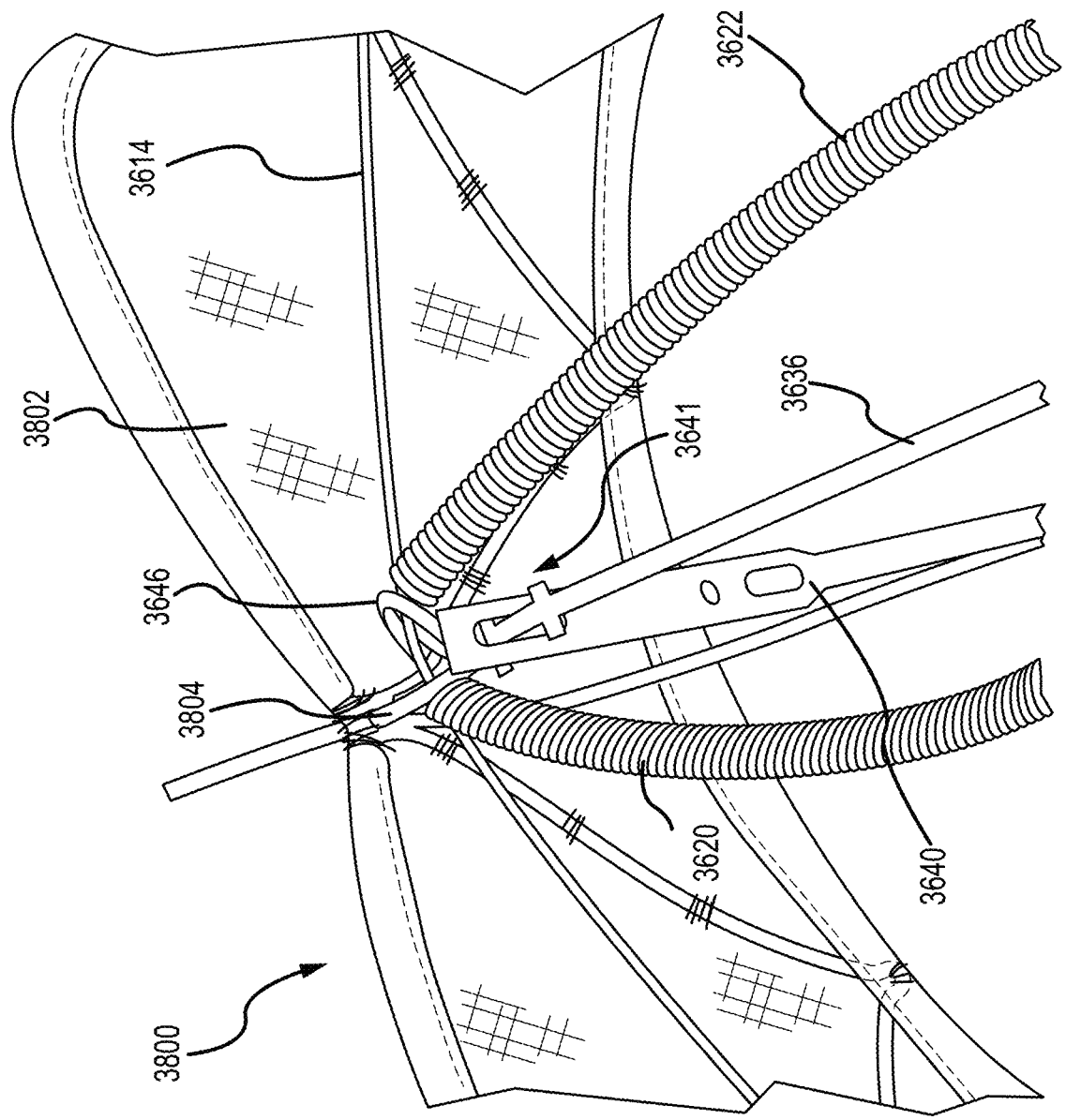
FIG. 59 is a detailed view illustrating coupling of an implant to the control arm assembly via a cinch line.

FIG. 59 is a detailed view of coupling between control arm assembly 3608 and implant 3800. As previously discussed, coupling of delivery device 3600 to implant 3800 is by cinch line 3614, which forms a loop through delivery device 3600 and about an inner circumference of implant 3800. More specifically, cinch line 3614 extends through delivery catheter 3604 (e.g., through cinch line tube 3620). Cinch line 3614 is then routed through apertures extending around each of control arm assembly 3608 and implant 3800. Cinch line 3614 is then rerouted back through delivery catheter 3604 (e.g., through cinch line tube 3622) to a proximal end of delivery catheter 3604.

In certain implementations, the apertures of implant 3800 may be in the form of hoops, loops, or rings (e.g., ring 3804) extending around an inner surface 3802 of implant 3800.

The apertures of control arm assembly 3608 may similarly be in the form of hoops, loops, or rings (e.g., ring 3646) coupled to control arm assembly 3608. For example, in the implementation of FIG. 58, ring 3646 is attached to and extends from proximal portion 3641 of distal arm 3640. In other implementations, distal arm 3640 or distal portion 3636 may define and include an integrally formed hole, port, or similar opening that functions as the aperture through which cinch line 3614 extends.

By routing cinch line 3614 through each of the apertures of control arm assembly 3608 and each of the apertures of implant 3800, implant 3800 can be coupled to delivery device 3600. Additionally, such an arrangement also enables cinch line 3614 to provide additional control and uniformity when expanding and collapsing implant 3800 during deployment and implantation. For example, given that cinch line 3614 extends around the circumference of implant 3800, applying tension to cinch line 3614 results in a distributed medial pulling force about implant 3800. As implant 3800 is collapsed, this distributed medial force encourages implant 3800 to collapse uniformly, thereby improving control and predictability during collapse of implant 3800. The distributed medial force may also act as a counterforce when expanding implant 3800, which, again, encourages implant 3800 to expand uniformly and improving control and predictability of implant expansion.

In certain implementations of this disclosure, delivery device 3600 may include a control assembly including control elements for adjusting expansion and collapse of control arm assembly 3608 and operation of cinch line 3614. Referring back to FIG. 55, for example, deployment control assembly 5500 includes an expansion handle 5504 that can be rotated to selectively expand and collapse implant 3800 when implant 3800 is coupled to control arm assembly 3608. For example, rotation of expansion handle 5504 may translate control arm shaft 3642 relative to delivery catheter 3604. As previously noted, such translation may push or pull proximal portion 3630 of control arm assembly 3608, thereby causing expansion of control arm assembly 3608. In other implementations, expansion handle 5504 may be replaced with other control elements, such as a lever, knob, or similar component for selectively translating control arm shaft 3642 relative to delivery catheter 3604.

Deployment control assembly 5500 further includes a tensioner 5506 for controlling tension on cinch line 3614. When assembled, tensioner 5506 couples to a first end of cinch line 3614 while a second end of cinch line 3614 may be fixed at another point on deployment control assembly 5500. Tensioner 5506 may be selectively movable, e.g., along a rail 5508, such that by proximally translating tensioner 5506, tension on cinch line 3614 can be increased. Conversely, by distally translating tensioner 5506, tension can be reduced.

In at least certain implementations, implant 3800 is released from delivery device 3600 by cutting cinch line 3614 at deployment control assembly 5500 and subsequently pulling cinch line 3614 from delivery catheter 3604.

XV. Control Assembly and Mounting

Previous sections of this disclosure describe alternative configurations for a control assembly of delivery device 3600. In general, such control assemblies provide various control elements for actuating various components of delivery device 3600. Among other things, such control elements include those for extending and retracting sheath 3616, steering delivery catheter 3604, extending and retracting extension member 3606, expanding and collapsing control arm assembly 3608, and controlling tension on cinch line 3614.

Figure 60:
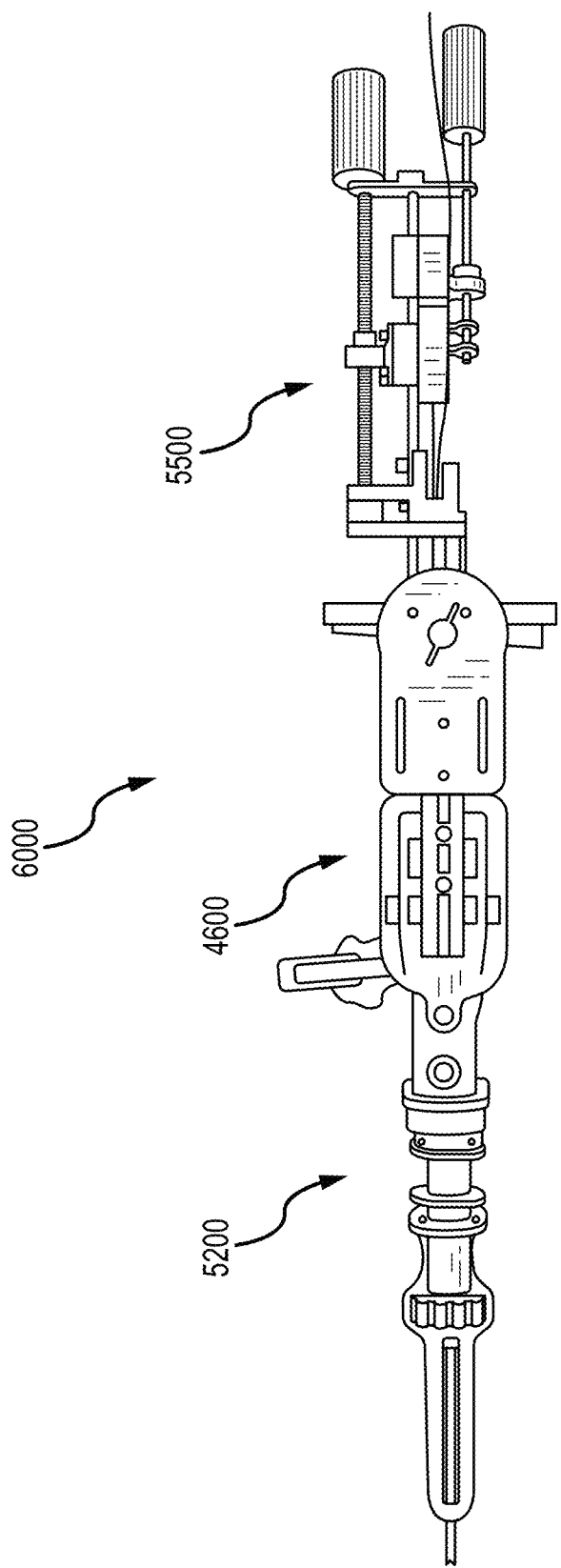
FIG. 60 is an illustration of a control assembly of a delivery device according to the present disclosure.

FIG. 60 is a proximal portion of delivery device 3600 and, in particular, a control assembly 6000 of delivery device 3600. As shown, control assembly 6000 combines various control assembly sections previously discussed in this disclosure. For example, control assembly 6000 combines (from most distal to most proximal) each of sheath control assembly 5200, steering control assembly 4600, and deployment control assembly 5500. Notably, control assembly 6000 is intended only as an example control assembly for use with delivery devices according to this disclosure and that provides various functions for delivering, deploying, and implanting valve repair implants. While not specifically illustrated other implementations of control assemblies may include alternative arrangements of control assembly sections and additional structural elements (e.g., an outer housing, grips, etc.), among other things.

Figure 61:
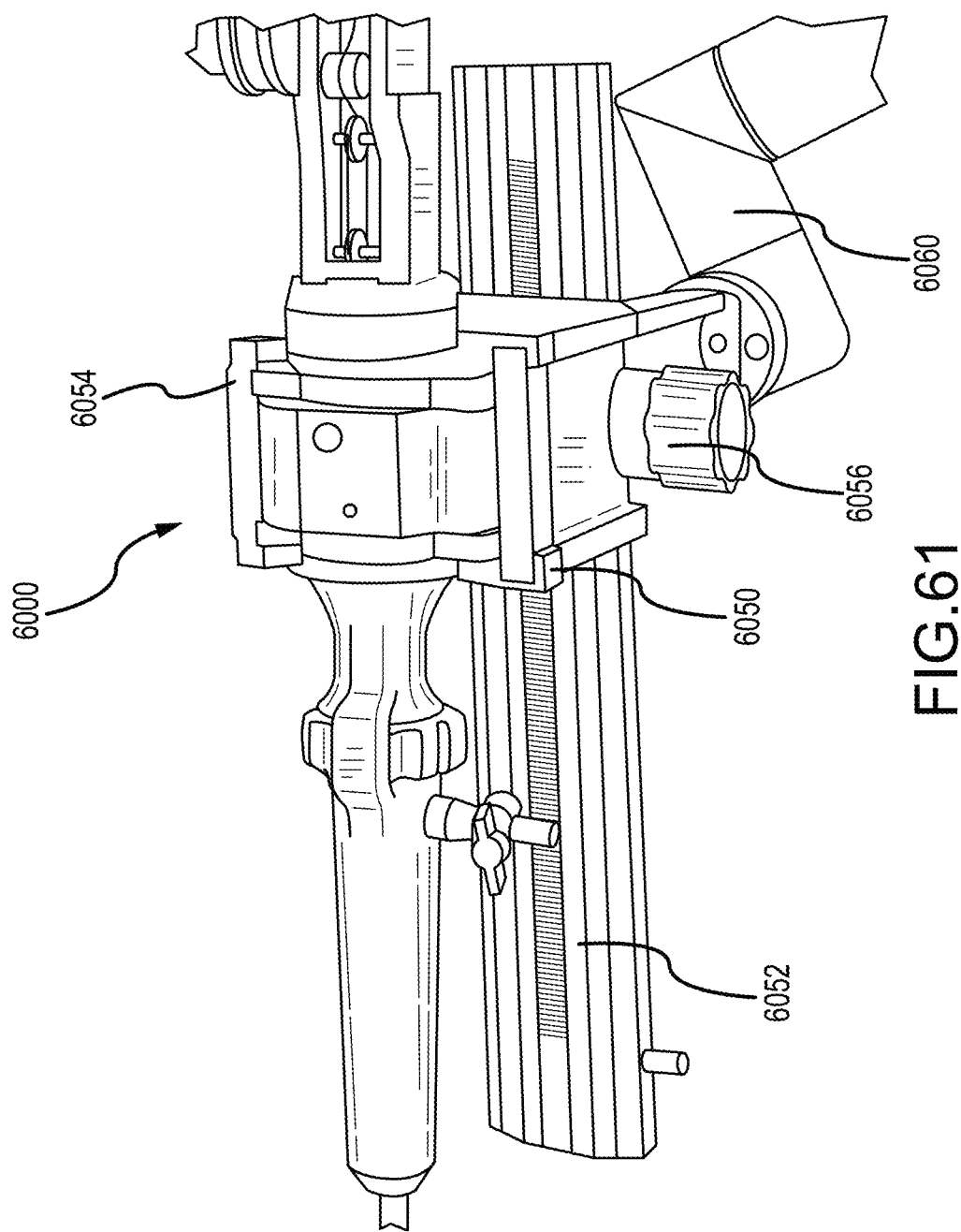
FIG. 61 is an illustration of a control assembly and mount for use with delivery devices of the present disclosure.

FIG. 61 is an example mounting arrangement for delivery device 3600, including control assembly 6000. In the example configuration, control assembly 6000 is received within a mount 6050 coupled to and supported by a rail 6052. Rail 6052, in turn, is coupled to an articulating arm 6060, which may be fixed to a bed, table, support stand, or similar stable structure.

Although other mounting configurations are contemplated, the configuration illustrated in FIG. 61 is advantageous in that it provides two additional degrees of freedom for delivery device 3600. First, mount 6050 includes a rotating cradle 6054 that receives delivery device 3600. Second, mount 6050 is coupled to rail 6052 by a stepper-type mount such that insertion of delivery device 3600 is controllable by a knob 6056. Mount 6050 may further include additional controls for locking each of rotating cradle 6054 and the position of mount 6050 on rail 6052.

XVI. Example Implantation Process

Figure 62:
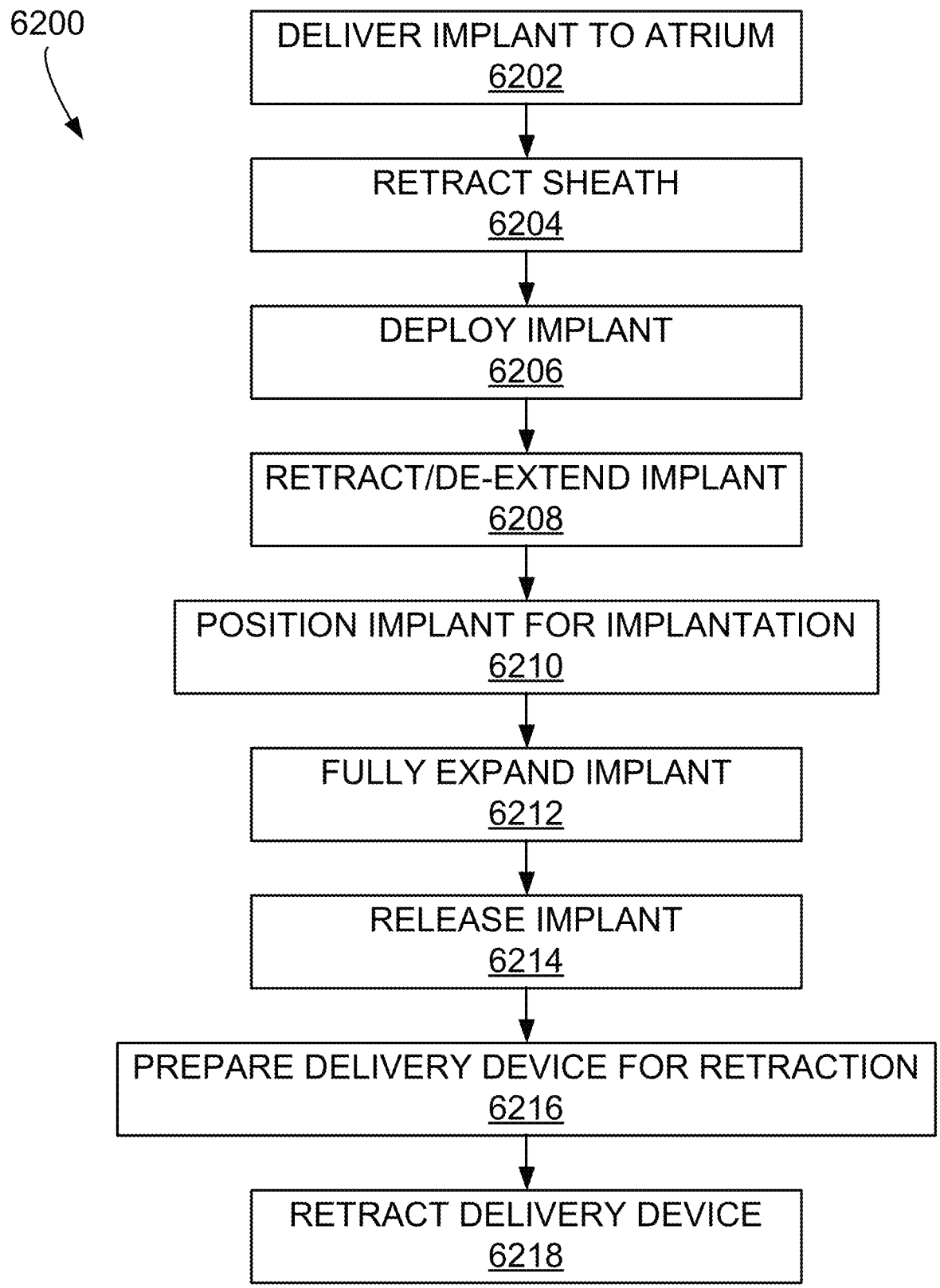
FIG. 62 is a flow chart illustrating a method of implanting a valve repair implant using a delivery device according to this disclosure.

To provide additional detail and context for the various features described in the preceding sections, FIG. 62 is a block diagram illustrating a method 6200 for implanting implant 3800 using delivery device 3600.

At step 6202, implant 3800 is delivered to a patient atrium, e.g., via an antegrade percutaneous route (e.g., a trans-femoral or trans-jugular route). During delivery, implant 3800 is coupled to a distal end of delivery device 3600 by cinch line 3614 with sheath 3616 extending over a distal end of delivery device 3600, including at least a portion of implant 3800. As previously discussed, coupling of implant 3800 to delivery device 3600 may include routing cinch line 3614 through a first set of apertures disposed around an interior circumference of implant 3800, such as a series of loops or rings distributed about the interior circumference of implant 3800. Cinch line 3614 is further routed through a second set of apertures of control arm assembly 3608, thereby coupling implant 3800 to control arm assembly 3608 using cinch line 3614. In at least some implementations, the apertures of control arm assembly 3608 may be rings coupled to proximal portions of the distal control arms of control arm assembly 3608. For example, FIG. 59 shows ring 3646 coupled to proximal portion 3641 of distal arm 3640.

In at least some implementations, navigating delivery device 3600 and implant 3800 to the implantation site may include routing delivery device 3600 along a guidewire previously inserted into the patient and extending to the atrium.

Step 6204 includes retracting sheath 3616 to facilitate subsequent deployment of implant 3800. As discussed in previous sections, retracting sheath 3616 may include manipulating a control of control assembly 6000 to proximally translate sheath 3616 relative to delivery catheter 3604.

Step 6206 includes deploying implant 3800. Deploying implant 3800 generally refers to the process of clearing implant 3800 from sheath 3616 and delivery catheter 3604 such that implant 3800 can be freely expanded, collapsed, and positioned for implantation. Deploying implant 3800 may include partially expanding implant 3800, e.g., by expanding control arm assembly 3608. For example, a user may partially expand control arm assembly 3608 by rotating a corresponding handle or knob of control assembly 6000. Deploying implant 3800 may also include at least partially extending implant 3800 distally relative to delivery catheter 3604. In at least some implementations, extending implant 3800 may include distally extending extension member 3606 relative to delivery catheter 3604 using a corresponding control of control assembly 6000.

Step 6208 includes retracting/de-extending implant 3800 relative to delivery catheter 3604 following at least partial expansion of implant 3800. As previously discussed, in certain implementations, initial deployment of implant 3800 may require that implant 3800 extend to a first distal extent beyond delivery catheter 3604, e.g., to permit clearance of implant 3800 from sheath 3616 and delivery catheter 3604. Once deployed, however, implant 3800 may be longitudinally retracted/de-extended to make the combination of the distal portion of delivery device 3600 and implant 3800 more compact. Among other things, the more compact configuration improves maneuverability of implant 3800 within the heart, thereby increasing the speed and accuracy with which implant 3800 can be positioned and implanted.

Step 6210 includes positioning implant 3800 for implantation. In at least certain implementations, positioning implant 3800 may include positioning implant 3800 such that an occlusive element of implant 3800 is at the level of the native leaflets or otherwise positioned to contact and interact with the native leaflets. During certain procedures, positioning implant 3800 may also include additional expanding, collapsing, and/or moving of implant 3800 to achieve proper positioning. Accordingly, step 6210 may include one or more of expanding/collapsing control arm assembly 3608, extending/retracting extension member 3606, steering delivery catheter 3604, or any other articulation of delivery device 3600 necessary to properly position implant 3800 within the heart.

Step 6212 includes fully expanding implant 3800 once implant 3800 is in position for implantation. Fully expanding implant 3800 may include expanding control arm assembly 3608 to or near its fullest extent. Notably, in most applications and when implant 3800 is properly positioned relative to the cardiac valve, such expansion will cause implant 3800 to interfere with and engage cardiac tissue. For example, implant 3800 may include outwardly protruding prongs shaped and positioned to engage tissue adjacent the valve.

Step 6214 includes releasing implant 3800 from delivery device 3600. Releasing implant 3800 from delivery device 3600 includes decoupling implant 3800 from delivery device 3600 by removing cinch line 3614. For example, cinch line 3614 may be cut at control assembly 6000 and subsequently pulled from delivery device 3600. During pulling, the cut end of cinch line 3614 passes through the apertures of control arm assembly 3608 and implant 3800, resulting in implant 3800 being decoupled from control arm assembly 3608.

Step 6216 includes preparing delivery device 3600 for retraction and removal from the patient. In general, preparation of delivery device 3600 includes collapsing delivery device 3600 to its fullest extent and sheathing distal portion 3602 of delivery device 3600. For example, preparing delivery device 3600 for retraction may include fully collapsing control arm assembly 3608, retracting/de-extending extension member 3606, and re-extending cinch line 3614 over the distal end of delivery device 3600.

Step 6218 includes retracting delivery catheter 3604 from the patient, substantially completing the implantation process.

XVII. Additional Alternative Implant and Occluder Designs

Figure 63A:
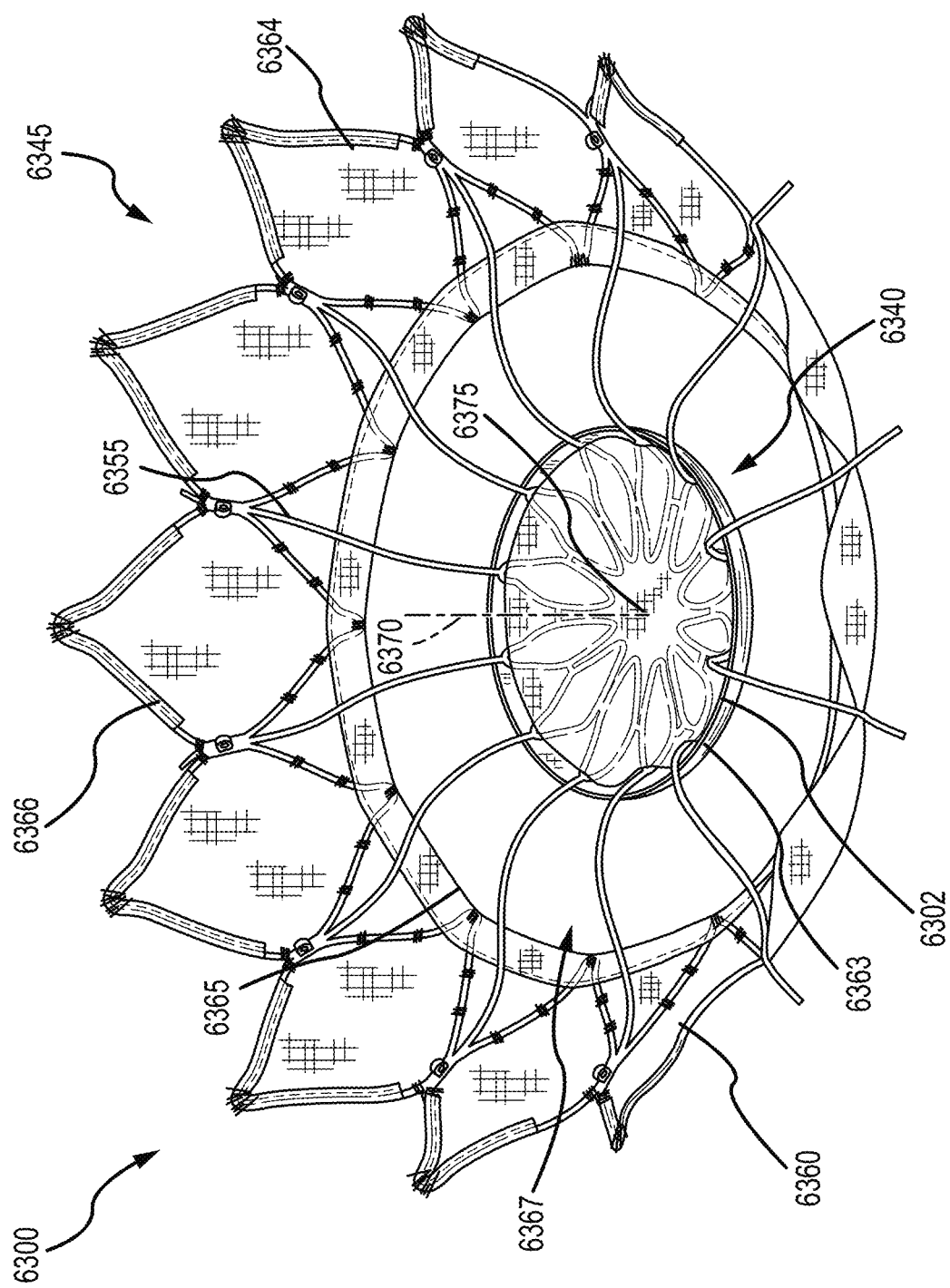
FIG. 63A is a proximal-side perspective view of another implant according to the present disclosure.
Figure 63B:
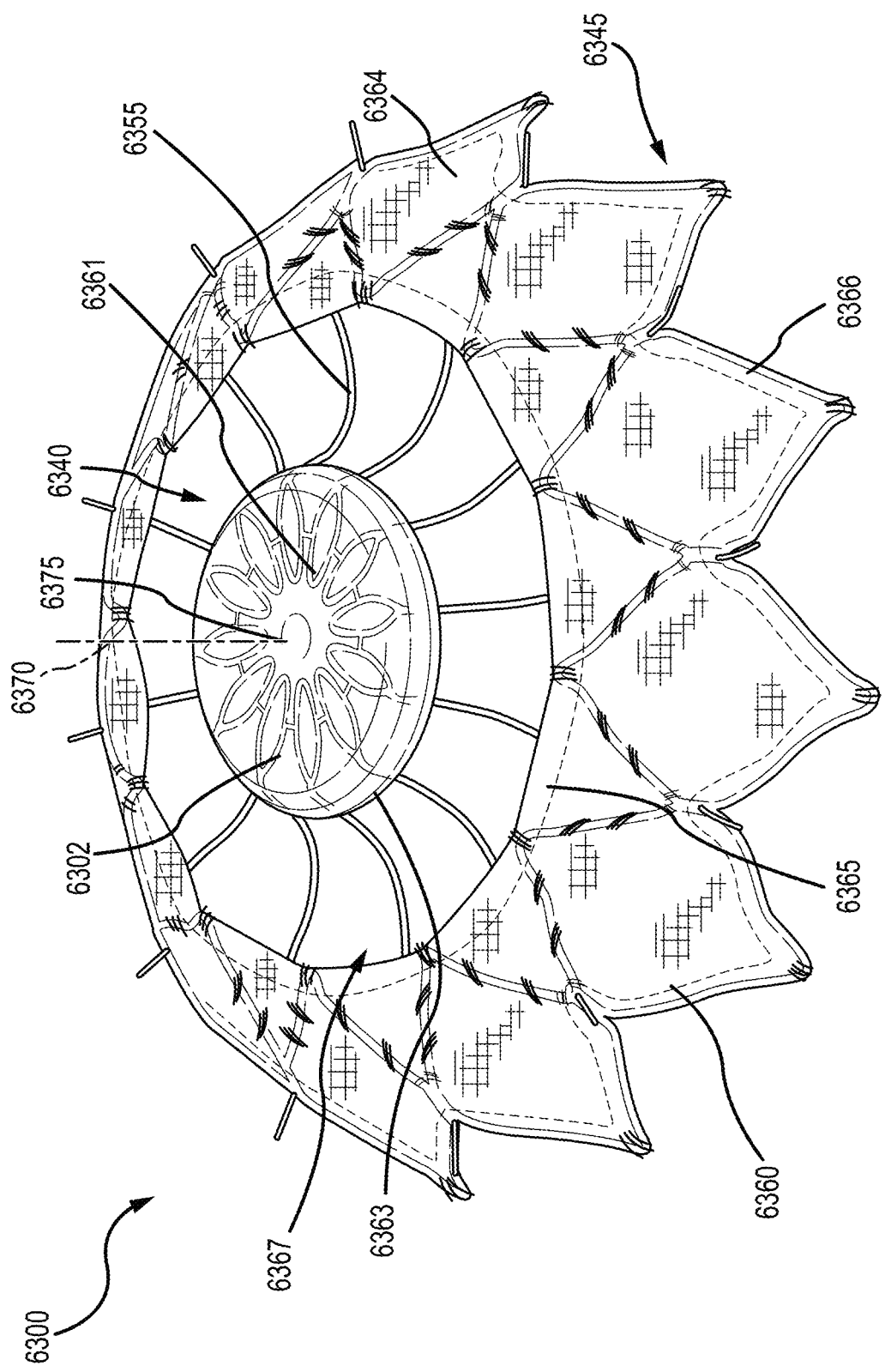
FIG. 63B is a distal-side perspective view of the implant of FIG. 63A.
Figure 63C:
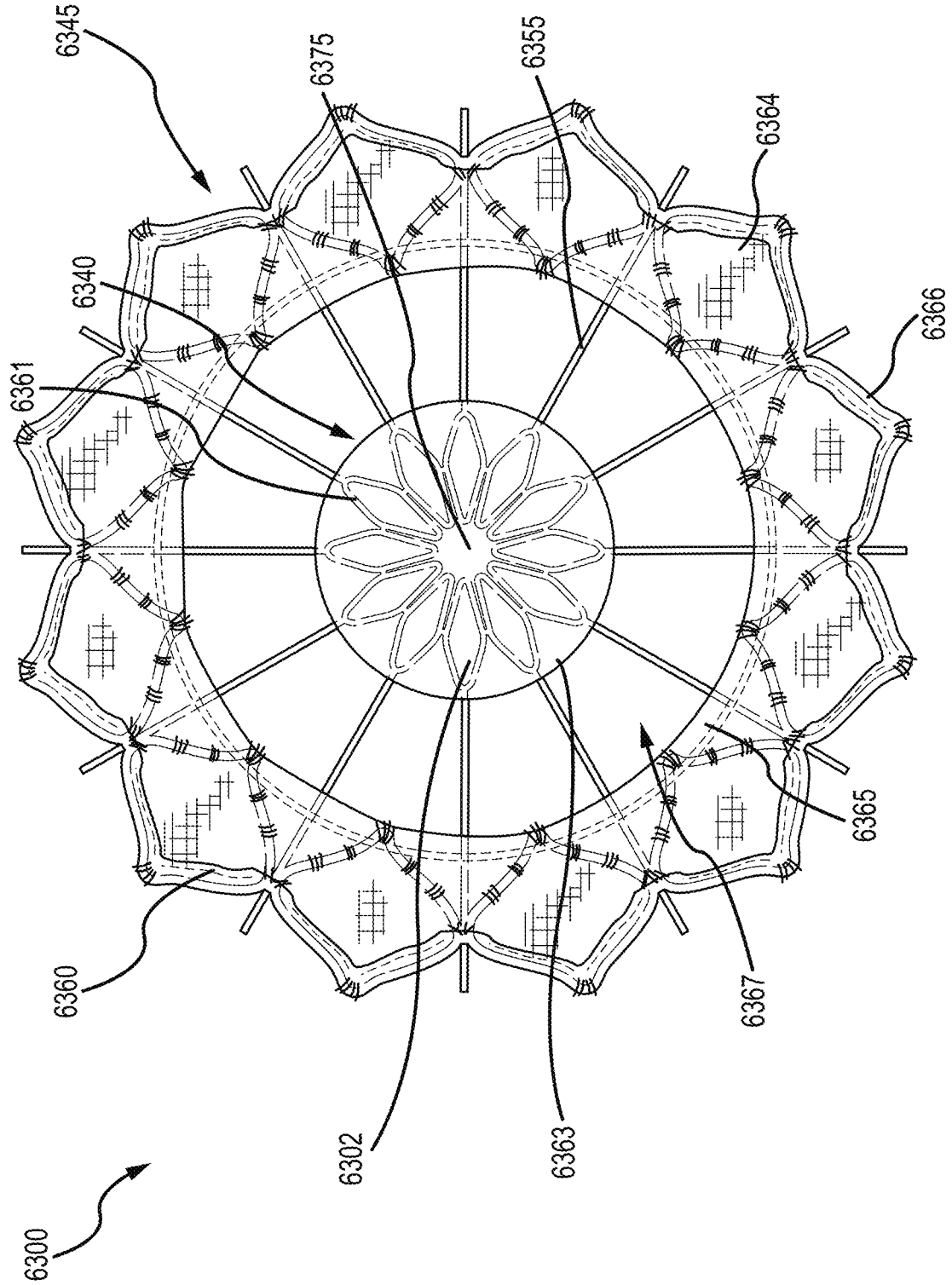
FIGS. 63C and 63D are distal views of the implant of FIG. 63A.
Figure 63D:
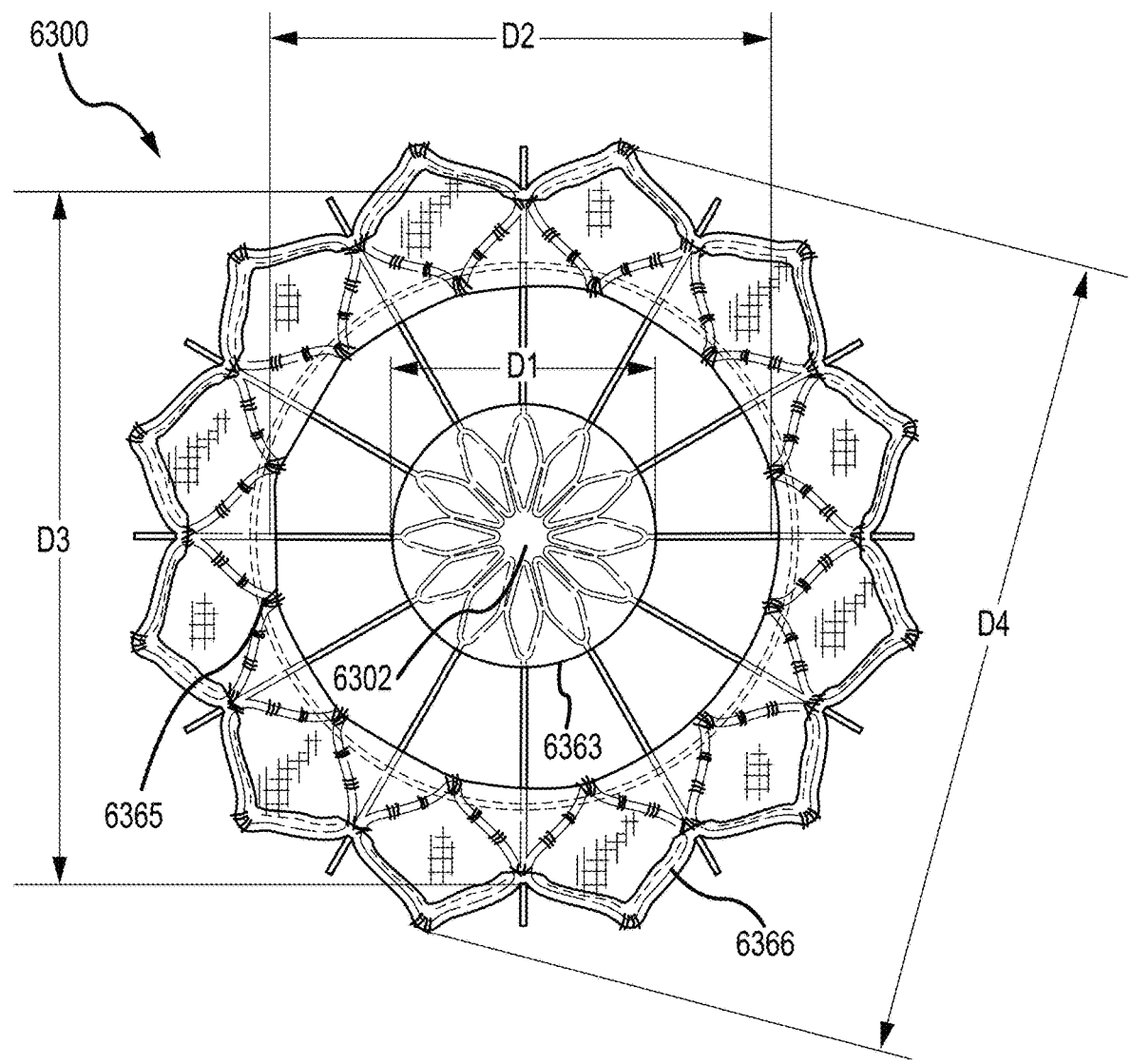
Figure 64A:
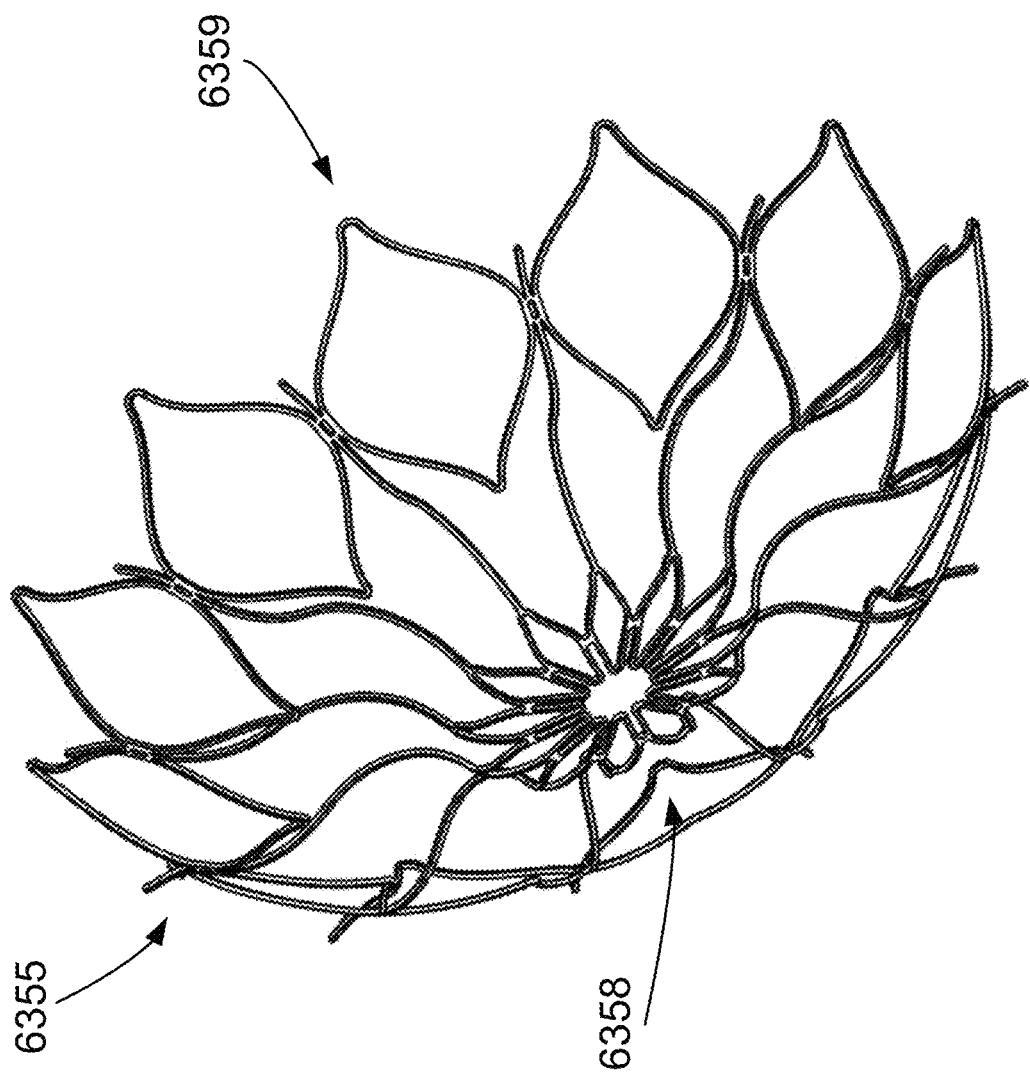
FIG. 64A-C are isometric, distal-side, and side elevation views of a frame of the implant of FIG. 63A.

FIGS. 63A-64N illustrate an implant 6300 according to another implementation of the present disclosure. Specifically, FIG. 63A is a perspective proximal-side (atrial-side when implanted) view of implant 6300 while FIGS. 63B and 63C are perspective and plan views of a distal side of implant 6300, respectively. FIG. 63D is the same as FIG. 63C albeit with various dimensions indicated. FIGS. 64A-64N illustrate a frame 6355 of implant 6300 and various details of frame 6355. FIGS. 63A-63C illustrate implant 6300 in an expanded state, such as when implant 6300 is implanted in a cardiac valve to be repaired.

As illustrated in FIGS. 63A-63D, implant 6300 generally includes a distal end 6340 and a proximal end 6345. Distal end 6340 serves as the leading end of implant 6300 during implantation and is directed toward the ventricle following implantation within the valve annulus. Implant 6300 further includes an occluder 6302 disposed at distal end 6340. Occluder 6302 is coupled to and supported on frame 6355. In contrast to previous occluders disclosed herein, which included bulb-type occluders (including those with sheet-style skirts) and sheet-type occluders, occluder 6302 is a cap-style occluder formed by laminating multiple sheets of material about a distal portion of frame 6355. Implant 6300 further includes an outer sheet 6360 supported by frame 6355. When in the expanded state, frame 6355 radiates laterally outward relative to a central longitudinal axis 6370 (indicated in FIGS. 63A and 63B) of implant 6300 with occluder 6302 forming a distal surface 6361 and outer sheet 6360 forming an annular surface 6364. Further details regarding occluder 6302 and outer sheet 6360 are illustrated and discussed below in the context of FIGS. 65A-65F for occluder 6302 and FIGS. 66A-67, respectively.

Distal surface 6361 formed by occluder 6302 includes a proximal radially outward edge 6363 while annular surface 6364 of outer sheet 6360 forms each of a distal radially inward edge 6365 and a proximal radially outward edge 6366. Proximal radially outward edge 6363 of distal surface 6361 and distal radially inward edge 6365 of annular surface 6364 define an opening 6367 between occluder 6302 and outer sheet 6360.

As with previous implants of this disclosure, implant 6300 may be transitioned into a collapsed state for delivery to the target implantation site. When collapsed, frame 6355, occluder 6302, and outer sheet 6360 may collapse symmetrically about central longitudinal axis 6370. Also, like previous implants of this disclosure, frame 6355 may be biased into expansion such that implant 6300 self-expands into the expanded state, e.g., to anchor itself within the target cardiac valve annulus.

Each of occluder 6302 and outer sheet 6360 are supported on frame 6355. In the specific example shown, occluder 6302 is coupled to and supported on frame 6355 by a bonding and lamination process. More specifically, at least one first layer of occluder 6302 is disposed on a distal surface of frame 6355 while at least one second layer of occluder 6302 is disposed on a proximal surface of frame 6355. Subsequent bonding of the layers (e.g., by application of an epoxy or other adhesive, heating, etc.) simultaneously forms occluder 6302 and couples occluder 6302 to frame 6355. In contrast, outer sheet 6360 is illustrated as being coupled to frame 6355 by sutures extending along distal radially inward edge 6365, proximal radially outward edge 6366, and frame 6355. Each of the lamination of occluder 6302 and the suturing of outer sheet 6360 to frame 6355 is described below in further details.

Implementations of this disclosure are not strictly limited to particular sizes or dimensions and may be modified or customized to meet the needs of patients and specific applications. Nevertheless, and without limitation to the scope of this disclosure, certain specific examples of dimensions are provided and indicated in FIG. 63D.

In certain implementations, occluder 6302 may have a diameter (D1) from and including about 16 mm to and including about 28 mm, with the maximum diameter generally corresponding to the diameter of occluder 6302 For example, occluder 6302 may a maximum diameter of about 22 mm.

In other implementations, outer sheet 6360 may have an inner diameter (D2) (e.g., the diameter of distal radially inward edge 6365) from and including about 36 mm to and including about 46 mm. For example, distal radially inward edge 6365 may have a diameter of about 41 mm.

As shown in FIG. 63D, each of outer sheet 6360 and frame 6355 may have a sinusoidal or otherwise varying proximal edge. In such implementations, proximal radially outward edge 6363 may be defined by each of a minimum diameter (D3) and a maximum diameter (D4). Among other things, a varying proximal edge balances robust anchoring of the implant within the valve annulus with reduced interference of the implant with native cardiac structures. More specifically, a sinusoidal proximal edge of frame 6355 and outer sheet 6360 provides robust anchoring and support by allowing frame 6355 to extend onto and to be distributed over a wider area about the valve annulus. In contrast, the sinusoidal edge of frame 6355 reduces the proximal portion of outer sheet 6360 as compared to similar configurations with the same maximum diameter but a circular proximal edge, thereby reducing the potential for interference between implant 6300 and other cardiac structures.

With the foregoing in mind, in at least certain implementations, the minimum diameter of proximal radially outward edge 6363 (D3) may be from and including about 48 mm to and including about 68 mm. For example, the minimum diameter of proximal radially outward edge 6363 may be approximately 58 mm. Similarly, the maximum diameter of proximal radially outward edge 6363 (D4) may be from and including about 58 mm to and including about 78 mm, but at least as large as the minimum diameter of proximal radially outward edge 6363. For example, in one specific example, the maximum diameter of proximal radially outward edge 6363 may be about 68 mm.

While this disclosure notes that a sinusoidal or varying configuration for proximal radially outward edge 6363 provides certain advantages, such a configuration is not necessary and implementations of this disclosure are not limited to configurations in which proximal radially outward edge 6363 varies. Accordingly, while not specifically illustrated in the context of implant 6300, this disclosure also contemplates that proximal radially outward edge 6363 of implant 6300 may be of constant diameter/circular.

While the height of implant 6300 is generally defined as the distance between distal extent 6375 and the proximal extent of proximal radially outward edge 6363. Like other aspects of implant 6300, the height of implant 6300 may vary, e.g., to accommodate variations in patient anatomy. In at least certain implementations, however, the overall height of implant 6300 may be from and including about 15 mm to and including about 25 mm. For example, the overall height of implant 6300 may be approximately 20 mm.

Further details regarding the construction of implant 6300 are provided with reference to FIGS. 64A-M, which illustrate frame 6355 in detail. More specifically, FIG. 64A is a distal isometric view of frame 6355, FIG. 64B is a distal elevation view of frame 6355, and FIG. 64C is an elevation view of frame 6355. FIGS. 64D and 64E are views of frame 6355 indicating specific features and elements of interest. FIGS. 64F-64K are detailed views of those features. FIG. 64L and FIG. 64M are side/elevation views of frame 6355 while FIG. 64N is a detailed view of a single spoke of frame 6355.

Referring first to FIGS. 64A-C, frame 6355 includes distal frame portion 6358, which supports occluder 6302 when fully assembled, and a proximal frame portion 6359, which supports outer sheet 6360. In general, each of distal frame portion 6358 and proximal frame portion 6359 include a set of circumferentially distributed petal portions configured to collapse and expand as implant 6300 is similarly collapsed and expanded during delivery and implantation.

While this disclosure contemplates that frame 6355 may be manufactured and assembled in various ways, in at least certain implementations, frame 6355 is formed as a unitary component by precision cutting a tubular substrate of material suitable for use in medical implants. For example, in at least certain implementations, frame 6355 is cut from high-cycle fatigue (HCF) nitinol tubing. The frame, as cut from the tubing, may be subsequently heated and bent into the final shape illustrated in the figures and described in the following section using a shape setting process consistent with the substrate material. Subsequent processing of the frame, such as electropolishing, passivation, deburring, cleaning, and the like, may also be applied to achieve the finished frame product.

As most clearly shown in FIG. 64B, distal frame portion 6358 may include radially extending and circumferentially distributed inner petal portions, such as inner petal portion 6380A and inner petal portion 6380B. The inner arcuate petal portions may be ovate, diamond-shaped, or otherwise have a similar elongate shape (e.g., generally diamond shaped albeit with rounded vertices and/or curved edges). Each inner petal portion may be defined by respective major and minor axes. For example, as shown in FIG. 64J, inner petal portion 6380A has a major axis 6381A that extends in a radial/longitudinal direction and a minor axis 6382A that extends in a substantially circumferential direction. In certain implementations, adjacent inner petal portions may be joined at or near the vertices along the minor axis. For example, and as indicated in FIG. 64J, inner petal portion 6380A and inner petal portion 6380B are joined at a junction 6384 disposed distal minor axis vertices of inner petal portion 6380A and inner petal portion 6380B.

Referring to FIG. 64B, proximal frame portion 6359 may similarly include outer petal portions that may be ovate, diamond-shaped, or have another elongate shape. Each such outer petal portion may be defined by respective major and minor axes. For example, and as shown in FIG. 64K, outer petal portion 6385A may have a major axis 6386A that extends in a substantially longitudinal direction and a minor axis 6387A that extends in a circumferential direction. In certain implementations, adjacent outer petal portions of proximal frame portion 6359 may be joined at or near the vertices along the minor axis (i.e., the co-vertices of the outer petal portions). For example, outer petal portion 6385A and outer petal portion 6385B are joined at a junction 6389 disposed at the corresponding co-vertices of outer petal portion 6385A and outer petal portion 6385B.

Referring back to FIG. 64B, frame 6355 generally includes members, struts, spokes, or similar elongate members. When frame 6355 is in a collapsed state, the spokes extend in a substantially longitudinal direction; however, as frame 6355 expands, the spokes/struts extend radially outward as well as proximally. As shown in FIG. 64B, a spoke/strut extends from each of the arcuate petal portions of the distal frame portion 6358 and, more specifically, from the proximal vertex of each of arcuate petal portion. For example, FIGS. 64B and 64J illustrate each of a spoke 6395A extending from a vertex 6396A of inner petal portion 6380A and a spoke 6395B extending from vertex 6396B of inner petal portion 6380B.

Referring again to FIG. 64B, each spoke extends from its corresponding inner petal portion of distal frame portion 6358 to a respective junction between outer arcuate petal portions of the proximal frame portion 6359. For example, FIG. 64M illustrates spoke 6395C terminating at junction 6389 between outer petal portion 6385A and outer petal portion 6385B.

Each spoke may further extend to form an anchor member (e.g., a spike, tine, or hook) disposed between adjacent outer petal portions. For example, each of FIGS. 64B and 64M include anchor member 6399 disposed between outer petal portion 6385A and outer petal portion 6385B and extending from junction 6389. As illustrated, anchor members are included between each pair of adjacent outer petal portions; however, this disclosure contemplates that more or fewer anchor members may be included and the distribution of anchor members about frame 6355 may vary. For example, in addition to anchor members disposed between adjacent outer petal portions, additional anchor members may extend from the distal vertex of one of more of the outer petal portions. As another non-limiting alternative, anchor members may extend from every other or every third junction between adjacent outer petal portions.

Figure 64F:
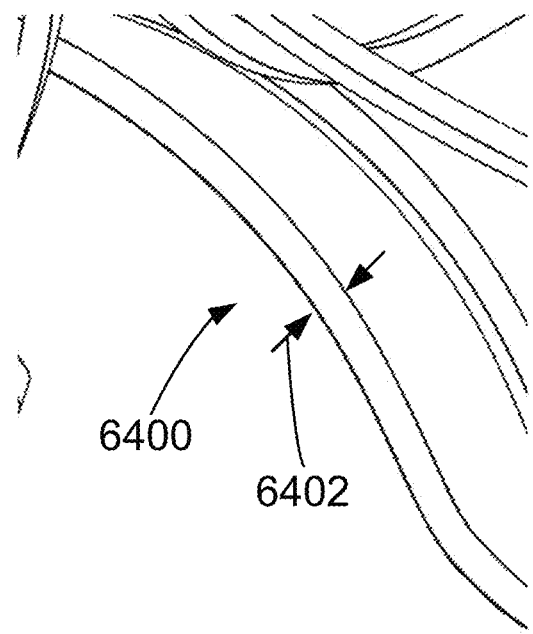
FIG. 64F is a detailed view of a spoke of the frame of FIGS. 64A-64E.

FIGS. 64D and 64E are views of frame 6355 indicating specific features and elements of interest, which are shown in detail in subsequent FIGS. 64F-64I. More specifically, FIG. 64D is a side elevation view of frame 6355 with frame 6355 oriented with a spoke/anchor member directed outward from the figure. In contrast, FIG. 64E is an angled side view of frame 6355 with frame 6355 oriented with an outer petal portion directed outward from the figure (i.e., at a 90-degree rotation relative to the view shown in FIG. 64D). As shown in FIG. 64D, FIG. 64F is a side elevation view of a portion of frame 6355 and, in particular, a detailed view of a spoke section 6400 extending that generally extends between an inner petal portion of frame 6355 and a junction between adjacent outer petal portions. For example, spoke section 6400 may correspond to sections of spoke 6395A and spoke 6395B extending between the inner petal portions of frame 6355 and their corresponding junctions of outer petal portions. The specific curvature of spoke section 6400 is discussed below in further detail in the context of FIGS. 64N-P. However, as shown in FIG. 64F, spoke section 6400 has a generally distally convex curvature. While the specific dimensions of spoke section 6400 may vary, in at least some implementations, spoke section 6400 may have a thickness 6402 from and including about 0.2 mm to and including about 0.4 mm. For example, in one specific implementation, thickness 6402 may be about 0.32 mm with a tolerance of +/−0.04 mm. In implementations in which frame 6355 is formed by cutting frame 6355 from a tubular substrate, thickness 6402 may correspond to the thickness of the tubular substrate.

Figure 64G:
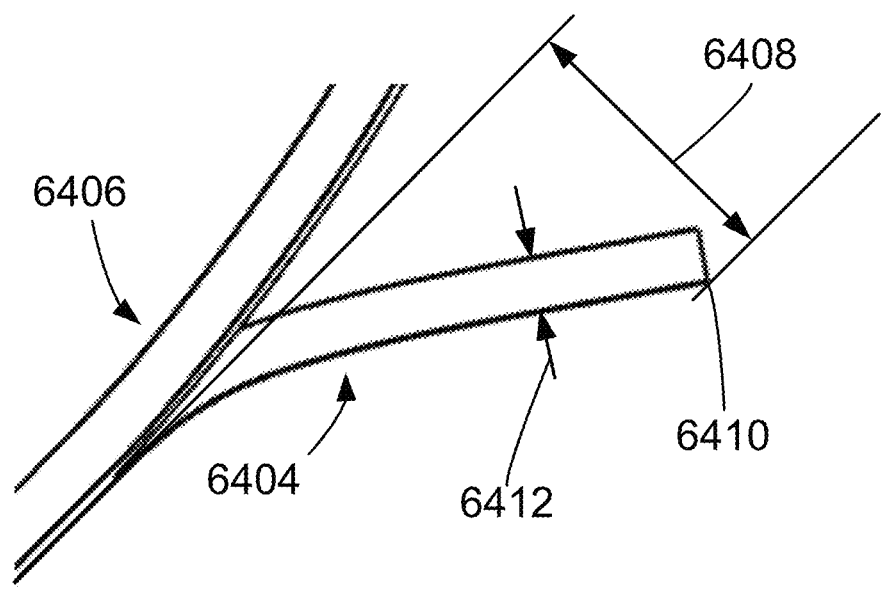
FIG. 64G is a detailed view of an anchor member of the frame of FIGS. 64A-64E, FIGS. 64H and 64I are detailed views of an outer petal portion of the frame of FIGS. 64A-64E.

As further shown in FIG. 64D, FIG. 64G is a side elevation view of an anchor member 6404 of frame 6355. For example, anchor member 6404 may correspond to anchor member 6399 of frame 6355 or any other anchor member distributed about frame 6355. As previously discussed, anchor members of implants according to this disclosure are generally configured to engage tissue surrounding the valve annulus to facilitate anchoring of the implant relative to the valve annulus during implantation. The specific size, shape, angle, and similar characteristics of anchor member 6404 may vary based on the application; however, FIG. 64G illustrates one non-limiting example configuration of anchor member 6404 that has demonstrated positive results in testing. As illustrated, anchor member 6404 extends from a junction 6406, which, as previously discussed, is generally located between adjacent outer petal portions. For example, junction 6389 of frame 6355 is shown in FIG. 64B as being located between outer petal portion 6385A and outer petal portion 6385B. As shown, anchor member 6404 may be integral with junction 6406 and may be formed by distally bending or curving anchor member 6404.

The performance characteristics of anchor member 6404 can be varied and controlled by modifying the geometry of anchor member 6404 and its geometric relationship (e.g., angle) relative to the other portions of 6355. For example, FIG. 64G indicates a depth 6408 or linear distance of anchor member 6404, which generally corresponds to a maximum linear distance between a tip 6410 of anchor member 6404 and the outer surface of a junction 6406 between adjacent outer petal portions (e.g., junction 6389 between outer petal portion 6385A and outer petal portion 6385B). While depth 6408 may vary, in at least some implementations, depth 6408 may be from about 1.0 mm to 3.5 mm. For example, in one specific implementation, depth 6408 may be about 2.2 mm with a tolerance of +/−0.4 mm.

Performance characteristics of anchor member 6404 can also be varied and controlled by modifying a thickness 6412 of anchor member 6404. While thickness 6412 may vary, in at least some implementation, thickness 6412 may be from and including about 0.2 mm to and including about 0.4 mm. For example, thickness 6412 may be about 0.32 mm with a tolerance of +/−0.04 mm. In implementations in which frame 6355 is formed by cutting frame 6355 from a tubular substrate, thickness 6412 may correspond to the thickness of the tubular substrate.

Figure 64H:
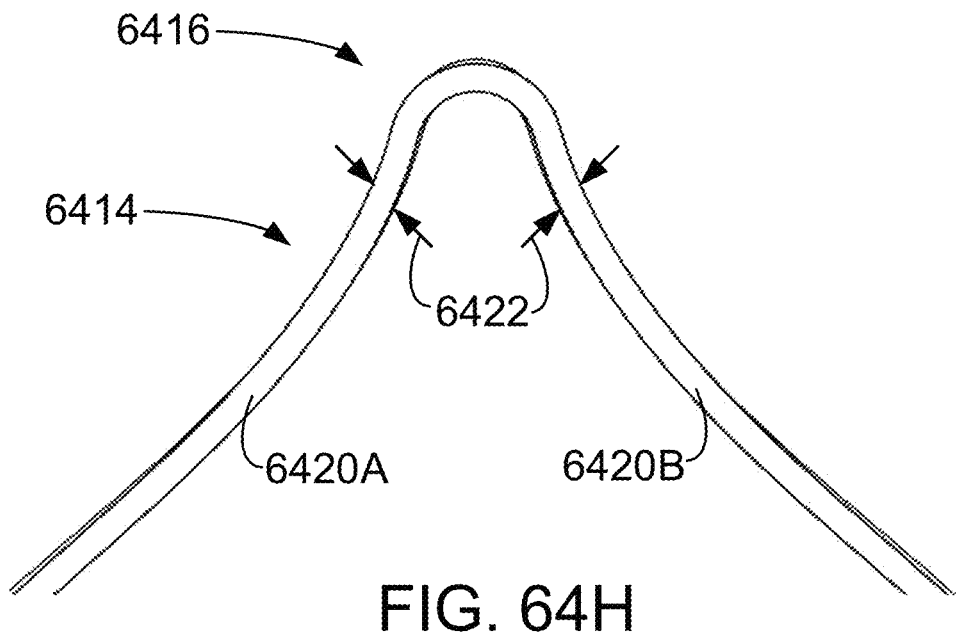
FIGS. 64D and 64E are additional views of the implant of FIG. 63A indicating the location of specific structures of the implant.
FIG. 64J is a detailed view of inner petal portions of the frame of FIGS. 64A-64E.
FIG. 64K is a detailed view of outer petal portions of the frame of FIGS. 64A-64E.
FIGS. 64L and 64M are dimensioned side views of the frame of FIGS. 64A-64E.
FIG. 64N is a detailed and dimensioned side view of a spoke of the frame of FIGS. 64A-64E.
Figure 64I:
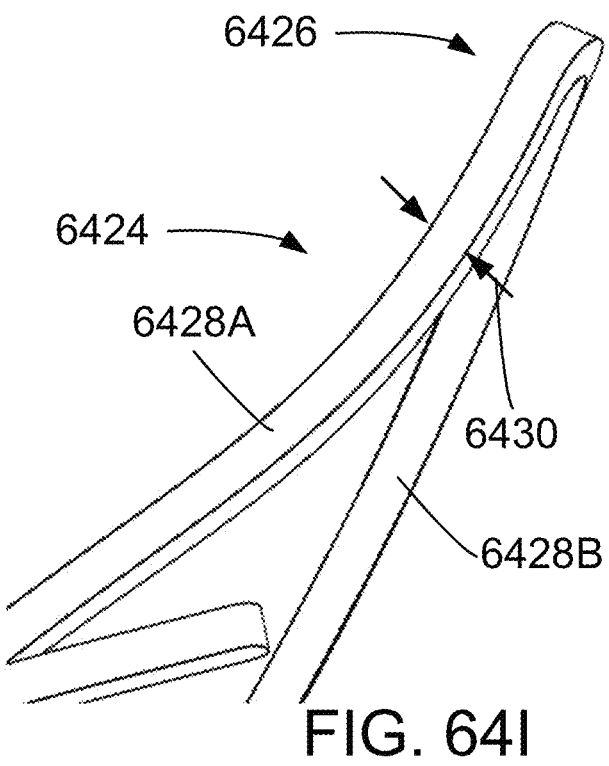
Figure 64J:
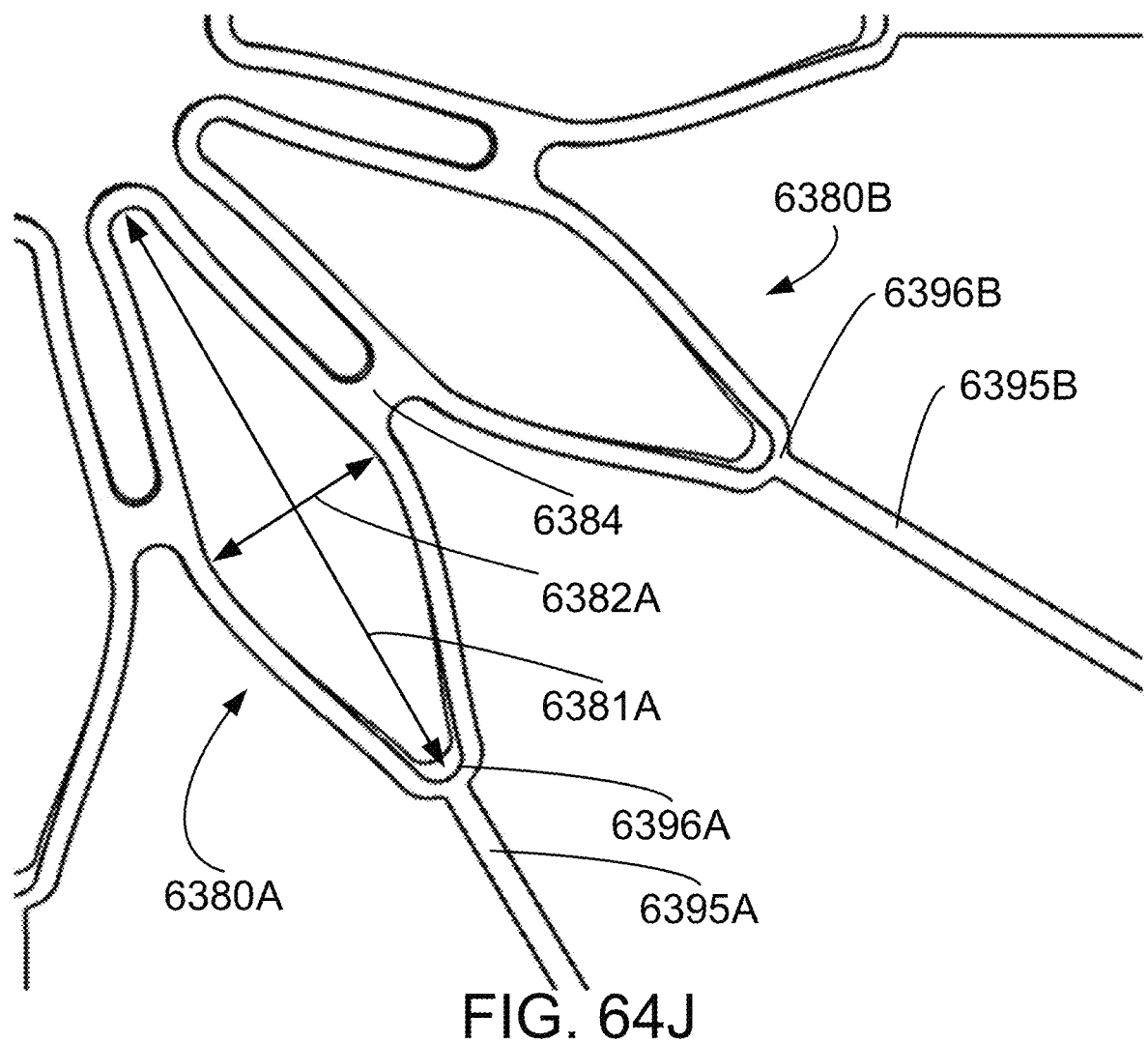
Figure 64K:
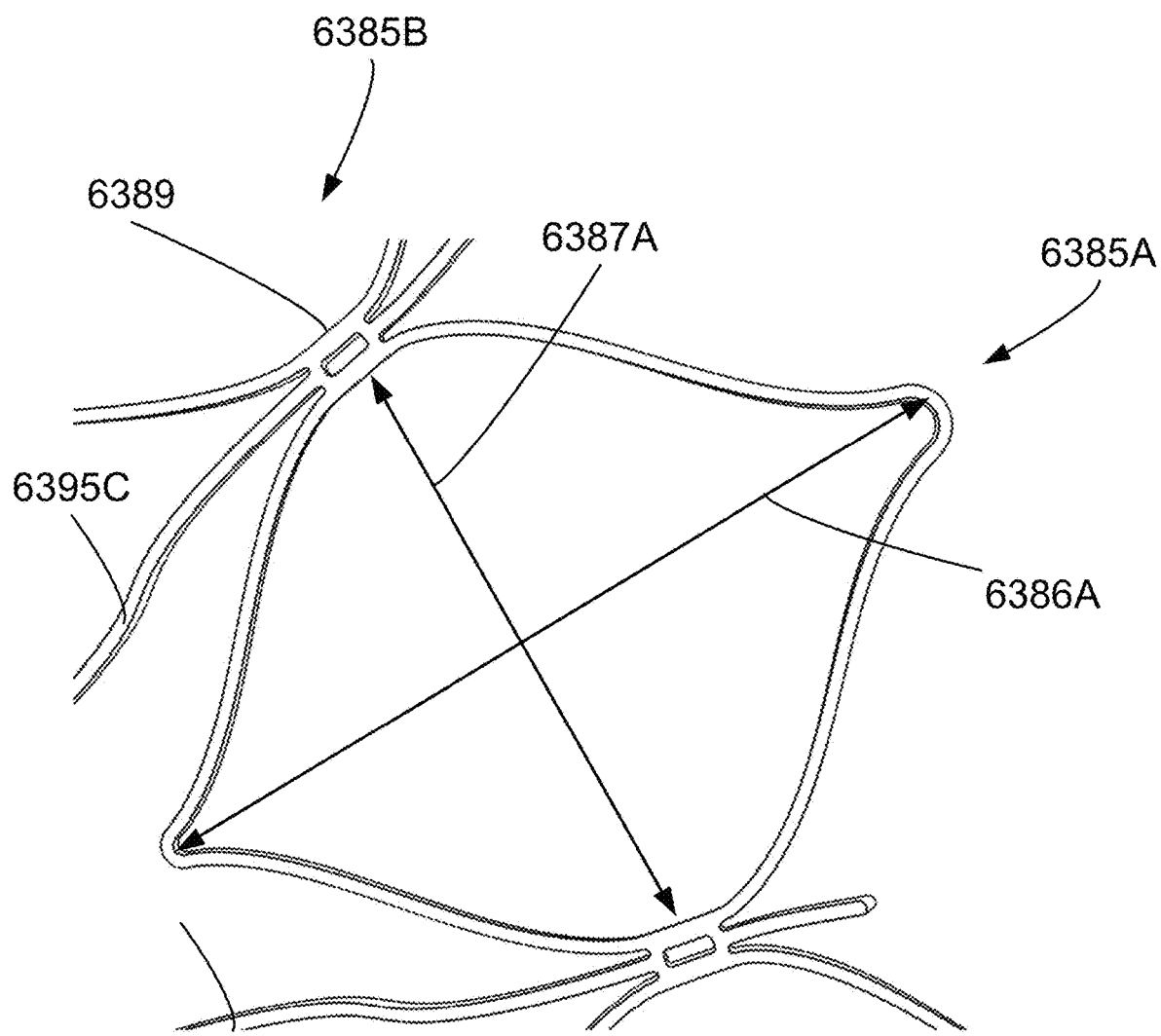
Figure 64L:
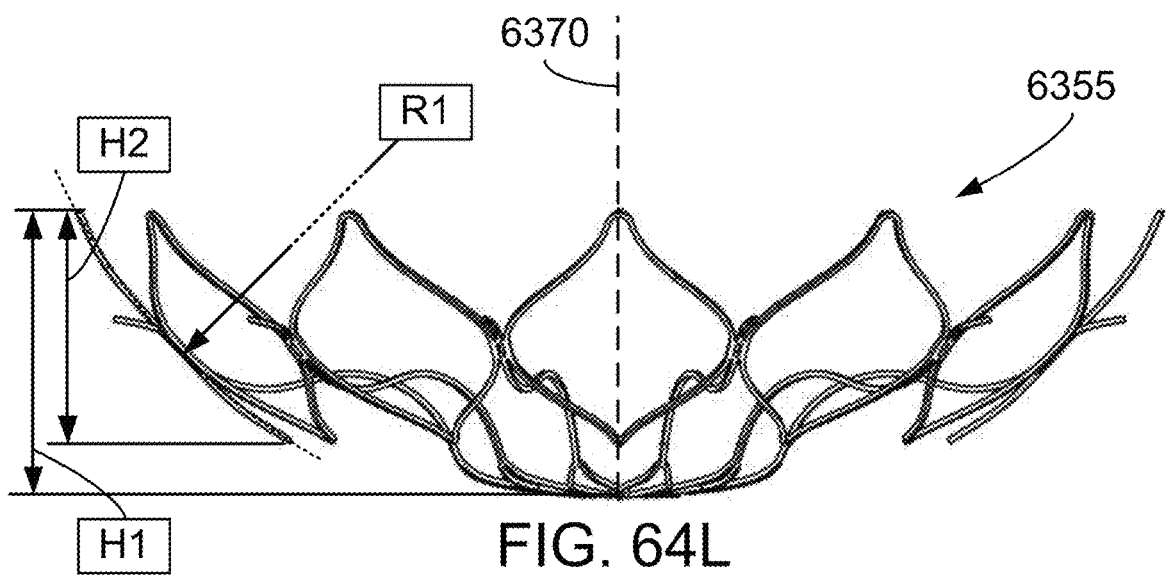
Figure 64M:
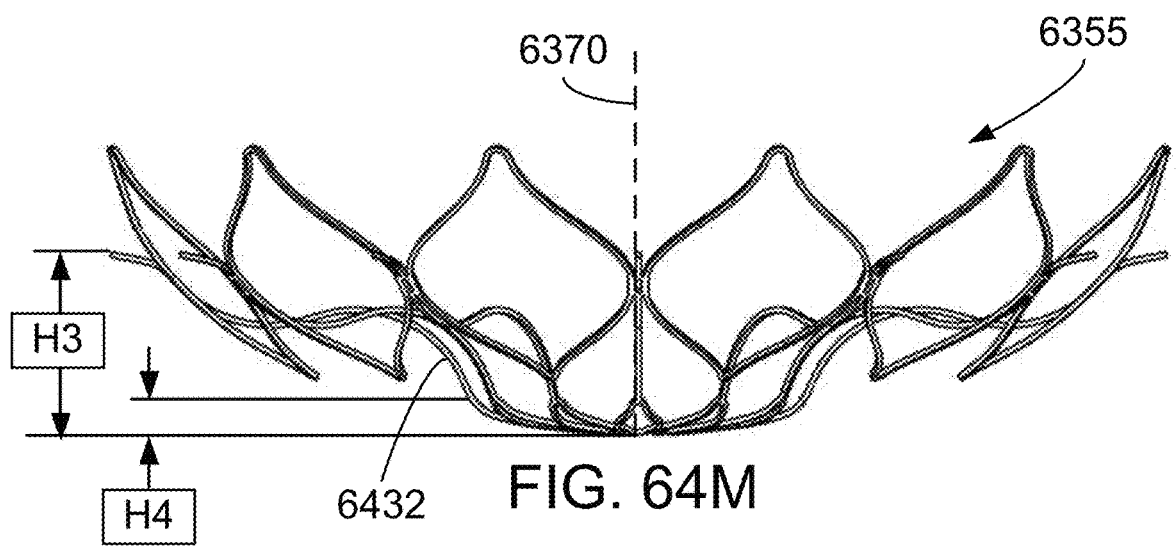

As indicated in FIG. 64E, FIGS. 64H and 64I are detailed views of respective outer petal portions and, specifically, proximal extents of the outer petal portions. More specifically, FIG. 64H illustrates an outer petal portion 6414 and, specifically, a detailed front view of a proximal chevron 6416 of outer petal portion 6414. FIG. 64I, in contrast, illustrates an outer petal portion 6424 and, in particular, a detailed side view of a proximal chevron 6426 of outer petal portion 6424.

Referring first to FIG. 64H, proximal chevron 6416 is formed at the junction of two petal sections, namely, petal section 6420A and petal section 6420B. As previously noted, in certain implementations of this disclosure, frame 6355 is laser cut from a tubular substrate such that certain dimensions may be controlled or otherwise dictated by the wall thickness of the tubular substrate. In contrast, when frame 6355 is cut from a tubular substrate, the width of petal section 6420A and petal section 6420B generally correspond to circumferential lengths of the tubular substrate and, as a result, are controlled and dictated by cuts made to the tubular substrate. Stated differently, the width of petal section 6420A and petal section 6420B can be varied and controlled and are not necessarily limited to any specific dimensions of the tubular substrate from which frame 6355 is cut. For example, FIG. 64H illustrates a width 6422 of each of petal section 6420A and petal section 6420B. While width 6422 may vary, in at least certain implementations, width 6422 may be from and including about 0.2 mm to and including about 0.4 mm. For example, in one specific implementation, width 6422 may be 0.32 mm with a tolerance of +/−0/04 mm.

Referring next to FIG. 64I, proximal chevron 6426 of outer petal portion 6424 is formed at the junction of two petal sections, namely, petal section 6428A and petal section 6428B, each of which generally has a thickness 6430. In certain implementations thickness 6430 may be controlled by or otherwise correspond to a wall thickness of a tubular substrate from which frame 6355 is cut. Thickness 6430 may vary; however, in at least certain implementations, thickness 6430 may be from and including about 0.2 mm to and including about 0.4 mm. For example, thickness 6412 may be about 0.32 mm with a tolerance of +/−0.04 mm.

Like previous frames discussed herein, frame 6355 may be formed from a variety of super-elastic and/or shape memory materials, including, for example, nickel-titanium alloys (e.g., Nitinol), which may be laser cut from a tube or in the form of drawn wire. The features defined in the shape memory materials may be defined therein via various cutting methods known in the art, include laser, water jet, electrical discharge machining (EDM), stamping, etching, milling, etc.

While illustrated as including 12 each of outer arcuate petal portions and inner arcuate petal portions, in other implementations, frame 6355 may include different numbers of inner and/or outer arcuate petal portions. For example, in certain example embodiments, frame 6355 may include between 10 and 14, between 8 and 16, or between 6 and 18 inner and outer arcuate petal portions. In other implementations, the number of inner arcuate petal portions may differ from the number of outer arcuate petal portions. Moreover, not every inner arcuate petal portion may be coupled to a corresponding spoke of frame 6355. For example, spokes may extend from only every other of inner arcuate petal portions.

As shown in the preceding figures, each inner arcuate petal portion is uniform as is each outer arcuate petal portion. In other implementations, the inner and outer arcuate petal portions may vary in any direction. For example, the inner arcuate petal portions may alternate between arcuate petal portions having a first major axis dimension and arcuate petal portions have a second major axis dimension different than the first major axis dimension.

Additional examples dimensions and features of frame 6355 are indicated in FIGS. 64L-64N. Specifically, FIGS. 64L and 64M are additional side views of frame 6355 with FIG. 64M being the view of FIG. 64L rotated approximately 90 degrees about the longitudinal axis 6370 of frame 6355. FIG. 64N is a detailed view of an example member 6432. The following discussion describes various dimensions and shapes of frame 6355 and its elements. As with other aspects of this disclosure, any specific dimensions and values should be considered non-limiting and are merely included as example values found to be suitable for use in certain valve repair procedures. Among other things, the dimensions described below may be modified and adjusted to account for differences in patient physiology.

Referring first to FIG. 64L, frame 6355 is shown with three dimensions indicated and generally related to the spokes and inner petal portions of frame 6355. First, overall height of frame 6355 is indicated as H1. In general, H1 corresponds to the distance between a distal and proximal extent of frame 6355 along central longitudinal axis 6370. In certain implementations and without limitation, H1 may be from and including about 15 mm to and including about 20 mm and, in one specific example may be approximately 17.5 mm with a tolerance of +/−0.5 mm.

FIG. 64L further includes dimension H2, which corresponds to longitudinal height of the outer petal portions as measured from the proximal extend of frame 6355. In certain implementations and without limitation, H2 may be from and including about 11 mm to and including about 16 mm and, in one specific example may be approximately 14 mm with a tolerance of +/−0.5 mm.

Finally, FIG. 64L includes dimension R1, which corresponds to a radius of curvature of the outer petal portions. In certain implementations and without limitation, R1 may be from and including about 15 mm to and including about 35 mm and, in one specific example may be approximately 25 mm.

Turning to FIG. 64M, frame 6355 is shown with two dimensions indicated. First, the height of the anchor members of frame 6355 relative to the distal extent of frame 6355 is indicated as H3. In certain implementations and without limitation, H3 may be from and including about 9 mm to and including about 15 mm and, in one specific example may be approximately 12 mm.

FIG. 64M further includes the height of the inner petal portions relative to the distal extent of frame 6355, which is indicated as H4. In certain implementations and without limitation, H4 may be from and including about 1.5 mm to and including about 3.5 mm and, in one specific example may be approximately 2.4 mm.

FIG. 64N is a cross-sectional view of frame 6355 focusing on a member 6432 of frame 6355 and with the remaining elements of frame 6355 removed for clarify. As indicated, member 6432 includes an anchor member 6434, a junction section 6436 (which corresponds to junctions between outer petal portions of frame 6355), a spoke 6438, and an inner petal portion 6440. FIG. 64N includes indicators for two curvatures and five height dimensions. As with the previous figures, the various dimensions are intended to be merely illustrative and can be readily adapted and modified, e.g., to accommodate differences in patient physiology.

Dimension H5 corresponds to a height of anchor member 6434 and junction section 6436. In certain implementations and without limitation, H5 may be from and including about 1 mm to and including about 4 mm and, in one specific example may be approximately 2 mm. Other example dimensions and characteristics of anchor member 6434 are provided above in the context of FIG. 64G.

Dimension H6 corresponds to a height of a proximally concave section 6439 of spoke 6438. Proximally concave section 6439 generally extends between junction section 6436 and a distally concave section 6441 of spoke 6438. As shown, proximally concave section 6439 is generally defined in FIG. 64N by a height H6 and a radius of curvature R2 with H6 corresponding to a distance between junction section 6436 and a distal extent of proximally concave section 6439. In certain implementations and without limitation, H6 may be from and including about 2 mm to and including about 4 mm and, in one specific example may be approximately 3 mm. Similarly, in certain implementations and without limitation, R2 may be from and including about 4 mm to and including about 10 mm and, in one specific example may be approximately 7 mm.

Dimension H7 corresponds to a difference between a distal extent of proximally concave section 6439 and a proximal extent of distally concave section 6441. In certain implementations and without limitation, H7 may be from and including about 0.25 mm to and including about 3 mm and, in one specific example may be approximately 1.25 mm.

Dimension H8 corresponds to a height of distally concave section 6441. Distally concave section 6441 generally extends between proximally concave section 6439 and inner petal portion 6440. As shown, distally concave section 6441 is generally defined in FIG. 64N by a height H8 and a radius of curvature R3 with H8 corresponding to a distance between a proximal extent of distally concave section 6441 and the beginning of inner petal portion 6440. In certain implementations and without limitation, H8 may be from and including about 2.5 mm to and including about 8.5 mm and, in one specific example may be approximately 5.5 mm. Similarly, in certain implementations and without limitation, R3 may be from and including about 4 mm to and including about 10 mm and, in one specific example may be approximately 7 mm.

Finally, dimension H9 corresponds to a height of inner petal portion 6440 and is generally defined as the distance between the end of proximally concave section 6439 and the distal extent of frame 6355. In certain implementations and without limitation, H9 may be from and including about 1.5 mm to and including about 4 mm and, in one specific example may be approximately 2.5 mm. Similarly, in certain implementations and without limitation, R4 may be from and including about 30 mm to and including about 50 mm and, in one specific example may be approximately 40 mm.

XVIII. Laminated Occluders for Valve Repair Implants

As previously discussed in the context of FIGS. 64A and 63B, implant 6300 includes occluder 6302. In contrast to bulb- and sheet-style occluders of other implementations provided in this disclosure, occluder 6302 has a multi-layered laminated structure and a general cap-like shape. Among other things, such occluders result in a generally lower profile and smaller overall height of implant 6300 while forming a relatively large distal surface of implant 6300 against which the native valve leaflets can seal, providing substantial reduction in regurgitation and other valve-related issues.

Figure 65A:
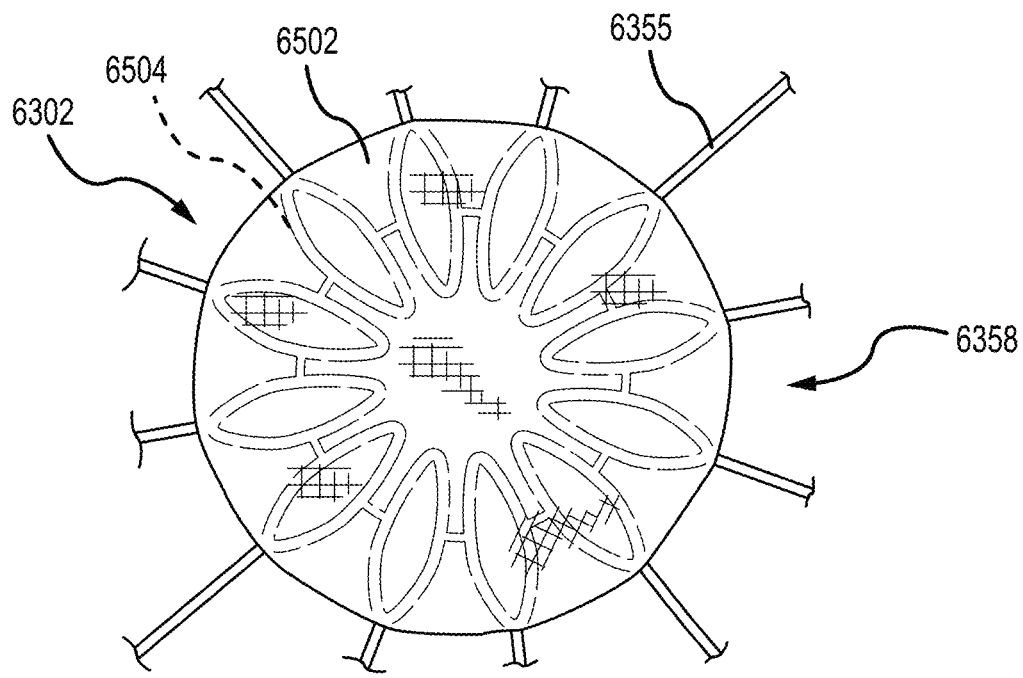
FIGS. 65A and 65B are a distal view and a proximal-side perspective view, respectively of a laminated occluder.
Figure 65B:
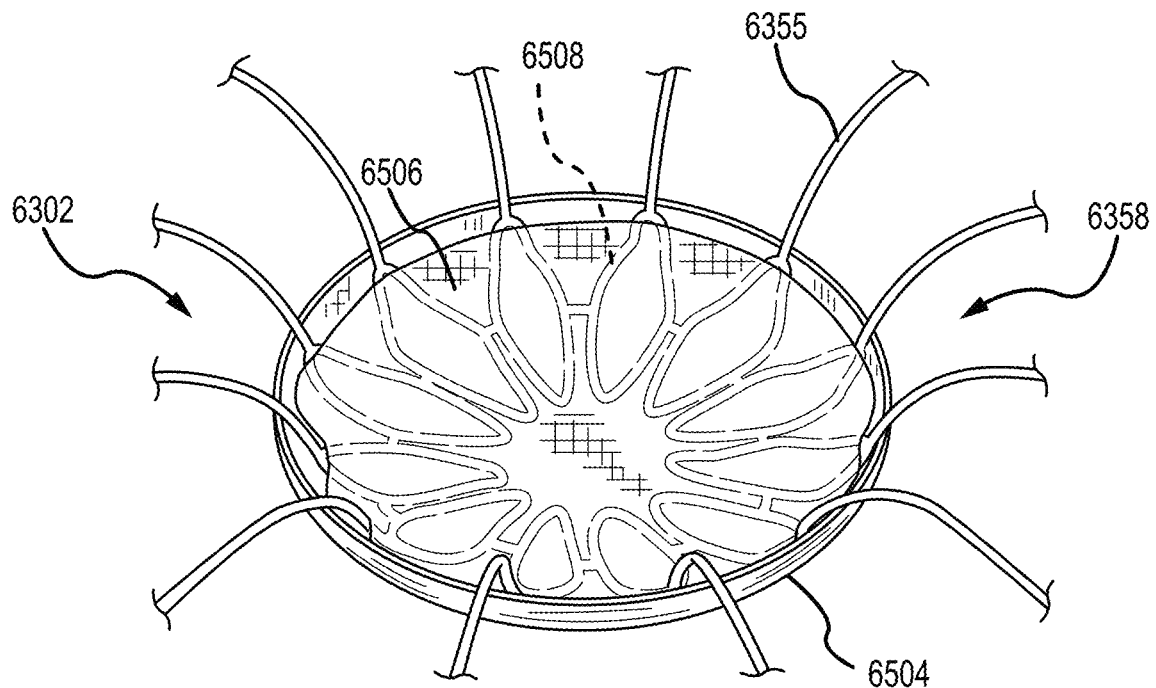
Figure 65C:
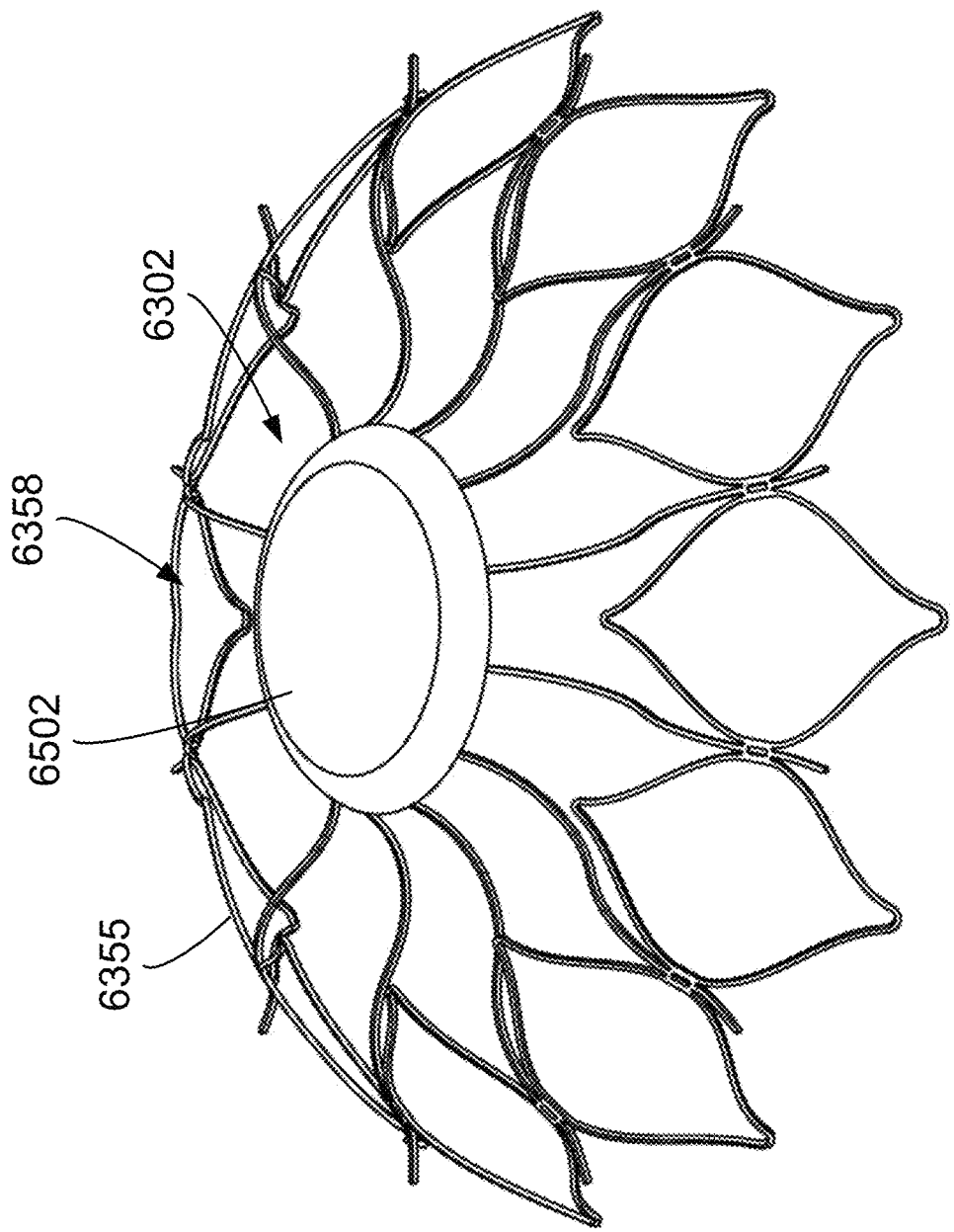
FIG. 65C is a distal-side isometric view of the frame of FIGS. 64A-64E with the laminated occluder attached.

FIGS. 65A and 65B are detailed views of occluder 6302 of implant 6300. More specifically, FIG. 65A is a distal view of occluder 6302 while FIG. 65B is an isometric view of occluder 6302. FIG. is a distal isometric view of frame 6355 and occluder 6302 of implant 6300 and is provided to illustrate occluder 6302 in the broader context of implant 6300 and frame 6355.

Referring to FIGS. 65A and 65B, occluder 6302 is generally formed directly onto distal frame portion 6358 of frame 6355. More specifically, occluder 6302 is formed onto the inner petal portions of distal frame portion 6358. While this disclosure contemplates that occluder 6302 may be formed onto distal frame portion 6358 in various ways, in at least one implementation, occluder 6302 is formed onto distal frame portion 6358 by applying a first sheet 6502 of substantially impervious material onto a distal surface 6504 (shown most clearly in FIG. 65D) of distal frame portion 6358. A second sheet 6506 of porous or semi-porous material is then disposed on a proximal surface 6508 of distal frame portion 6358 such that second sheet 6506 substantially overlaps first sheet 6502 with the inner petal portions of distal frame portion 6358 disposed between first sheet 6502 and second sheet 6506. An epoxy, adhesive, or similar bonding material is then applied to proximal surface 6508 of distal frame portion 6358 such that it penetrates second sheet 6506 and, once cured, bonds second sheet 6506 to first sheet 6502 and the inner petal portions of distal frame portion 6358.

Figure 65D:
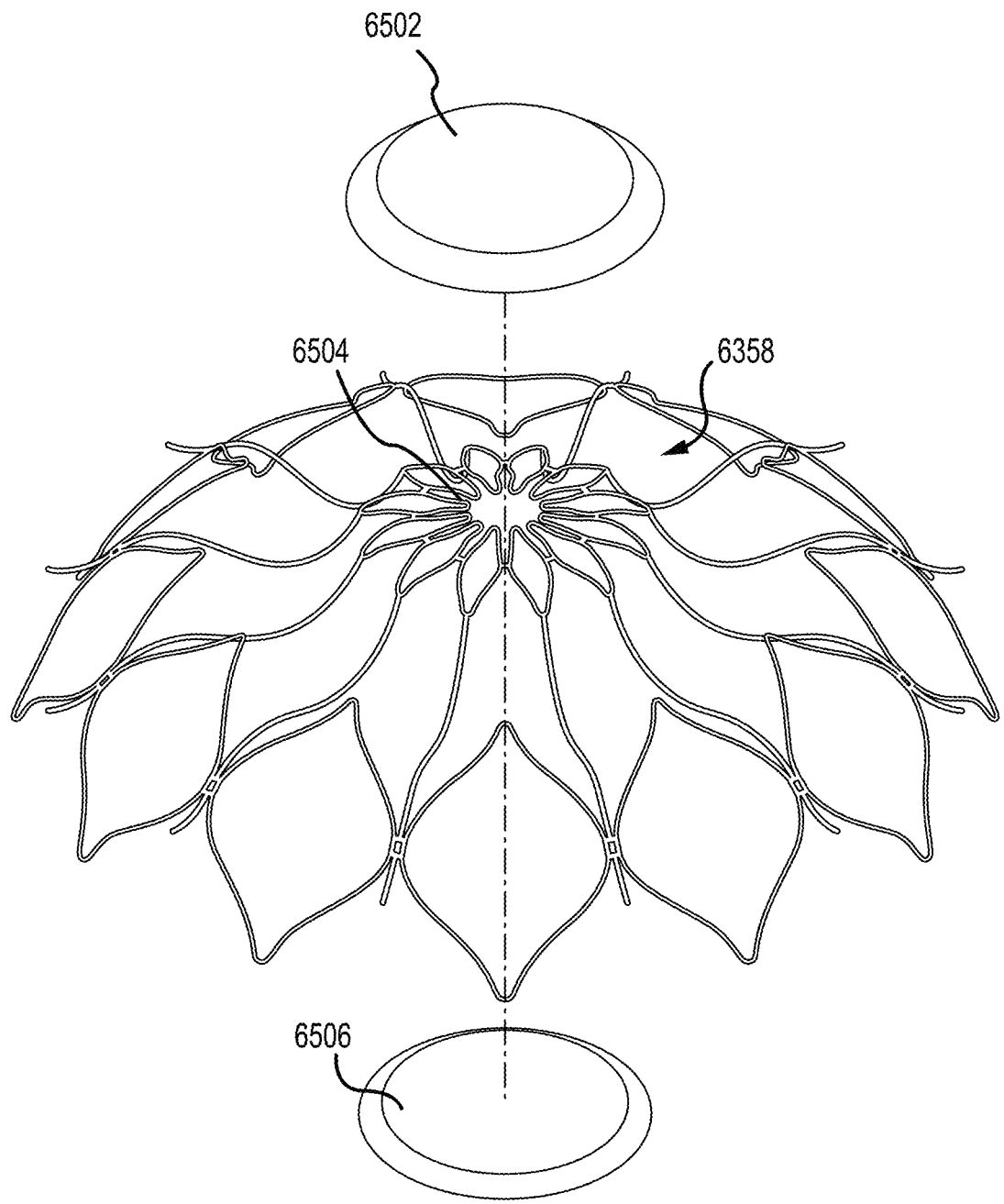
FIG. 65D is an exploded view of the frame and laminated occluder of FIG. 65C.

FIG. 65D is an exploded view of occluder 6302 and frame 6355. As shown, each of first sheet 6502 and second sheet 6506 are cut and shaped to be received onto and bonded to distal frame portion 6358 of frame 6355. The specific materials and process for forming occluder 6302 may vary in implementations of this disclosure; however, in at least one example implementation, first sheet 6502 is formed from an engineering polymer that is biocompatible and has low porosity. In certain implementations, for example, first sheet 6502 may be formed from expanded polytetrafluoroethylene (ePTFE) or a similar polymer. Second sheet 6506, in contrast, may be formed from a substantially more porous and flexible material. By way of non-limiting example, in certain implementations second sheet 6506 is formed from a porous and biocompatible fabric, such as a woven polyethylene terephthalate (PET) material. For example, in some implementations, the material of second sheet 6506 may be the same as or similar to that used for outer sheet 6360 of implant 6300 (shown in FIG. 63A).

While this disclosure contemplates that different materials may be used to bond first sheet 6502 and second sheet 6506 to each other and to distal frame portion 6358, in one example implementation, bonding is achieved using a combination of a siloxane segmented polyurethane and a polymer precursor, such as tetrahydrofuran (THF). During assembly, the polyurethane is solved in the THF and the resulting mixture is applied to second sheet 6506 and proximal surface 6508 of distal frame portion 6358 following layering of first sheet 6502 and second sheet 6506 onto distal frame portion 6358. The relatively high viscosity of the polyurethane/THF mixture allows for relatively easy penetration of second sheet 6506, encapsulation of the fibers of second sheet 6506, and flow into the volume between first sheet 6502 and second sheet 6506 containing distal frame portion 6358. Following subsequent curing, the polyurethane/THF mixture provides a robust, consistent, and substantially impermeable bond between first sheet 6502 and second sheet 6506. Notably, polyurethane and certain polyurethane-based compounds are capable of curing/setting without application of additional heat which may cause frame 6355 to deform or lose shape.

Figure 65E:
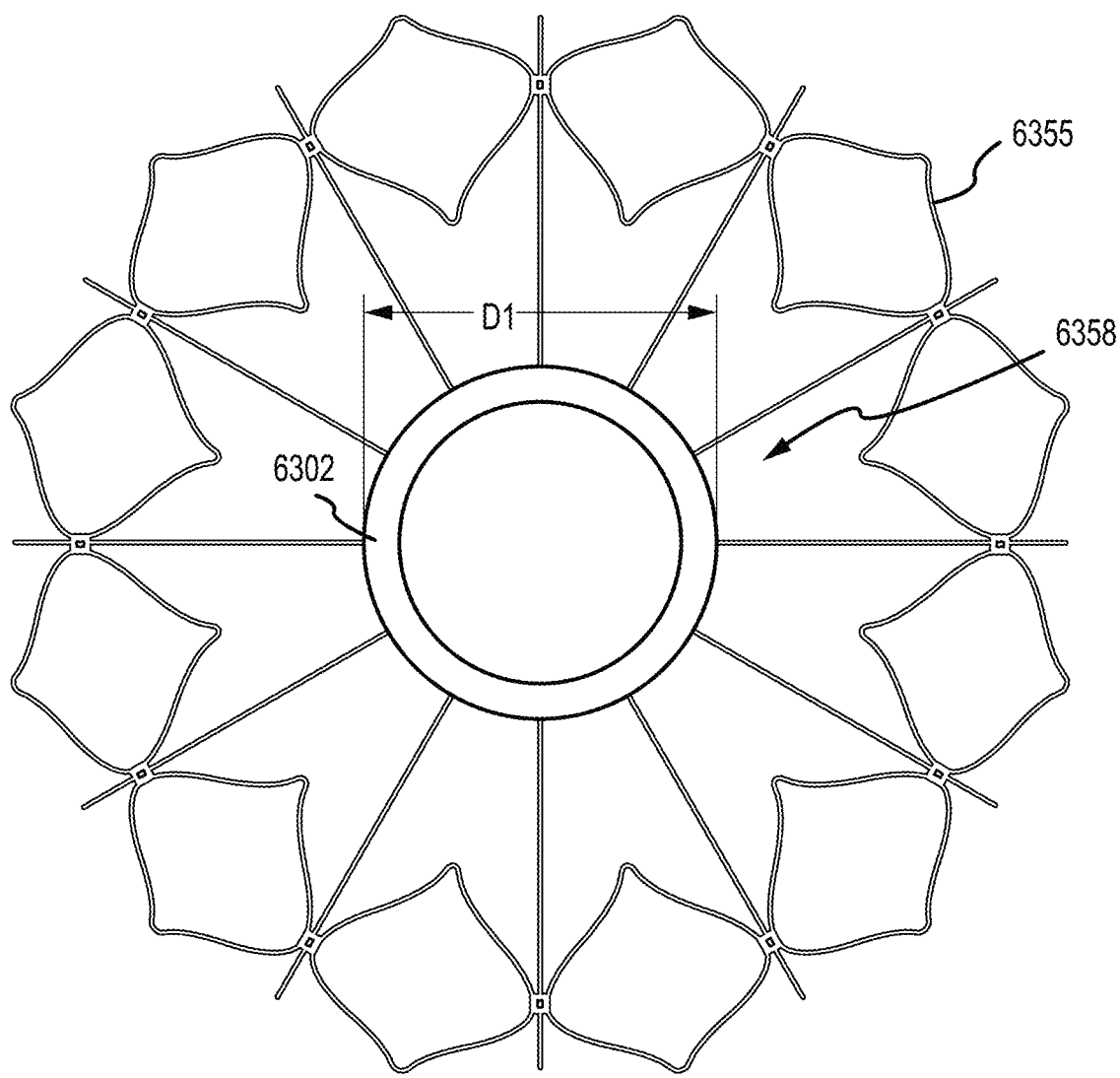
FIGS. 65E and F are dimensioned distal and elevation views of the frame and laminated occluder of FIG. 65C.
Figure 65F:
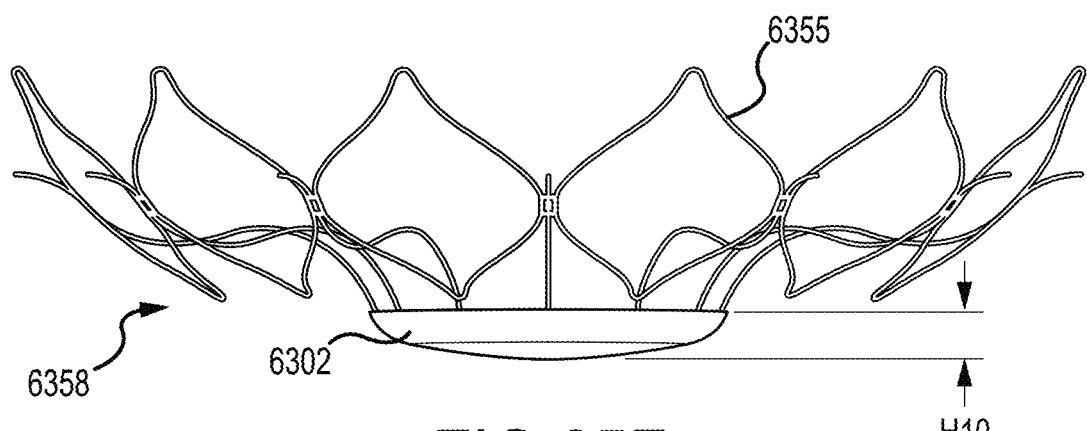

FIGS. 65E and 65F are distal and side elevation views of frame 6355 including occluder 6302 following bonding of occluder 6302 to frame 6355. As shown in FIG. 65 and as previously discussed in the context of FIG. 64D, occluder 6302 may generally have a diameter D1. While D1 may vary in applications of the present disclosure, in certain implementations, D1 may be from and including about 16 mm to and including about 28 mm. In other implementations, D1 may be from and including about 20 mm to and including about 22 mm. In one specific implementation, D1 is about 21.4 mm with a tolerance of +/−0.5 mm.

Referring to FIG. 65F, occluder 6302 may also be constructed to have a defined height, as indicated by dimension H10. As shown, H10 generally corresponds to the distance between a distal tip of occluder 6302 (which generally corresponds to the distal extent of implant 6300) and a proximal edge of occluder 6302 (e.g., proximal radially outward edge 6363 shown in FIGS. 63A and 64B). H10 may vary; however, in certain implementations, H10 may be from and including about 3.0 mm to and including about 5 mm. For example, in one implementation H10 is approximately 4 mm with a tolerance of +/−0.5 mm.

Figure 66A:
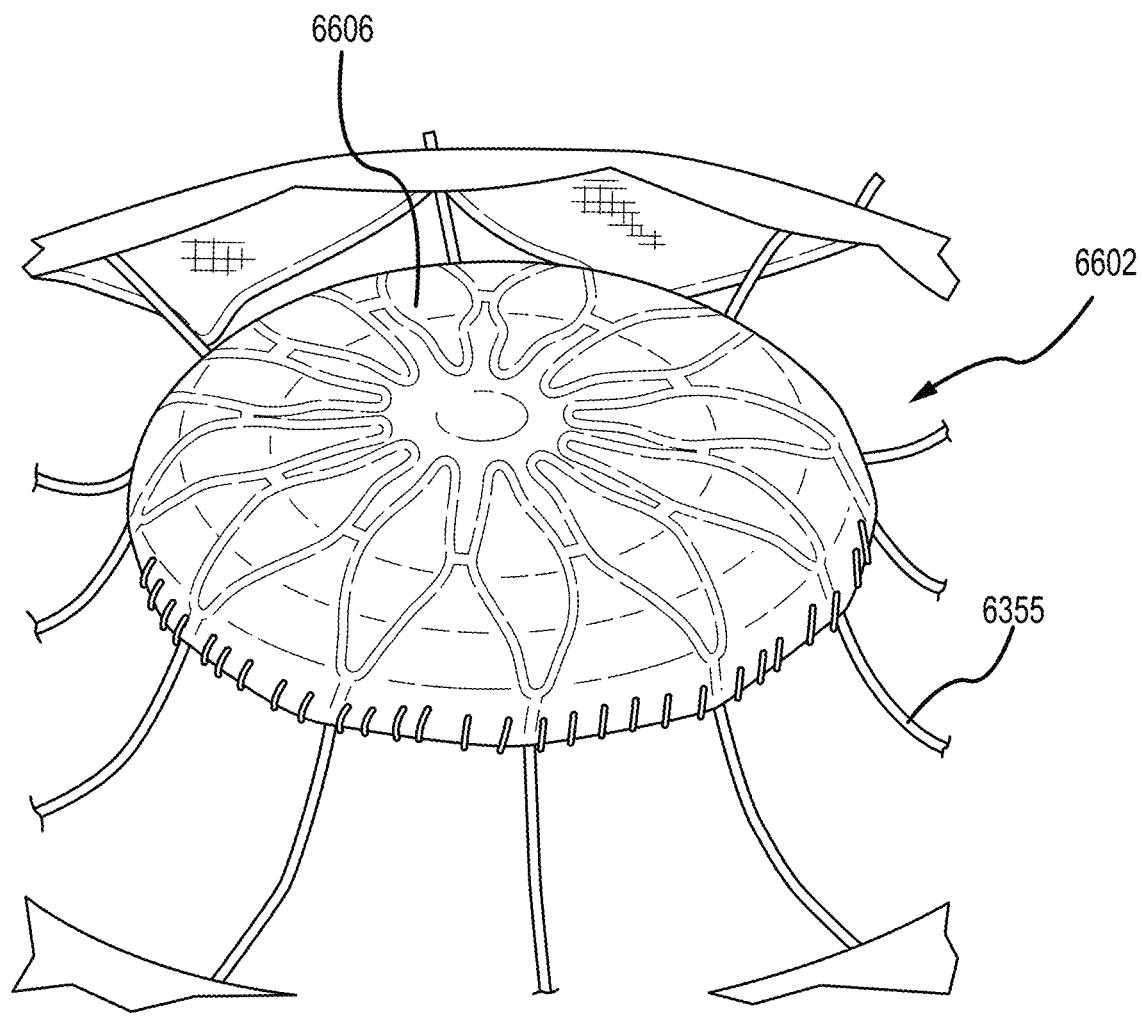
FIG. 66A is a distal-side perspective view of an alternative laminated occluder including a proximally convex back.
Figure 66B:
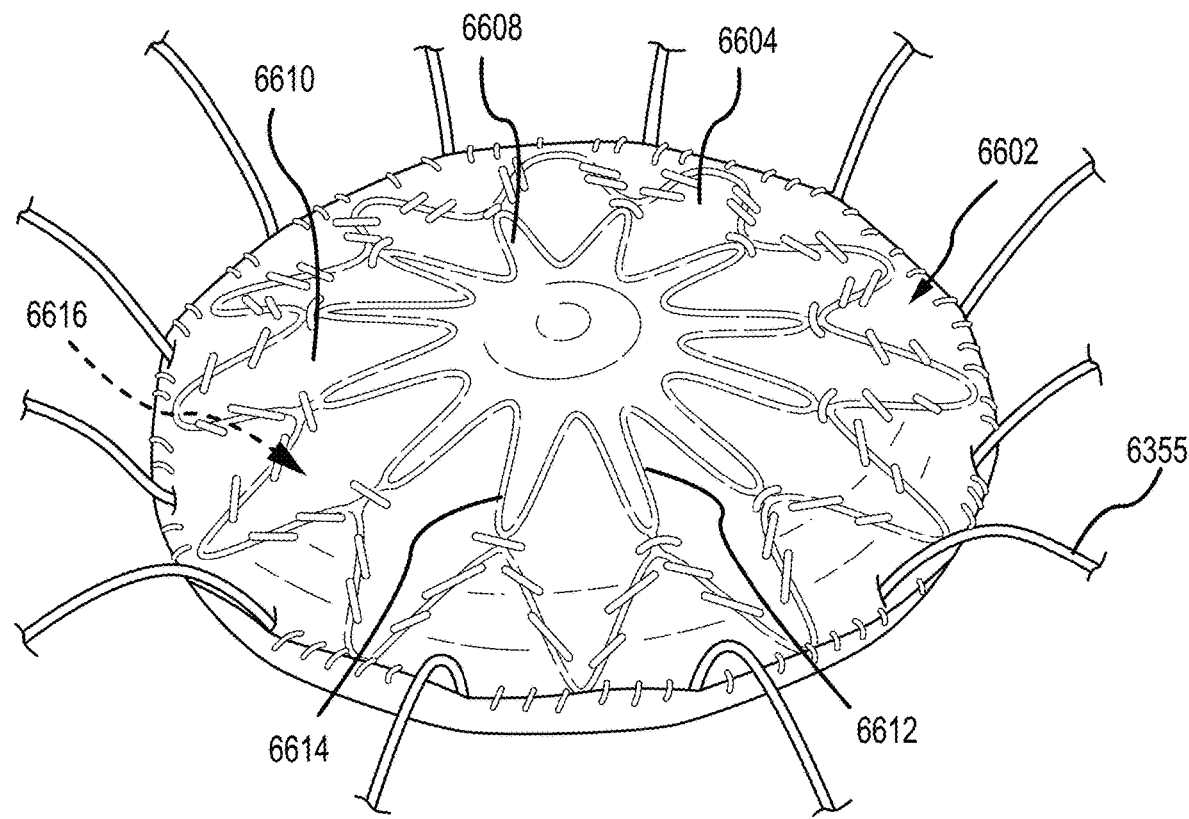
FIG. 66B is a proximal-side perspective view of the alternative laminated occluder of FIG. 66A.

FIGS. 66A and 66B illustrate an occluder 6602 that may be used for implant 6300 and other implants according to this disclosure as an alternative or variation of occluder 6302. Specifically, FIG. 66A is a distal view of alternative occluder 6602 as coupled to frame 6355 of implant 6300 while FIG. 66B is a proximal view of occluder 6602 similar assembled as implant 6300.

As discussed above and illustrated in FIGS. 65A-65F, occluder 6302 has a concave proximal surface. In contrast and as most clearly illustrated in FIG. 66B, occluder 6602 is configured to have a proximal surface 6604 that is convex. Among other things, convex proximal surface 6604 can provide benefits to hemodynamic flow across implant 6300 by more effectively directing flow around occluder 6602.

As shown in FIGS. 66A and 66B, occluder 6602 may have a multi-part construction including a distal section 6606 coupled to a proximal section 6608. Distal section 6606 is distally concave and may be substantially similar to occluder 6302. Proximal section 6608, in contrast, is distally concave and is coupled to distal section 6606 such that occluder 6602 has an overall pillow shape. As shown in FIGS. 66A and 66B, proximal section 6608 is coupled to distal section 6606 by suturing distal section 6606 to proximal section 6608; however, this disclosure contemplates that proximal section 6608 may be coupled to distal section 6606 using other methods, such as adhesives, epoxies, welding/bonding, and the like.

Proximal section 6608 may be constructed in various ways; however, in the implementation shown in FIG. 68B, proximal section 6608 includes a sheet 6610 and an internal frame 6612. Internal frame 6612 is shown as having a star-shaped construction including radially extending arms, such as arm 6614. Each arm is coupled to sheet 6610, e.g., by a suture, thereby attaching sheet 6610 to internal frame 6612 such that internal frame 6612 imparts a curved shape to sheet 6610. In at least certain implementations, internal frame 6612 may be formed using techniques similar to those used in forming frame 6355. For example, internal frame 6612 may be cut (e.g., laser cut) from tube-shaped substrate (e.g., a nitinol tube), treated, and formed into the star-like shape shown in FIG. 68B.

Sheet 6610 may similarly be formed from various materials; however, in certain implementations, sheet 6610 may be formed from a porous material, such as the woven PET used for second sheet 6506 of occluder 6302 and outer sheet 6360 of implant 6300. Among other things, using a porous material allows an internal volume 6616 of occluder 6602 to be flushed of air in preparation for delivery and implantation. Following implantation, the porosity of sheet 6610 may permit some blood to flow into internal volume 6616; however, sheet 6610 substantially limits blood flow out of internal volume 6616, such that blood entering into internal volume 6616 eventually fills and clots within internal volume 6616, forming a thrombus that effectively results in occluder 6602 having a substantially solid body that directs blood flow around occluder 6602.

In certain alternative implementations, internal volume 6616 may be filled with an epoxy, solidifying gel, solid insert, or similar material or object that substantially fills internal volume 6616 prior to delivery and implantation. In other implementation, internal volume 6616 may contain a hydromorphic polymer, hydrogel, or similar substance that expands when exposed to a fluid, e.g., blood, such that the material expands to fill internal volume 6616 following implantation. In still other alternative implementations, occluder 6602 may have a substantially solid construction. For example, occluder 6602 may be in the form of a substantially solid biocompatible body having an overall shape similar to that of occluder 6602 shown in FIGS. 66A and 66B and that can be readily coupled to distal frame portion 6358 to form occluder 6602.

XIX. Outer Sheet Construction and Assembly

As previously discussed in the context of FIG. 63A, implant 6300 includes outer sheet 6360, which extends circumferentially about a proximal portion of frame 6355. Outer sheet 6360 provides various functions including, but not limited to, protecting tissue around the valve annulus from frame 6355, facilitating alignment of implant 6300 within the valve annulus, and anchoring implant 6300 at its implantation location (e.g., through tissue ingrowth into outer sheet 6360). Further details regarding construction and assembly of outer sheet 6360 are now provided with reference to FIGS. 67A-67D.

Figure 67A:
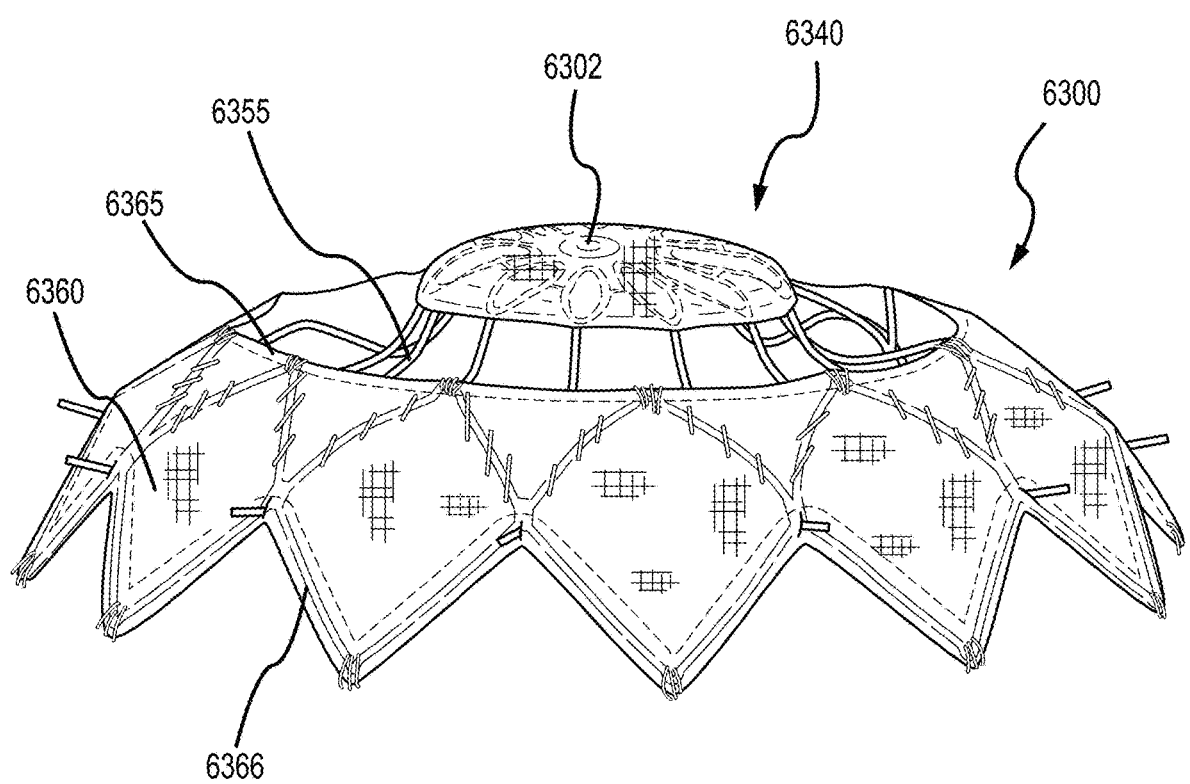
FIG. 67A is an elevation view of the implant of FIG. 63A illustrating an outer sheet coupled to the implant frame.

FIG. 67A is a side view of the distal face of implant 6300. As shown, implant 6300 includes occluder 6302 at distal end 6340 and coupled to frame 6355. Implant 6300 further includes outer sheet 6360, which extends circumferentially about a proximal portion of frame 6355 and is also coupled to and supported by frame 6355. Although the shape of outer sheet 6360 may vary, in the implementation shown in FIG. 67A, distal radially inward edge 6365 of outer sheet 6360 is circular and while proximal radially outward edge 6366 has a sinusoidal/repeating shape.

Figure 67B:
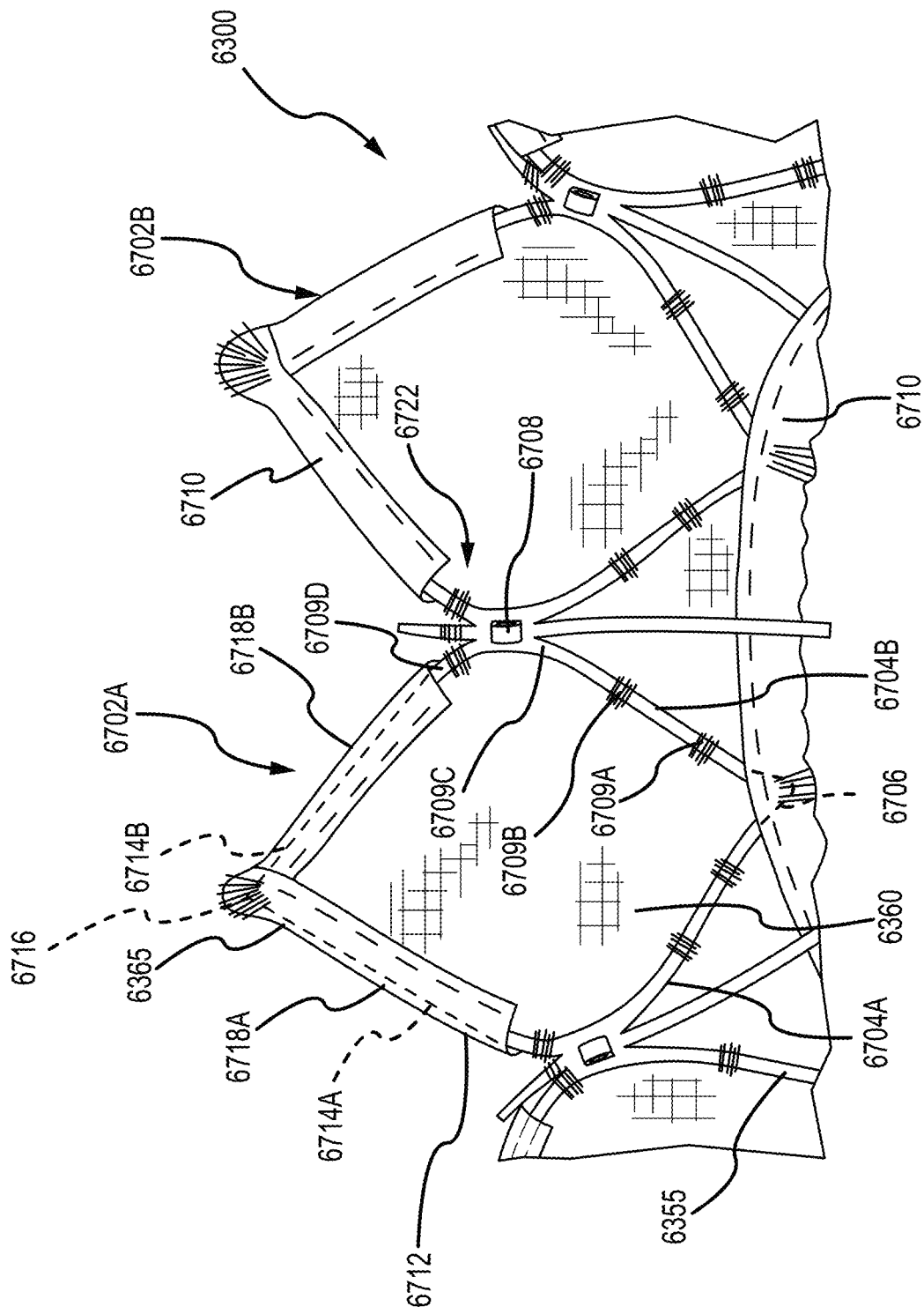
FIGS. 67B-D are detailed views of the coupling between the outer sheet and frame of the implant of FIG. 63A.

FIG. 67B is a proximal side view of a section of frame 6355 and outer sheet 6360 of implant 6300 and further illustrates assembly of outer sheet 6360 to frame 6355. The specific view shown in FIG. 67B illustrates coupling of outer sheet 6360 to each of a first outer petal portion 6702A and a second outer petal portion 6702B of frame 6355.

Outer sheet 6360 is shown as being coupled to frame 6355 using both suture loops and hemming. For example, first outer petal portion 6702A includes a frame section 6704A and a frame section 6704B, with frame section 6704B extending between a distal vertex 6706 of first outer petal portion 6702A and a junction 6708 formed between first outer petal portion 6702A and second outer petal portion 6702B. Along frame section 6704B, three suture loops 6709A-6709C are placed to couple outer sheet 6360 to frame 6355. Additional sutures loops are distributed about junction 6708 to further reinforce the coupling of junction 6708 to frame 6355. An additional suture 6709D is positioned proximal junction 6708 for further reinforcing the coupling between outer sheet 6360 and frame 6355 around junction 6708.

Outer sheet 6360 is also coupled to frame 6355 by hems extending along each of the proximal and distal edges of frame 6355. For example, a first hem 6710 extends along radially inward edge 6365, enveloping the distal vertices of the outer petal portions (e.g., distal vertex 6706 of first outer petal portion 6702A). A second hem 6712 extends along proximal radially outward edge 6366, conforming to the variable shape of proximal radially outward edge 6366.

As shown, second hem 6712 is discontinuous and made up of discrete hem sections corresponding to the proximal halves of each outer petal portion. For example, first outer petal portion 6702A includes a first petal segment 6714A and a second petal segment 6714B that extend proximally and meet at a proximal vertex 6716. Outer sheet 6360 includes a first hem segment 6718A and a second hem segment 6718B that correspond to and contain first petal segment 6714A and second petal segment 6714B, respectively, with first hem segment 6718A folded over second hem segment 6718B.

Second hem 6712 is shown as being discontinuous between petal portions, e.g., at junction 6708. Despite this continuity, the suture used to form the discrete sections of second hem 6712 may be continuous and may be routed across the junctions between petal portions. For example, FIG. 67B shows a suture segment 6722 that crosses junction 6708 and is continuous between first hem segment 6718A and second hem segment 6718B.

Figure 67D:
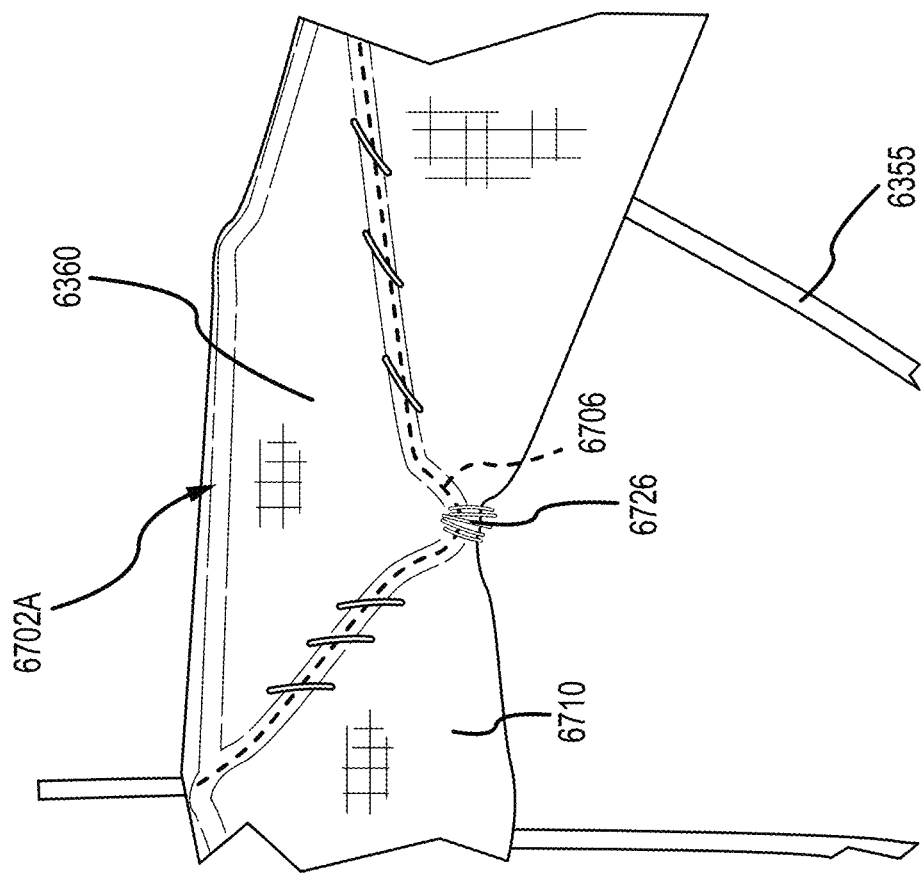
Figure 67C:
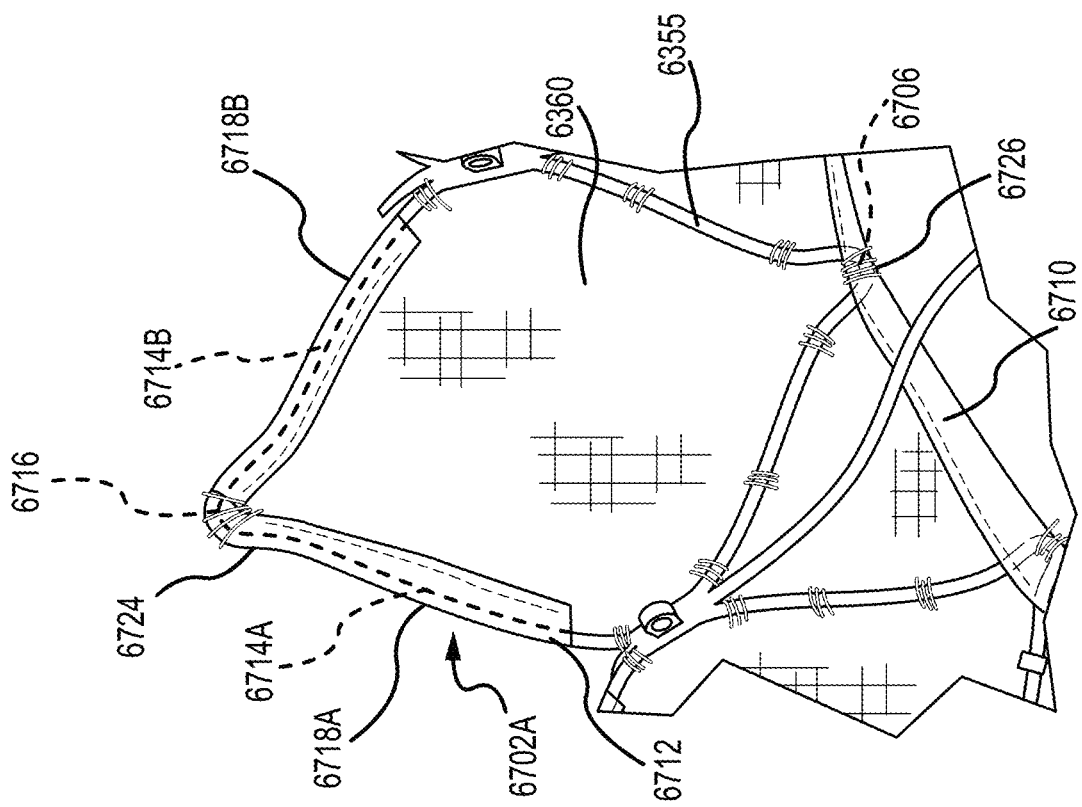

FIGS. 67C and 67D illustrate proximal vertex 6716 and distal vertex 6706, respectively, in further detail. As shown in each figure, a suture wrap may be formed at one or both of proximal vertex 6716 and distal vertex 6706. For example, a proximal suture wrap 6724 is shown in FIG. 67C extending around proximal vertex 6716 while a distal suture wrap 6726 is shown in each of FIGS. 67C and 67D extending around distal vertex 6706. Including suture wraps as shown provides several notable advantages. As a first example, each of the suture wraps provides robust and reinforced coupling of outer sheet 6360 to frame 6355. The suture wraps also provide additional padding around the vertices of the outer petal portions of frame 6355. Finally, the suture wraps may fill gaps between hem segments. For example, proximal suture wrap 6724 is disposed between first hem segment 6718A and second hem segment 6718B and may fill/cover any gap that may be present between the two segments despite the folding of first hem segment 6718A over second hem segment 6718B.

Figure 68:
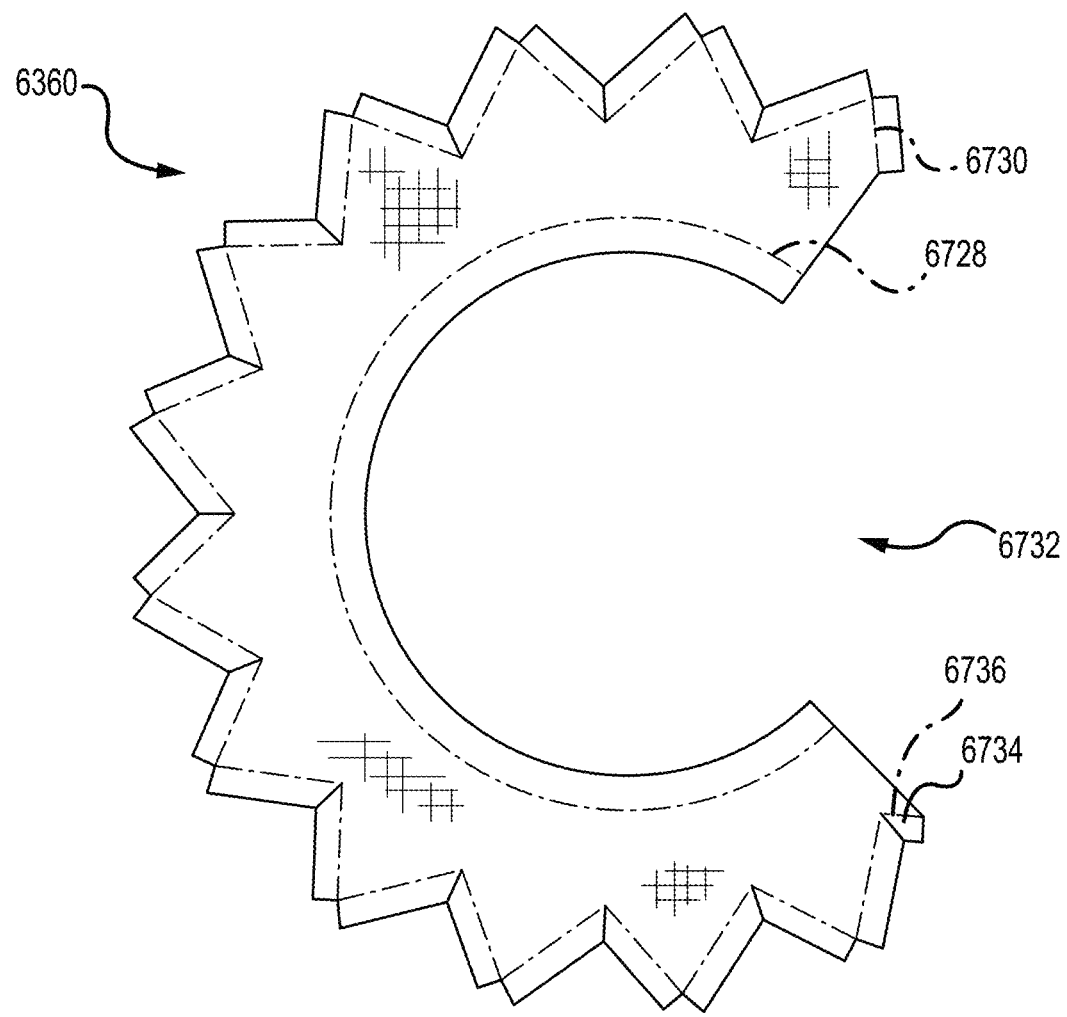
FIG. 68 illustrates the outer sheet prior to attachment to the frame.

FIG. 68 shows an example of outer sheet 6360 prior to coupling onto frame 6355. As shown, outer sheet 6360 is a single piece of woven PET material that is cut (e.g., laser cut) to conform to frame 6355 and to include various tabs, etc., to form any hems required to couple outer sheet 6360 to frame 6355. FIG. 68 further indicates a first fold line 6728 corresponding to first hem 6710 and a series of second fold lines 6730 corresponding to second hem 6712.

In one example assembly process and following cutting of outer sheet 6360, outer sheet 6360 is wrapped around frame 6355 as shown in the preceding figures and sutured/stitched onto frame 6355. Such suturing/stitching generally includes forming each of first hem 6710 and second hem 6712 and forming any additional suture loops (e.g., suture loops 6709A-6709D). To facilitate wrapping of outer sheet 6360 about frame 6355, outer sheet 6360 includes an open side 6732 that is closed as outer sheet 6360 is wrapped about frame 6355. To facilitate this process, outer sheet 6360 may include an additional tab, such as tab 6734, to keep outer sheet 6360 in a closed configuration while being coupled to frame 6355. Following initial wrapping of outer sheet 6360 about frame 6355, tab 6734 may be folded inward (e.g., along fold line 6736) and held in place by a suture/stitch. Doing so maintains an approximate shape of outer sheet 6360 and facilitates folding and forming of the various hems and suture loops necessary to securely couple outer sheet 6360 to frame 6355.

The foregoing discussion provides one example of construction and assembly of outer sheet 6360. In particular, the example included cutting outer sheet 6360 from a sheet of suitable material (e.g., woven PET) and attaching outer sheet 6360 to frame 6355 using a combination of hems and suture loops. In suture-reliant implementations, coupling of outer sheet 6360 to frame 6355 may be achieved using a monofilament suture, a multifilament suture, or a combination of mono- and multifilament sutures. Also, this disclosure contemplates that outer sheet 6360 may be coupled to frame 6355 using sutures, adhesives, welding, or any combination thereof. For example, in certain implementations, one of heat welding or ultrasonic welding may be used to close the various hems illustrated in the preceding figures. As another example, polyurethane, silicone, or a similarly suitable and biocompatible adhesive, epoxy, bonding agent, etc., may be employed. This disclosure also contemplates that multiple fixation techniques may be used to couple outer sheet 6360 to frame 6355. For example, adhesive may be initially used to perform an initial or partial coupling of outer sheet 6360 to outer sheet 6360 but may be supplemented or reinforced by suturing, welding, etc.

XX. Implants Including Eyelets for Cinch Line Routing

Implant delivery systems of the present disclosure generally rely on two mechanisms for controlling expansion and collapse of implants during delivery. First, during delivery, implants according to this disclosure may be disposed on a control arm assembly of the delivery tool. The control arm assembly includes control arms configured to radially expand and contract in response to manipulation of a corresponding control of a handle assembly of the delivery tool. The control arm is coupled to the frame of the implant such that as a clinician expands the control arms radially outward, the implant expands. Similarly, as the clinician retracts the control arms radially inward, the implant is pulled inward and collapsed.

In addition to the control arms, delivery systems according to the present disclosure may include one or more cinch lines. The one or more cinch lines are routed through the delivery tool and made to extend circumferentially about the frame of the implant. In implementations including a single cinch line, the cinch line may be routed from a handle assembly, through the catheter assembly of the delivery system (e.g., through a cinch line tube extending through the catheter assembly), about the full circumference of the implant, and back through the catheter assembly to the handle assembly.

In contrast, in implementations including multiple cinch lines, each cinch line may be similarly routed through delivery catheter assembly, but only partially about the circumference of the implant. For example, in an implementation including two cinch lines, each cinch line may extend about approximately half of the circumference of the implant and meet at a retention location. Each cinch line may terminate in a loop or similar feature through which a retention pin or cable may be passed to retain the cinch lines during delivery and implantation.

During delivery and implantation, the one or more cinch lines provide various functions and benefits. In general, the one or more cinch lines retain the implant on the control arms; however, by maintaining tension of the one or more cinch lines during expansion and collapse of the implant, the uniformity of expansion and collapse can be substantially improved due to the cinch lines distributing expansion/ collapse forces evenly about the implant. Relatedly, maintain tension on the one or more cinch lines also provides improve responsiveness of the implant expansion and collapse controls by reducing or eliminating slack that may need to be overcome before manipulation of a control by the clinician results in corresponding movement of the implant.

Regardless of whether one or more cinch lines are included, following delivery and implantation of the implant, the cinch lines must be decoupled from the implant to permit release of the implant and subsequent removal of the delivery system. In implementations including a single cinch line that forms a large loop through the delivery system, the cinch line may be cut at a proximal location and subsequently pulled through the catheter assembly. In implementations including multiple cinch lines retained by a retention cable at the implant, the retention cable may be retracted to release the cinch lines, which may then be retracted through the delivery catheter. This process and an example handle assembly for sequencing of retention cable and cinch line retraction is described below in further detail in the context of FIGS. 83A-86D.

Smooth and reliable retraction of the cinch lines is a critical part of the implantation process. For example, if the cinch lines bind, snag, or become otherwise restricted as they are retracted, the resulting pulling on the implant may result in the implant to shift within the valve annulus or, in certain extreme cases, to become partially or fully dislodged from its implantation location.

To avoid or reduce the likelihood of such situations, implementations of this disclosure include various features for more reliable and consistent routing of cinch lines and, in particular, consistent retraction of cinch lines during release of the implant from the delivery system. For example, in the implementation shown in FIG. 59, routing rings (e.g., ring 3646) are coupled to the control arms of delivery device 3600 and cinch line 3614 is routed through each of the routing rings and corresponding rings (e.g., ring 3804) coupled to the frame of implant 3800.

As another alternative, which is discussed in further detail in this section, improved cinch line routing is provided by a series of eyelets coupled to the implant frame. More specifically, specially designed eyelets are coupled to the frame of the implant such that the eyelets are distributed circumferentially about the radially inward surface of the implant. In one specific implementation, the junctions between adjacent outer petal portions of the implant frame include a slot through which the separately manufactured eyelets are inserted. In contrast to the rings included in the implementation shown in FIG. 59, the eyelets are rigidly retained using one or more coupling techniques and form a consistent and reliable path for the one or more cinch lines about the circumference of the implant. Additional features, such as a smooth, radius inner bore, reduce the likelihood of cinch lines binding or snagging as they are retracted through the eyelets, thereby improving the overall reliability and consistency with which the cinch lines can be retracted during release of the implant from the delivery device.

Figure 69A:
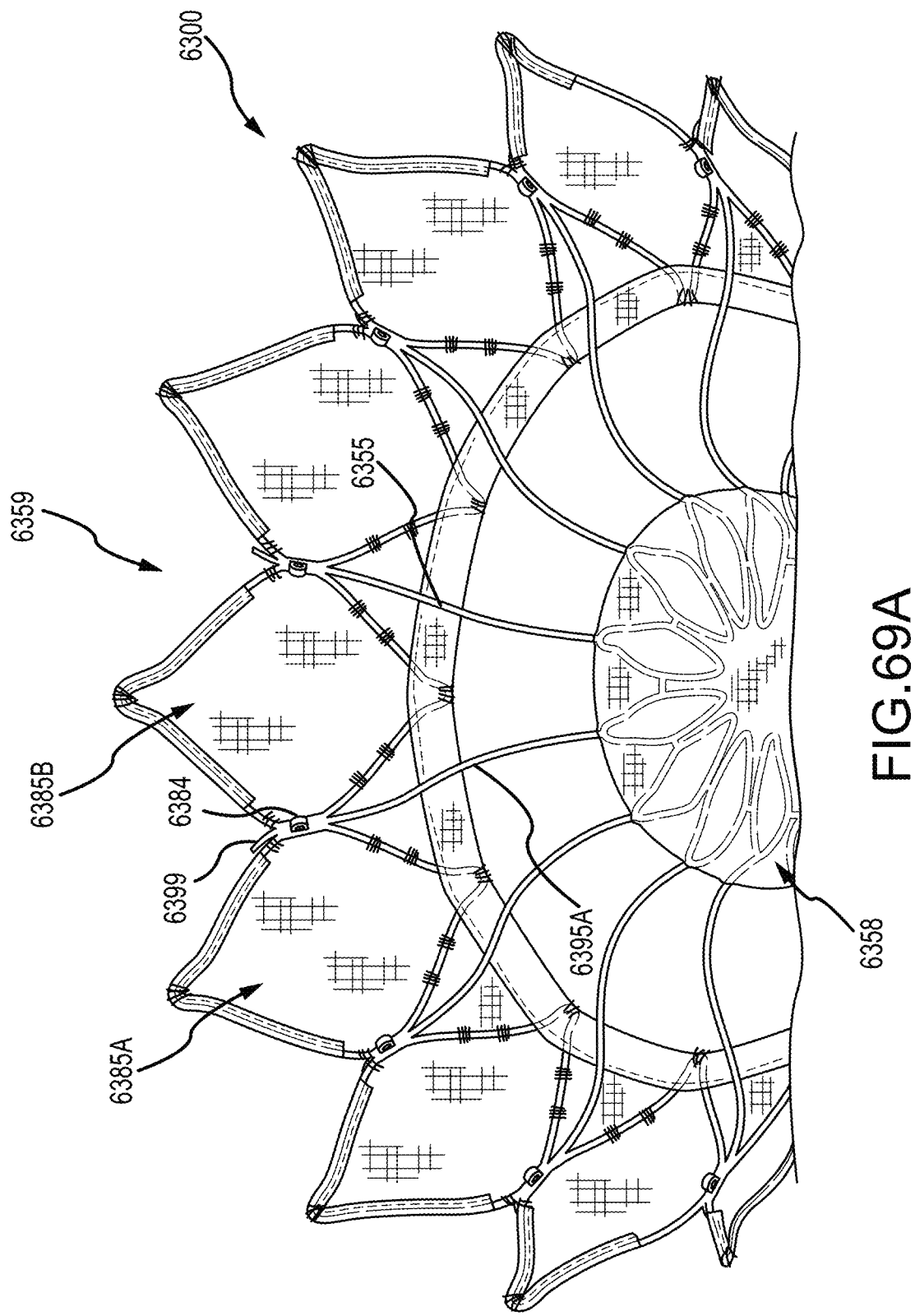
FIG. 69A is a proximal-side perspective view of the implant of FIG. 63A illustrating eyelets distributed about the frame of the implant.
Figure 69B:
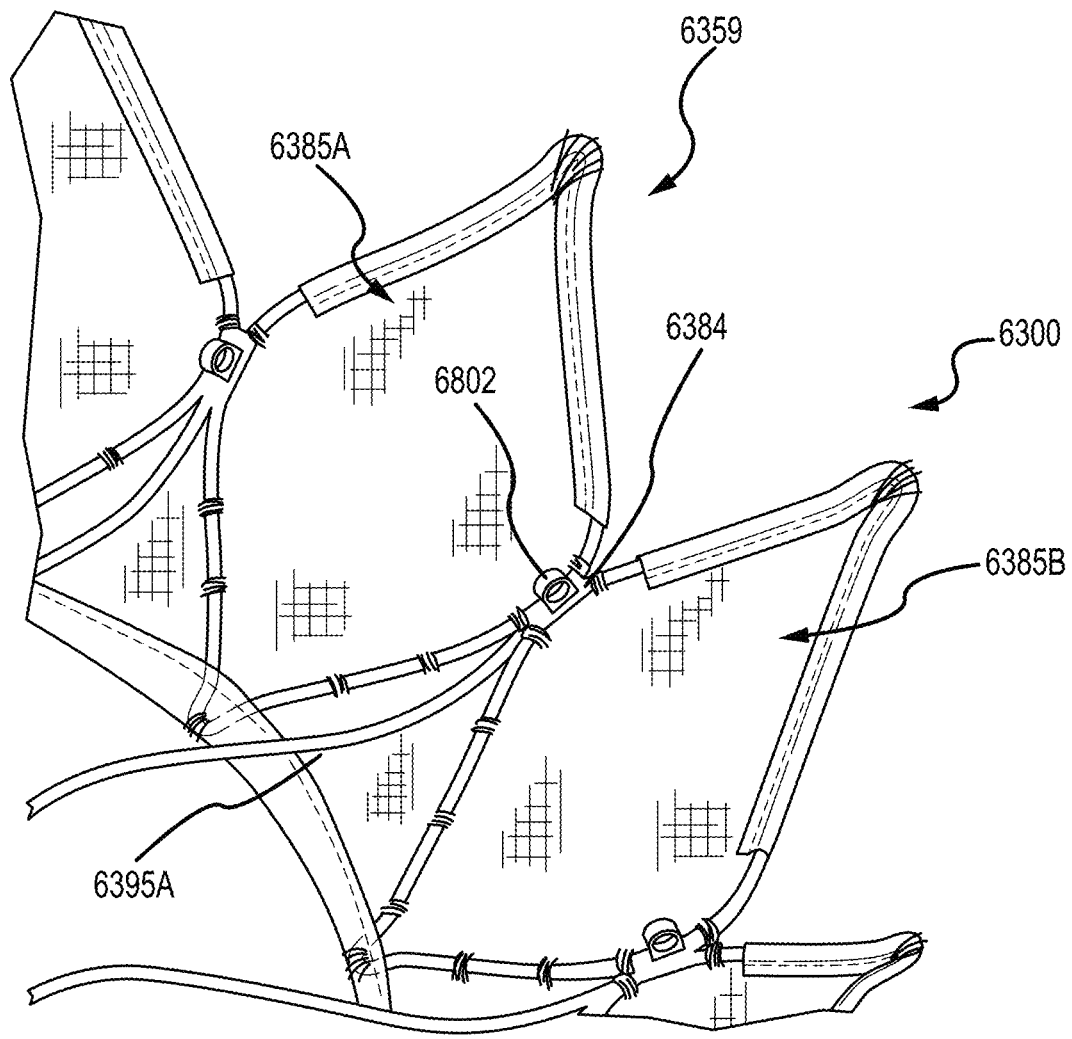
FIG. 69B is a detailed view of the implant of FIG. 63A further illustrating eyelets of the implant.

FIGS. 69A and 69B are a partial proximal view and a detailed proximal view, respectively, of implant 6300. Implant 6300 is discussed in detail in previous sections; however, implant 6300 generally includes frame 6355, which includes a series of circumferentially distributed spokes that extend from a distal frame portion 6358 to a proximal frame portion 6359. Proximal frame portion 6359 includes a series of circumferentially distributed outer petal portions, such as outer petal portion 6385A and outer petal portion 6385B. Each pair of outer petal portions meet at a junction, such as junction 6384. Each junction further connects with one of the spokes extending from distal frame portion 6358. For example, junction 6384 connects outer petal portion 6385A, outer petal portion 6385B, and spoke 6395A. In at least certain implementations, an anchor member, such as anchor member 6399 may also extend from junction 6384.

In certain implementations of this disclosure, each junction of frame 6355 may further include an eyelet for use in routing one or more cinch line about the inner surface of implant 6300. For example, FIG. 69B illustrates an eyelet 6802 located at and coupled to junction 6384. Additional eyelets are also shown coupled to adjacent junctions. In certain implementations, each junction of frame 6355 may include a respective eyelet such that the eyelets extend about the full circumference of implant 6300 and enable corresponding and complete routing of one or more cinch lines about implant 6300.

Figure 70:
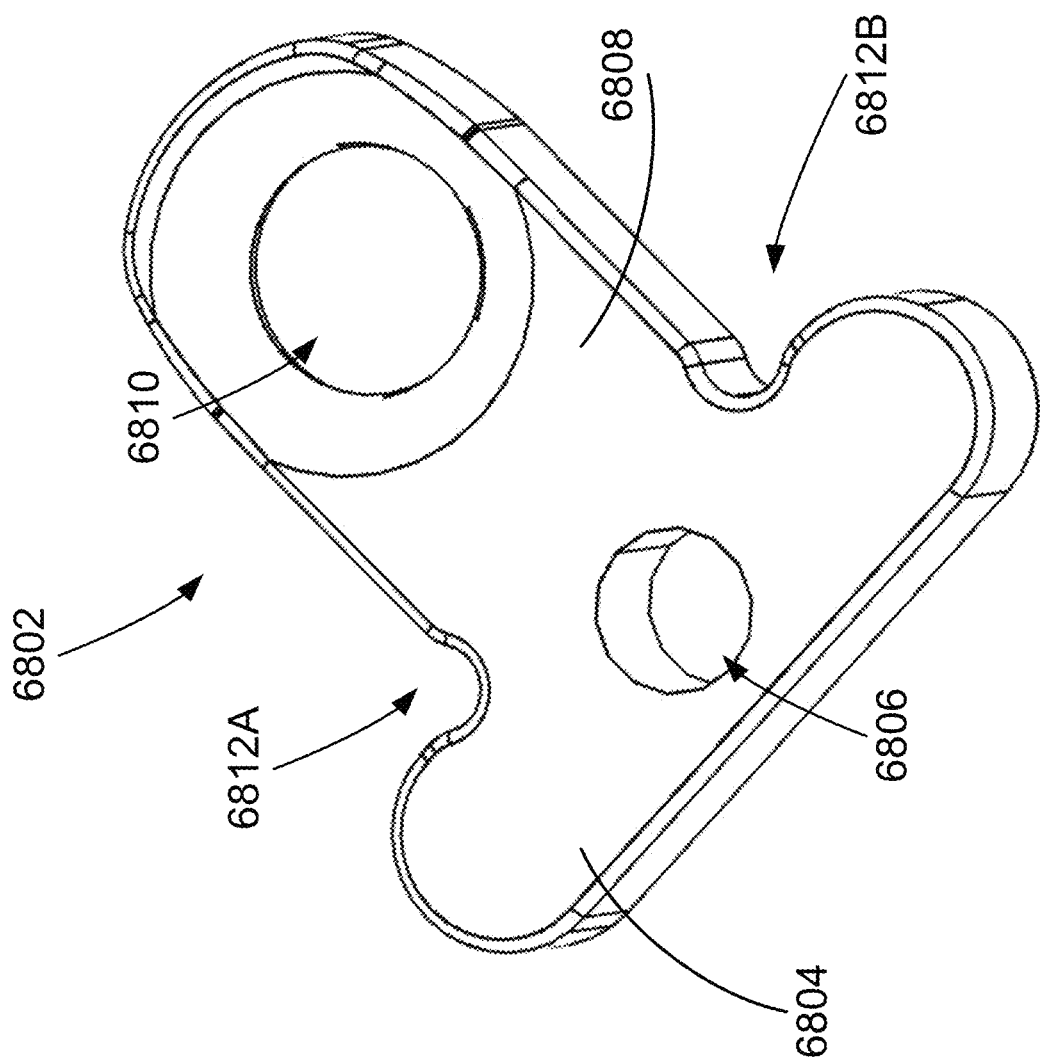

FIG. 70 is an isometric view of eyelet 6802, while FIGS. 71A-C are plan, bottom, and cross-sectional views of eyelet 6802, respectively. As shown in the figures, eyelet 6802 generally includes a shank 6804 extending in a first direction and a body 6808 extending perpendicularly from shank 6804. In certain implementations, shank 6804 defines a retention hole 6806 that may be used to couple eyelet 6802 to frame 6355 using a suture loop or similar coupling element. Body 6808 similarly defines a cinch line hole 6810 that extends through body 6808 and that is generally sized and shaped to permit threading of the cinch line through cinch line hole 6810.

As shown in FIG. 70, an undercut may be made on either side of body 6808 where body 6808 meets shank 6804. For example, FIG. 70 indicates undercut 6812A on a first side of body 6808 and undercut 6812B on an opposite side of body 6808. As discussed below in further detail, undercut 6812A and undercut 6812B facilitate flush contact between shank 6804 and the proximal side of junction 6384 when eyelet 6802 is assembled with frame 6355.

FIGS. 71A-71C illustrate additional views of eyelet 6802 including various dimensions. As in other aspects of this disclosure, the specific dimensions of eyelet 6802 may vary and any ranges or dimensions specifically mentioned in this disclosure in this and other sections are intended merely as examples that reflect certain positive outcomes during development and testing.

Referring first to FIG. 71A, dimension W1 corresponds to a width of body 6808, dimension D5 corresponds to a diameter of the through hole of cinch line hole 6810, H11 corresponds to an offset between the top extent of shank 6804 and the beginning of the radius of cinch line hole 6810, and D6 corresponds to a diameter of retention hole 6806. In certain implementations, W1 may be from and including about 0.9 mm to and including about 1.0 mm and, in one specific example is approximately 0.927 mm with a tolerance of +/−0.02 mm. In certain implementations, D5 may be from and including about 0.55 mm to and including about 0.6 mm and, in one specific example is approximately 0.527 mm with a tolerance. In certain implementations, H11 may be from and including about 0.55 mm to and including about 0.65 mm and, in one specific example is approximately 0.596 mm with a tolerance of +/−0.02 mm. In certain implementations, D6 may be from and including about 0.35 mm to and including about 0.4 mm and, in one specific example is approximately 0.38 mm.

FIG. 71B is a bottom view of eyelet 6802 and includes dimensions W2, which corresponds to the width of shank 6804, and T1, which corresponds to the thickness of eyelet 6802. In certain implementations, W2 may be from and including about 1.8 mm to and including about 2.0 mm and, in one specific example is approximately 1.875 mm with a tolerance of +/−0.02 mm. In certain implementations, T1 may be from and including about 0.3 mm to and including about 0.4 mm and, in one specific example is approximately 0.36 mm with a tolerance of +/−0.02 mm.

Finally, FIG. 71C is a cross-sectional view of body 6808 across cinch line hole 6810 as indicated in FIG. 71A. As shown, in at least certain implementations, cinch line hole 6810 may have radiused or otherwise machined sides to eliminate any sharp edges that may catch or otherwise impede cinch line retraction. The radius of cinch line hole 6810 is indicated as R5 in FIG. 71C. In certain implementations, R5 may be from and including about 0.15 mm to and including about 0.20 mm and, in one specific example is approximately 0.18 mm.

Figure 72:
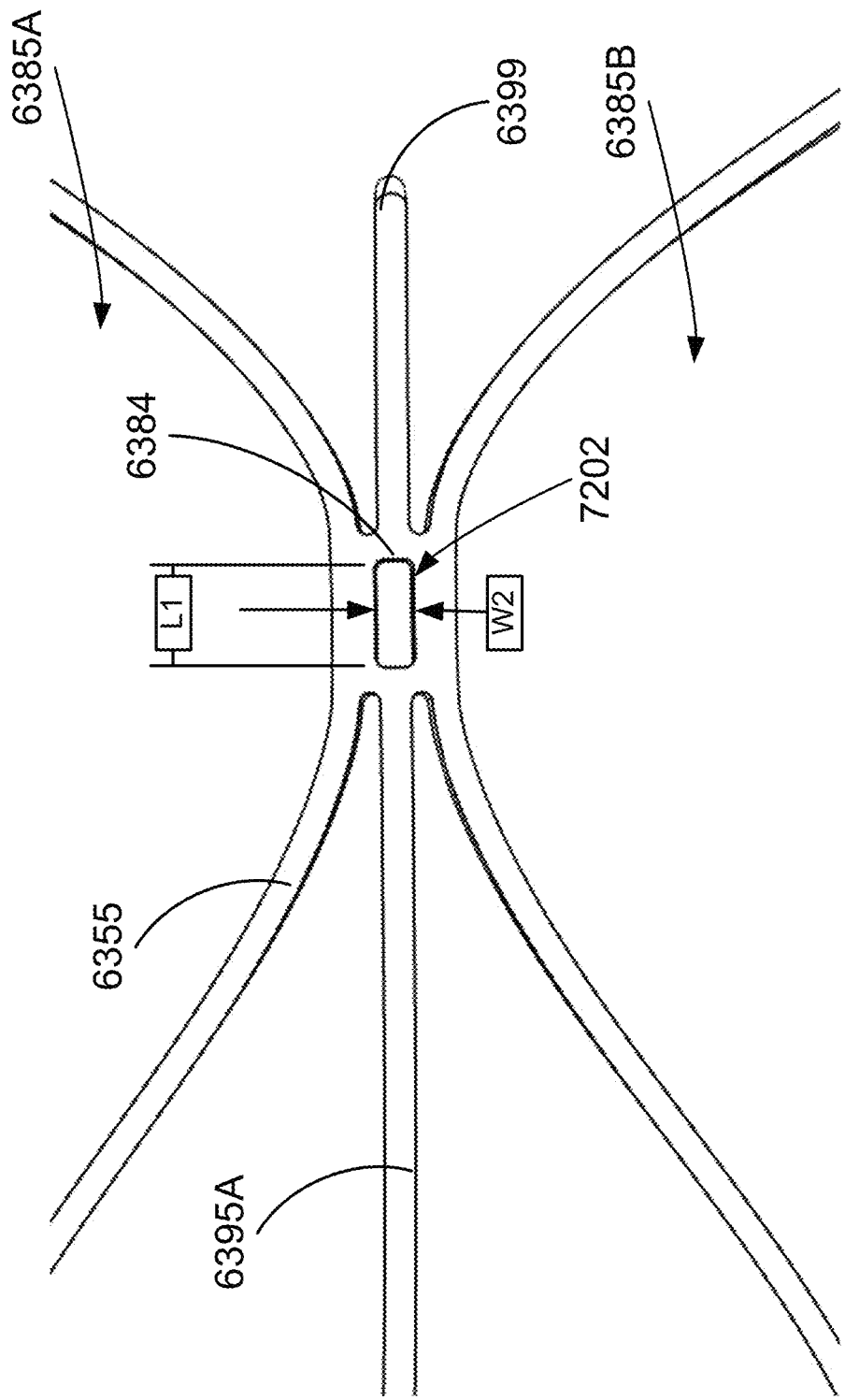
FIG. 72 is a detailed view of a junction of the frame of the implant of FIG. 63A including a slot for receiving an eyelet.

FIG. 72 is a detailed view of junction 6384 with eyelet 6802 removed. More specifically, FIG. 72 is a detailed view from a perspective orthogonal to a slot 7202 on a distal side of frame 6355. As previously discussed, junction 6384 provides a connection location between spoke 6395A, outer petal portion 6385A, and outer petal portion 6385B, and anchor member 6399 may extend outward from junction 6384.

Slot 7202 is defined by and extends through junction 6384 and is shaped to receive eyelet 6802. For example, in certain implementations, slot 7202 may be laser cut or otherwise formed in the same process as the rest of frame 6355 (e.g., a process by which frame 6355 is laser cut from a tubular substrate, such as a nitinol tube). Slot 7202 may vary in size and shape depending on the scale of frame 6355 and, more specifically, the size and shape of eyelet 6802. Nevertheless, in certain implementations, slot 7202 may generally have a width W2 and a length L1, with W2 corresponding to a dimension extending perpendicular to spoke 6395A and L extending parallel to spoke 6395A. Although dimensions of W and L may vary, in certain implementations, W may be from and including about 0.3 mm to and including about 0.5 mm. For example, W2 may be approximately 0.405 mm with a tolerance of +/−0.03 mm. Similarly, L1 may vary in different implementations of this disclosure; however, in certain implementations, L1 may be from and including about 0.75 mm to and including about 1.5 mm. In one specific example, L1 is approximately 1.075 mm with a tolerance of +/−0.03 mm.

Figure 73A:
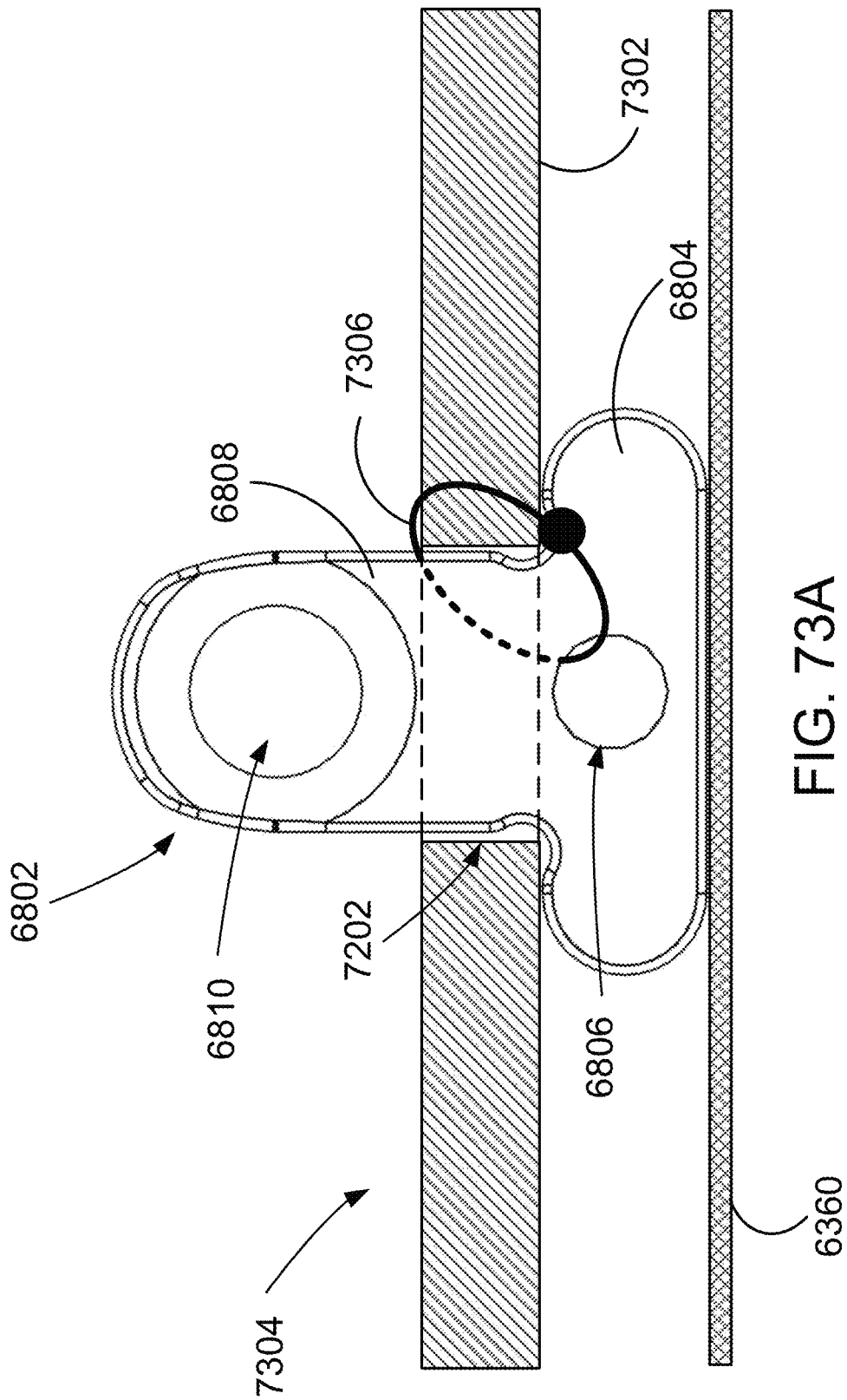
FIGS. 73A and 73B are cross-sectional views of the implant of FIG. 63A illustrating coupling of the eyelet to the frame with FIG. 73B further illustrating coupling of the implant to a delivery device control arm.

FIG. 73A is a cross-sectional view of junction 6384 with eyelet 6802 installed. As shown, eyelet 6802 is inserted through slot 7202 such that shank 6804 of eyelet 6802 abuts a distal surface 7302 of junction 6384 and cinch line hole 6810 extends to a proximal side 7304 of junction 6384, with the contact between shank 6804 and distal surface 7302 precluding further proximal movement by eyelet 6802. Eyelet 6802 is shown as being coupled to junction 6384 by a suture loop 7306 that extends about junction 6384 and is threaded through retention hole 6806 of eyelet 6802. In other implementations, eyelet 6802 may be retained within slot 7202 using alternative or additional means. For example, eyelet 6802 may be bonded to junction 6384 using an adhesive or by a welding process. As another alternative slot 7202 and body 6808 of eyelet 6802 may be sized such that an interference fit is formed between slot 7202 and body 6808 that positively retains eyelet 6802 within slot 7202. As further illustrated in FIG. 73A, outer sheet 6360 is generally disposed distal shank 6804 when implant 6300 is fully assembled. Accordingly, outer sheet 6360 may also be fitted to abut and apply proximal force to shank 6804 to facilitate retention of eyelet 6802 within slot 7202.

Figure 73B:
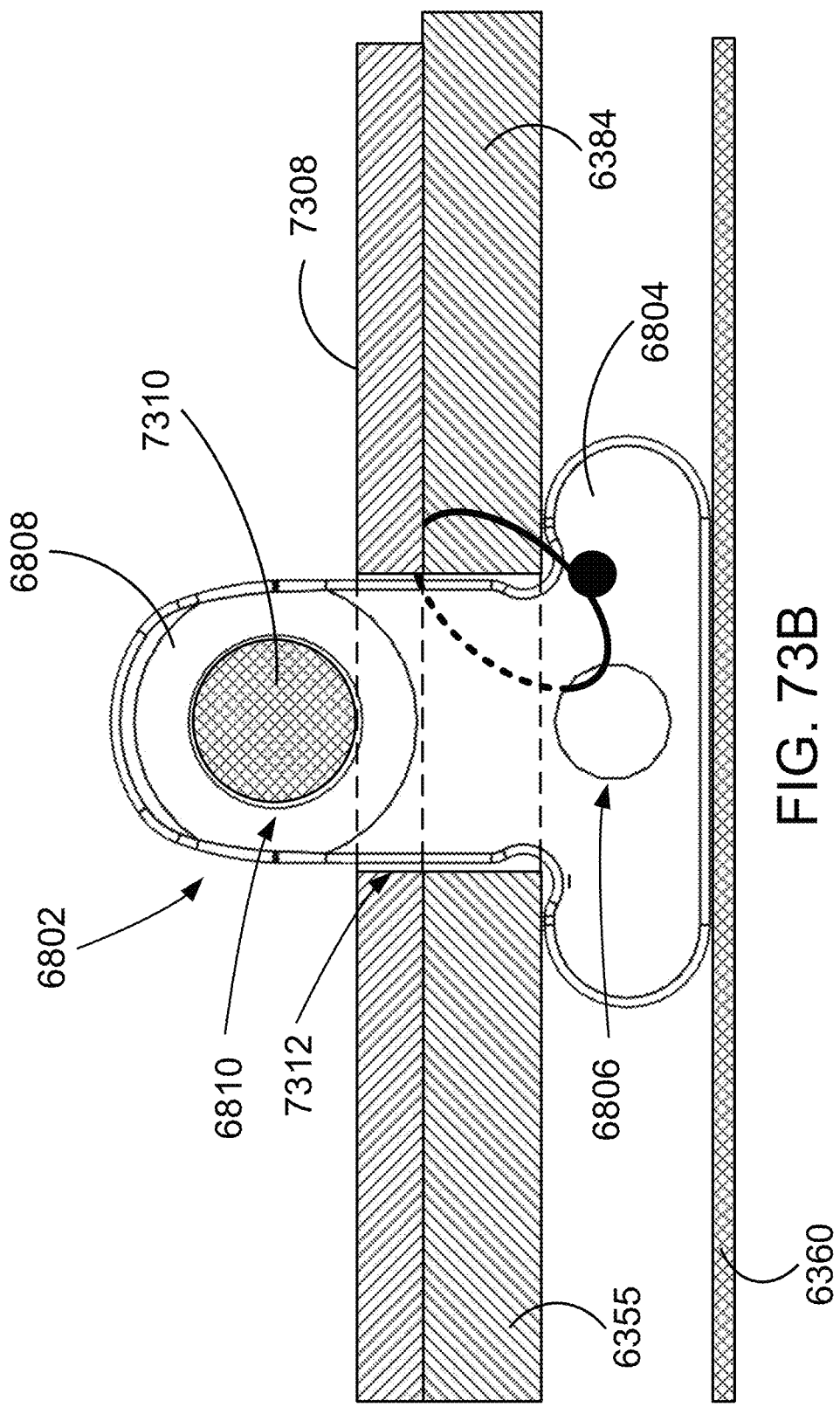

FIG. 73B is similarly a cross-sectional view of junction 6384 with eyelet 6802 installed albeit with implant 6300 coupled to a control arm 7308 of a delivery tool and with a cinch line 7310 routed through cinch line hole 6810 of eyelet 6802. As shown, control arm 7308 includes a hole or slot 7312 shaped to receive body 6808 of eyelet 6802. Following insertion of eyelet body 6808 through slot 7312, cinch line 7310 can be routed through cinch line hole 6810, thereby retaining implant 6300 onto control arm 7308. This general assembly process is then repeated for each eyelet of implant 6300 and each corresponding control arm of the delivery device.

Following placement of implant 6300, cinch line 7310 is released (e.g., by cutting and pulling or retraction of a retention pin/cable) and retracted. During retraction, cinch line 7310 passes through cinch line hole 6810. Once cinch line 7310 is clear of cinch line hole 6810, control arm 7308 is separable from eyelet 6802, thereby enabling release of implant 6300 from the delivery tool.

This disclosure contemplates that eyelet 6802 may be formed and manufactured using various materials and processed. Nevertheless, in one specific implementation, eyelet 6802 is formed from titanium that is precision machined, cleaned, and electropolished prior to assembly with frame 6355.)

XXI. Delivery Tools Including Internal Tubes with Modified Flexibility

FIGS. 36-44 illustrated various features and components of delivery device 3600, which is a non-limiting example of an implant delivery device according to this disclosure. As described in the context of FIGS. 36-44, delivery device 3600 includes delivery catheter 3604, which is the primary steerable element of delivery device 3600. Delivery device 3600 further includes various tubes and shafts within delivery catheter 3604 for performing various functions of delivery device 3600. For example, tube 3626 provides a conduit through which control arm shaft 3642 and control arm assembly 3608 extend.

In addition to providing protection and support for control arm shaft 3642 and control arm assembly 3608, in at least some implementations, tube 3626 is also extendible and retractable relative to delivery catheter 3604 to facilitate positioning of the implant during the implantation process. An implementation of this disclosure capable of such extension and retraction and corresponding control mechanisms is illustrated in FIGS. 79A-79D and discussed further below.

In general, extension and retraction of distal tube 3626 requires that distal tube 3626 have sufficient axial strength and rigidity to transfer longitudinal forces imparted at a handle assembly of the delivery system efficiently and responsively. However, given that delivery catheter 3604 is steerable, distal tube 3626 must also be sufficiently flexible to permit steering of delivery catheter 3604 without imparting substantial resistance.

To address these challenges, among others, this disclosure provides for an internal tube for an implant delivery system that is both stiff enough to transfer forces necessary for extension and retraction of an implant supported on the distal end of the tube and flexible enough so as not to substantially impact steering and control of the delivery catheter within which the tube is contained. As described below in further detail, these goals are achieved by forming a substantial length of the tube with a uniform and relatively stiff construction. Certain distal sections of the tube that generally correspond to the steerable sections of the delivery catheter further include slits, cutouts, helical cuts, or similar features that locally reduce bending stiffness of the tube without substantially altering axial strength and force transfer characteristics. In some implementations, such stiffness reduction features may be configured to reduce stiffness of the tube to bending along a specific plane or in a specific direction, e.g., along a plane corresponding to a steering plane of the delivery catheter, while maintaining rigidity with respect to bending in other directions.

Figure 74:
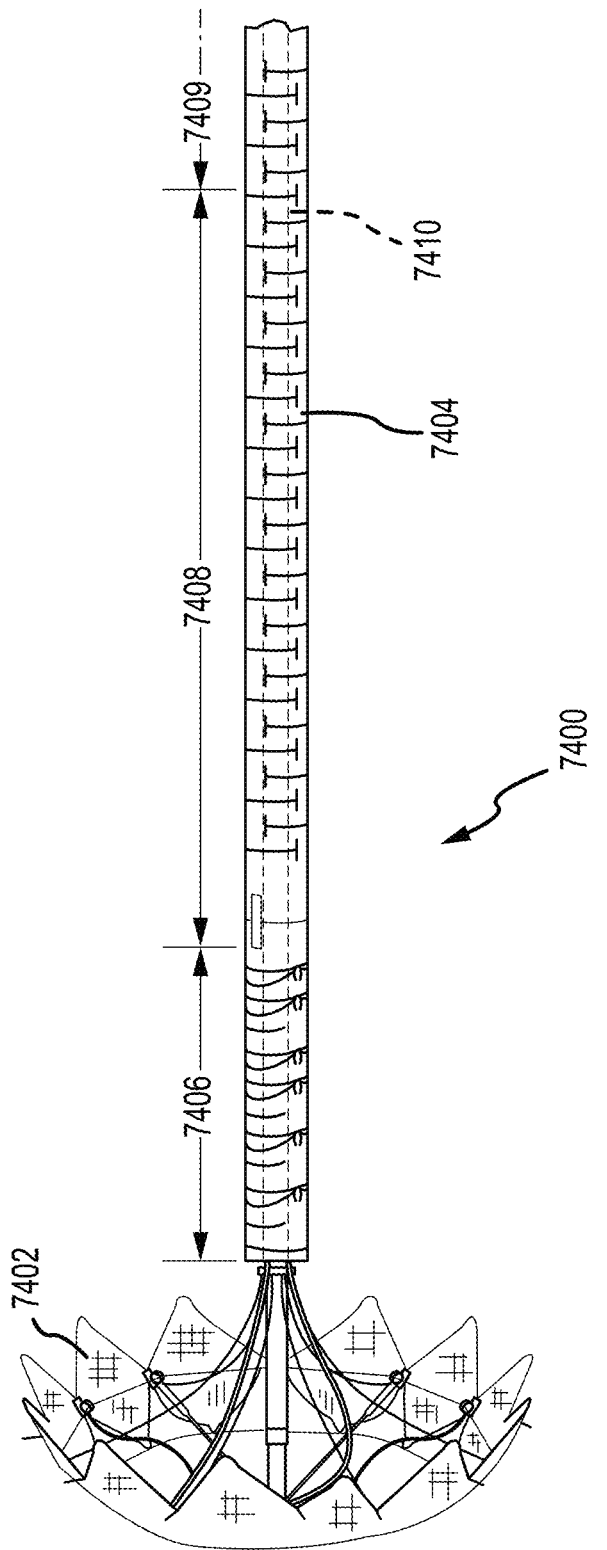
FIG. 74 is an elevation view of an example delivery system and implant, the delivery system including a catheter assembly.

FIG. 74 illustrates an example delivery system 7400 for an implant 7402. Delivery system 7400 generally corresponds to delivery device 3600, discussed above. As noted in the context of delivery device 3600, delivery system 7400 includes a steerable catheter 7404 including multiple steerable sections. While other configurations and steering arrangements of steerable catheter 7404 are contemplated by and within the scope of this disclosure, steerable catheter 7404 generally includes a distal steerable section 7406 steerable along a first plane (e.g., plane 4506, shown in FIG. 45A with bending along plane 4506 further illustrated in FIGS. 45B and 45C) and a proximal steerable section 7408 steerable along two planes (e.g., plane 4508 and plane 4510 shown in FIG. 45A with steering along the planes shown in FIGS. 45D and 45E and FIGS. 45F-45H, respectively). In certain implementations, the first steering plane of proximal steerable section 7408 may be coplanar with the steering plane of distal steerable section 7406 when steerable catheter 7404 is in a neutral/straight configuration while the second steering plane of proximal steerable section 7408 may be orthogonal to the first steering plane of proximal steerable section 7408. Steerable catheter 7404 may also include one or more non-steerable catheter sections, such as non-steerable catheter section 7409. For example, non-steerable catheter section 7409 may extend from proximal steerable section 7408 to a handle assembly of delivery system 7400.

Delivery system 7400 includes an internal tube 7410. The specific functions of internal tube 7410 may vary; however, in at least certain implementations internal tube 7410 enables routing of elongate elements through steerable catheter 7404. In delivery system 7400, internal tube 7410 is also translatable relative to steerable catheter 7404 to facilitate positioning and placement of implant 7402 during delivery and implantation. An example of such extension and retraction is provided below in the context of FIGS. 79A-80B, which illustrate and describe extension and retraction of an inner tube and a corresponding handle mechanism for performing extension/retraction.

While this disclosure contemplates that internal tube 7410 may have a substantially uniform structure, in at least certain implementations internal tube 7410 is divided into sections with varying stiffnesses and properties related to bending of the particular section. Certain sections may also have non-uniform stiffness, such as by having a first stiffness when bent along a first plane and/or in a first direction and a second, different stiffness when bent along a second plane and/or in a second direction.

Figure 75:
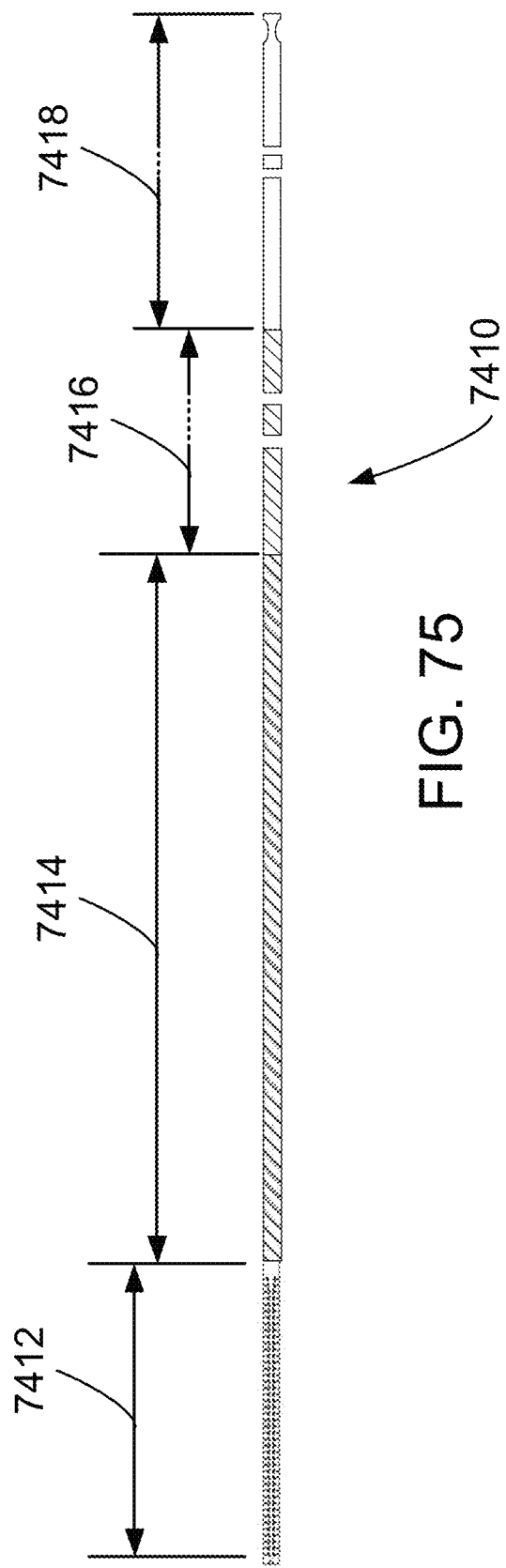
FIG. 75 is an elevation view of an internal tubular member of the catheter assembly of FIG. 74.

FIG. 75 illustrates internal tube 7410 removed from delivery system 7400. As shown, internal tube 7410 is generally divided into four sections, each of which has a different structure. While implementations of this disclosure may vary, internal tube 7410 specifically includes a distal tube section 7412, a first medial section 7414, a second medial tube section 7416, and a proximal tube section 7418. Each section of internal tube 7410 may correspond to a particular section of steerable catheter 7404. For example, in the implementation shown, distal tube section 7412 may correspond to distal steerable section 7406, first medial section 7414 may correspond to proximal steerable section 7408, second medial tube section 7416 may correspond to a distal segment of non-steerable catheter section 7409, and proximal tube section 7418 may correspond to a proximal segment of non-steerable catheter section 7409.

Although the specific construction of internal tube 7410 may vary, in at least certain implementations, internal tube 7410 is formed as a unitary tubular structure. Material of internal tube 7410 may similarly vary; however, in one specific implementation, internal tube 7410 is formed from stainless steel or a similar biocompatible material. In at least one implementation, internal tube 7410 is formed from a tube having an outer diameter from and including about 2.5 mm to and including about 3.5 mm with a wall thickness from and including about 0.1 mm to and including about 0.5 mm. For example, in one specific implementation, internal tube 7410 has an outer diameter of approximately 3 mm and a wall thickness of 0.25 mm.

Figure 76A:
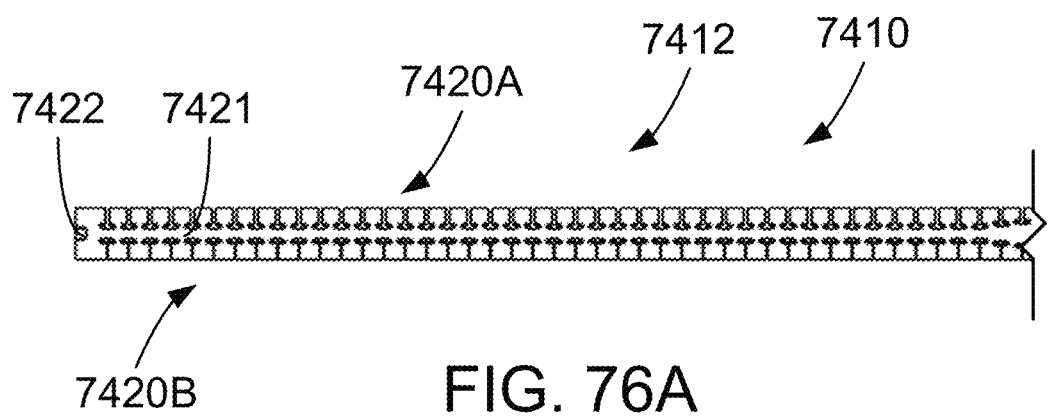
FIGS. 76A-76D are detailed views of specific sections of the internal tubular member of FIG. 75.

FIGS. 76A-76D illustrate each section of internal tube 7410 in further detail. FIG. 76A is a side view of distal tube section 7412 of internal tube 7410. When assembled with steerable catheter 7404, distal tube section 7412 generally corresponds to distal steerable section 7406.

As noted above, in the specific implementation illustrated in FIG. 74, distal steerable section 7406 of steerable catheter 7404 is bidirectionally steerable along a single plane. To accommodate such bending of distal steerable section 7406, distal tube section 7412 may be configured to have reduced stiffness to bending along the steering plane of distal steerable section 7406.

In one specific implementation, stiffness of distal tube section 7412 is modified by a series of cuts distributed longitudinally along distal tube section 7412. More specifically, distal tube section 7412 includes first cuts 7420A extending along a first side of distal tube section 7412 and second cuts 7420B extending along a second side of distal tube section 7412. First cuts 7420A and second cuts 7420B reduce the stiffness of distal tube section 7412 relative to bending in the directions of the sides along which the cuts extend. In contrast, relatively higher stiffness is maintained for bending in directions orthogonal to the cut sides due to "spines" (e.g., spine 7421) that extend along distal tube section 7412 between the sets of cuts. When internal tube 7410 is disposed within steerable catheter 7404, first cuts 7420A and second cuts 7420B are generally oriented perpendicular to the steering plane of distal steerable section 7406 such that resistance to bending by distal tube section 7412 along the steering plane is reduced.

As illustrated in FIG. 76A, each of first cuts 7420A and second cuts 7420B terminate in a bulbous cutout, resulting in an overall dog-bone shape to each of the cuts. The dog-bone shape generally reduces interference of the internal cut surfaces during bending. Among other things, doing so promotes more uniform bending of distal tube section 7412 and avoids binding of distal tube section 7412 during bending.

To maintain proper orientation between internal tube 7410 and steerable catheter 7404 a keyway 7422 or similar alignment feature of distal tube section 7412 may mate with a corresponding feature of steerable catheter 7404.

While FIG. 76A illustrates lateral cuts for reducing bending stiffness along one plane, this disclosure contemplates that lateral cuts may also be used to reduce stiffness of a given section of internal tube 7410 to bending along multiple planes. For example, internal tube 7410 may be modified by including additional cuts orthogonally offset from first cuts 7420A and second cuts 7420B and disposed between adjacent cuts of first cuts 7420A and second cuts 7420B. By doing so, stiffness of internal tube 7410 may also be reduced to bending along a second plan orthogonal to the first plane corresponding to first cuts 7420A and second cuts 7420B. More generally, by angularly offsetting the lateral cuts along internal tube 7410, internal tube 7410 can be made to have reduced stiffness along any number and direction of bending planes. Stiffness along a given bending plane may be controlled by modifying the density, kerf, depth, or other similar characteristics of the cuts corresponding to the bending plane. Accordingly, in implementations in which internal tube 7410 has controlled stiffness in multiple directions or along multiple planes, the cut characteristics for each plane may be modified and controlled to impart specific bending characteristics for the direction/plane.

Figure 76B:
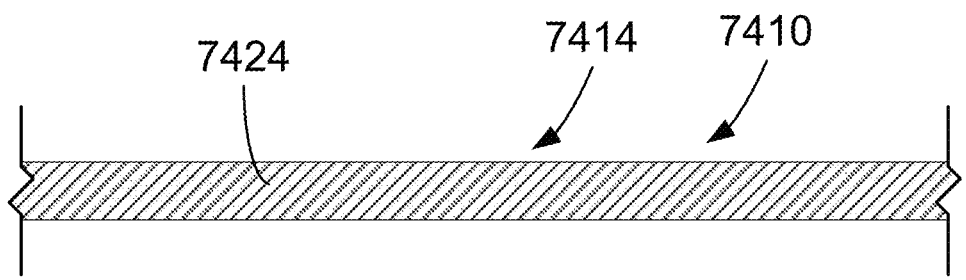

FIG. 76B is a side view of first medial section 7414 of internal tube 7410. As noted above, in the specific implementation illustrated in FIG. 74, proximal steerable section 7408 of steerable catheter 7404 is steerable along two orthogonal planes. To accommodate such bending, first medial section 7414 may be configured to have omnidirectionally reduced stiffness to bending.

In one specific implementation, stiffness of first medial section 7414 is modified by one or more helical cuts, such as helical cut 7424, extending along the length of first medial section 7414. Given that helical cut 7424 extends around the entirety of first medial section 7414, it reduces stiffness of first medial section 7414 omnidirectionally relative to stiffness of first medial section 7414 absent any such cuts.

Figure 76C:
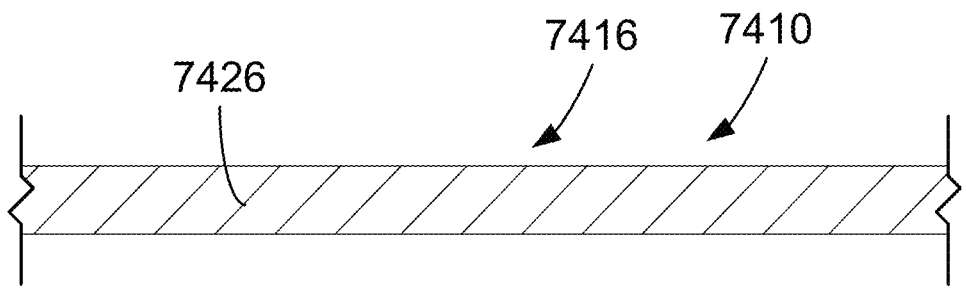

FIG. 76C is a side view of second medial tube section 7416 of internal tube 7410. As noted above, in the specific implementation illustrated in FIG. 74, second medial tube section 7416 may correspond to a distal segment of non-steerable catheter section 7409 of steerable catheter 7404.

While not requiring the flexibility to accommodate steering, reduced stiffness of second medial tube section 7416 may nevertheless be desirable in certain applications and procedures. For example, during delivery of an implant to the valve annulus using delivery system 7400, the distal segment of non-steerable catheter section 7409 corresponding to second medial tube section 7416 is near and may even extend into the heart. As such, the distal segment of non-steerable catheter section 7409 may contact and exert forces on tissue and structures of and surrounding the heart, particularly during changes in insertion and/or rotation of steerable catheter 7404. In general, internal tube 7410 structurally reinforces steerable catheter 7404 and contributes to the contact forces between steerable catheter 7404 and surrounding tissue. So, by reducing the stiffness of second medial tube section 7416, the degree of structural reinforcement provided to the distal segment of non-steerable catheter section 7409 and corresponding contact forces exerted by non-steerable catheter section 7409 can be reduced.

In one specific implementation, stiffness of second medial tube section 7416 is modified by one or more helical cuts, such as helical cut 7426, extending along the length of second medial tube section 7416. Given that helical cut 7426 extends around the entirety of second medial tube section 7416, it reduces stiffness of second medial tube section 7416 omnidirectionally. Compared to helical cut 7424 of first medial section 7414, helical cut 7426 of second medial tube section 7416 is illustrated as having a greater pitch, resulting in a smaller reduction in the stiffness of second medial tube section 7416.

Figure 76D:
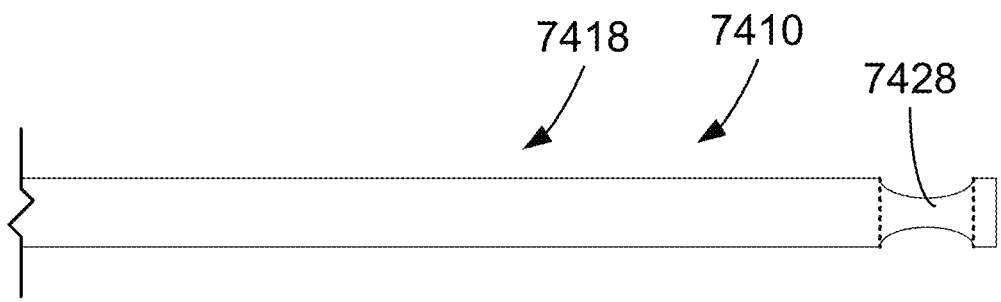

FIG. 76D is a side view of proximal tube section 7418 of internal tube 7410. As shown, proximal tube section 7418 does not include any specific modifications to change the general stiffness of proximal tube section 7418. However, as shown, proximal tube section 7418 may include a coupling feature 7428, such as an elongate through hole, for coupling to a handle of delivery system 7400 and maintaining rotational alignment of internal tube 7410 with respect to steerable catheter 7404 while permitting longitudinal translation of internal tube 7410 relative to steerable catheter 7404.

This disclosure contemplates various aspects of the cuts illustrated in FIGS. 76A-76C may be modified to impart different stiffness reductions to internal tube 7410 and to tune the stiffness of internal tube 7410 for a given application. For example, with reference to the lateral cuts shown in FIG. 76A, cut density (i.e., cuts per unit length of internal tube 7410), kerf width, cut depth, and similar characteristics may be modified to modify the stiffness. Similarly, with respect to the helical cuts shown in FIGS. 76B and 76C, pitch, kerf, helix angle, and similar characteristics may be modified to alter the stiffness of internal tube 7410.

While FIGS. 76A-76C illustrate cuts through a wall of internal tube 7410, this disclosure also contemplates that any cuts may extend only partially through the wall of internal tube 7410, with the depth of the cut being generally proportional to the stiffness reduction provided by the cut. This disclosure also contemplates that the stiffness of sections of internal tube 7410 may be modified in other ways including, but not limited to, varying wall thickness, varying tube material, varying tube shape, and the like.

The specific dimensions of internal tube 7410 may vary. However, in certain implementations, internal tube 7410 may be from and including about 1400 mm to and including about 1800 mm. For example, in one implementation, internal tube 7410 may be approximately 1540 mm in length. Each section of internal tube 7410 may similarly vary in length. For example, in one implementation, distal tube section 7412 may be from and including about terminate in a distal end including a keyway or similar non-rotational feature that is from and including about 40 mm to and including about 80 mm in length. For example, distal tube section 7412 may be approximately 60 mm in length. In certain implementations, first medial section 7414 may be from and including about 90 mm to and including about 130 mm. For example, first medial section 7414 may be approximately 110 mm in length. In certain implementations, the spiral cut of first medial section 7414 may have a pitch from and including about 0.4 mm to and including about 0.6 mm, e.g., 0.5 mm. In some implementations, the spiral cut of first medial section 7414 is continuous; however, in others, it may be an interrupted cut with cut lengths of approximately 2 mm to 4 mm interspersed with uncut sections of approximately 0.5 mm to approximately 0.8 mm. More generally, however, each of distal tube section 7412 and first medial section 7414 may be approximately the same length as the corresponding steerable sections of the delivery catheter with which they are paired and within which they are disposed. Second medial tube section 7416 may similarly vary in length. For example, in certain implementations, second medial tube section 7416 may be from and including about 500 mm to and including about 700 mm in length. In one specific example, second medial tube section 7416 is approximately 630 mm in length. In certain implementations in which second medial tube section 7416 is spiral cut, the spiral cut of second medial tube section 7416 may have a pitch from and including about 1 mm to and including about 2 mm, e.g., 1.5 mm. The spiral cut of second medial tube section 7416 may similarly be uninterrupted or interrupted. When the spiral cut is interrupted, it may include cut segments from and including about 3 mm to and including about 4 mm, e.g., 3.5 mm, and uncut segments of 0.5 mm to 1.2 mm, e.g., 0.9 mm. Finally, in certain implementations, proximal tube section 7418 may be from and including about 600 mm to and including about 800 mm and, in one specific example, is approximately 740 mm.)

XXII. Delivery Tool Handles for Delivery of Expandable Implants

Delivery tools according to this disclosure generally include a handle assembly with various control elements and a catheter assembly extending form the handle assembly. During delivery of an implant, the implant is retained within at least partially within a distal end of the catheter assembly. Following insertion of the catheter assembly and location of the distal end of the catheter assembly by a clinician, the clinician deploys the implant from the distal end of the catheter assembly. Deployment generally includes fully exposing the implant, such as by retracting a protective sheath and/or distally extending the implant from the distal end of the catheter assembly, and once exposed, expanding the implant into an expanded configuration for implantation. Following final positioning and implantation of the now-expanded implant, the clinician detaches the implant from the distal end of the catheter assembly and retracts the delivery tool from the patient.

The foregoing process requires substantial control and manipulation of the delivery tool and the implant including, but not limited to, steering of the catheter assembly, extension and retraction of the implant relative to the catheter assembly, expansion and contraction of the implant, and release of the implant. An example steering mechanism and corresponding handle features and functions are discussed above in the context of FIGS. 45A-49. As noted in the context of those figures, the handle assembly may include levers or similar steering control elements configured to steer sections of the catheter assembly independently and in multiple directions. For example, FIGS. 45A-45H illustrate one example implementation in which a distal portion of the catheter assembly is separated into a proximal steering section and a distal steering section, each of which is independently articulable.

In addition to steering of the catheter, certain implementations of this disclosure include elements for controlling each of rotation and insertion of the catheter assembly. For example, FIG. 61 illustrates an example delivery device mount that includes a rail and cradle supporting the delivery device. The cradle is movable/translatable along the rail (e.g., by turning a corresponding knob) to control insertion. The cradle also includes a rotatable mount for the delivery device such that the delivery device may be rotated within the cradle while maintaining longitudinal alignment.

Figure 77A:
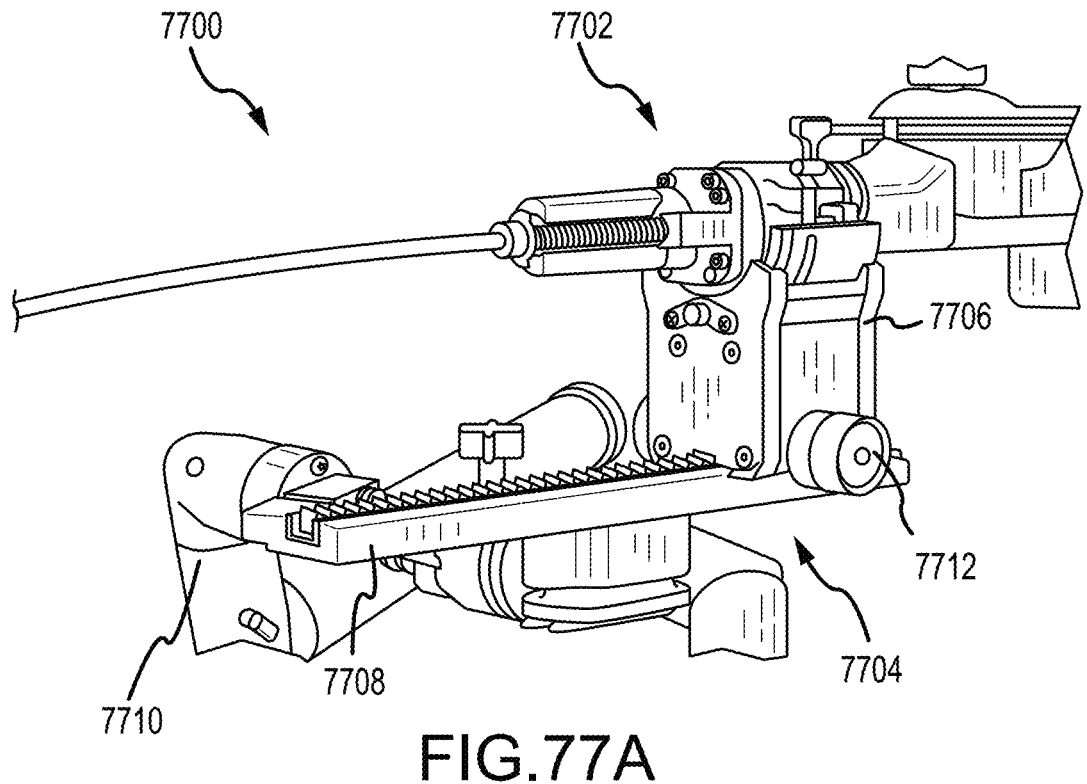
FIGS. 77A and 77B are perspective views of a mounting assembly and delivery system illustrating insertion of the delivery system.
Figure 77B:
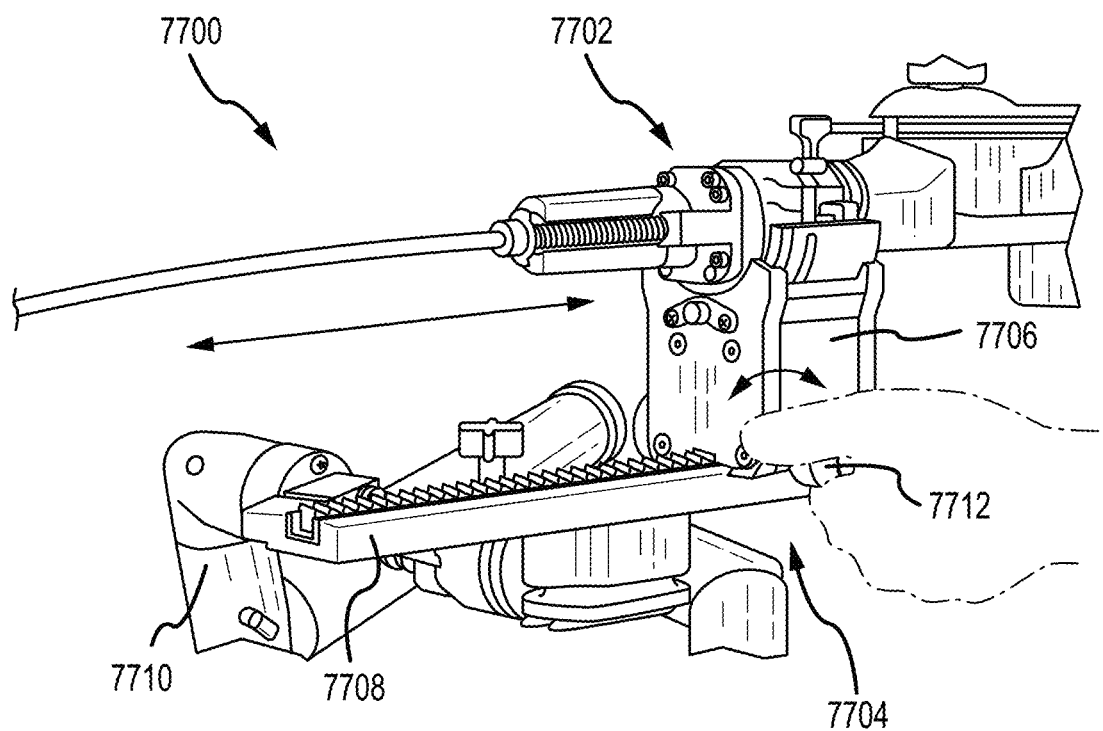

FIGS. 77A-78C illustrate a similar mounting arrangement for enabling both insertion and rotation of a delivery device. FIG. 77A is an illustration of an implant delivery system 7700 including a delivery device 7702 supported by a mounting assembly 7704 including a cradle 7706. Cradle 7706 is supported by a rail 7708 supported by an articulating arm 7710. While not shown in the figures, articulating arm 7710 may be coupled to a patient bed or similar fixture within an operating environment. Similar to the mounting arrangement shown in FIG. 61, cradle 7706 includes a stepper-type articulation system that is manually driven by a knob 7712. More specifically, as a clinician rotates knob 7712 (as shown in FIG. 77B), cradle 7706 translates along rail 7708 in a corresponding direction, thereby controlling insertion of delivery device 7702.

Figure 78A:
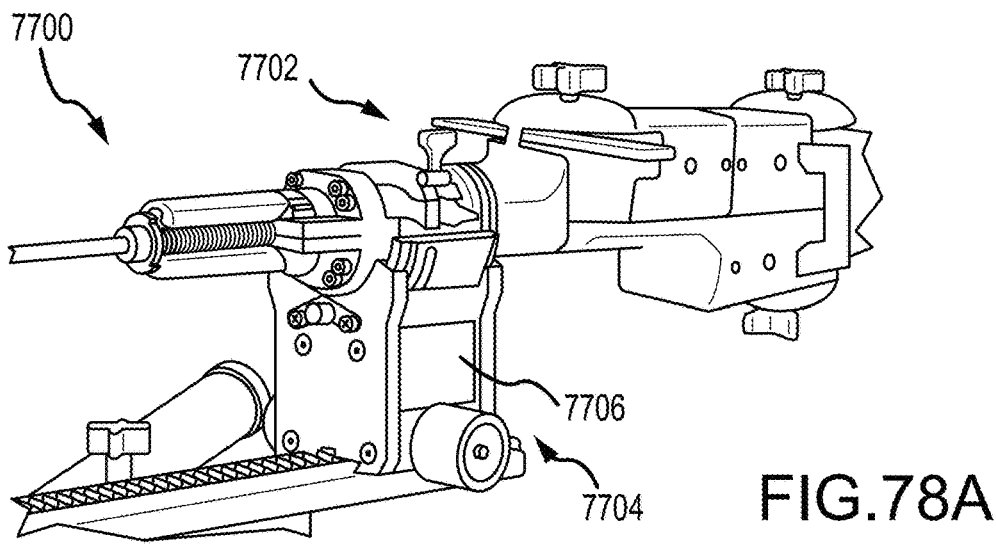
FIGS. 78A-78C are additional views of the mounting assembly and delivery system of FIGS. 77A and 77B illustrating rotation of the delivery system.
Figure 78B:
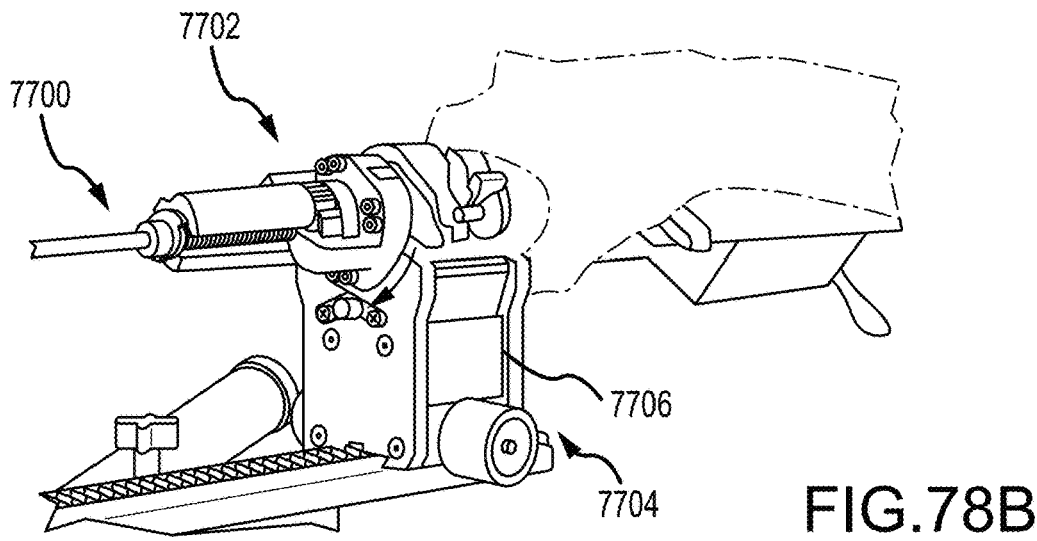
Figure 78C:
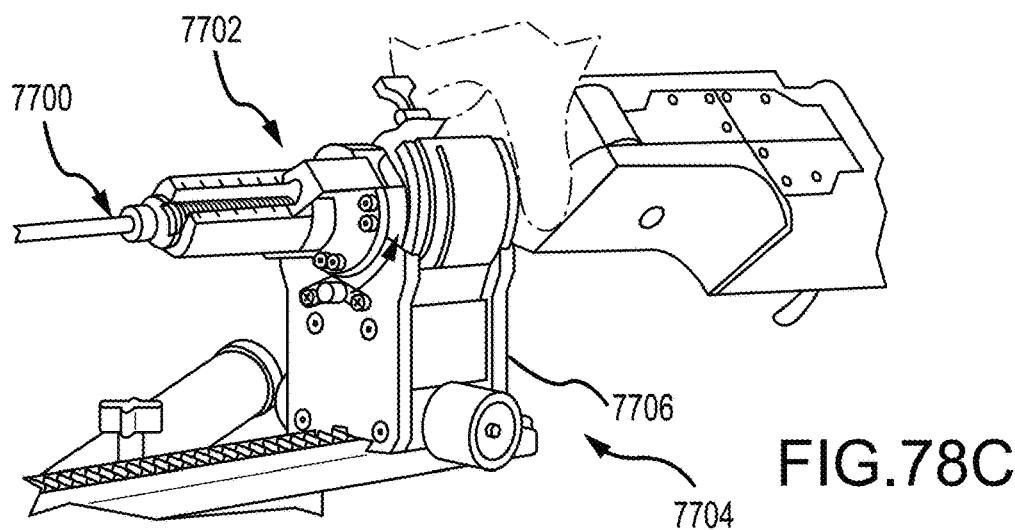

FIGS. 78A-78C illustrate rotation of delivery device 7702 within cradle 7706 of mounting assembly 7704. FIG. 78A illustrates delivery device 7702 in a neutral position. To modify rotational position of delivery device 7702, a clinician may manually rotate delivery device 7702 within cradle 7706. FIG. 78B illustrates delivery system 7700 during manual rotation of by a clinician in a first direction from the neutral position of FIG. 78A while FIG. 78C illustrates delivery device 7702 following rotation by a clinician in an opposite direction from neutral. Notably, during rotation in either direction, the longitudinal axis of delivery device 7702 is maintained in a fixed location. While the amount of rotation provided by mounting assembly 7704 may vary, in at least certain implementations, mounting assembly 7704 may be configured to provide up to and including about 180 degrees of total rotation for delivery device 7702, e.g., 90 degrees in either a clockwise or counterclockwise direction relative to neutral.

In addition to rotation and insertion, delivery systems according to the present disclosure can be actuated and controlled in other ways with corresponding control elements included in their handle assemblies. By way of non-limiting example, such additional degrees of freedom and articulation may include extension of an implant relative to a distal end of a delivery catheter, controlled expansion and contraction of the implant prior to release, and controlled release of the implant from the distal end of the delivery catheter, each of which is discussed below in further detail.

First, FIGS. 79A-80B illustrate an example implementation of a delivery device 7900 having a handle assembly 7902. Like other delivery devices and systems of this disclosure, delivery device 7900 generally includes a steerable catheter assembly 7904. An implant 7950 may be disposed on a distal end 7906 of the catheter assembly 7904 for delivery and implantation. The catheter assembly 7904 includes a steerable catheter body 7908 and an extension tube 7910. During operation and as discussed in the context of FIGS. 54A and 54B and FIGS. 74-76E, extension tube 7910 may be extended and retracted relative to distal end 7906 to facilitate positioning, orientation, and placement of implant 7950 relative to the valve annulus.

In one example tricuspid valve repair procedure, implant 7950 is maintained in a retracted and sheathed configuration during delivery of distal end 7906 of delivery device 7900 into the right atrium and with implant 7950 coupled to distal end 7906. With distal end 7906 in the right atrium, the clinician unsheathes and expands implant 7950 and aligns implant 7950 to be normal to the tricuspid valve annulus, e.g., by steering catheter assembly 7904. Once aligned, extension tube 7910 is extended to translate implant 7950 into the valve annulus for subsequent release.

FIGS. 79A-79D illustrate general operation of handle assembly 7902 of delivery device 7900 to perform extension and retraction of implant 7950. More specifically, FIGS. 79A and 79C are illustrations of handle assembly 7902 with extension tube 7910 and implant 7950 in a fully extended configuration and during retraction, respectively. Similarly, FIGS. 79B and 79D are illustrations of distal end 7906 of delivery device 7900 with extension tube 7910 and implant 7950 in a fully extended configuration and during retraction, respectively.

Extension and retraction of extension tube 7910 and implant 7950 is achieved by an extension control element 7912 of handle assembly 7902. In the specific implementation shown, extension control element 7912 is in the form of an extension knob 7914 that is rotatable by a clinician to selectively extend and retract extension tube 7910. More specifically, rotation of extension control element 7912 in a first direction (e.g., clockwise) results in extension of extension tube 7910 while rotation in a second, opposite direction (e.g., counterclockwise) results in retraction of extension tube 7910.

FIGS. 79A and 79C generally illustrate handle assembly 7902 having a housing 7916. Housing 7916 includes an aperture 7918 to visually communicate the state of delivery device 7900 and, in particular, extension of extension tube 7910 and implant 7950. This disclosure contemplates that various techniques may be used to visually indicate extension of extension tube 7910 and implant 7950; however, as shown in FIGS. 79A and 79C, extension/retraction of extension tube 7910 is generally communicated by the relative position of a shuttle indicator 7922 disposed on an extension shuttle 7924. Extension tube 7910 is coupled to and extends distally from extension shuttle 7924 such that translation of extension shuttle 7924 corresponds to translation of extension tube 7910. So, as the clinician extends and retracts extension tube 7910 and implant 7950, extension shuttle 7924 translates within aperture 7918, moving the location of shuttle indicator 7922 and communicating translation of extension tube 7910. A scale 7926 is coupled to housing 7916 adjacent shuttle indicator 7922 and includes markers corresponding to various degrees of extension and retraction of extension tube 7910 to communicate the current extension/retraction state to the clinician.

Figure 80A:
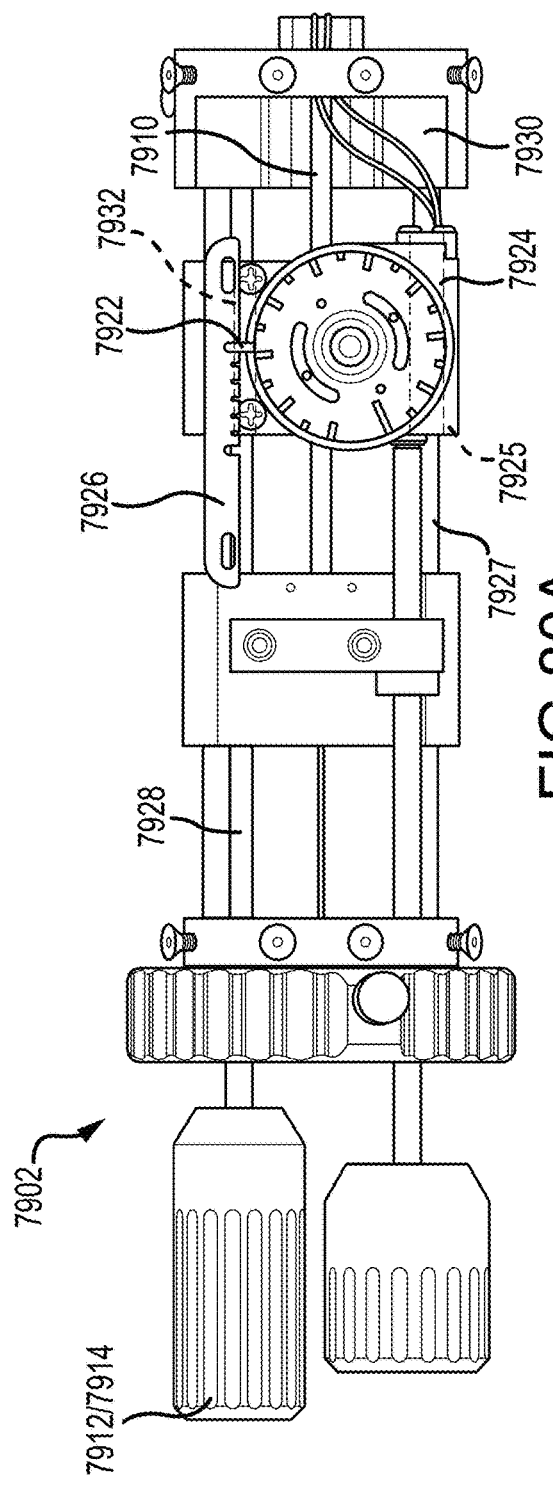
FIGS. 80A and 80B are internal views of the handle assembly in the extended and retracted states, respectively.
Figure 80B:
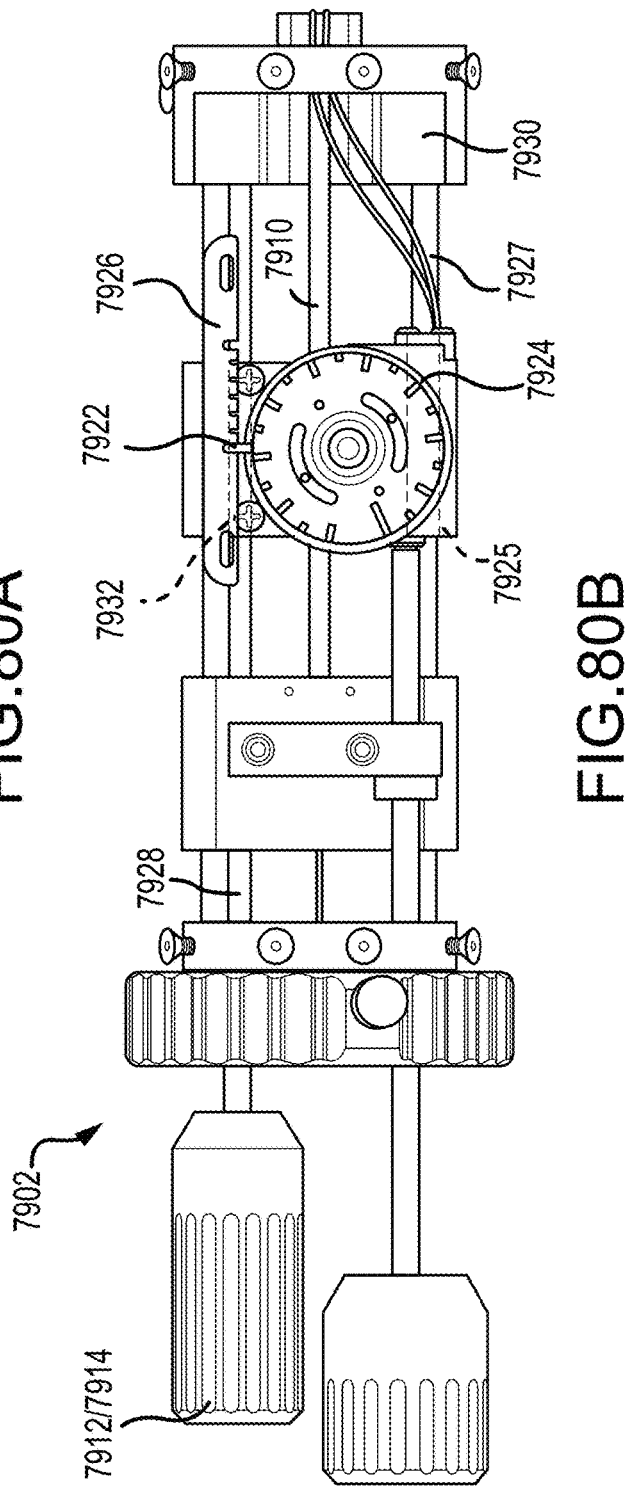

FIGS. 80A and 80B illustrate delivery device handle assembly 7902 with housing 7916 removed and are intended to explain operation of handle assembly 7902 to extend and retract extension tube 7910. More specifically, FIG. 80A illustrates handle assembly 7902 in a first state corresponding to extension tube 7910 being in a fully extended configuration (e.g., similar to that illustrated in FIGS. 79A and 79B) while FIG. 80B illustrates handle assembly 7902 in a second state corresponding to extension tube 7910 being in a fully retracted configuration (e.g., similar to that illustrated in FIGS. 79C and 79D). Shuttle indicator 7922 is also included in FIGS. 80A and 80B in position but decoupled from housing 7916 for purposes of more clearly illustrating shuttle indicator 7922 and its relationship with extension shuttle 7924.

Handle assembly 7902 is operable to selectively extend and retract extension tube 7910 between the fully extended configuration shown in FIG. 80A and the fully retracted configuration shown in FIG. 80B by rotation of extension knob 7914. Extension knob 7914 can be rotated in either direction to selectively extend and retract extension tube 7910 and can be used to translate extension tube 7910 into a fully extended configuration, a fully retracted configuration, or any intermediate (e.g., partially extended/retracted) configuration.

Extension knob 7914 is coupled to an extension shaft 7928 that extends distally from extension knob 7914 into housing 7916 and is coupled to a distal member 7930 of housing 7916, thereby longitudinally fixing extension shaft 7928. Extension shaft 7928 is at least partially threaded and extends through a threaded hole 7932 of extension shuttle 7924. As shown, extension shuttle 7924 further may include one or more guide bores (e.g., guide bore 7925) through which corresponding guide members (e.g., guide member 7927) extend to maintain alignment of and to support extension shuttle 7924 and along which extension shuttle 7924 translates. As extension knob 7914 is rotated, extension shaft 7928 longitudinally drives extension shuttle 7924 along the guide members and, as a result, extends or retracts extension tube 7910 based on the direction of rotation of extension knob 7914.

Figure 81A:
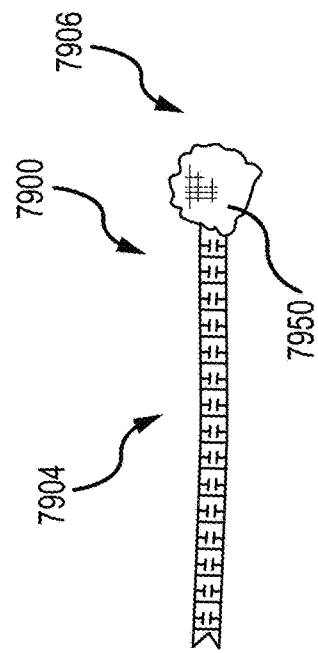
FIGS. 81A and 81B are elevation views of the handle assembly and the distal end of the delivery system illustrating the system in a collapsed state.
Figure 81B:
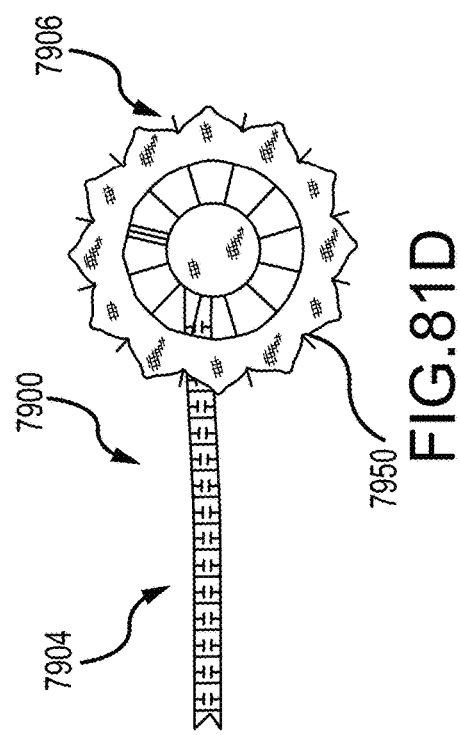
Figure 81C:
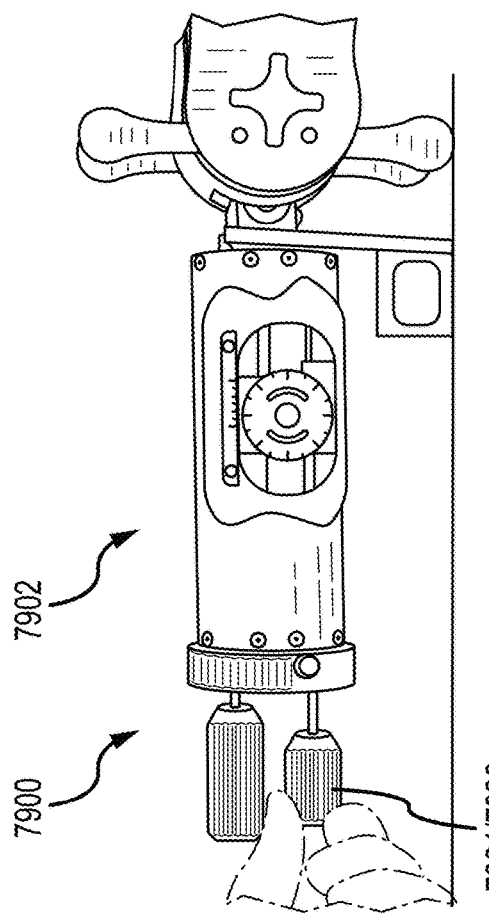
FIGS. 81C and 81D are elevation views of the handle assembly and the distal end of the delivery system illustrating the system in an expanded state.
Figure 81D:
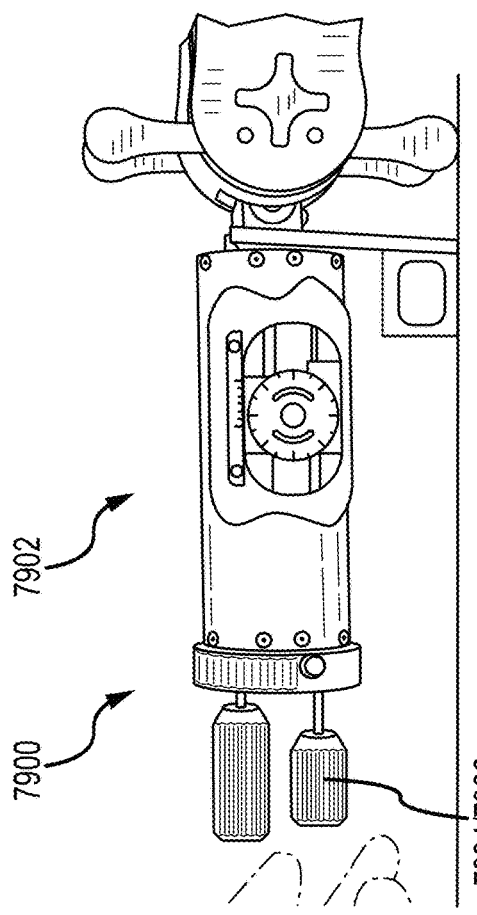

FIGS. 81A-81D illustrate operation of a second control mechanism of handle assembly 7902 and, specifically, a control mechanism configured to selectively expand and collapse implant 7950. FIGS. 81A and 81B illustrate delivery device 7900 in a first configuration in which implant 7950 is in a collapsed state. As shown in FIG. 81A, handle assembly 7902 includes an expansion control element 7934 in the form of an expansion knob 7936. During operation and following unsheathing and extension of implant 7950 from the distal end of catheter assembly 7904, expansion knob 7936 is rotatable to selectively expand and collapse implant 7950. FIGS. 81C and 81D, for example, illustrate delivery device 7900 in a second configuration in which implant 7950 has been fully expanded by rotation of expansion knob 7936 in a first direction. In the illustrated implementation, expansion knob 7936 is bidirectionally rotatable such that implant 7950 can be selectively expanded and collapsed between the fully expanded state in FIG. 81D, the fully collapsed state in FIG. 81B, or any intermediate state of expansion/collapse.

While the specific mechanical configuration of delivery devices and implants according to this disclosure may vary, expansion and collapse of the implant by the delivery device during delivery generally requires two actions. Expansion is generally achieved by applying radially outward and circumferentially distributed force to the implant. For example, as previously discussed in the context of delivery device 3600 in FIGS. 38-44, delivery device 3600 includes circumferentially distributed control arms (such as the control arms of control arm assembly 3608 shown in FIGS. 42 and 43) that can be made to extend radially and apply radially outward force by longitudinal translation of control arm shaft 3642.

To facilitate uniform and controlled expansion of the implant, delivery devices according to this disclosure also include one or more cinch lines configured to be run circumferentially about the implant during deployment. For example, delivery device 3600 is a single cinch line implementation with cinch line 3614 indicated in FIG. 38. As discussed below in the context of release mechanisms for delivery device 7900, the specific implementation of delivery device 7900 generally includes two, simultaneously controllable cinch lines. In other implementations, delivery devices of this disclosure may include one or more than two cinch lines as described below in further detail in the context of implant release controls. During expansion of the implant and as radially outward force is applied by the control arms, the one or more cinch lines of the delivery device are paid out while maintaining the cinch lines under tension. Among other things, maintaining tension on the cinch lines distributes the radial forces applied by the control arms around the circumference of the implant and improves general responsiveness of expansion/collapse of the implant to manipulation of a corresponding control element (e.g., expansion knob 7936 of handle assembly 7902).

Collapsing the implant similarly involves coordinated movement of the control arms and while maintaining tension on one or more cinch lines. In contrast to expansion of the implant during which the control arms are made to extend radially outward by distal translation of the control arm shaft, collapse is achieved by radially collapsing the control arms by proximally translating the control arm shaft. During collapse, tension is maintained on the one or more cinch lines extending about the implant to facilitate uniform collapse of the implant with good responsiveness to manipulation of the corresponding control element (e.g., expansion knob 7936 of handle assembly 7902).

In summary, expansion of the implant involves radial extension of the control arms by distal translation of the control arm shaft and a corresponding payout of the one or more cinch lines under tension as the implant expands. Similarly, collapse of the implant involves radially retraction of the control arms by proximal translation of the control arm shaft and a corresponding retraction of the one or more cinch lines that maintains tension on the one or more cinch lines as the implant collapses.

In certain implementations, translation of the control arm shaft and cinch line tension may be independently controllable by a clinician using corresponding control elements of the delivery device handle. In other implementations, such as delivery device 7900, control arm shaft translation and cinch line control are synchronized to operation of a single control element, i.e., expansion knob 7936. Stated differently, rotation of expansion knob 7936 in a first direction results in both distal translation of a control arm shaft (and, as a result, radial expansion of the control arms) and a synchronized and proportional paying out of the one or more cinch lines to maintain tension on the one or more cinch lines. Rotation of expansion knob 7936 in a second direction results in both proximal translation of the control arm shaft (and, as a result, radial retraction of the control arms) and a synchronized and proportional retraction of the one or more cinch lines to maintain tension on the one or more cinch lines.

Figure 82A:
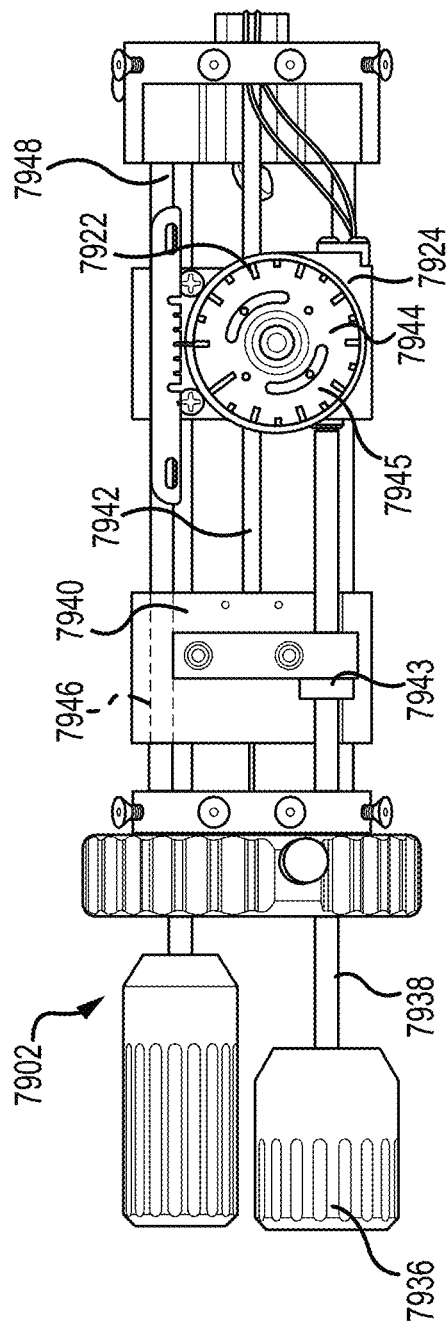
FIG. 82A is an internal view of the handle assembly in the collapsed state.
Figure 82B:
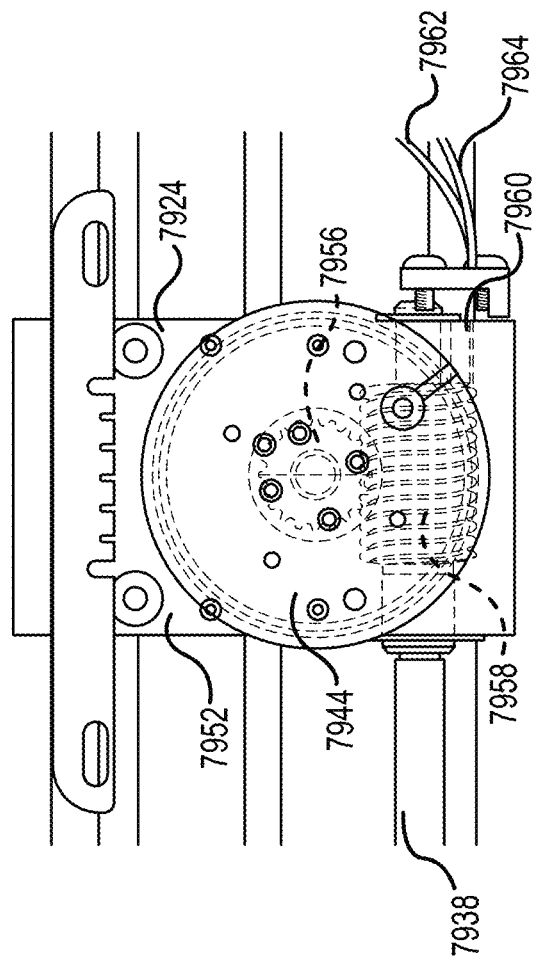
FIG. 82B is a detailed view of a cinch line mechanism of the handle assembly.
Figure 82C:
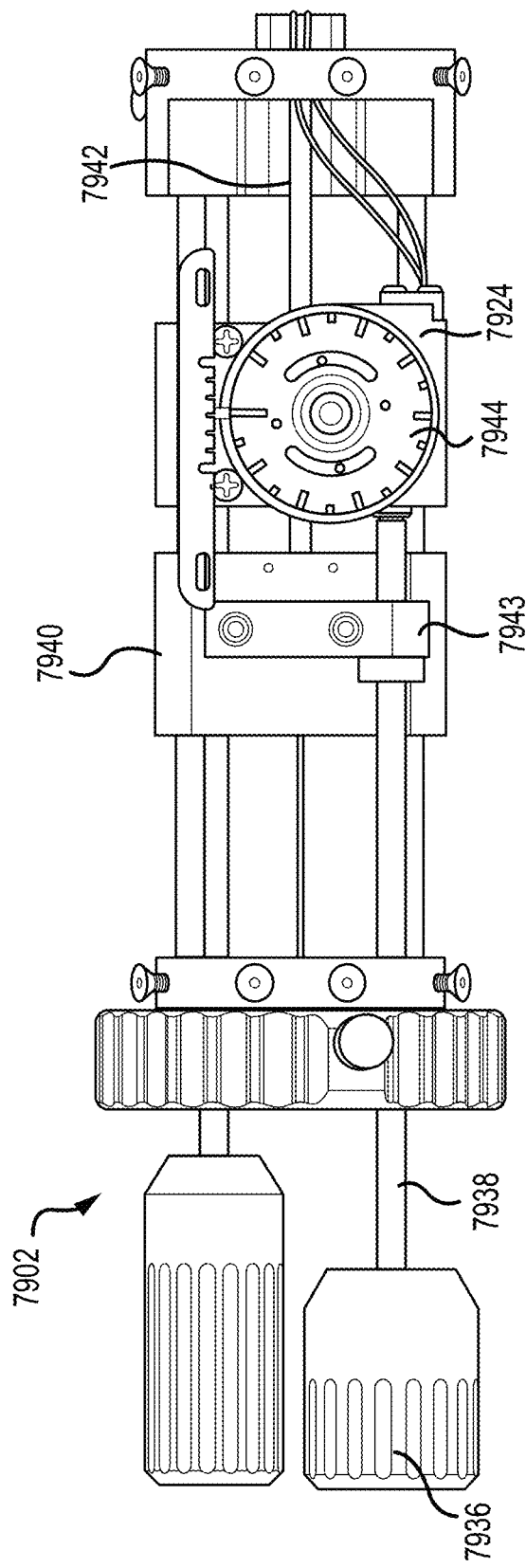
FIG. 82C is an internal view of the handle assembly in the expanded state.

An example mechanism for achieving synchronized control arm shaft and cinch line manipulation is illustrated in FIGS. 82A-82C, which illustrate handle assembly 7902 with housing 7916 removed. More specifically, FIG. 82A illustrates handle assembly 7902 in a state corresponding to full collapse of the implant 7950 (e.g., as shown in FIGS. 81A and 81B), FIG. 82B shows a partially transparent detailed view of extension shuttle 7924, and FIG. 82C illustrates handle assembly 7902 in a state corresponding to full expansion of implant 7950 (e.g., as shown in FIGS. 81C and 81D).

Referring first to FIG. 82A, expansion knob 7936 is coupled to an expansion shaft 7938 that extends from expansion knob 7936 into housing 7916. Expansion shaft 7938 terminates proximally at extension shuttle 7924 and is coupled to extension shuttle 7924 such that expansion shaft 7938 remains longitudinally fixed relative to extension shuttle 7924. As described below in further detail, rotation of expansion shaft 7938 generally drives rotation of a spool 7944 supported on extension shuttle 7924. Notably, while rotation of expansion knob 7936 causes rotation of spool 7944, rotation of expansion knob 7936 does not cause translation of extension shuttle 7924 and corresponding extension/retraction of extension tube 7910 and implant 7950. Stated differently, expansion and collapse of the implant is controllable independent of longitudinal translation of implant 7950 by extension tube 7910.

Housing 7916 further contains an expansion shuttle 7940 coupled to a control arm shaft 7942. Expansion shuttle 7940 includes a threaded coupling 7943 or similar threaded structure through which expansion shaft 7938 extends. Expansion shuttle 7940 may further include one or more guide bores (e.g., guide bore 7946) through which corresponding guide members (e.g., guide member 7948) may extend to maintain alignment of expansion shuttle 7940 and guide translation of expansion shuttle 7940 within housing 7916. As expansion shaft 7938 is rotated, expansion shaft 7938 longitudinally drives expansion shuttle 7940 along the guide members and, as a result, extends or retracts control arm shaft 7942 based on the direction of rotation of expansion knob 7936.

As previously noted, operation of expansion knob 7936 effects both translation of control arm shaft 7942 and corresponding payout or retraction of the one or more cinch lines of delivery device 7900. FIG. 82B illustrates extension shuttle 7924 in partial transparency for purposes of illustrating cinch line control by rotation of expansion knob 7936. As shown, extension shuttle 7924 includes spool 7944, which is supported on a body 7952 by a gear 7956 that is threadedly engaged to a worm gear 7958 coupled to expansion shaft 7938. As a clinician rotates expansion shaft 7938 using expansion knob 7936, worm gear 7958 drives gear 7956, causing rotation of spool 7944. As illustrated, a tether 7960 extends around spool 7944 and is coupled to each of a first cinch line 7962 and a second cinch line 7964. As spool 7944 rotates in response to rotation of expansion knob 7936, tether 7960 spools onto or is paid out from spool 7944, thereby retracting or paying out each of first cinch line 7962 and second cinch line 7964.

Referring back to FIG. 82A, spool 7944 may include a faceplate 7945 that may further include markings for indicating the relative rotation of spool 7944. Given that spool 7944 rotates in response to expansion and contraction of implant 7950, markings on faceplate 7945 or similar markings on spool 7944 or extension shuttle 7924 indicating the relative rotation of spool 7944 may be used to communicate the degree to which implant 7950 is expanded/collapsed.

As noted above, rotating expansion knob 7936 results in simultaneous translation of expansion shuttle 7940 (translating control arm shaft 7942) and corresponding retraction/payout of the one or more cinch lines of handle assembly 7902. Synchronization between these two functions is primarily dictated by the interaction between worm gear 7958 and gear 7956, which collectively form a gearbox or similar transmission system. More specifically, the gear ratio between worm gear 7958 of control arm shaft 7942 and gear 7956 coupled to spool 7944 dictates the relationship between rotation of expansion shaft 7938 and the rotation of spool 7944. Given that expansion shaft 7938 is coupled to and directly drives expansion shuttle 7940 and that spool 7944 drives retraction and payout of the one or more cinch lines, the gear ratio between worm gear 7958 and gear 7956 also dictates the relationship between translation of control arm shaft 7942 and payout/retraction of the one or more cinch lines.

Synchronizing the one or more cinch lines with translation of the control arms involves modifying the circumference formed by the one or more cinch lines about the implant with changes in the radius of the implant resulting from extension and retraction of the control arms. In general, one unit of radial change in the implant results in approximately $2\pi$ units of circumferential change. Accordingly, worm gear 7958, gear 7956, and spool 7944 are sized and configured such that rotation of expansion shaft 7938 resulting in one unit of radial expansion (or contraction) by the control arms results in approximately $2\pi$ units of total cinch line payout (or retraction). Notably, in implementations in which two or more cinch lines are included, the $2\pi$ units of total cinch line payout or retraction may be distributed among multiple cinch lines. So, for example, in an implementation including two cinch lines, worm gear 7958, gear 7956, and spool 7944 would be configured to impart approximately $\pi$ units of payout/retraction of each cinch line for each unit of radial expansion/contraction of the control arms.

XXIII. Delivery Tool Handles for Sequenced Implant Release

Following delivery and placement of an implant using delivery devices of this disclosure, a clinician releases the implant from the distal end of the delivery device within the valve annulus.

FIGS. 83A-83H are illustrations and corresponding schematic diagrams illustrating an example implant release sequence according to this disclosure. The sequence illustrated in FIGS. 83A-83H occurs subsequent to placement and implantation of implant 7950. Accordingly, while the figures illustrate implant 7950 and delivery device 7900 in space, in practice, implant 7950 would be implanted in the valve annulus and retained in position by its frame and retention features, such as barbs or hooks, of the frame.

Figures 83A, 83B:
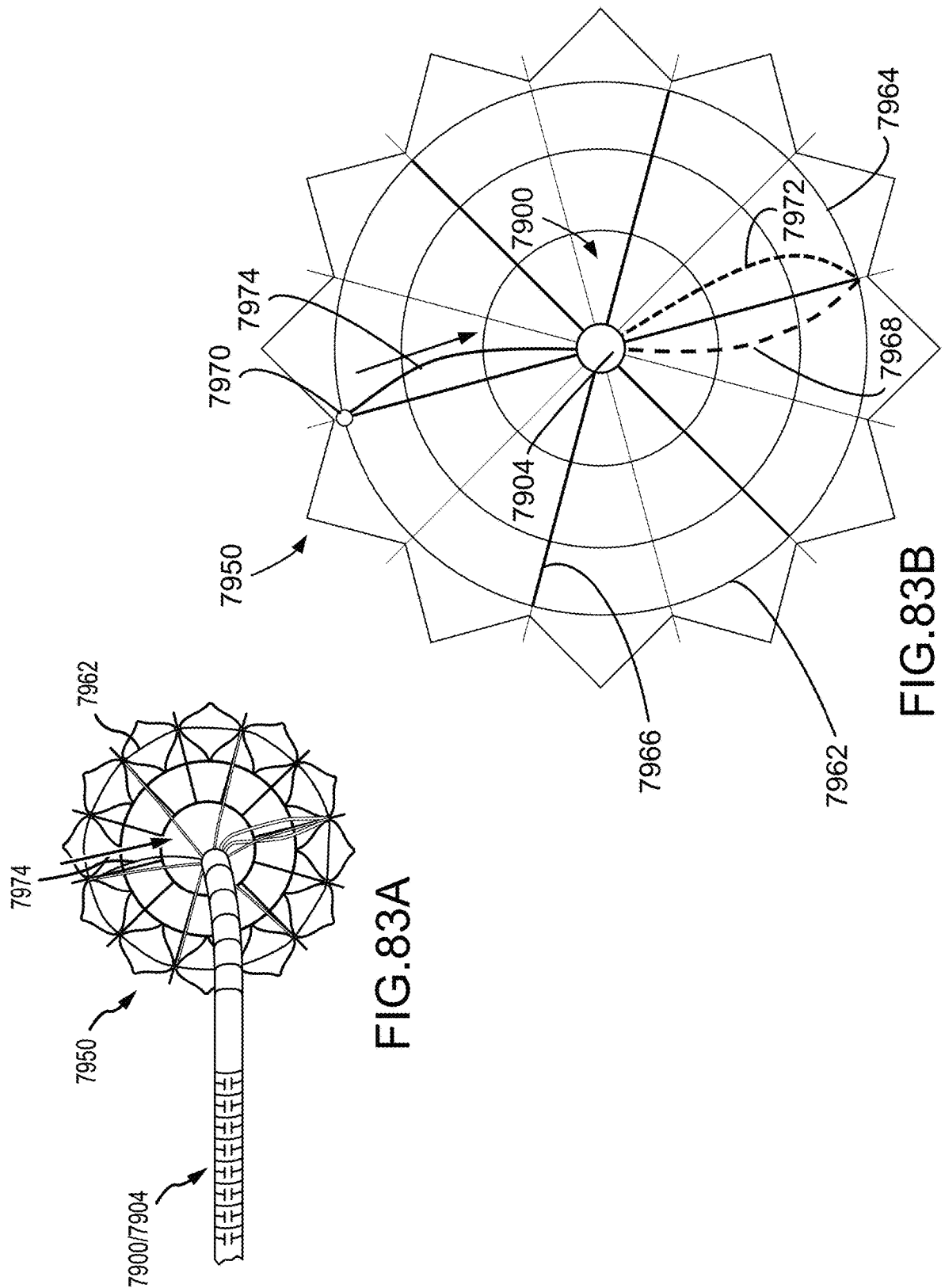

FIG. 83A is an illustration of implant 7950 coupled to catheter assembly 7904 and FIG. 83B is a proximal schematic view of implant 7950 at an initial stage of releasing implant 7950 from catheter assembly 7904. As shown in FIG. 83B, implant 7950 is supported on control arms (e.g., control arm 7966) of delivery device 7900 and maintained on the control arms by first cinch line 7962 and second cinch line 7964. Friction and/or interference between mating portions of the control arms and the frame of the implant may further facilitate retention of implant 7950 on the control arms.

Each cinch line is routed from a distal end of catheter assembly 7904 about a portion of implant 7950 to a retention location. For example, first cinch line 7962 extends from a first cinch line tube 7968 extending from catheter assembly 7904 and is routed about a first half of implant 7950 to a retention location 7970. Similarly, second cinch line 7964 extends from a second cinch line tube 7972 about a second half of implant 7950 to retention location 7970. As previously discussed in this disclosure, routing of each of the cinch lines may include passing each cinch line through a series of retention features distributed about the frame of implant 7950 and/or the control arms. For example, as described previously in this disclosure, such retention features may include a series of circumferentially distributed eyelets or loops configured to facilitate coupling of implant 7950 to the control arms of delivery device 7900 using one or more cinch lines.

In the state illustrated in FIG. 83B, first cinch line 7962 and second cinch line 7964 meet at retention location 7970 and are held in place by a controllable retention element. In the implementation shown, the controllable retention element is a retention cable 7974 extending from catheter assembly 7904 to retention location 7970. At retention location 7970, retention cable 7974 is threaded through loops or similar features at the terminal ends of first cinch line 7962 and second cinch line 7964 to retain first cinch line 7962 and second cinch line 7964.

To initiate decoupling of implant 7950 from delivery device 7900, a clinician releases retention cable 7974 to free each of first cinch line 7962 and second cinch line 7964 from retention location 7970. As shown in FIG. 82B, for example, releasing retention cable 7974 may including proximally retracting or pulling retention cable 7974 into catheter assembly 7904.

This disclosure contemplates that a single cinch line may be used to couple implant 7950 to delivery device 7900. In such implementations, the single cinch line extends around the full circumference of implant 7950 and is retained, e.g., by retention cable 7974 or similar retention member, adjacent the same location where the cinch line first begins its circumferential route around implant 7950.

This disclosure further contemplates that more than two cinch lines may be included and routed in various ways about the implant and retained by one or more retention members/retention cables. For example, in the implementation shown in FIG. 83A, first cinch line tube 7968 and second cinch line tube 7972 open at approximately the same location such that first cinch line 7962 and second cinch line 7964 are routed in opposite directions about implant 7950. In an alternative implementation, first cinch line tube 7968 and second cinch line tube 7972 may open at locations offset by approximately 180 degrees (e.g., on opposite sides of implant 7950) such that first cinch line 7962 and second cinch line 7964 may be routed in the same direction (e.g., both clockwise or both counterclockwise) about implant 7950. Notably, in such cases, delivery device 7900 may include two retention members/retention cables with each retention member retaining and retractable to release a respective one of the cinch lines. In yet other example implementations, delivery device 7900 may include four cinch lines and four cinch line tubes. In one such implementation, the cinch lines tubes may be offset by 90 degrees and cinch lines extending from each cinch line tube may be routed in a common direction about a quarter of the implant. In such implementations, each cinch line may have a corresponding retention member retractable to release the cinch line.

In another four-tube/four-cinch line implementation, pairs of cinch line tubes may be disposed on opposite sides of implant 7950 with cinch lines extending from each tube about a quarter of implant 7950. So, for example, distal outlets of two cinch line tubes may be located at a 12 o'clock position of implant 7950 with a first cinch line routed clockwise from a first tube to a 3 o'clock position and a second cinch line routed from the 12 o'clock position to a 9 o'clock position. Distal outlets of two additional cinch line tube may be disposed at a 6 o'clock position of implant 7950 with one cinch line routed clockwise from the 6 o'clock position to the 9 o'clock position and a second cinch line routed counterclockwise from the 6 o'clock position to the 3 o'clock position. The two cinch lines routed to the 9 o'clock position may then be retained by a first retention member while the two cinch lines routed to the 3 o'clock position may be retained by a second retention member.

The foregoing arrangement and routing principles may be expanded to support any suitable number of cinch lines and cinch line tubes with the cinch lines routed in either direction about implant 7950.

FIG. 83C is an illustration of implant 7950 coupled to catheter assembly 7904 and FIG. 83D is a proximal schematic view of implant 7950 at a subsequent stage of release. Following initial retraction of retention cable 7974 to release each of first cinch line 7962 and second cinch line 7964, each of the cinch lines may be similarly retracted into catheter assembly 7904. As shown in FIGS. 83C and 83D, retracting each of first cinch line 7962 and second cinch line 7964 may include retracting or pulling each of the cinch lines into their respective cinch line tubes (e.g., first cinch line 7962 into first cinch line tube 7968 and second cinch line 7964 into second cinch line tube 7972).

In the specific implementation shown, retraction of retention cable 7974, first cinch line 7962, and second cinch line 7964 is coordinated such that first cinch line 7962 and second cinch line 7964 begin retraction prior to full retraction of retention cable 7974. In other implementations, retraction of first cinch line 7962 and second cinch line 7964 may be delayed until full retraction of retention cable 7974 into catheter assembly 7904 or, more generally, any time subsequent to initial retraction of retention cable 7974 and release of the cinch lines from retention location 7970.

FIG. 83E is an illustration of implant 7950 coupled to catheter assembly 7904 and FIG. 83F is a proximal schematic view of implant 7950 at a further stage of release. FIGS. 83E and 83F illustrate a stage in the release operation prior to full retraction of first cinch line 7962 into first cinch line tube 7968 and second cinch line 7964 into second cinch line tube 7972. As shown, retention cable 7974 has been fully retracted into catheter assembly 7904. Each of first cinch line 7962 and second cinch line 7964 have also been substantially retracted into its respective tube. Accordingly, with the exception of the final frame spoke and control arm pair adjacent the outlets of the cinch line tubes, implant 7950 is decoupled from delivery device 7900.

Figure 83G:
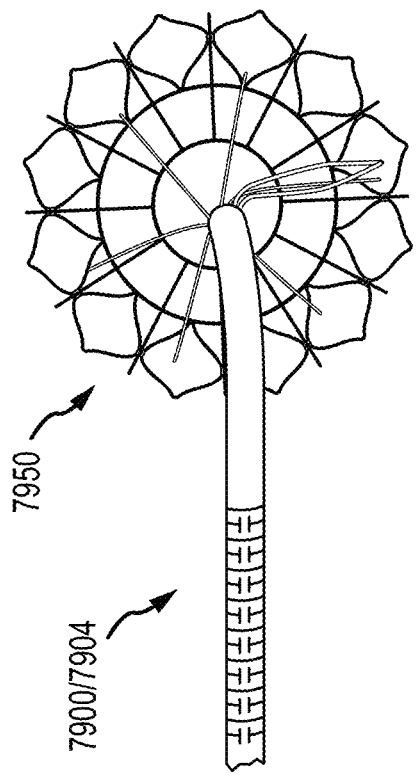
Figure 83H:
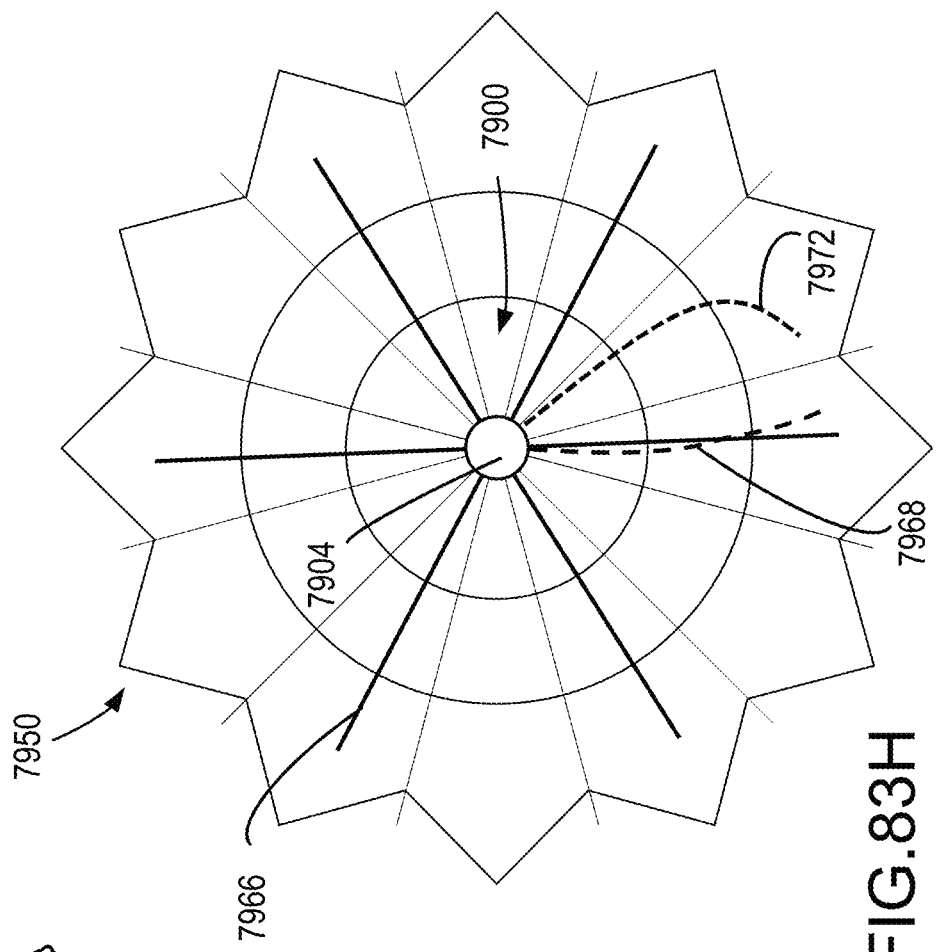

FIG. 83G is an illustration of implant 7950 and catheter assembly 7904 and FIG. 83H is a proximal schematic view of implant 7950 at a final stage of release. More specifically, each of first cinch line 7962 and second cinch line 7964 are fully retracted and, as a result, implant 7950 is no longer coupled to the control arms of delivery device 7900, as illustrated by the rotational offset between the control arms and frame spokes shown in FIG. 83H.

In certain implementations, implant 7950 may be positively retained on the control arms of delivery device 7900 following full retraction of the cinch lines. In such cases, the control arms of delivery device 7900 may be decoupled from implant 7950 by a slight retraction of the control arms, a rotation of the control arms, or another similar movement of the control arms relative to implant 7950 which, as noted above, would be implanted into and retained by tissue around the valve annulus during the release procedure. More generally, the fit between implant 7950 and control arms is such that no or relatively minimal force is required to disengage implant 7950 from delivery device 7900 following removal of the cinch lines. To the extent that implant 7950 and delivery device 7900 are designed to have positive retention without the cinch lines in place, the corresponding fit between implant 7950 and elements of delivery device 7900 should be designed such that decoupling force is substantially less than forces that would result in dislodging of implant 7950 from the valve annulus.

Following release, the control arms and any other components extending from a distal end of catheter assembly 7904 may be retracted into catheter assembly 7904 and/or sheathed in preparation for removal of delivery device 7900 from the patient.

In general, the foregoing process involves sequential steps of retracting retention cable 7974 sufficiently to release first cinch line 7962 and second cinch line 7964 then retracting each of first cinch line 7962 and second cinch line 7964 to fully release implant 7950 from delivery device 7900. To ensure this sequence occurs in the proper order and with proper timing, handle assemblies of delivery devices according to this disclosure may include a single control mechanism for retracting the retention cables and cinch lines for release.

Figure 84:
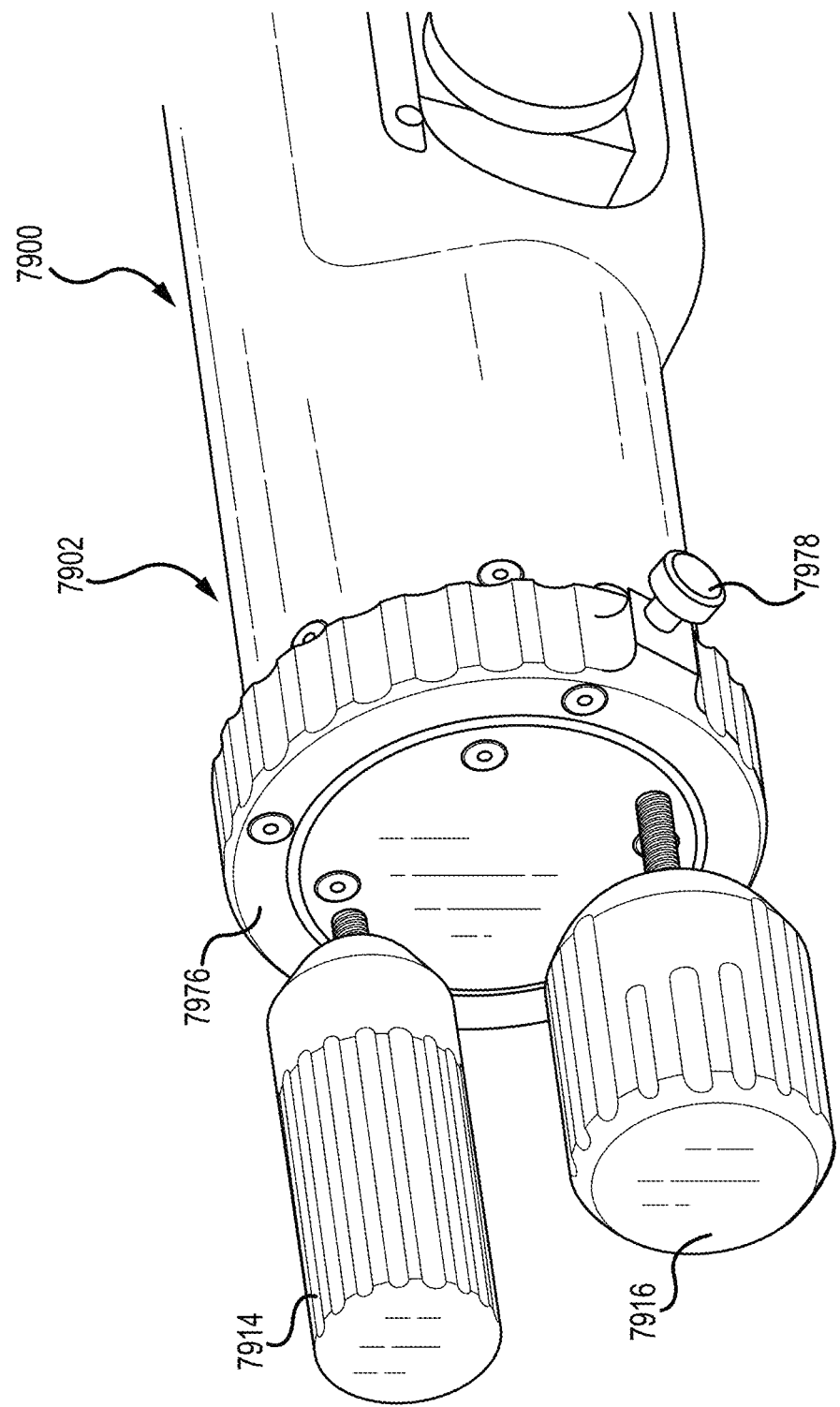
FIG. 84 is a perspective view of a handle assembly including a control ring for releasing an implant from a delivery system.

FIG. 84 is a proximal view of handle assembly 7902 of delivery device 7900. As shown, handle assembly 7902 includes each of extension knob 7914 and expansion knob 7936 for controlling extension and expansion of implant 7950 when implant 7950 is coupled to the distal end of delivery device 7900 during delivery and implantation.

FIG. 84 further illustrates a release mechanism in the form of a control ring 7976. As described below in further detail, control ring 7976 is rotatable to release implant 7950 from delivery device 7900. More specifically, rotation of control ring 7976 results in retraction of retention cable 7974, first cinch line 7962, and second cinch line 7964 (shown in the previous figures) in the correct sequence and with proper timing for release of implant 7950 from delivery device 7900. As shown in FIG. 84, control ring 7976 may be locked in position by a lock 7978 (e.g., a locking screw or similar locking mechanism that prevents rotation of control ring 7976) during delivery and placement of implant 7950. Once implant 7950 is positioned with in the valve annulus, lock 7978 may be unlocked to permit rotation of control ring 7976 and release of implant 7950 from delivery device 7900.

Given mechanical conventions of counterclockwise rotation corresponding to retraction (e.g., for screws or similar threaded fasteners), examples discussed in this disclosure generally rely on counterclockwise rotation of control ring 7976 to retract cinch lines and retention cables to release of implant 7950 from delivery device 7900. Nevertheless, it should be understood that the concepts taught in this disclosure can be readily adapted into a configuration in which release results from clockwise rotation of control ring 7976 instead.

Further details of the operation of control ring 7976 are now provided with reference to FIGS. which illustrate handle assembly 7902 with housing 7916 removed. Referring first to FIG. handle assembly 7902 includes a proximal member 7980 or frame element on which control ring 7976 is rotationally supported. Proximal member 7980 defines aperture 7982 through which release lines extend and that is generally aligned with a ring orifice 7977 extending through control ring 7976. In the specific implementation shown, the release lines include a retention tether 7984 and a cinch line tether 7986.

Retention tether 7984 is coupled to a proximal end of retention cable 7974 (shown, e.g. in FIGS. 83B and 83D) such that proximally pulling retention tether 7984 results in retraction of retention cable 7974. As described above in the context of FIGS. 83A and 83B, retention cable 7974 generally retains first cinch line 7962 and second cinch line 7964 during implant delivery and deployment and retraction of retention cable 7974 releases first cinch line 7962 and second cinch line 7964 for subsequent detachment of implant 7950 from delivery device 7900.

Cinch line tether 7986 forms a loop about each of first cinch line 7962 and second cinch line 7964 such that proximal pulling of cinch line tether 7986 results in retraction of each of first cinch line 7962 and second cinch line 7964. As noted above in the context of FIGS. 83C-83H, following release of first cinch line 7962 and second cinch line 7964 by retraction of retention cable 7974, retraction of first cinch line 7962 and second cinch line 7964 generally causes the cinch lines to retract through coupling features (e.g., eyelets) configured to facilitate retention of implant 7950 on delivery device 7900, thereby allowing detachment of implant 7950 from delivery device 7900.

The looping of cinch line tether 7986 about each of first cinch line 7962 and second cinch line 7964 is more clearly illustrated in FIG. 85B, which is a detailed view of handle assembly 7902 in the area of extension shuttle 7924. As shown, tether 7986 loops about and is used to pull/retract each of first cinch line 7962 and second cinch line 7964 simultaneously. However, in other implementations, separate tethers may be included for each of first cinch line 7962 and second cinch line 7964.

As previously noted, implementations of this disclosure may include more than two cinch lines and/or more than a single retention element. In implementations including more than two cinch lines, cinch line tether 7986 may be looped around or otherwise coupled to each of the cinch lines to perform simultaneously retraction of the cinch lines. Alternatively, the handle assembly may include multiple cinch line tethers coupled to approximately the same location on control ring 7976 such that each of the cinch line tethers is pulled simultaneously. As another alternative, retraction of one or more cinch lines may be staggered by coupling the cinch lines or corresponding cinch line tethers for each group to different locations about control ring 7976.

Similarly, in implementations with multiple retention elements, each retention element may be coupled to a common retention element tether that, in turn, is coupled to and pullable by control ring 7976. By doing so, each of the retention elements may be simultaneously pulled by rotating control ring 7976. Alternatively, the retention elements or tethers coupled to subgroups of the retention elements may be coupled to locations around control ring 7976 such that rotation of control ring 7976 results in sequenced pulling of the retention elements. In general, however, the retention elements are sequenced to be retracted prior to pulling of the cinch lines such that the cinch lines are released by the retention elements and able to be retracted.

Figure 85C:
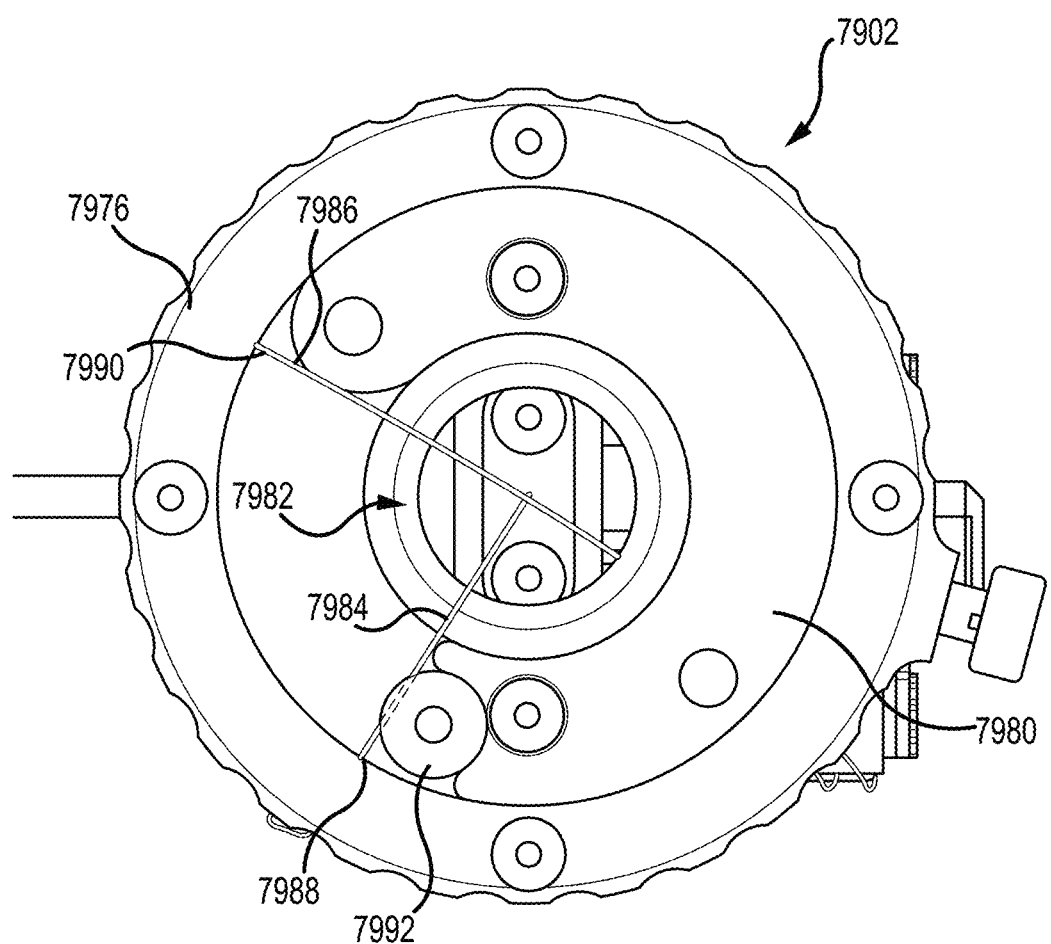
FIG. 85C is a proximal internal view of the handle assembly of FIG. 84.

FIG. 85C is a proximal view of handle assembly 7902 with housing 7916 removed and further illustrating routing of retention tether 7984 and cinch line tether 7986. As shown, retention tether 7984 generally extends along the longitudinal axis of handle assembly 7902 through aperture 7982 and is coupled to a first attachment location 7988 on control ring 7976. Cinch line tether 7986 similarly extends through aperture 7982 and is coupled to a second attachment location 7990 on control ring 7976, second attachment location 7990 being angularly offset from first attachment location 7988. Due to the coupling of retention tether 7984 and cinch line tether 7986 to control ring 7976, rotation of control ring 7976 about and relative to proximal member 7980 results in angular movement of retention tether 7984 and cinch line tether 7986 about aperture 7982. FIG. 85C further indicates a protrusion 7992 (e.g., a spindle, hub, capstan, or similar structure) is coupled to and extends proximally from proximal member 7980 between control ring 7976 and aperture 7982 in the path of retention tether 7984 and cinch line tether 7986 during rotation of control ring 7976.

FIGS. 86A-86D are schematic illustrations of the view shown in FIG. 85C illustrating an example release sequence of implant 7950 from delivery device 7900 from the perspective of the release control. FIG. 86A illustrates essentially the same configuration as FIG. 85C and corresponds to a state prior to beginning a release process. As noted above in the context of FIG. 85C, in this state, retention tether 7984 and cinch line tether 7986 extend through aperture of proximal member 7980 and couple to control ring 7976 at first attachment location 7988 and second attachment location 7990, respectively. Protrusion 7992 is positioned between aperture 7982 and control ring 7976 and along the rotational path of the tethers.

FIG. 86B, illustrates handle assembly 7902 following a first counterclockwise rotation of control ring 7976. The state shown in FIG. 86B corresponds to a stage in the implant release process following initial retraction of retention cable 7974 and which generally corresponds to a state immediately after that shown in FIG. 83B. More specifically, the state shown in FIG. 86B occurs after initial retraction of retention cable 7974 but prior to retraction of first cinch line 7962 and second cinch line 7964.

As shown in the transition between FIGS. 86A and 86B, rotation of control ring 7976 results in a corresponding rotation of first attachment location 7988 for retention tether 7984 about aperture 7982. Rotation of first attachment location 7988 causes contact and interference between retention tether 7984 and protrusion 7992 and corresponding wrapping of retention tether 7984 around protrusion 7992. Protrusion 7992 functions like a pulley or post and increases the length of retention tether 7984 necessary to extend between aperture 7982 and first attachment location 7988. As a result, retention tether 7984 is pulled through aperture 7982 proximally pulling and retracting retention cable 7974.

Rotation of control ring 7976 similarly results in a corresponding rotation of second attachment location 7990 for cinch line tether 7986 about aperture 7982. However, in contrast to retention tether 7984, cinch line tether 7986 is not made to contact protrusion 7992 and the length of cinch line tether 7986 extending between aperture 7982 and second attachment location 7990 remains constant. So, rotation of control ring 7976 as shown in the transition between FIGS. 86A and 86B does not result in pulling of cinch line tether 7986 and first cinch line 7962 and second cinch line 7964 remain unretracted.

FIG. 86C illustrates handle assembly 7902 following further rotation of control ring 7976. In the illustrated state, cinch line tether 7986 is about to but has not yet contacted protrusion 7992. As a result, the length of cinch line tether 7986 extending from aperture 7982 to second attachment location 7990 is the same as in FIGS. 86A and 86B and pulling/retraction of the cinch lines has not yet started. In contrast, the additional rotation of control ring 7976 has resulted in further pulling of retention tether 7984 to accommodate the increased distance between aperture 7982 and first attachment location 7988. As a result, the transition from the state shown in FIG. 86B to that shown in FIG. 86C results in further pulling of retention tether 7984 and further retraction of retention cable 7974.

FIG. 86D illustrates handle assembly 7902 following even further rotation of control ring 7976. Again, this rotation results in further rotation of first attachment location 7988 and second attachment location 7990 about aperture 7982. As in the previous figures, further rotation of first attachment location 7988 results in additional pulling of retention tether 7984 and further retraction of retention cable 7974 due to the contact between retention tether 7984 and protrusion 7992. Rotation of control ring 7976 from the state shown in FIG. 86C to that of FIG. 86D also results in contact between cinch line tether 7986 and protrusion 7992 and initiating pulling of cinch line tether 7986 through aperture 7982. Given the looping of cinch line tether 7986 about first cinch line 7962 and second cinch line 7964, the pulling of cinch line tether 7986 results in retraction of first cinch line 7962 and second cinch line 7964.

With retention tether 7984 and cinch line tether 7986 now in contact with protrusion 7992, further rotation of control ring 7976 results in further retraction of retention cable 7974, first cinch line 7962, and second cinch line 7964. In certain implementations, handle assembly control ring 7976 may include a stop, indicators, or similar features to indicate when control ring 7976 has been sufficiently rotated to sufficiently retract each of retention cable 7974, first cinch line 7962, and second cinch line 7964 to release implant 7950 from delivery device 7900.

As shown in FIGS. 86A-86D, sequential retraction of retention cable 7974 followed by the cinch lines is achieved by rotation of control ring 7976 triggering pulling of retention tether 7984 followed by cinch line tether 7986. More specifically, rotation of control ring 7976 in a release direction first causes retention tether 7984 to contact protrusion 7992, initiating pulling of retention tether 7984 and retention cable 7974. Subsequent rotation of control ring 7976 eventually causes contact between cinch line tether 7986 and protrusion 7992, initiating pulling of cinch line tether 7986 and the cinch lines.

This disclosure contemplates that the timing and sequencing for pulling of the retention components and the cinch line components can be modified in various ways. For example, by changing the angular offset between the attachment locations on control ring 7976 for retention tether 7984 and cinch line tether 7986, sequencing of cinch line pulling relative to retention cable pulling can be modified. In general, increasing the angular offset between the attachment locations results in pulling of the cinch lines initiated later in the process of retracting the retention cable. Conversely, decreasing the angular offset between the attachment locations results in retraction of the cinch lines beginning earlier in the process of retracting the retention cable. Protrusion 7992 may also be modified to change timing and sequencing of the release operation. For example, the rate at which the tethers are pulled per unit of rotation of control ring 7976 is generally a function of the size of protrusion 7992. As a result, increasing or decreasing the circumference/perimeter of protrusion 7992 can be used to increase or decrease the rate at which the tethers are pulled (all other things being equal).

XXIV. Structural Mounting of Delivery System

FIGS. 77A-78C illustrate implant delivery system 7700, which includes delivery device 7702 and mounting assembly 7704. As described in the context of those figures, mounting assembly 7704 is generally configured to support delivery device 7702 and may include various features for controlled operation of delivery device 7702. For example, FIGS. 77A and 77B illustrate longitudinal translation of delivery device 7702 relative to mounting assembly 7704 by rotation of knob 7712 to perform insertion/retraction of delivery device 7702. FIGS. 78A-78C similarly illustrate manual rotation of delivery device 7702 within mounting assembly 7704. Additional details regarding mounting assemblies are provided below with specific reference to FIGS. 87A-87L, which illustrate mounting assembly 8700 and various components of mounting assembly 8700. Mounting assembly 8700 is substantially like mounting assembly 7704 of FIGS. 78A-78C, so unless otherwise stated, the description of mounting assembly 7704 provided earlier in this disclosure is generally applicable to mounting assembly 8700.

Figure 87A:
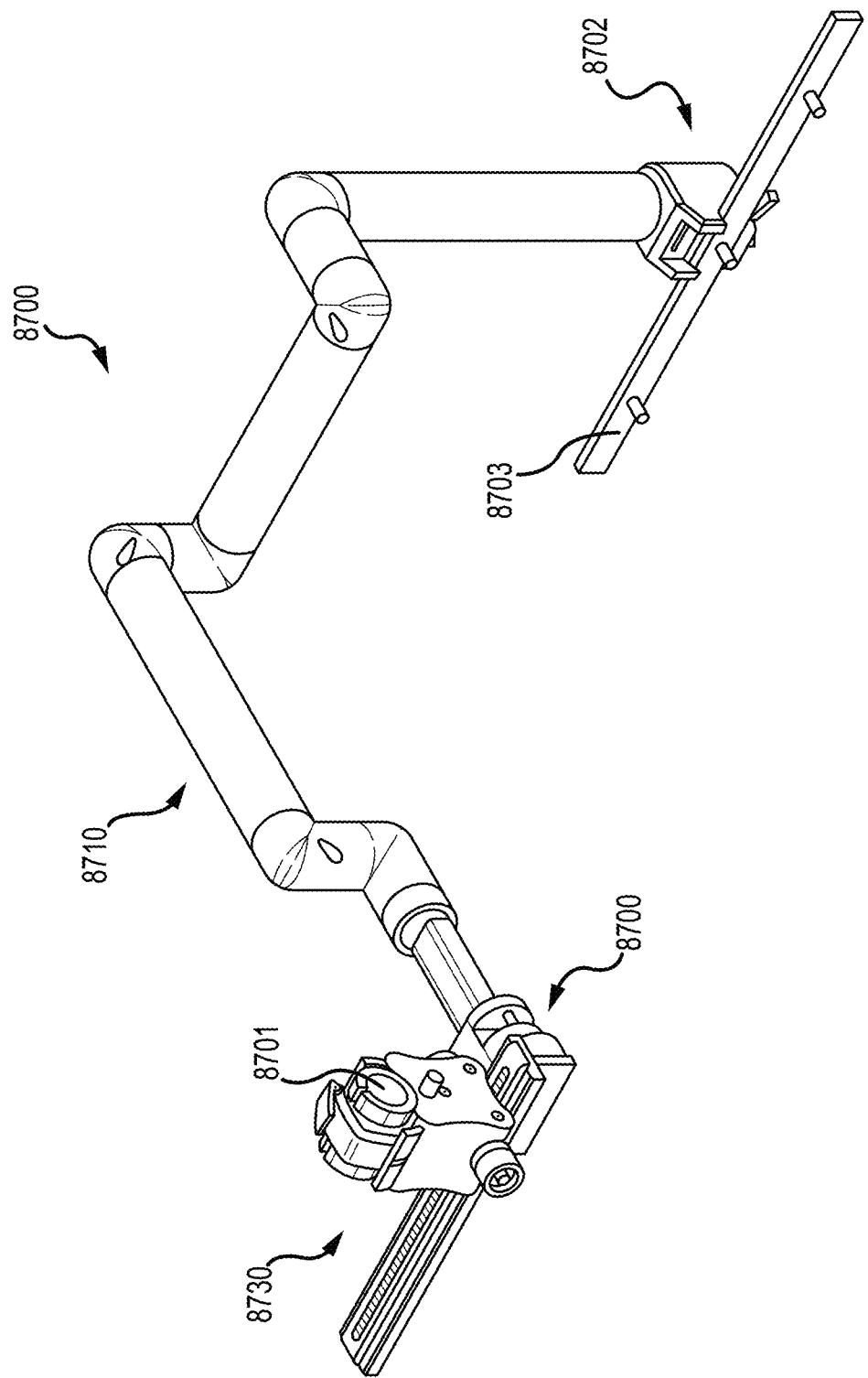
FIG. 87A is an isometric view of a mounting assembly for use with delivery devices according to this disclosure.

FIG. 87A is an isometric view of a mounting assembly 8700 according to the present disclosure. Mounting assembly 8700 includes a structural coupling 8702, an arm assembly 8710, and a handle mount assembly 8730. FIG. 87A further includes a handle assembly element 8701 and a structural element 8703.

As shown, mounting assembly 8700 is coupled to and supported by structural element 8703. More specifically, structural coupling 8702 couples to structural element 8703 with arm assembly 8710 coupled to and extending from structural coupling 8702. Arm assembly 8710 may be any suitable structure for supporting and adjusting the position and orientation of handle mount assembly 8730. As shown, arm assembly 8710 is a universal articulating arm structure including multiple manipulable and lockable joints. This disclosure contemplates that other support structures may be used to support and maintain position of handle mount assembly 8730 during use, arm assembly 8710 is included as a specific example that includes degrees of freedom and flexibility that are conducive to use with delivery devices of this disclosure.

Handle mount assembly 8730 is coupled to and extends from arm assembly 8710. During use, handle mount assembly 8730 receives and provides direct support of a delivery device, as reflected by handle assembly element 8701. As noted in the context of 77A-78C and as further discussed below, handle mount assembly 8730 may further include elements for facilitating insertion and rotation of a delivery device while maintaining a longitudinal axis of the delivery device in a fixed location.

In general, handle assembly element 8701 corresponds to a portion of a delivery device according to this disclosure. More specifically, handle assembly element 8701 corresponds to a handle assembly of a delivery device and is provided in the figures to illustrate how delivery devices of this disclosure are received and supported by mounting assembly 8700. This disclosure contemplates that each of handle assembly element 8701 may vary and, as such, handle assembly element 8701 is intended only as a non-limiting example of a delivery device structure that may be received and supported by mounting assembly 8700.

Structural element 8703 is intended to reflect an environmental structure, such as a bed rail, to which mounting assembly 8700 may be coupled and that supports mounting assembly 8700. Like handle assembly element 8701, structural element 8703 is provided as a non-limiting example of a structure to which mounting assembly 8700 may be coupled. Accordingly, any specific aspects of structural element 8703 shown in the figures should be considered non-limiting. For example, this disclosure contemplates that structural element 8703 may vary in size and shape from that shown in the figures or that mounting assembly 8700 may be coupled to structures other than bed rails, including stand-alone mounting systems that do not rely on other capital equipment within the operating theater.

Figure 87B:
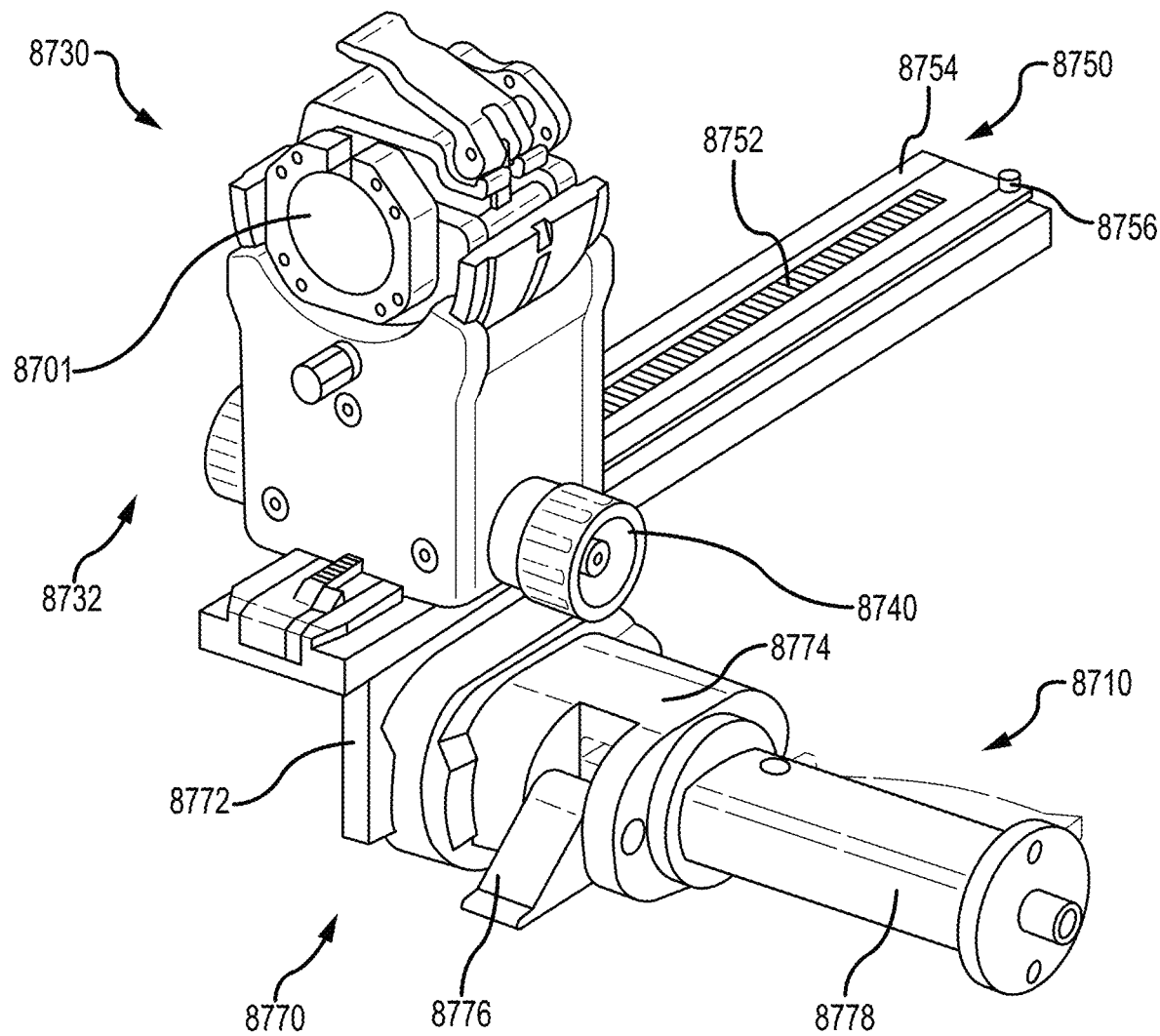
FIG. 87B is an isometric view of a handle mount assembly of the mounting assembly of FIG. 87A.

FIG. 87B is an isometric view of handle mount assembly 8730 and a terminal portion of arm assembly 8710 including an interface block 8774. Handle mount assembly 8730 includes a carriage assembly 8732 coupled to and movable along a rail assembly 8750. Rail assembly 8750 includes a rail 8752 and a frame 8754. Carriage assembly 8732 and rail assembly 8750 are selectively coupled to arm assembly 8710 by an interface 8770. Interface 8770 includes a rail-side interface element in the form of a plate 8772 that is receivable by interface block 8774. As shown, interface block 8774 further includes a locking control 8776 in the form of a lever that can be selectively engaged and disengaged to fix and release plate 8772 from interface block 8774, thereby permitting selective attachment and removal of handle mount assembly 8730 from arm assembly 8710. FIG. 87B further includes an extension member 8778 coupled to and extending from interface block 8774 and that couples interface block 8774 to the remainder of arm assembly 8710. In general, extension member 8778 is configured to mate with and to be coupled with a terminal end of arm assembly 8710.

In the implementation shown, carriage assembly 8732 includes a manually driven stepper-type drive system. More specifically, carriage assembly 8732 is retained on rail assembly 8750 by a dove-tail type mating arrangement. Carriage assembly 8732 includes knobs (such as knob 8740) that are rotatable to provide controlled translation of carriage assembly 8732 along rail assembly 8750. For example, knob 8740 may be coupled to an internal gear or cog of carriage assembly 8732 that mates with rail 8752 of rail assembly 8750 such that rotation of knob 8740 rotates the internal gear or cog and drives carriage assembly 8732 along rail 8752.

Figure 87C:
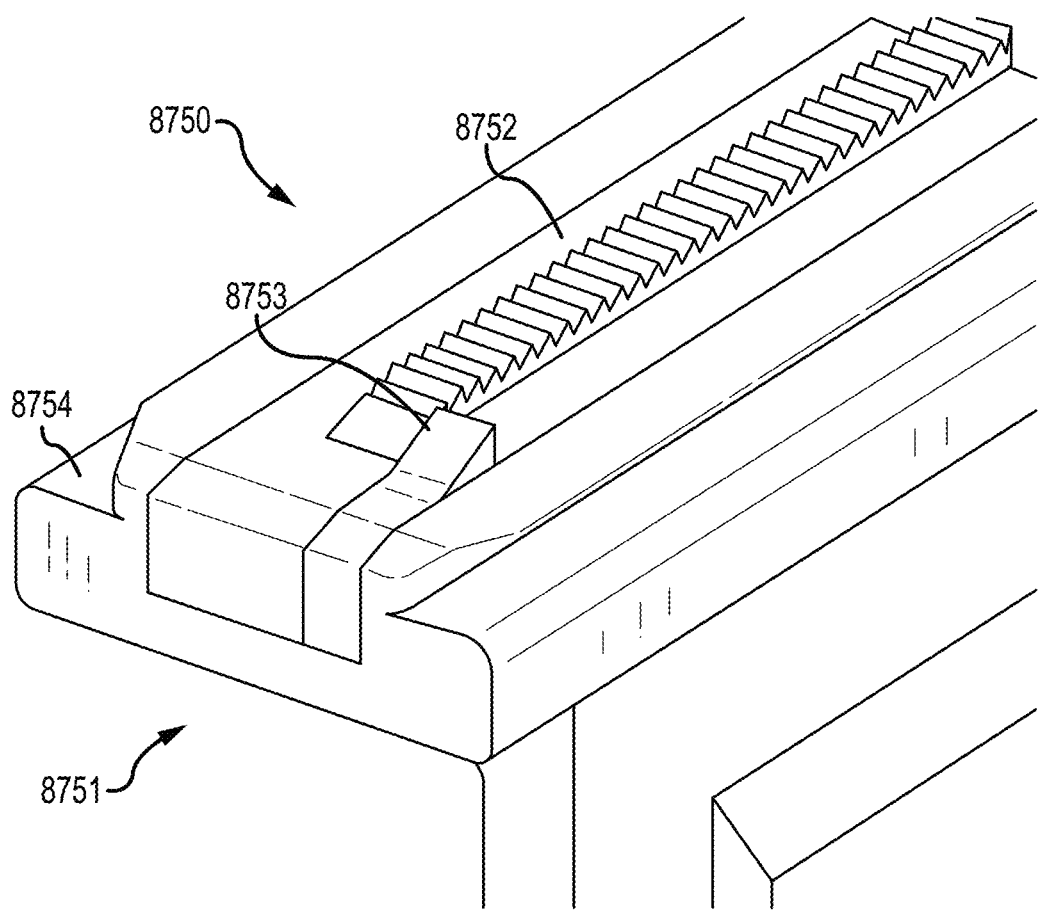
FIG. 87C is a detailed view of a rail assembly of the of the mounting assembly of FIG. 87A.

FIG. 87C is a detailed isometric view of rail assembly 8750. More specifically, FIG. 87C illustrates a distal portion of rail 8752 and frame 8754. As shown, rail assembly 8750 may have an open end 8751 to facilitate attachment and removal of carriage assembly 8732 from rail assembly 8750. In certain implementations, rail assembly 8750 may include a retention feature, such as stop 8753 that generally retains carriage assembly 8732 on rail 8752, but that can be selectively disengaged to permit sliding of carriage assembly 8732 off rail 8752 at open end 8751. For example, stop 8753 is generally biased into the configuration shown in FIG. 87C to retain carriage assembly 8732 on rail 8752; however, stop 8753 may be depressed, removed, or otherwise disengaged to permit sliding of carriage assembly 8732 off open end 8751. Referring to FIG. 87B, frame 8754 is shown as further including an optional stop 8756 protruding from a proximal portion of frame 8754 and that limits proximal travel of carriage assembly 8732 along rail 8752.

FIGS. 87D and 87E isometric views of rail assembly 8750, carriage assembly 8732 and interface 8770 in a decoupled state. As shown in FIG. 87D, plate 8772 is coupled to an underside of frame 8754 and includes a retention structure 8773. Interface block 8774 includes a face 8779 shaped to receive retention structure 8773 (e.g., having a groove or channel shaped to the correspond to the exterior surface of the U-shaped retention structure) and further includes a locking pillar 8775 shaped to be received within an internal channel 8777 defined on an inner surface of retention structure 8773. As specifically shown in FIG. 87D, retention structure 8773 is in the form of a U-shaped channel with a groove or channel extending along the inner surface of the U-shaped structure. During operation, locking pillar 8775 is manipulable to selectively engage internal channel 8777 to lock interface block 8774 to plate 8772.

Figure 87G:
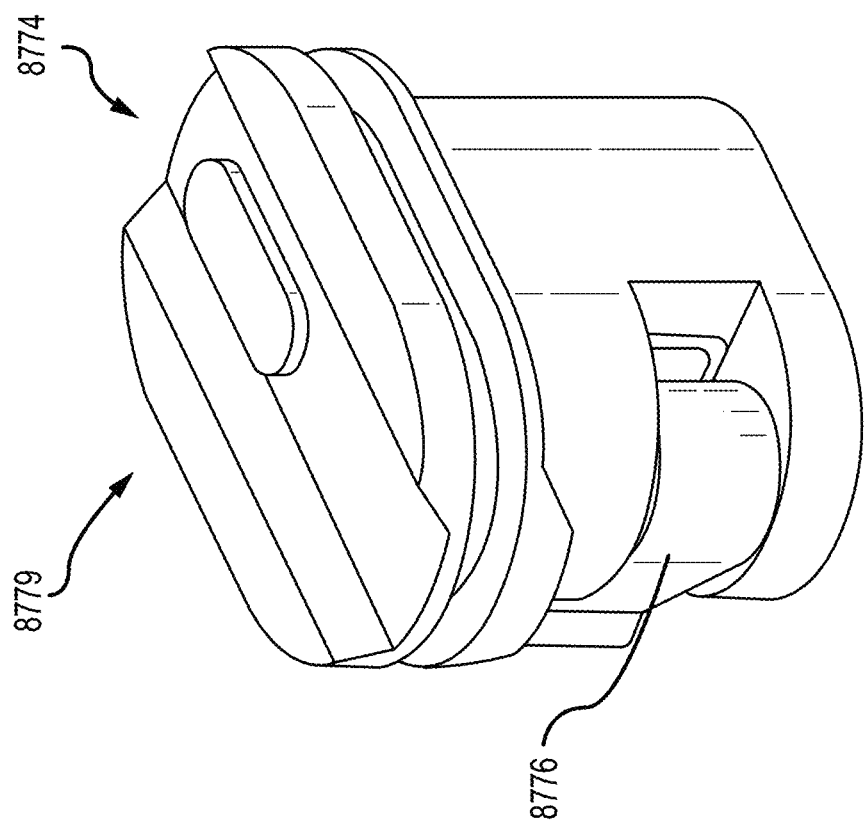
FIGS. 87F and 87G are isometric views of an interface block of the mounting assembly of FIG. 87A in a disengaged and engage state, respectively.
Figure 87F:
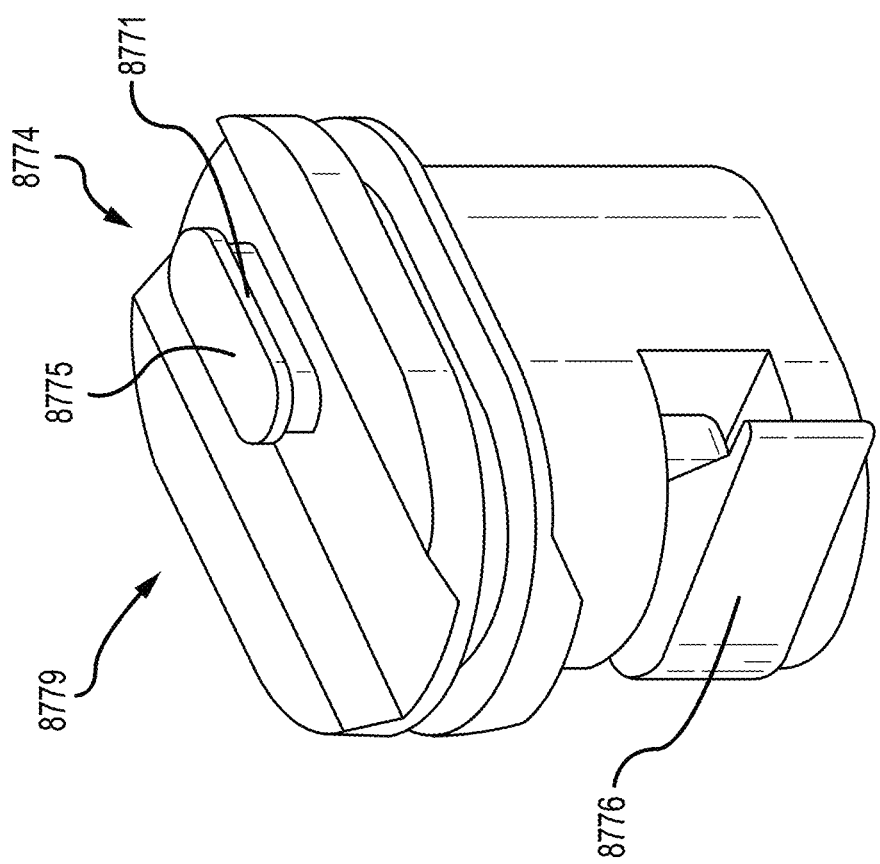
Figure 87H:
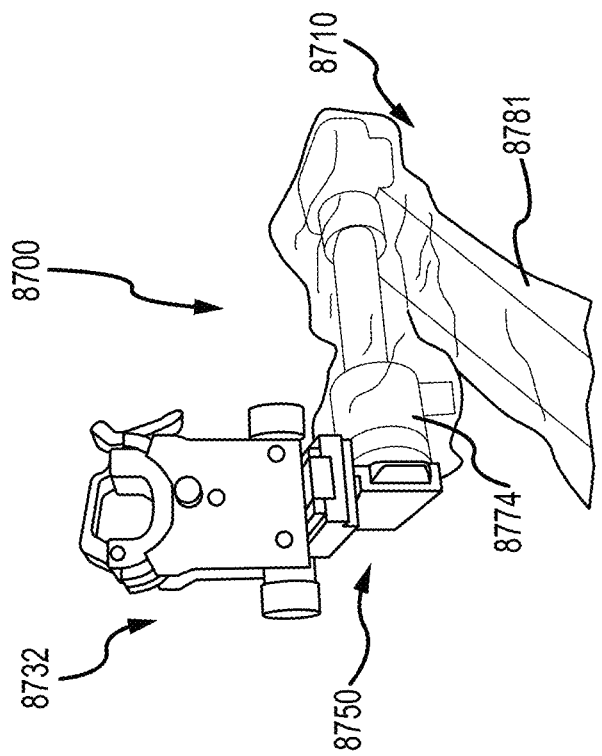
FIGS. 87H and 87I are perspective views of the mounting assembly of FIG. 87A including a sterile drape.

FIGS. 87G and 87H illustrate interface block 8774 in an open/unlocked state and a closed/locked state, respectively. In the illustrated implementations, interface block 8774 transitions between the open/unlocked state of FIG. 87G to the closed/locked state of FIG. 87H in response to actuation of locking control 8776. As shown, locking control 8776 is in the form of a cam-style lever that drives locking pillar 8775 between a raised position (shown in FIG. 87G) and a retracted position (shown in FIG. 87H). In operation, plate 8772 is slid onto interface block 8774 while locking pillar 8775 is in the open configuration shown in FIG. 87G. More specifically, plate 8772 is slid onto interface block 8774 such that a lip 8771 of locking pillar 8775 is received within internal channel 8777 of retention structure 8773. Locking control 8776 is then actuated to retract locking pillar 8775 into interface block 8774, thereby locking interface block 8774 to plate 8772.

Figure 87I:
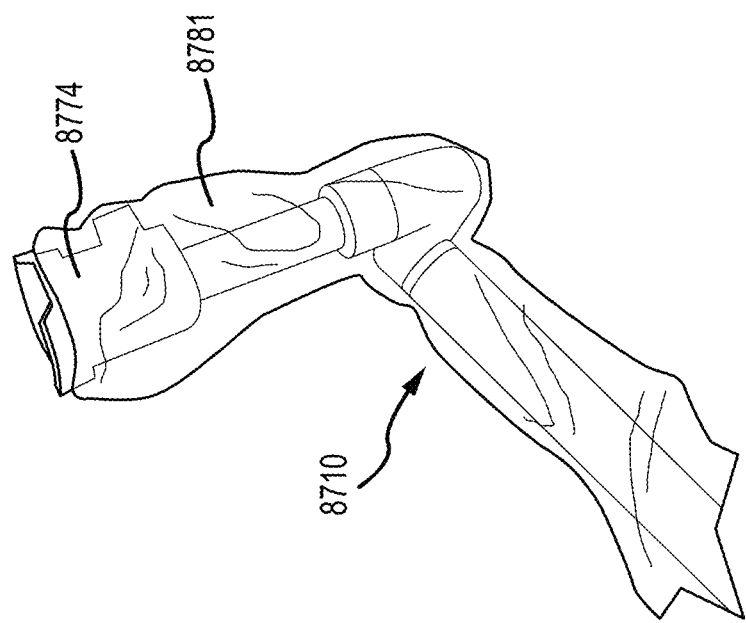

Among other advantages, the specific coupling arrangement illustrated in FIGS. 87D and 87E can facilitate maintaining a sterile operating environment. FIGS. 87H and 87I, for example, are perspective views of mounting assembly 8700 with and without carriage assembly 8732 coupled to interface block 8774. As shown in the figures, interface block 8774 and arm assembly 8710 may be covered in a sterile drape 8781 such that between surgeries carriage assembly 8732 and rail assembly 8750 may be readily detached from arm assembly 8710 for disposal or sterilizing. With carriage assembly 8732 and arm assembly 8710 removed, a used drape can be readily slid off arm assembly 8710 and replaced with a new, sterile drape, thereby eliminating or reducing the need to re-sterilize the underlying arm assembly 8710.

Figure 87K:
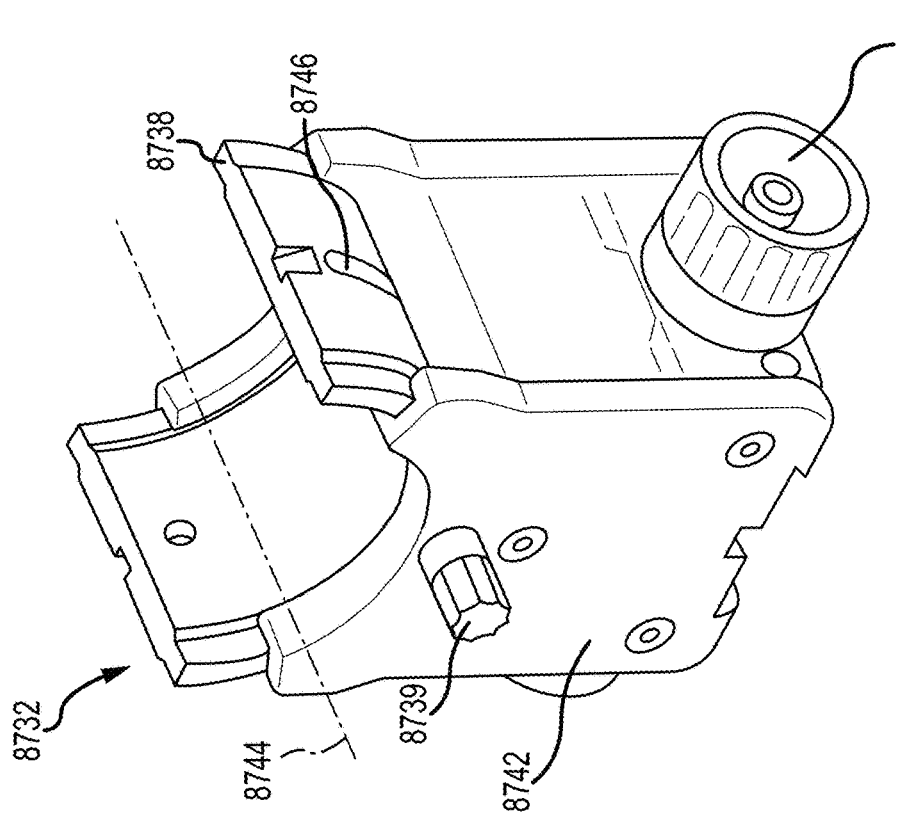
FIGS. 87J and 87K are isometric views of a carriage assembly of the mounting assembly of FIG. 87A.
Figure 87J:
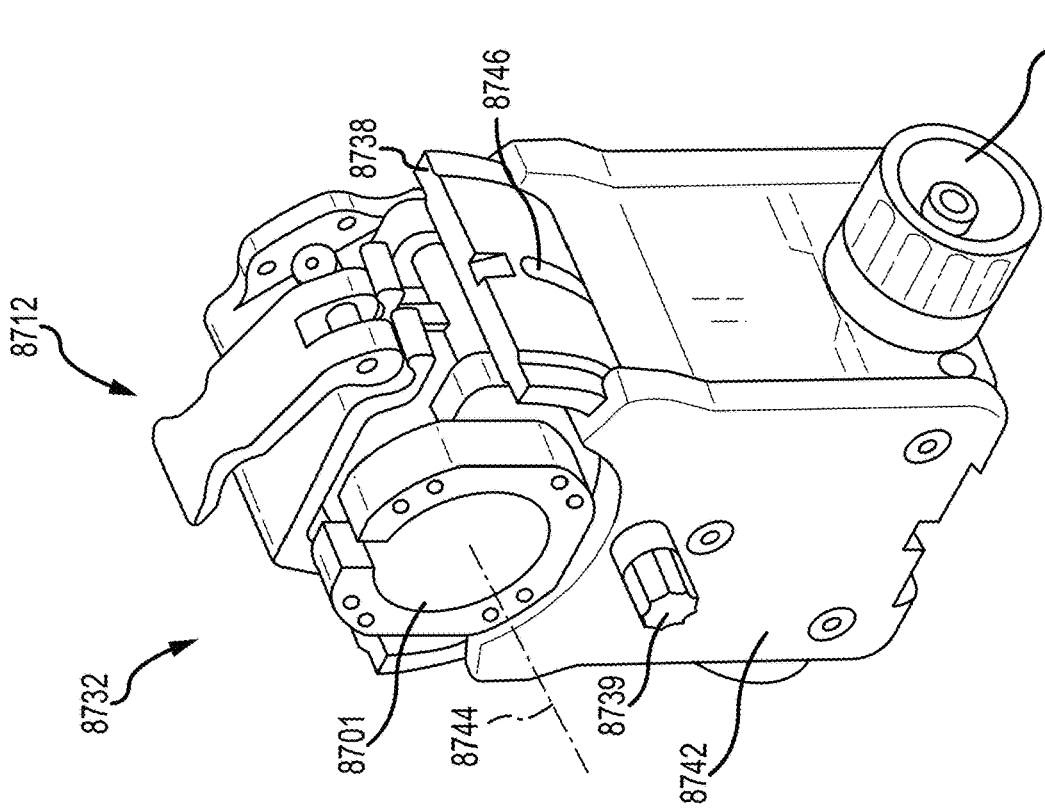

FIGS. 87J and 87K are isometric views of carriage assembly 8732. More specifically, FIG. 87J illustrates carriage assembly 8732 including a yoke 8712 and retaining handle assembly element 8701. FIG. 87K illustrates carriage assembly 8732 with yoke 8712 removed to better show a rotating collar 8738.

As previously discussed, carriage assembly 8732 includes a knob 8740 rotatable to drive carriage assembly 8732 along rail 8752 of rail assembly 8750. Such translation of carriage assembly 8732 can be used to control insertion of a delivery device coupled to mounting assembly 8700. Implementations of this disclosure may also enable rotation of the delivery device relative to carriage assembly 8732. For example, as most clearly shown in FIG. 87K, carriage assembly 8732 may include a rotating collar 8738. Rotating collar 8738 is coupled to and supported by a body 8742 of carriage assembly 8732 and is rotatable relative to body 8742 about a longitudinal axis 8744, which corresponds to a longitudinal axis of the delivery device when retained by carriage assembly 8732. In at least some implementations, rotation of rotating collar 8738 may be guided by a slot 8746 or similar guide element of rotating collar 8738 that mates with a corresponding structure of body 8742 (not shown). An example of such rotation is shown in FIGS. 78A-78C, which illustrate rotation of delivery device 7702 within cradle 7706. As further shown in FIGS. 87J and 87K, carriage assembly 8732 may include a rotational lock (e.g., locking knob 8739) configured to selectively lock and unlock rotating collar 8738 in position.

Figure 87L:
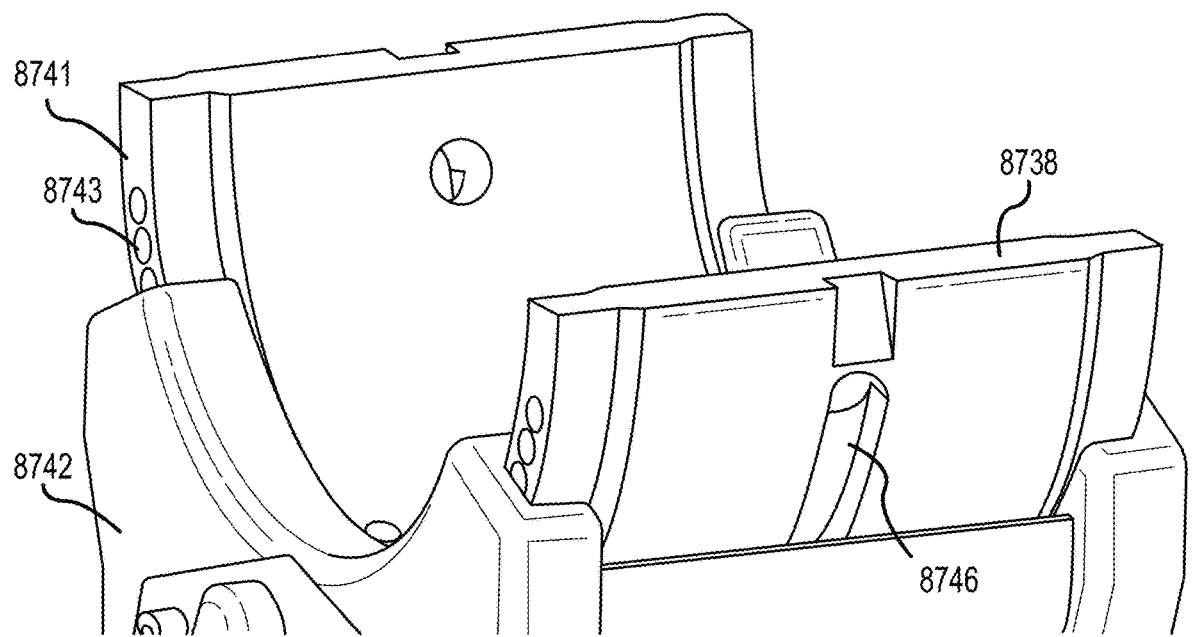
FIG. 87L is a detailed view of the carriage assembly as shown in FIG. 87K.

In at least certain implementations, carriage assembly 8732 may be configured to facilitate discrete rotation of rotating collar 8738. For example, FIG. 87L is a detailed view of carriage assembly 8732 as presented in FIG. 87L. As shown, rotating collar 8738 includes a proximal face 8741 that further includes a series of detents (e.g., detent 8743). Carriage assembly 8732 may include one or more corresponding protrusions (not shown) such that as a clinician or operator rotates rotating collar 8738, rotating collar 8738 transitions between discrete rotational positions due to engagement of the protrusion with the detents.

Figure 87M:
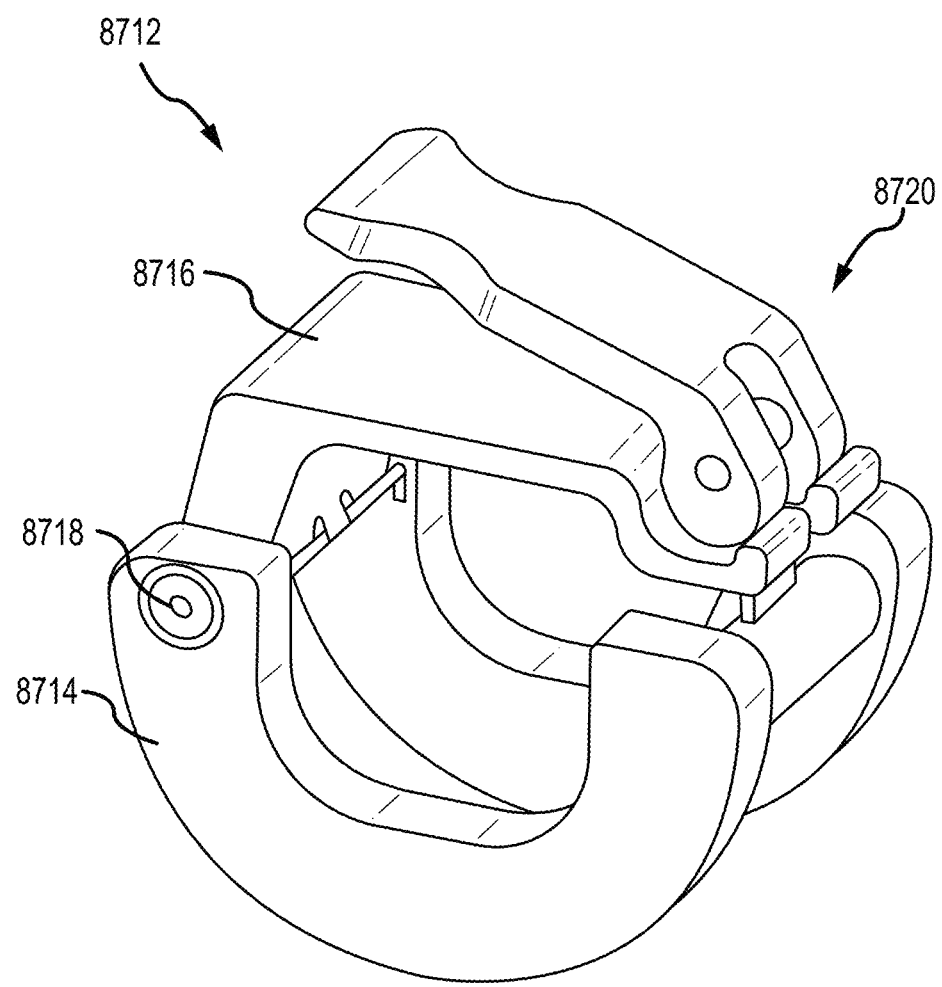
FIG. 87M is an isometric view of a yoke of the mounting assembly of FIG. 87A.

FIG. 87M is an isometric view of yoke 8712, which, as illustrated in FIG. 87I, is coupled to and retained by rotating collar 8738 when carriage assembly 8732 is fully assembled. As shown in FIG. 87M, yoke 8712 includes a lower member 8714 and an upper member 8716 coupled to lower member 8714 by a hinge 8718 or similar joint. Each of lower member 8714 and upper member 8716 are generally shaped to conform to and receive a portion of a delivery tool, e.g., as shown in the previous figures by retention of assembly element 8701 by yoke 8712. Although this disclosure contemplates other styles of closure mechanisms, yoke 8712 includes a cam-style latching mechanism 8720 configured to clamp upper member 8716 relative to lower member 8714 and about the delivery device.

Figure 87N:
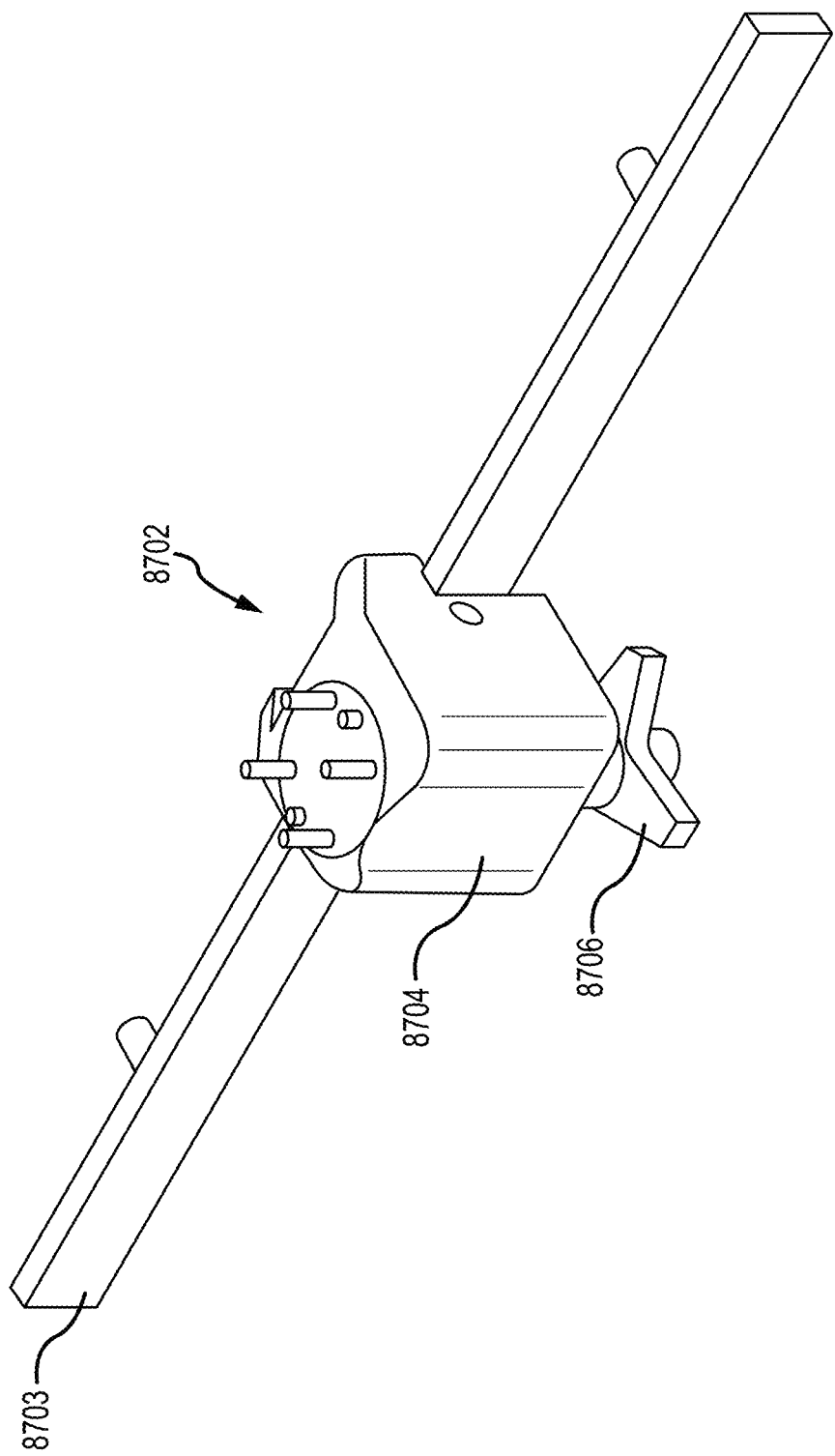
FIG. 87N is an isometric view of a structural coupling of the mounting assembly of FIG. 87A.

FIG. 87N is an isometric view of structural coupling 8702 and structural element 8703. As previously noted, structural coupling 8702 is coupleable to structural element 8703 or other capital equipment within an operating environment to support mounting assembly 8700. As illustrated, structural coupling 8702 includes a body 8704 shaped to receive or otherwise mate with structural element 8703. Structural coupling 8702 further includes a locking or retention mechanism (e.g., locking knob 8706) adapted to affix structural coupling 8702 to structural element 8703 once positioned on structural element 8703.

Mounting assembly 8700 is intended to illustrate one example mounting structure suitable for use with delivery devices of this disclosure. This disclosure contemplates that the various components and features of mounting assembly 8700 illustrated in the figures and discussed above can be replaced or modified with one or more other alternative components. For example, arm assembly 8710 may be substituted with any other suitable articulating or non-articulating assembly capable of supporting delivery devices of this disclosure in position relative to a patient. Similarly, while mounting assembly 8700 is illustrated as including structural elements for providing controlled insertion and rotation of delivery devices, either functionality may be omitted. As another example, mounting assembly 8700 includes cam-style locking mechanisms for several components. Such locking mechanisms are generally easy and intuitive to articulate in a surgical context; however, other locking mechanisms may be used in their place. For example, yoke 8712 is illustrated in FIG. 87K as including a cam-style latching mechanism 8720; however, cam-style latching mechanism 8720 may be readily substituted with a screw-type lock, a magnetic latch, a tie down, or other suitable mechanism.

XXV. Control Arm Assembly Including Cantilevered Control Arms

FIGS. 56-58 illustrate an example implementation of a delivery device 3600 according to the present disclosure and described in further detail, above. As shown in those figures, delivery device 3600 generally includes a control arm assembly 3608 at distal portion 3636 of delivery device 3600. Control arm assembly 3608 includes multiple control arm pairs distributed around an extension member 3606. Extension member 3606 is selectively extendable and retractable relative to delivery catheter 3604 to facilitate deployment of implant 3800.

Each control arm pair of control arm assembly 3608 includes a proximal arm 3634 coupled to a respective distal arm 3640. During operation, a control shaft disposed within delivery catheter 3604 and coupled to a proximal end of each of the proximal control arms of control arm assembly 3608 is translatable to selectively extend and retract the proximal control arms. As the proximal control arms are extended, diverter 3628 directs the proximal arms in a lateral and outward direction. Due to the coupling of the distal control arms to their respective proximal control arms, this lateral extension of the proximal control arms results in similar lateral and outward movement of the distal control arms, thereby expanding control arm assembly 3608. Such expansion of control arm assembly 3608 causes similar expansion of implant 3800, which is generally coupled to and supported by control arm assembly 3608 during delivery and implantation. Collapse of the implant can be similarly achieved by retracting the control shaft, which retracts the proximal control arms, laterally contracts the coupling of the distal and proximal control arms, and collapses control arm assembly 3608, thereby collapsing implant 3800.

As shown in FIGS. 57 and 58, each of the control arm pairs of delivery device 3600 generally include a proximal control arm, e.g., proximal arm 3634, and a respective distal control arm, e.g., distal arm 3640. More specifically, and with reference to FIG. 58, proximal portion 3641 of distal arm 3640 is coupled to distal portion 3636 of proximal arm 3634 by a T-and-slot style joint in which a T-shaped protrusion 3637 of proximal arm 3634 is inserted through and subsequently rotated to be retained by aperture 3639 of distal arm 3640. Notably, the coupling of distal arm 3640 and proximal arm 3634 in delivery device 3600 is at or near the end of the control arms.

Among other advantages, the control arm coupling and arrangement of delivery device 3600 and control arm assembly 3608 results in a substantially maximum moment arm for distal arm 3640 and efficient transfer of forces applied to proximal arm 3634 (e.g., by translating the control shaft) to distal arm 3640. As illustrated in FIG. 56, however, coupling the distal end of the proximal control arms at or near the proximal ends of the distal control arms generally limits the degree to which control arm assembly 3608 may be retracted during delivery and implantation. For example, FIG. 56 illustrates delivery device 3600 in a fully collapsed and fully or near fully retracted state. Further retraction of control arm assembly 3608 into delivery catheter 3604 from the state shown in FIG. 56 generally results in interference between control arm assembly 3608 and the distal end of delivery catheter 3604, precluding further retraction.

Since the control arm assembly is a generally rigid body and protrudes from the distal end of the delivery catheter, the degree to which the control arm assembly can retract relative to the delivery catheter contributes to the general maneuverability of the implant during delivery and implantation. More specifically and all other things being relatively equal, a control arm assembly that is further retractable into the delivery catheter will reduce the non-steerable length at the distal end of the delivery device, improving the maneuverability of the distal end and, by extension, an implant coupled to the distal end.

Figure 88A:
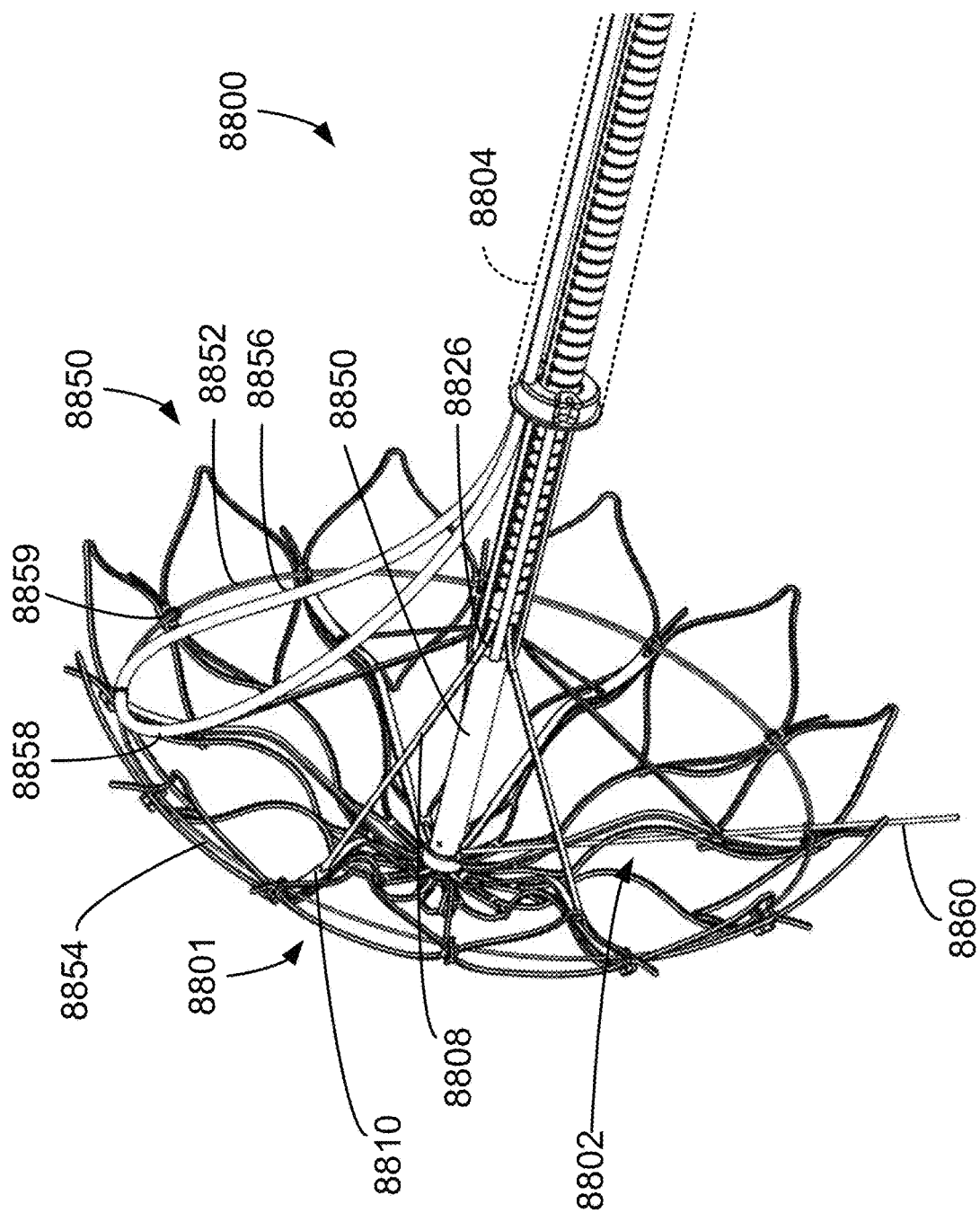
FIG. 88A is an isometric view of a distal portion of a delivery device and implant according to an implementation of this disclosure.
Figure 88B:
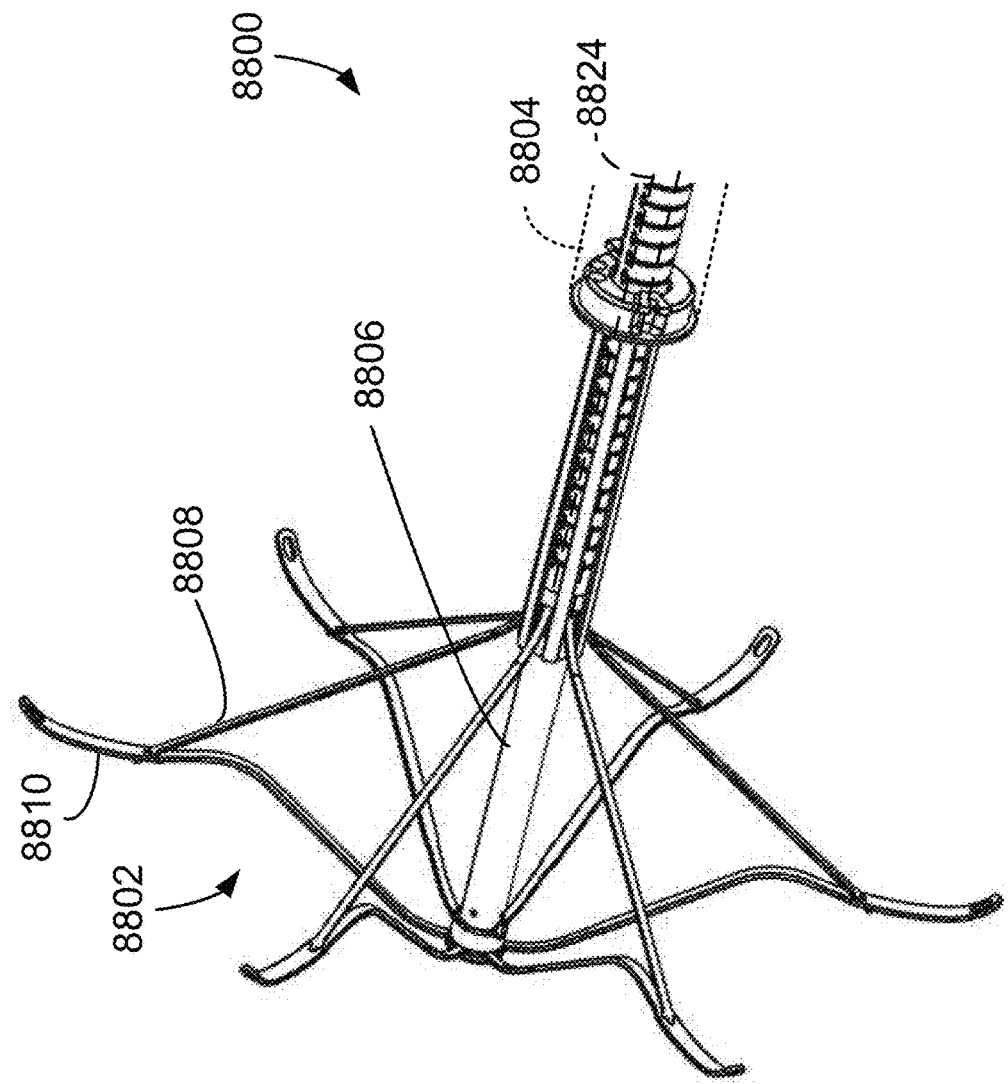
FIG. 88B is the view of FIG. 88A with select components removed to better illustrate a control arm assembly.
Figure 88C:
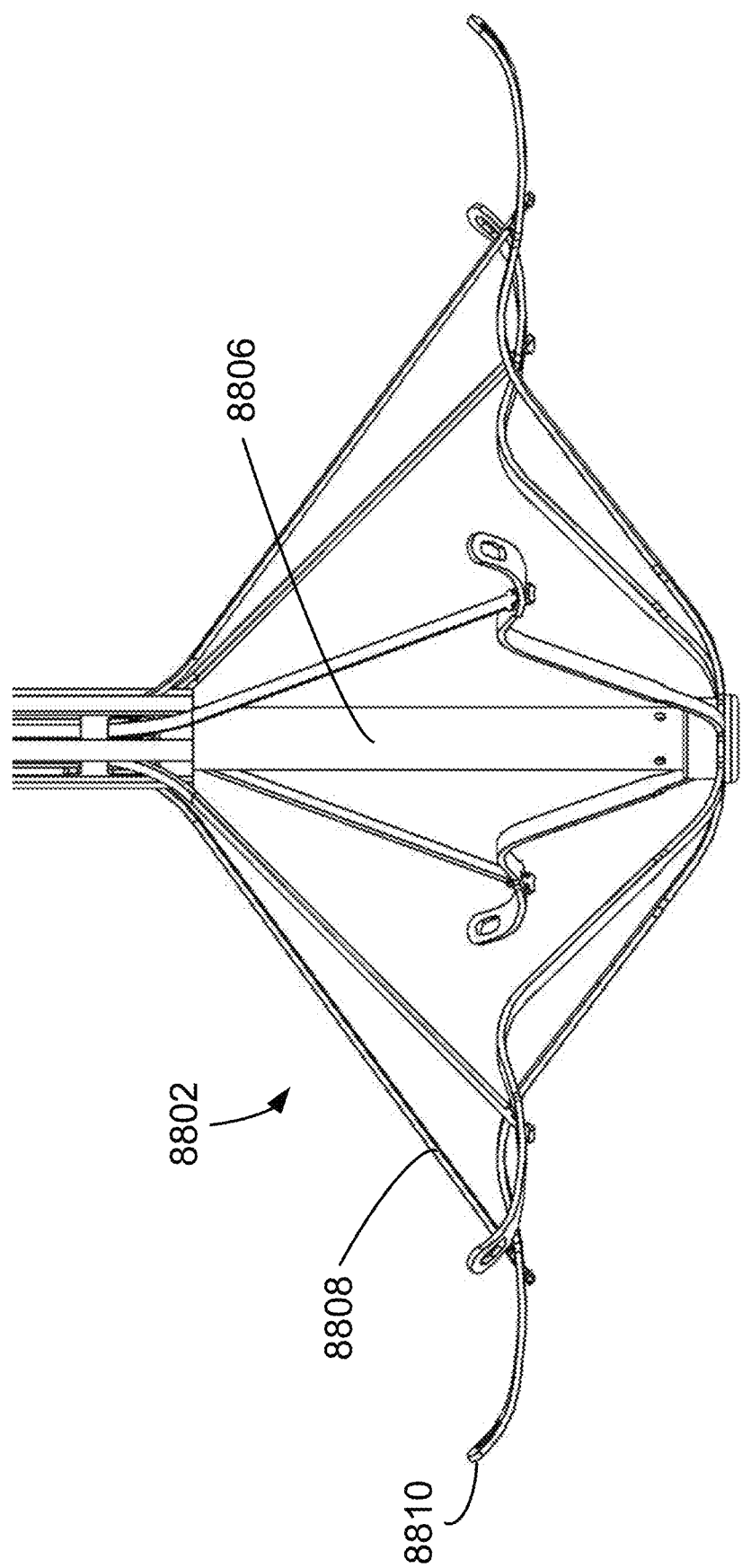
FIG. 88C is a side elevation view of the control arm assembly of FIG. 88B.
Figure 88D:
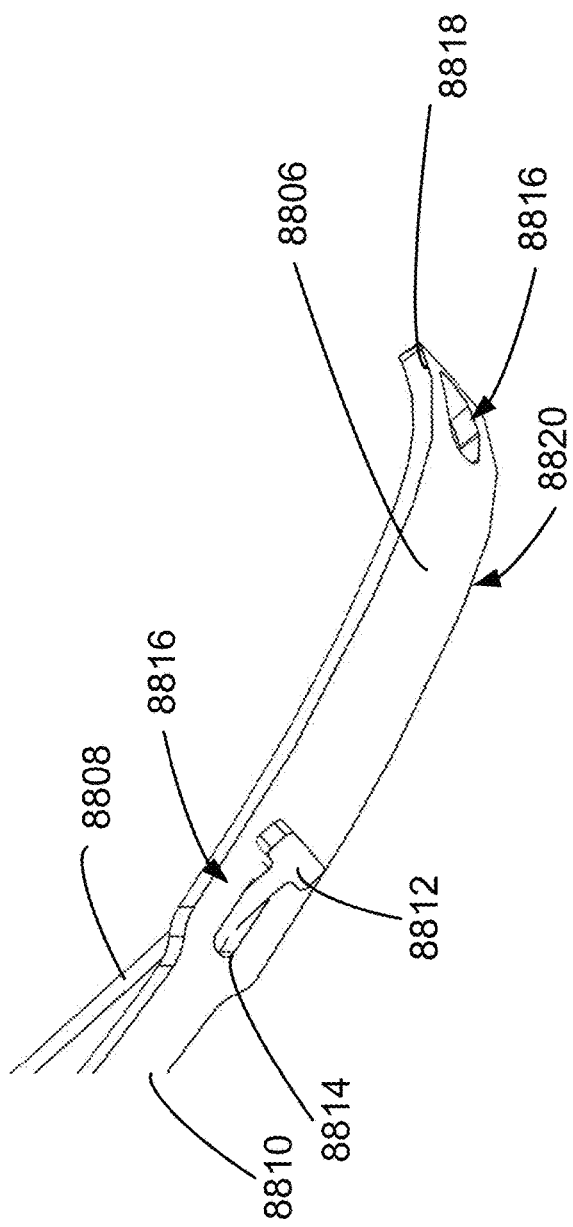
FIGS. 88D and 88E are detailed views of a joint between control arms of the control arm assembly of FIG. 88B.
Figure 88E:
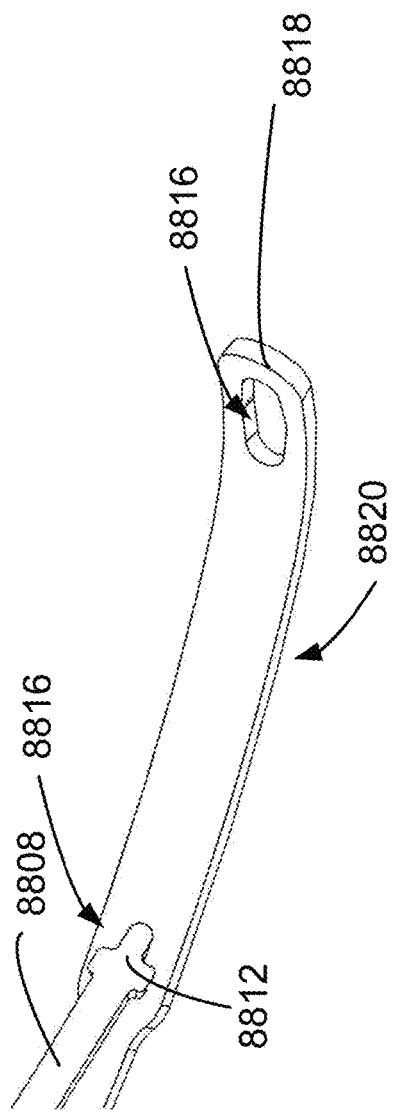
Figure 88F:
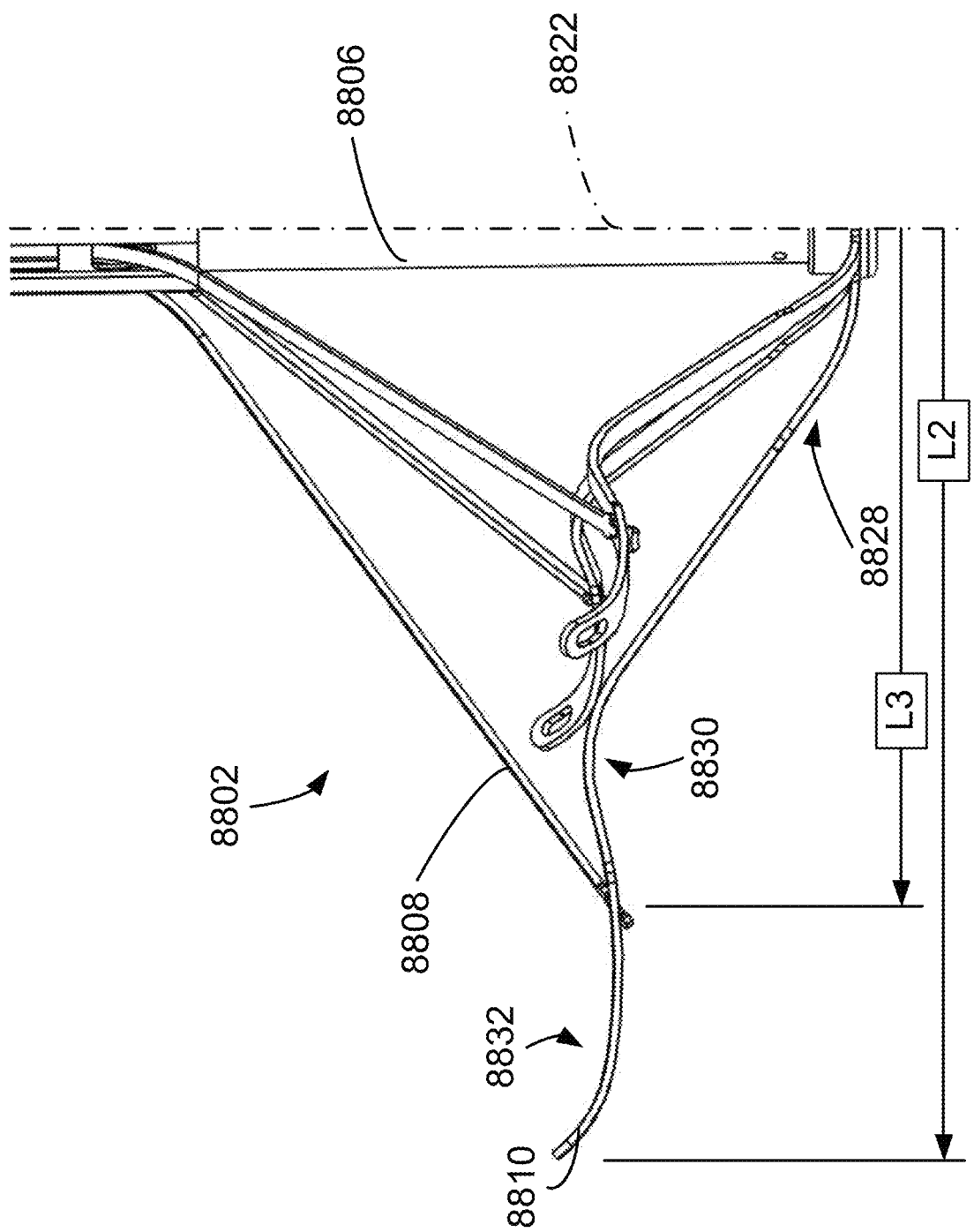
FIG. 88F is a partially dimensioned side view of the control arm assembly of FIG. 88B.
Figure 89:
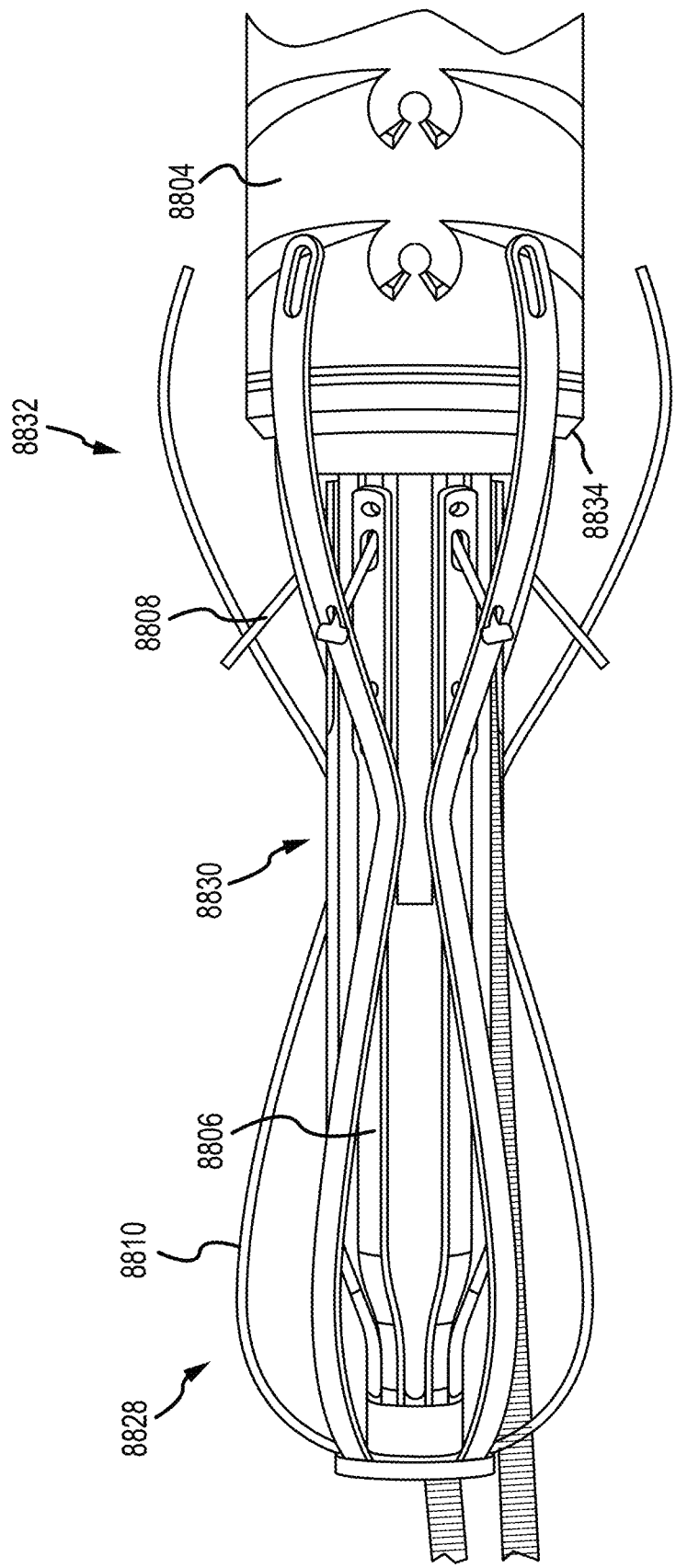

With the foregoing in mind, FIGS. 88A-89 illustrate an alternative configuration of a delivery device 8800 including a control arm assembly 8802 for selectively expanding and collapsing an implant 8850 and that is extendible from a delivery catheter 8804. In contrast to control arm assembly 3608 of delivery device 3600, in which coupling of the control arm pairs is positioned near the ends of the proximal and distal control arms, control arm assembly 8802 includes control arm pairs in which coupling of the proximal control arm and the distal control arm is positioned away from the end of the distal control arm such that a portion of the distal control arm is cantilevered. This configuration enables further retraction of control arm assembly 8802 into delivery catheter 8804 during delivery as compared to control arm assembly 3608, improving maneuverability of the distal end of delivery catheter 8804 and facilitating improved positioning and orientation of implant 8850.

FIG. 88A is a proximal perspective view of a distal end 8801 of delivery device 8800 with implant 8850 coupled to control arm assembly 8802. For clarity, delivery catheter 8804 is shown in FIG. 88A in dashed lines and occluder and outer skirt of implant 8850 are omitted. Control arm assembly 8802 is coupled to and distributed about an extension member 8806, which is selectively extendible from and retractable into delivery catheter 8804. So, for example, delivery catheter 8804 will generally be kept in a fully or near fully retracted state during delivery of the implant to minimize the unsteerable distal length of delivery device 8800. Following approximate placement of implant 8850, extension member 8806 is extended (in conjunction with retraction of a sheath (not shown) extending about the distal end of delivery device 8800) from delivery catheter 8804, deploying implant 8850 and permitting expansion of implant 8850 prior to final positioning/orientation and placement within the valve annulus.

As illustrated and as previously discussed in other sections of this disclosure, implant 8850 is coupled to control arm assembly 8802 by a first cinch line 8852 and a second cinch line 8854 that extend from a first cinch line tube 8856 and a second cinch line tube 8858, respectively, about a circumference of implant 8850. Implant 8850 includes eyelets (e.g., eyelet 8859) that extend proximally through slots formed in the distal control arms of control arm assembly 8802 with each of the cinch lines routed through the eyelets on a proximal side of the control arms, e.g., as illustrated in FIG. 73B. Each of first cinch line 8852 and second cinch line 8854 are held in position by a retention member 8860 that is retractable into delivery catheter 8804 through extension member 8806 to allow for retraction of first cinch line 8852 and second cinch line 8854 and release of implant 8850 from control arm assembly 8802.

FIG. 88B is the same perspective of FIG. 88A, albeit with implant 8850 and the cinch line-related elements of delivery device 8800 removed for clarity while FIG. 88C is a side elevation view of control arm assembly 8802. With reference to FIGS. 88B and 88C, control arm assembly 8802 generally includes a series of control arm pairs distributed about extension member 8806. In the specific example of delivery device 8800, control arm assembly 8802 includes six control arms pairs distributed at 60-degree offsets; however, other implementations of this disclosure may include more or fewer control arm pairs with different distributions.

Each control arm pair includes a proximal control arm, e.g., proximal control arm 8808, coupled to a respective distal control arm, e.g., distal control arm 8810. As shown in FIGS. 88D and 88E, coupling of proximal control arm 8808 to distal control arm 8810 may be based on a T-and-slot type coupling like the coupling arrangement discussed above in the context of FIG. 58. More specifically, proximal control arm 8808 includes a T- or I-shaped protrusion 8812 that is inserted through a corresponding aperture 8814 of distal control arm 8810 and rotated such that distal control arm 8810 is retained by protrusion 8812 and resulting in a coupling 8816 connecting proximal control arm 8808 and distal control arm 8810 in a hinge-like manner. Notably, coupling 8816 is disposed at a location distal a proximal end 8818 of distal control arm 8810 such that proximal end 8818 extends beyond coupling 8816 and forms a cantilevered section 8820 of distal control arm 8810.

Referring to FIG. 88B, the proximal control arm of each control arm pair of control arm assembly 8802 may be coupled to or drivable by a control shaft 8824 disposed within delivery catheter 8804. More specifically, as delivery catheter 8804 is translated distally, the proximal control arms are made to extend distally and radially outward (e.g., due to being directed outwardly by a diverter 8826). As the proximal control arms extend radially outward, they push the distal control arms outward as well, thereby expanding control arm assembly 8802. Conversely, if control arm assembly 8802 is in an expanded state and control shaft 8824 is proximally translated, the proximal control arms of control arm assembly 8802 are retracted and radially collapsed, resulting in corresponding radially collapse of the distal control arms to which the proximal control arms are coupled.

FIG. 88F illustrates proximal control arm 8808 and distal control arm 8810 in further detail with certain dimensions indicated. As shown in FIG. 88E, when fully expanded, distal control arm 8810 extends a length L2 relative to a longitudinal axis 8822 of delivery device 8800. In certain implementations, L2 may be from and including about 20 mm to and including about 40 mm. For example, L2 may be about 27 mm. In contrast, coupling 8816 is located at a length L3 relative to longitudinal axis 8822. In certain implementations, L3 may be from and including about 15 mm to and including about 20 mm, but not greater than L2. For example, L3 may be about 20 mm. More generally, L3 may be based on a relationship to L2. For example, in certain implementations L3 may be positioned at a location that is approximately within a central two-thirds of L2. As another example, L3 may be from and including about 40% to and including about 90% of L2. For example, L3 may be about 75% of L2.

As shown in FIG. 88F, each of the distal control arms may include various curved sections such that the distal control arms generally conform to other elements of delivery device 8800 when the distal control arms are in a collapsed state. For example, distal control arm 8810 includes each of a distal bend 8828, a medial bend 8830, and a proximal bend 8832 adapted to conform distal control arm 8810 to extension member 8806 and delivery catheter 8804.

FIG. 89 is a perspective view of delivery device 8800 with control arm assembly 8802 in a collapsed state, as shown, distal control arm 8810 is coupled to proximal control arm 8808 and is shaped to generally conform to extension member 8806 and delivery catheter 8804. More specifically, distal bend 8828 of distal control arm 8810 directs a first portion of distal control arm 8810 toward and along extension member 8806. Medial bend 8830 then directs a medial section of distal control arm 8810 radially outward and around a tip 8834 of delivery catheter 8804. Finally, proximal bend 8832 redirects distal control arm 8810 radially inward toward or parallel to delivery catheter 8804. Stated differently, the various curves of distal control arm 8810 result in a shape of distal control arm 8810 that generally conforms to the distal end of the various components of delivery device 8800. Notably, the shape of distal control arm 8810 enables retraction of control arm assembly 8802 such that a proximal extend of control arm assembly 8802 is positioned proximally beyond a distal end of delivery catheter 8804, reducing the non-steerable length of delivery catheter 8804. In at least certain implementations, the curved shape of distal control arm 8810 also results in a bulbous shape, particularly when sheathed, that is readily navigable through physiological lumens of the patient.

XXVI. Alternative Example Implantation Process

Figure 90:
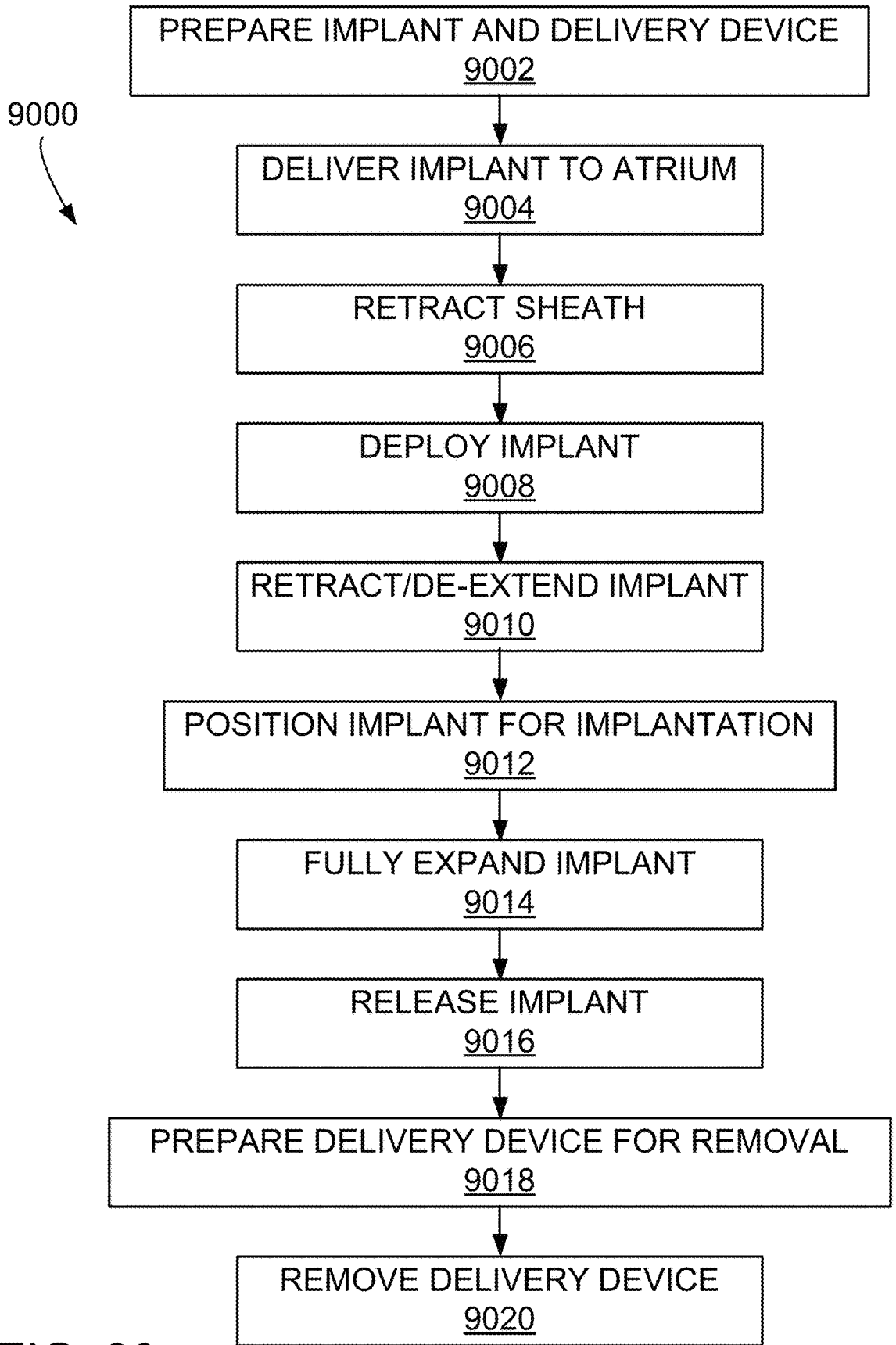

To provide additional detail and context for the various features described in the preceding sections, FIG. 90 is a block diagram illustrating a method 9000 for implanting an implant using delivery device, each of the implant and delivery device according to various aspects of this disclosure.

At step 9002, the implant and the delivery device are prepared for the implantation process. In general, preparation of the implant on the delivery device includes coupling the implant to a distal end of the delivery device, inserting the implant into a sheath/delivery catheter of the delivery device, and mounting the delivery device within the operating theater.

As described throughout this disclosure, coupling of the implant to the delivery device generally includes routing one or more cinch about the implant in a manner that couples the implant to a control arm assembly of the delivery device. For example, as illustrated in FIG. 73B, the implant may include circumferentially distributed eyelets (e.g., eyelet 6802) that extend proximally through both a frame (e.g., frame 6355) of the implant and control arms (e.g., control arm 7308) of the control arm assembly such that an aperture (e.g., cinch line hole 6810) of the eyelet is positioned proximal both the frame and control arm. A cinch line is then routed through the aperture and fixed (e.g., using a retractable retention member), thereby coupling the implant to the control arm assembly. FIG. 59 illustrates an alternative implementation in which cinch lines are routed through rings coupled to each of control arms of the control arm assembly and the implant frame such that cinch lines run through the rings similarly couples the implant to the control arm assembly.

In at least some implementations, coupling of the implant to the delivery device may also be facilitated through mating of corresponding elements of the implant and the control arm assembly. For example, referring back to FIG. 73B, eyelet 6802 may be sized and shaped to be press fit through slot 7312 of control arm 7308, thereby providing additional positive retention of the implant on the control arm assembly.

Coupling of the implant to the delivery device is generally performed with the delivery device in an extended position. For example, as previously discussed, the delivery device generally includes an internal tubular member coupled to the control arm assembly and that is longitudinally translatable relative to the delivery catheter of the delivery device. During delivery and implantation, such extension and retraction facilitates positioning and orientation of the implant without requiring substantial steering or insertion of the delivery catheter. Accordingly, during preparation of the delivery device and implant, the delivery device may be placed in a fully or partially extended state. following coupling of the implant to the control arm assembly of the delivery device, the implant may be radially compressed and the control arm assembly retracted such that the implant is partially retracted into the delivery catheter and/or is coverable by an extendible sheath of the delivery device.

With the implant coupled to the delivery device and sheathed, the delivery device may be coupled to a mount assembly, such as the mount assembly described above in the context of FIGS. 87A-87N.

As noted in the context of FIGS. 87H and 87I, preparation of the implant and delivery device may also include preparation of the mounting assembly on which the delivery device is supported, such as by sterilizing and/or applying a sterile drape to the mounting assembly prior to coupling the delivery device to the mounting assembly.

At step 9004, the implant is delivered to a patient atrium, e.g., via an antegrade percutaneous route (e.g., a trans-femoral or trans-jugular route). Navigating the delivery device and implant to the implantation site may include routing the delivery device along a guidewire previously inserted into the patient and extending to the atrium.

Navigating the delivery device and implant may include one or more of a combination of steering the delivery catheter of the delivery device, modifying insertion of the delivery device, modifying rotation of the delivery device, or any similar movement and manipulation of the delivery device. In certain implementations, at least some of the maneuverability of the delivery catheter and the delivery device may be provided by insertion and rotation control elements of the mounting assembly to which the delivery device is attached. For example, the mounting assembly of FIGS. 87A-87N includes a stepper-type control knob that may be rotated to control insertion of the delivery device and a manually rotatable collar that can be rotationally indexed to modify a rotation of the delivery device.

As noted, navigating the implant may also include steering the delivery catheter of the delivery device. In certain implementations, the delivery catheter may include multiple steerable sections. For example, in the specific example illustrated in FIGS. 45A-45H, delivery catheter 3604 includes a distal steerable section 4502 and a proximal section proximal steerable section 4504 with distal steerable section 4502 steerable along a first plane and proximal steerable section 4504 steerable along each of the first plane and a second plane orthogonal to the first plane (both relative to delivery catheter 3604 being in a neutral steering configuration). As described and illustrated in the context of FIG. 46, steering may be achieved in certain implementation, by a collection of levers disposed at the handle assembly of the delivery device with each handle manipulable to control steering of a corresponding section of the delivery catheter along a specific plane.

Step 9006 includes retracting the sheath extending around the distal end of the delivery device, including the implant, to facilitate subsequent deployment of the implant. As discussed in previous sections, retracting of the sheath may include manipulating a corresponding control of the delivery device handle assembly to proximally translate the sheath relative to the delivery catheter, thereby exposing the distal end of the delivery device and the implant.

Step 9008 includes deploying the implant. Deploying the implant generally refers to the process of clearing the implant from the sheath and the distal end of the delivery catheter such that the implant can be freely expanded, collapsed, and positioned for implantation.

In at least certain implementations, clearing the implant from the sheath and the distal end of the delivery catheter may include distally extending the implant relative to the delivery catheter. For example, FIGS. 79A-80B illustrate an example handle assembly mechanism configured to longitudinally translate the implant relative to the delivery catheter. More specifically, the handle assembly shown includes a rotatable knob that drives an internal shuttle of the handle assembly. The shuttle, in turn, is coupled to an extension shaft that extends through the delivery catheter and terminates in the control arm assembly to which the implant is coupled. Operating the rotatable knob translates the shuttle within the handle assembly, thereby driving the extension shaft and, as a result, the control arm assembly and implant. As noted in FIGS. 74-76D, in at least certain implementations, the extension member may include sections of selectively modified flexibility such that the extension shaft does not substantially impact the steerability of the delivery catheter within which the extension shaft extends.

Deploying the implant may further include expanding the implant following clearance of the sheath and the delivery catheter. As described in the context of FIGS. 81A-82O, expansion of the implant may be performed by rotation of an expansion control, e.g., a rotatable knob, of the handle assembly. In one specific implementation, expansion is achieved by actuation (e.g., rotation) of the expansion control, which results in simultaneous proximal translation of a control arm shaft and corresponding payout of the cinch lines coupling the control arm assembly to the implant. Proximal translation of the control arm shaft causes the control arm pairs of the control arm assembly to expand laterally. Given the coupling of the implant to the control arm assembly and the biasing of the implant into expansion, expansion of the control arm assembly drives and/or permits natural expansion of the implant into an expanded state. Notably, payout of the cinch lines is generally coordinated by the handle assembly such that the cinch lines are maintained in tension as the implant expands. Doing so improves the uniformity with which the implant expands while improving the responsiveness of the implant to actuation of the expansion controls.

Step 9010 includes retracting/de-extending the implant relative to the delivery catheter following at least partial expansion of the implant in step 9008. Among other things, such retraction of the implant relative to the delivery catheter reduces the non-steerable length at the distal end of the delivery device. With less non-steerable length, the implant can be more readily and accurately manipulated within the atrium to facilitate proper alignment of the implant with the valve annulus. In certain implementations, the retraction of step 9010 may be performed by reversing the extension mechanism discussed above in the context of step 9008. So, for example, the extension control (e.g., the rotatable knob corresponding to extension) of the handle assembly may be actuated in an opposite direction to proximally retract the shuttle of the handle assembly. Doing so also retracts the extension shaft, thereby retracting the now-expanded implant relative to the delivery catheter.

Step 9012 includes positioning the implant for final implantation. Among other things, such positioning may include aligning or approximately aligning a longitudinal axis of the implant with a valve axis normal to the valve annulus. Positioning the implant may further include adjusting the height of the implant relative to the valve annulus such that an occluder of the implant is positioned to interact with or otherwise contact the native leaflets of the patient valve. Positioning the implant may include additional expanding, collapsing, and/or moving of the implant to achieve proper positioning of the implant relative to the valve annulus. Moving of the implant may include, without limitation, one or more of changing rotation and insertion of the delivery device, steering of the delivery catheter, and extending/retracting the implant relative to the delivery catheter, as described in previous steps.

Step 9014 includes fully expanding the implant once in position for implantation. As noted above in the context of step 9008, expanding the implant generally includes operating an expansion control of the handle assembly that simultaneously expands the control arm assembly to which the implant is coupled and pays out the cinch line extending around the implant. By fully expanding the implant, within the valve annulus, the implant is made to interfere with and engage cardiac tissue. For example, the implant may include outwardly protruding prongs or tines shaped and positioned to engage tissue adjacent the valve during the expansion process.

Step 9016 includes releasing the implant from the delivery device by decoupling the implant from the control arm assembly of the delivery device. A full description of an example release process and corresponding handle mechanisms for achieving release of the implant are described above in the context of FIGS. 83A-86D. In general, however, certain release processes include coordinate release and retraction of the cinch lines coupling the implant to the control arm assembly. For example, in certain implementations, the handle assembly includes a control element (e.g., a rotating ring) that, when actuated first pulls one or more retention members that pin the cinch lines extending around the implant in position. Further rotation of the control element then initiates pulling of the cinch lines into the delivery catheter, thereby decoupling the control arm assembly and the implant. In implementations in which the control arm assembly and implant are further coupled by a press fit or similar loose-fitting joint, full release of the implant from the control arm assembly/delivery device may further include retracting the control arm assembly (e.g., by operating the extension mechanism to retract the control arm assembly) or by applying a similar proximal force on the control arm assembly (e.g., by retracting or rotating the delivery device, steering the delivery catheter, or performing a similar actuation of the delivery device).

Step 9018 includes preparing the delivery device for retraction and removal from the patient. In general, preparation of the delivery device includes fully collapsing and retracting the control arm assembly and re-sheathing the distal portion of the delivery device. Finally, at step 9020, the delivery device may be removed from the patient. In certain cases, removal of the delivery device from the patient includes both retraction of the delivery device and steering of the catheter into a substantially neutral position as the distal end of the delivery device exits the atrium. Following removal of the delivery device from the atrium, the delivery catheter may be fully extracted from the patient back along the surgical route used during insertion.

XXVII. Illustrative Aspects of the Present Disclosure

Illustrative examples of the disclosure include, but are not limited to the following:

Aspect 1-1. A delivery tool for an implantable medical device including a handle body; a threaded shaft extending within the handle body; a shuttle threadedly engaged with the threaded shaft and configured to translate along the threaded shaft in response to rotation of the threaded shaft; a gear assembly drivable by rotating the threaded shaft; a spool coupled to the gear assembly such that the spool is rotatable in response to rotation of the threaded shaft and simultaneously with translation of the shuttle; a control arm shaft coupled to the shuttle and extending distally from the handle body, the control arm shaft translatable by translating the shuttle; and a control arm assembly coupled to a distal end of the control arm shaft, wherein the control arm assembly is laterally expandable in response to translation of the control arm shaft.

Aspect 1-2. The delivery tool of Aspect 1-1 further including an extension member extending distally relative to the distal end of the control arm shaft, wherein the control arm assembly further includes: a proximal control arm coupled to a distal end of the control arm assembly; and a distal control arm, wherein: a proximal end of the distal control arm is coupled to the proximal control arm at a coupling location, and a distal end of the distal control arm is coupled to a distal end of the extension member.

Aspect 1-3. The delivery tool of Aspect 1-1 further including at least one cinch line coupled to the spool and extending distally from the handle body such that rotation of the spool results in a change in length of the cinch line extending from the spool.

Aspect 1-4. The delivery tool of Aspect 1-1 further including a plurality of cinch lines coupled to the spool and extending distally from the handle body such that rotation of the spool results in a simultaneously change in length of each of the plurality of cinch lines extending from the spool.

Aspect 1-5. The delivery tool of Aspect 1-1, wherein the gear assembly includes a worm gear coupled to the threaded shaft and a worm wheel engaged with the worm gear and coupled to the spool.

Aspect 1-6. The delivery tool of Aspect 1-1 further including a user input actuatable to rotate the threaded shaft.

Aspect 1-7. The delivery tool of Aspect 1-6, wherein the user input is a knob coupled to a proximal end of the threaded shaft.

Aspect 1-8. The delivery tool of Aspect 1-1, wherein the threaded shaft is a first threaded shaft and the delivery tool further includes a second threaded shaft configured to simultaneously translate each of the gear assembly, the shuttle, and the threaded shaft.

Aspect 1-9. The delivery tool of Aspect 1-8 further including a gear assembly shuttle coupled to the gear assembly and threadedly engaged with the second threaded shaft, the gear assembly shuttle configured to move along the second threaded shaft in response to rotation of the second threaded shaft.

Aspect 1-10. The delivery tool of Aspect 1-8 further including a first user input actuatable to rotate the first threaded shaft and a second user input actuatable to rotate the second threaded shaft.

Aspect 1-11. The delivery tool of Aspect 1-8, wherein the first user input is a first knob coupled to a proximal end of the first threaded shaft and the second user input is a second knob coupled to a proximal end of the second threaded shaft.

Aspect 2-1. A delivery tool for an implantable medical device including: a handle body; a threaded shaft extending within the handle body; a shuttle threadedly engaged with the threaded shaft and configured to translate along the threaded shaft in response to rotation of the threaded shaft; an extension shaft coupled to the shuttle and extending distally from the handle body, the extension shaft translatable by translating the shuttle; and a control arm assembly coupled to a distal end of the control arm shaft, wherein the control arm assembly is longitudinally translatable in response to translation of the extension shaft and laterally expandable independent of being longitudinally translated by the extension shaft.

Aspect 2-2. The delivery tool of Aspect 2-1 further including an extension member coupled to and extending distally from the extension shaft.

Aspect 2-3. The delivery tool of Aspect 2-2, wherein the control arm assembly further includes each of a proximal control arm and a distal control arm, wherein: a proximal end of the distal control arm is coupled to the proximal control arm at a coupling location, and the proximal control arm is drivable to laterally translate the coupling location, thereby selectively expanding the control arm assembly.

Aspect 2-4. The delivery tool of Aspect 2-1 further including an expansion assembly configured to drive expansion and collapse of the control arm assembly independent of longitudinally translating the control arm assembly.

Aspect 2-5. The delivery tool of Aspect 2-4, wherein longitudinally translating the control arm assembly further longitudinally translates the expansion assembly.

Aspect 3-1. A delivery tool for an implantable medical device including: a handle body; a frame element supported by the handle body, the frame element defining an aperture and having a longitudinal axis extending through the aperture; a control ring defining a ring orifice and supported by the frame element, wherein the control ring is rotatable about the longitudinal axis and includes a line coupling location; and a protrusion extending into the ring orifice at a radial offset from the longitudinal axis, wherein the protrusion is configured to interfere with a control line extending from the aperture to the line coupling location following a rotation of the control ring.

Aspect 3-2. The delivery tool of Aspect 3-1 further including a lock configured to selectively prevent rotation of the control ring relative to the frame element.

Aspect 3-3. The delivery tool of Aspect 3-1, wherein: the line coupling location is a first line coupling location, the control ring includes a second release line coupling location angularly offset from the first release line coupling location; and the protrusion is further configured to interfere with a second control line extending from the aperture to the second line coupling location in response to a further rotation of the control ring.

Aspect 3-4. The delivery tool of Aspect 3-3 further including the first control line and a retention element, wherein the first control line is coupled to the retention element such that interference of the first control line with the protrusion results in proximal retraction of the retention element.

Aspect 3-5. The delivery tool of Aspect 3-4 further including a cinch line, wherein the retention element is configured to retain a distal end of the cinch line prior to proximal retraction of the retention element and to release the distal end of the cinch line when retracted.

Aspect 3-6. The delivery tool of Aspect 3-5, wherein the cinch line is one of a plurality of cinch lines and the retention element is configured to retain each of the plurality of cinch lines prior to proximal retraction of the retention element and to release each of the plurality of cinch lines when retracted.

Aspect 3-7. The delivery tool of Aspect 3-3 further including the second control line and a cinch line, wherein the second control line is configured such that interference of the second release line with the protrusion results in proximal retraction of the cinch line.

Aspect 3-8. The delivery tool of Aspect 3-7, wherein the cinch line is configured to be routed about a portion of the implantable medical device to distribute forces about the implantable medical device during at least one of expansion and contraction of the implantable medical device.

Aspect 3-9. The delivery tool of Aspect 3-3 further including the second release line and a plurality of cinch lines, wherein the second release line is configured to proximally retract each cinch line of the plurality of cinch lines.

Aspect 3-10. The delivery tool of Aspect 3-9, wherein: a proximal end of each cinch line of the plurality of cinch lines is anchored within the handle body, the second release line forms a loop within the handle body, and each cinch line of the plurality of cinch lines extends through the loop such that retraction of the second release line proximally retracts each of the plurality of cinch lines. Aspect 4-1. A delivery tool for an implantable medical device including: a handle body;

a tubular body extending distally from the handle body; and a control arm assembly coupled to a distal end of the tubular body, wherein: the control arm assembly is selectively expandable in a lateral direction, and the tubular body includes a proximal steerable section and a distal steerable section, the proximal steerable section being independently steerable from the distal steerable section.

Aspect 4-2. The delivery tool of Aspect 4-1, wherein the distal steerable section is steerable along a first plane and the proximal steerable section is steerable along each of the first plane and a second plane orthogonal to the first plane.

Aspect 4-3. The delivery tool of Aspect 4-1 further including an extension tube disposed within the tubular body and configured to longitudinally translate independent of the tubular body to selectively extend the control arm assembly relative to the tubular body, wherein the extension tube includes an extension tube section having modified flexibility with respect to bending along a steering plane of the tubular body.

Aspect 4-4. The delivery tool of Aspect 4-3, wherein the extension tube section includes a plurality of longitudinal cuts extending along the extension tube section and perpendicular to the steering plane.

Aspect 4-5. The delivery tool of Aspect 4-3, wherein the extension tube section includes a helical cut extending along the extension tube section.

Aspect 4-6. The delivery tool of Aspect 4-1 further including an extension tube disposed within the tubular body and configured to longitudinally translate independent of the tubular body to selectively extend the control arm assembly relative to the tubular body, wherein: the distal steerable section is steerable along a first plane, the proximal steerable section is steerable along each of the first plane and a second plane orthogonal to the first plane, the extension tube includes a distal extension tube section having modified flexibility with respect to bending along the first plane, the extension tube includes a proximal extension tube section having modified flexibility with respect to bending along each of the first plane and the second plane.

Aspect 4-7. The delivery tool of Aspect 4-6, wherein the distal extension tube section includes a plurality of longitudinal cuts extending along the distal extension tube section and perpendicular to the first plane.

Aspect 4-8. The delivery tool of Aspect 4-6, wherein the proximal extension tube section includes a helical cut extending along the extension tube section.

Aspect 4-9. The delivery tool of Aspect 4-3, wherein the extension tube is formed from nitinol.

Aspect 5-1. A cardiac valve repair implant including: a central occluder; a frame extending about a central longitudinal axis from the central occluder and self-biasing from a collapsed state to an expanded state, the frame including: an inner frame portion supporting the central occluder; a plurality of spokes extending proximally from the central portion and forming a circumference about the central longitudinal axis; and expandable outer cells disposed between adjacent spokes of the plurality of spokes; and an outer sheet supported on a proximal portion of the frame and extending circumferentially about the proximal portion of the frame, wherein when the frame is in the expanded state, the outer sheet and the central occluder define an annulus between the outer sheet and the central occluder centered about the central longitudinal axis.

Aspect 5-2. The cardiac valve repair implant of Aspect 5-1, wherein the outer sheet is formed from a knit polyethylene terephthalate material.

Aspect 5-3. The cardiac valve repair implant of Aspect 5-1, wherein a distal edge of the outer sheet is circular about the central longitudinal axis.

Aspect 5-4. The cardiac valve repair implant of Aspect 5-1, wherein a proximal edge of the outer sheet is sinusoidal.

Aspect 5-5. The cardiac valve repair implant of Aspect 5-1, wherein a proximal edge of the outer sheet varies between a first proximal extend and a second proximal extent different than the first proximal extent.

Aspect 5-6. The cardiac valve repair implant of Aspect 5-1, wherein the outer sheet is coupled to the frame by one or more hems.

Aspect 5-7. The cardiac valve repair implant of Aspect 5-6, wherein the outer sheet is coupled to the frame by a first hem extending along a proximal edge of the frame and a second hem extending about a proximal edge of the annulus.

Aspect 5-8. The cardiac valve repair implant of Aspect 5-1, wherein each of the expandable outer cells includes a proximal tip and a distal tip and wherein a suture is wrapped about at least one of the proximal tip and the distal tip.

Aspect 6-1. A cardiac valve repair implant including: a central occluder including a central longitudinal axis; a frame extending from the central occluder, the frame including a central portion supporting the central occluder and a plurality of spokes extending from the central portion and distributed circumferentially about the central longitudinal axis; an outer sheet supported on a proximal portion of the frame and extending circumferentially about the proximal portion of the frame; and a plurality of eyelets distributed circumferentially about the central longitudinal axis, each eyelet of the plurality of eyelets coupled to and extending from a respective spoke of the plurality of spokes.

Aspect 6-2. The cardiac valve repair implant of Aspect 6-1, wherein the outer sheet is retained on an outer side of the frame and the plurality of eyelets extend opposite the outer sheet.

Aspect 6-3. The cardiac valve repair implant of Aspect 6-1, wherein a spoke of the plurality of spokes defines a slot through which an eyelet of the plurality of eyelets extends.

Aspect 6-4. The cardiac valve repair implant of Aspect 6-3, wherein: the eyelet includes a body portion defining a through hole and a shank portion coupled to the body portion, the shank portion has a width greater than the body portion, and the eyelet is received by the slot such that the body portion extends through the slot to a first side of the spoke and the shank is retained on a second side of the spoke opposite the first side.

Aspect 6-5. The cardiac valve repair implant of Aspect 6-3, wherein the eyelet defines a retention hole and the eyelet is coupled to the frame by a suture loop extending through the retention hole and around the frame.

Aspect 6-6. The cardiac valve repair implant of Aspect 6-1, wherein each of eyelets includes a radiused through hole.

Aspect 7-1. A cardiac valve repair implant comprises: a central occluder including a central longitudinal axis; a frame extending proximally from the central occluder, the frame centered about and forming a circumference around the central longitudinal axis of the central occluder and self-biasing from a collapsed state to an expanded state; and an outer sheet supported on a proximal portion of the frame, wherein when the frame is in the expanded state, the outer sheet forms an annular surface defining an inner circular opening centered about the central longitudinal axis of the central occluder, wherein: the frame including an inner portion coupled to and supporting the central occluder, and the central occluder has a laminated construction including a first sheet disposed on a distal side of the inner frame portion coupled to a second sheet disposed on a proximal side of the inner frame portion.

Aspect 7-2. The cardiac valve repair implant of Aspect 7-1 wherein the central occluder has a distally concave shape.

Aspect 7-3. The cardiac valve repair implant of Aspect 7-1, wherein the first sheet is formed from a substantially impermeable material.

Aspect 7-4. The cardiac valve repair implant of Aspect 7-3, wherein the second sheet is formed from a permeable material.

Aspect 7-5. The cardiac valve repair implant of Aspect 7-4, wherein the second sheet is bonded to the first sheet by a liquid bonding material applied to the second sheet.

Aspect 7-6. The cardiac valve repair implant of Aspect 7-1, wherein the first sheet is formed from expanded polytetrafluoroethylene (ePTFE).

Aspect 7-7. The cardiac valve repair implant of Aspect 7-1, wherein the second sheet is formed from a fabric.

Aspect 7-8. The cardiac valve repair implant of Aspect 7-7, wherein the fabric including woven polyethylene terephthalate (PET).

Aspect 7-9. The cardiac valve repair implant of Aspect 7-1, wherein the first sheet is coupled to the second sheet using a polyurethane compound.

Aspect 7-10. The cardiac valve repair implant of Aspect 7-9, wherein the polyurethane compound including a siloxane segmented polyurethane and a polymer precursor.

Aspect 7-11. The cardiac valve repair implant of Aspect 7-10, wherein the polymer precursor is such as tetrahydrofuran (THF).

Aspect 7-12. The cardiac valve repair implant of Aspect 7-1, wherein the central occluder further comprises a proximal cap.

Aspect 7-13. The cardiac valve repair implant of Aspect 7-12, wherein the proximal cap including a frame element and a proximal sheet coupled to the frame element.

Aspect 7-14. The cardiac valve repair implant of Aspect 7-13, wherein the proximal sheet is formed from a porous material.

Aspect 7-15. The cardiac valve repair implant of Aspect 7-12, wherein the proximal cap has a distally convex shape.

Aspect 7-16. The cardiac valve repair implant of Aspect 7-12, wherein the proximal cap and the second sheet define an internal volume of the central occluder.

Aspect 7-17. The cardiac valve repair implant of Aspect 7-16, wherein the internal volume is filled with aa solid or expandable material.

Aspect 7-18. The cardiac valve repair implant of Aspect 7-12, wherein the proximal cap is coupled to at least one of the first sheet and the second sheet by a suture extending around the circumference of the central occluder.

XXVIII. Conclusion

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

In general, while the embodiments described herein have been described with reference to particular embodiments, modifications can be made thereto without departing from the spirit and scope of the disclosure. Note also that the term "including" as used herein is intended to be inclusive, i.e. "including but not limited to."

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

We claim:

1. A delivery device for cardiac valve repair implants, the delivery device comprising:
   a delivery catheter;
   an extension member protruding from a distal end of the delivery catheter; and
   a control arm assembly releasably coupleable to a valve repair implant, the control arm assembly including a control arm pair, wherein the control arm pair includes:
   a distal control arm coupled to and extending proximally from a distal end of the extension member; and
   a proximal control arm coupled to a proximal portion of the distal control arm, wherein the proximal control arm is extendable from the distal end of the delivery catheter by pushing the proximal control arm, and wherein the control arm assembly is configured to laterally expand in response to extending the proximal control arm.

2. The delivery device of claim 1, wherein the control arm pair is one of a plurality of control arm pairs of the control arm assembly, each control arm pair including a respective distal control arm and a respective proximal control arm.

3. The delivery device of claim 2, wherein each proximal control arm of each control arm pair is simultaneously extendable from the distal end of the delivery catheter to laterally expand the control arm assembly.

4. The delivery device of claim 2, further comprising a control arm shaft disposed within the delivery catheter, wherein:
   the control arm shaft is coupled to a proximal portion of the control arm assembly and is translatable relative to the delivery catheter, and
   each proximal control arm of each control arm pair is simultaneously extendable from the distal end of the delivery catheter to laterally expand the control arm assembly by translating the control arm shaft.

5. The delivery device of claim 1, further comprising a control assembly coupled to a proximal end of the delivery catheter and a control arm extension member shaft extending through the delivery catheter and coupled to the proximal control arm, the control assembly including a control for selectively extending and retracting the proximal control arm by translating the control arm extension member shaft.

6. The delivery device of claim 1, further comprising a diverter disposed distal the distal end of the delivery catheter, wherein the diverter directs the proximal control arm laterally as the proximal control arm is extended from the distal end of the delivery catheter.

7. The delivery device of claim 1, wherein the distal control arm is rigidly coupled to the distal end of the extension member such that, as the proximal control arm is extended from the distal end of the delivery catheter, the distal control arm bends laterally.

8. The delivery device of claim 1, wherein the extension member is selectively extendable from the distal end of the delivery catheter.

9. The delivery device of claim 8 further comprising a control assembly coupled to a proximal end of the delivery catheter, the control assembly including a control for selectively extending and retracting the extension member from the distal end of the delivery catheter.

10. The delivery device of claim 1 further comprising a control assembly coupled to a proximal end of the delivery catheter and an extension member shaft extending through the delivery catheter and coupled to the extension member, the control assembly including a knob rotatable to selectively extend and retract the proximal control arm by translating the extension member shaft.

11. The delivery device of claim 1 further comprising a sheath disposed about the delivery catheter, wherein the sheath is translatable from a first position in which the sheath extends over the extension member and a second position in which the extension member is at least partially exposed.

12. The delivery device of claim 1, wherein:
the delivery catheter includes a first steerable portion and a second steerable portion,
the first steerable portion is distal the second steerable portion, and
the first steerable portion is steerable independent of the second steerable portion.

13. The delivery device of claim 12, wherein the first steerable portion and the second steerable portion are steerable along a common plane.

14. The delivery device of claim 13, wherein the second steerable portion is further steerable along a second plane orthogonal to the common plane.

15. The delivery device of claim 1, wherein the proximal control arm is coupled to a proximal end of the distal control arm.

16. The delivery device of claim 1, wherein the proximal control arm is coupled to a location of the distal control arm within a proximal half of the distal control arm.

17. The delivery device of claim 1, wherein the distal control arm includes a distal curvate section that is distally concave and a proximal curvate section that is proximally concave.

18. The delivery device of claim 1 further comprising at least one cinch line extending through the delivery catheter and selectively retractable and extendable relative to the delivery catheter.

19. The delivery device of claim 18 further comprising a control assembly coupled to a proximal end of the delivery catheter, the control assembly including a control for each of simultaneously expanding the control arm assembly and paying out the at least one cinch line and simultaneously collapsing the control arm assembly and retracting the at least one cinch line.

20. A delivery device for cardiac valve repair implants, the delivery device comprising:
a delivery catheter;
an extension member protruding from a distal end of the delivery catheter; and
a control arm assembly releasably coupleable to a valve repair implant, the control arm assembly including a plurality of control arm pairs distributed circumferentially about the extension member, wherein each control arm pair of the plurality of control arm pairs includes:
a distal control arm coupled to and extending proximally from a distal end of the extension member; and
a proximal control arm coupled to a proximal portion of the distal control arm, wherein the proximal control arm is extendable from the distal end of the delivery catheter by pushing the proximal control arm, and wherein the control arm assembly is configured to laterally expand in response to extending the proximal control arm.

21. The delivery device of claim 20, further comprising a control arm extension member shaft extending through the delivery catheter and coupled to each proximal control arm of the plurality of control arm pairs, wherein the control arm extension member shaft is selectively translatable relative to the delivery catheter to expand and contract the control arm assembly.

22. The delivery device of claim 20 further comprising at least one cinch line extending through the delivery catheter and selectively retractable and extendable relative to the delivery catheter.

23. The delivery device of claim 22 further comprising a control assembly coupled to a proximal end of the delivery catheter, the control assembly including a control for each of simultaneously expanding the control arm assembly and paying out the at least one cinch line and simultaneously collapsing the control arm assembly and retracting the at least one cinch line.

24. The delivery device of claim 20, wherein:
the delivery catheter includes a first steerable portion and a second steerable portion,
the first steerable portion is distal the second steerable portion,
the first steerable portion is steerable independent of the second steerable portion,
each of the first steerable portion and the second steerable portion are steerable along a common plane; and
the second steerable portion is further steerable along a second plane orthogonal to the common plane.

25. A delivery device for cardiac valve repair implants, the delivery device comprising:
a delivery catheter;
an extension member protruding from a distal end of the delivery catheter; and
a control arm assembly releasably coupleable to a valve repair implant, the control arm assembly including a control arm pair, wherein the control arm pair includes:
a distal control arm coupled to and extending proximally from a distal end of the extension member; and
a proximal control arm coupled to a proximal portion of the distal control arm, wherein the proximal control arm is extendable from the distal end of the delivery catheter by pushing the proximal control arm, and wherein the control arm assembly is configured to laterally expand in response to extending the proximal control arm, wherein the delivery catheter includes a distal portion including a plurality of independently steerable sections.

26. The delivery device of claim 25, wherein the plurality of independently steerable sections includes a first steerable section and a second steerable section and each of the first steerable section and the second steerable section is steerable along a common plane.

27. The delivery device of claim 26, wherein the first steerable section is distal the second steerable section and the second steerable section is further steerable along a second plane orthogonal to the common plane.

28. The delivery device of claim 25, wherein the control arm pair is one of a plurality of control arm pairs of the control arm assembly, each control arm pair including a respective distal control arm and a respective proximal control arm.

29. The delivery device of claim 28, further comprising a control arm shaft disposed within the delivery catheter, wherein:
   the control arm shaft is coupled to a proximal portion of the control arm assembly and is translatable relative to the delivery catheter, and
   each proximal control arm of each control arm pair is simultaneously extendable from the distal end of the delivery catheter to laterally expand the control arm assembly by translating the control arm shaft.

30. The delivery device of claim 25, wherein the extension member is selectively extendable from the distal end of the delivery catheter.

* * * * *